US011834756B2

(12) United States Patent
Pawlosky et al.

(10) Patent No.: US 11,834,756 B2
(45) Date of Patent: Dec. 5, 2023

(54) METHODS AND COMPOSITIONS FOR PROTEIN AND PEPTIDE SEQUENCING

(71) Applicant: Google LLC, Mountain View, CA (US)

(72) Inventors: Annalisa Marie Pawlosky, Mountain View, CA (US); Michael Gibbons, Livermore, CA (US); Sara Ahadi, San Mateo, CA (US); Shirley Jing Shao, Sunnyvale, CA (US); Anna Le, San Jose, CA (US); Ali Bashir, San Francisco, CA (US); Marc Berndl, Mountain View, CA (US); Michelle Therese Hoerner Dimon, Redwood City, CA (US); Lauren Schiff, Encino, CA (US)

(73) Assignee: Google LLC, Mountain View, CA (US)

( * ) Notice: Subject to any disclaimer, the term of this patent is extended or adjusted under 35 U.S.C. 154(b) by 228 days.

(21) Appl. No.: 17/019,121

(22) Filed: Sep. 11, 2020

(65) Prior Publication Data

US 2021/0079557 A1    Mar. 18, 2021

Related U.S. Application Data

(60) Provisional application No. 62/900,440, filed on Sep. 13, 2019.

(51) Int. Cl.
| | |
|---|---|
| *C12Q 1/68* | (2018.01) |
| *C40B 30/04* | (2006.01) |
| *C40B 70/00* | (2006.01) |
| *C12Q 1/6806* | (2018.01) |
| *C40B 40/04* | (2006.01) |
| *C12Q 1/6869* | (2018.01) |

(52) U.S. Cl.
CPC .......... *C40B 30/04* (2013.01); *C12Q 1/6806* (2013.01); *C12Q 1/6869* (2013.01); *C40B 40/04* (2013.01); *C40B 70/00* (2013.01); *C12Q 2525/205* (2013.01)

(58) Field of Classification Search
None
See application file for complete search history.

(56) References Cited

U.S. PATENT DOCUMENTS

| | | |
|---|---|---|
| 2003/0198970 A1 | 10/2003 | Roberts |
| 2009/0264300 A1 | 10/2009 | Franch et al. |
| 2016/0060687 A1 | 3/2016 | Zhu |
| 2017/0211133 A1 | 7/2017 | Landegren |
| 2018/0320224 A1 | 11/2018 | Gaublomme et al. |
| 2021/0079398 A1 | 3/2021 | Pawlosky et al. |
| 2021/0102248 A1 | 4/2021 | Pawlosky et al. |
| 2021/0171937 A1 | 6/2021 | Pawlosky et al. |
| 2022/0155300 A1 | 5/2022 | Tsai et al. |

FOREIGN PATENT DOCUMENTS

WO    WO 2017070309    4/2017

OTHER PUBLICATIONS

Flanigon, Multiplex protein detection with DNA readout via mass spectrometry, N. Biotechnol., 30(2): 153-158, 2013 (Year: 2013).
Flanigon, Multiplex protein detection with DNA readout via mass spectrometry, N. Biotechnol., 30(2): 153-158, 2013, Supplement. (Year: 2013).
Hansen, Sensitive ligand-based protein quantification using immune-PCR: A critical review of single-probe and proximity ligation assays, BioTechniques, 56: 217-228, 2014. (Year: 2014).
Abreu et al., "Global signatures of protein and mRNA expression levels," Molecular BioSystems, 2009, 5(12):1512-26.
Almasi et al., "Development of a single stranded DNA aptamer as a molecular probe for Incap cells using cell-selex," Avicenna journal of medical biotechnology, Jul. 2016, 8(3):104.
Berezhnoy et al., "Isolation and optimization of murine IL-10 receptor blocking oligonucleotide aptamers using high-throughput sequencing," Molecular Therapy, Jun. 2012, 20(6):1242-50.
Bergman et al., "Chemical C-terminal protein sequence analysis: improved sensitivity, length of degradation, proline passage, and combination with Edman degradation," Analytical biochemistry, Mar. 2001, 290(1):74-82.
Blind et al., "Aptamer Selection Technology and Recent Advances," Molecular Therapy—Nucleic Acids, Jan. 2015, 4:e223.
Bouchard et al., "Discovery and development of therapeutic aptamers," Annual review of pharmacology and toxicology, Feb. 2010, 50:237-57.
Casagranda et al., "InBasic Protein and Peptide Protocols," Human Press, 1994, 335-349.
Chen et al., "Conservation and sustainable use of medicinal plants: problems, progress, and prospects," Chinese medicine, Dec. 2016, 11(1):37.
Chen et al., "Development of cell-SELEX technology and its application in cancer diagnosis and therapy," International journal of molecular sciences, Dec. 2016, 17(12):2079.
Cheng et al., "Diversity of spotted fever group Rickettsia infection in hard ticks from Suifenhe," Chinese-Russian border Ticks Tick Borne Dis., 2016, 7:715-9.
De Sousa Abreu et al., "Absolute protein expression profiling estimates the relative contributions of transcriptional and translational regulation," Mol. Biosyst., 2009, 5(12):1512-26.
Diatchenko et al., "Suppression subtractive hybridization: a method for generating differentially regulated or tissue-specific cDNA probes and libraries," Proceedings of the National Academy of Sciences, Jun. 1996, 93(12):6025-30.

(Continued)

*Primary Examiner* — Christopher M Gross
(74) *Attorney, Agent, or Firm* — Fish & Richardson P.C.

(57) ABSTRACT

This disclosure describes methods and compositions for protein and peptide sequencing.

21 Claims, 70 Drawing Sheets

(62 of 70 Drawing Sheet(s) Filed in Color)

Specification includes a Sequence Listing.

(56) References Cited

OTHER PUBLICATIONS

Fujishima et al., "A mechanically bendable superhydrophobic steel surface with self-cleaning and corrosion-resistant properties," Journal of Materials Chemistry A., 2015, 3(27):14263-71.
Fujishima et al., "An overhang-based DNA block shuffling method for creating a customized random library," Scientific Reports, May 2015, 5:9740.
Gnirke et al., "Solution hybrid selection with ultra-long oligonucleotides for massively parallel targeted sequencing." Nature biotechnology, Feb. 2009, 27(2):182-9.
Gordon et al., "Click-PD: A quantitative method for base-modified aptamer discovery," bioRxiv, Jan. 2019, 1:626572.
Hallman et al., "A clinical histologic study of bovine hydroxyapatite in combination with autogenous bone and fibrin glue for maxillary sinus floor augmentation: results after 6 to 8 months of healing," Clinical Oral Implants Research, Apr. 2001, 12(2):135-43.
Hoon et al., "Aptamer selection by high-throughput sequencing and informatic analysis," Biotechniques, Dec. 2011, 51(6):413-6.
Horspool et al., "Development of a targeted polymorph screening approach for a complex polymorphic and highly solvating API," Journal of pharmaceutical sciences, Sep. 2010, 99(9):3874-86.
Horspool et al., "Efficient assembly of very short oligonucleotides using T4 DNA Ligase," BMC research notes, Dec. 2010, 3(1):1-9.
Jia et al., "High-throughput recombinant protein expression in *Escherichia coli*: current status and future perspectives," Open biology, Aug. 2016, 6(8):160196.
Jung et al., "Massively parallel biophysical analysis of CRISPR-Cas complexes on next generation sequencing chips," Cell, Jun. 2017, 170(1):35-47.
Little et al, An exonuclease induced by bacteriophage λ II. Nature of the enzymatic reaction, Journal of Biological Chemistry, Feb. 1967, 242(4):679-86.
Loakes et al., "5-Nitroindole as an universal base analogue," Oxford University Press, Aug. 1994, 22(20):4039-4043.
Marin-Palomo et al., "Microresonator-based solitons for massively parallel coherent optical communications," Nature, Jun. 2017, 546(7657):274-9.
McKeague et al., "Challenges and opportunities for small molecule aptamer development," Journal of nucleic acids, Jan. 2012.
Miteva et al., "Proteomics-based methods for discovery, quantification, and validation of protein-protein interactions," Analytical chemistry, Jan. 2013, 85(2):749-68.
Mitsis et al., "Characterization of the interaction of lambda exonuclease with the ends of DNA," Nucleic acids research, Aug. 1999, 27(15):3057-63.
NanoPoreTech.com [online], "Protein Analysis," Aug. 2017, retrieved on Nov. 16, 2020, retrieved from URL<https://nanoporetech.com/applications/protein-analysis>, 1 page.
Pfeiffer et al, "Customised nucleic acid libraries for enhanced aptamer selection and performance," Current Opinion in Biotechnology, Dec. 2017, 48:111-8.
Pham et al., "High-throughput protein sequencing. Analytical chemistry," Feb. 2003, 75(4):875-82.
Rodriques et al., "A theoretical analysis of single molecule protein sequencing via weak binding spectra," PloS one, Mar. 2019, 14(3):e0212868.
Schiess et al., Targeted proteomic strategy for clinical biomarker discovery, Molecular oncology, Feb. 2009, 3(1):33-44.
Scoville et al., Selection of DNA aptamers for ovarian cancer biomarker CA125 using one-pot selex and high-throughput sequencing, Journal of nucleic acids, Oct. 2017.

Setlem et al., "Immuno affinity SELEX for simple, rapid, and cost-effective aptamer enrichment and identification against aflatoxin B1," Frontiers in microbiology, Dec. 2016, 7:1909.
Sheynkman et al., "Proteogenomics: integrating next-generation sequencing and mass spectrometry to characterize human proteomic variation," Annual review of analytical chemistry, Jun. 2016, 9:521-45.
Swaminathan et al., A theoretical justification for single molecule peptide sequencing, PLoS Comput Biol, Feb. 2015, 11(2):e1004080.
Swaminathan et al., "Highly parallel single-molecule identification of proteins in zeptomole-scale mixtures," Nature biotechnology, Nov. 2018, 36(11):1076-82.
Takahashi et al., "High throughput sequencing analysis of RNA libraries reveals the influences of initial library and PCR methods on SELEX efficiency," Scientific reports, Sep. 2016, 6(1):1-4.
Tucker et al., "G-quadruplex DNA aptamers and their ligands: structure, function and application," Current pharmaceutical design, May 2012, 18(14):2014-26.
Tuerk et al., "Systematic evolution of ligands by exponential enrichment: RNA ligands to bacteriophage T4 DNA polymerase," Science, Aug. 1990, 249(4968):505-10.
Vogel et al., "Insights into the regulation of protein abundance from proteomic and transcriptomic analyses," Nature Reviews Genetics, Apr. 2012, 13(4):227-32.
Wang et al, "QCM-based aptamer selection and detection of *Salmonella typhimurium*," Food Chemistry, Apr. 2017, 15;221:776-82.
Watt et al., "The unexpected awakening of Chaitén volcano, Chile," Transactions American Geophysical Union, Jun. 2009, 90(24):205-6.
Yates et al., "Proteomics by mass spectrometry: approaches, advances, and applications," Annual review of biomedical engineering, Aug. 2009, 11:49-79.
Zhou et al., "Aptamers as targeted therapeutics: current potential and challenges," Nature Reviews Drug Discovery, Mar. 2017, 16(3):181-202.
Zhou et al., "Engineered fibroblast growth factor 19 reduces liver injury and resolves sclerosing cholangitis in Mdr2-deficient mice," Hepatology, Mar. 2016, 63(3):914-29.
Zhuo et al, "Recent advances in SELEX technology and aptamer applications in biomedicine," International journal of molecular sciences, Oct. 2017, 18(10):2142.
Alam et al., "Poly-Target Selection Identifies Broad-Spectrum RNA Aptamers," Mol. Therapy: Nucleic Acids, Dec. 7, 2018, 13:605-619.
Cho et al., "Quantitative selection of DNA aptamers through microfluidic selection and high-throughput sequencing," PNAS, Aug. 31, 2010, 107(35):15373-15378.
Morris et al., "High affinity ligands from in vitro selection: Complex targets," PNAS USA, Mar. 17, 1998, 95(6):2902-2907.
Schutze et al., "Probing the SELEX Process with Next-Generation Sequencing," PLOS One, Dec. 29, 2011, 6(12):e29604, 10 pages.
Yang et al., "Selection of aptamers for AMACR detection from DNA libraries with different primers," RSC Advances, May 23, 2018, 8:19067-19074.
PCT International Preliminary Report on Patentability in International Application No. PCT/US2020/050574, dated Mar. 24, 2022, 11 pages.
Gu et al, "Multiplex single-molecule interaction profiling of DNA-barcoded proteins" Nature, 2014, 14 pages.
PCT International Search Report and Written Opinion in International Application No. PCT/US2020/050574, dated Feb. 9, 2021, 19 pages.
Lu et al., "Absolute protein expression profiling estimates the relative contributions of transcriptional and translational regulation," Nature Biotechnology, Jan. 2007, 25(1):117-124.
Chen, "Replacing antibodies with aptamers in lateral flow immunoassay," Biosensors and Bioelectronics, Sep. 15, 2015, 42 pages.

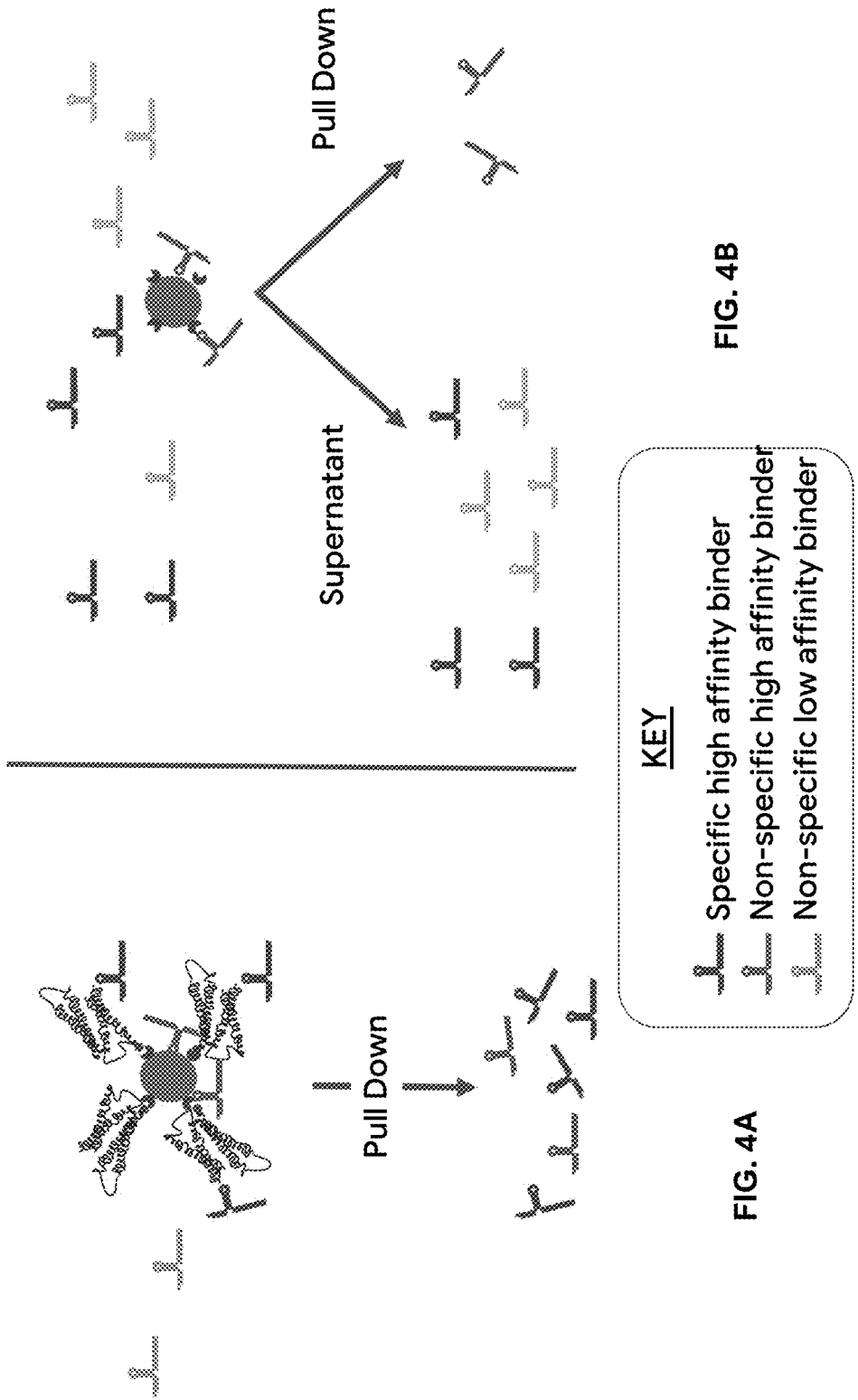

FIG. 31A dsDNA Lego

FIG. 31B ssDNA or RNA Lego

Top 20 Most Common Sequences (Counts out of 100,000 reads)

Fake SELEX

Brady1_fs_r3_S1_L001_R1_001.fastq.gz
Sampled 100000 reads

| Sequence | Counts |
|---|---|
| CACCGCATCCTGAGGCCGGTGTGAGGGCACGAAGTCTGGAGAAT | 7 |
| TGACTAGTACATGACCACTTGAGACCACGCACTAAGGCCCGAAC | 5 |
| CTAGCCATGGTCAGTGCCCTTACCCTCAGAGCGGAAGTACCTGATATGAAT | 4 |
| CACCGCATCCTGAGGCCTGGTGGAGGGCACGAAGTCTGGTTGAAT | 3 |
| TGACTAGTACAATGACCACTTGACCACGCACGCACTAAGGCCCAAG | 3 |
| CTAGCCATGGTCCCTTCAGTGCTTCATGTTAGTATGAAAGCCTTAAGACT | 3 |
| GAACCCATGGTCAGTGCCCTTACCCTCAGAGCGGAAGTACCTAAAAAAA | 3 |
| CTAGCCATCCTGAGGCCGGTGTGAGGCGGAAGTCGGAAGTACCTGATTTGACT | 3 |
| CCAACCGGTTCTGGGCGCTATCGGCTASCTCTTGGAGAGAAATGACT | 3 |
| CTAGCCATGGTGCCGTATCCCTGAGGCCGGAAGTACCTGATATGACT | 2 |
| CACCGCATCCTGAGGCCGGTGTGAGGGCACGAAGTCTGGCTAGACT | 2 |
| CACCGCATCCGAGGCCGGTGTGAGGGCACGAAGTCTGGTTGAAA | 2 |
| CACCGCATCCATCCTGAGGCCGGTGGTGGAGGGCACGAAGTCTGGTGACT | 2 |
| GCTAGAACACGCCTTCATTCARTCARATAGAAACTTTACAGTCTTGACT | 2 |
| GAACCCATGGTCAGTGCCTCATGTTAGTATGAAAGCCTTAAAAAT | 2 |
| GAACCCATGGTCAGTGCCTCAGTGTTAGTATGAAAGCTTATTGACT | 2 |

SELEX

Brady1_r3_S1_L001_R1_001.fastq.gz
Sampled 100000 reads

| Sequence | Counts |
|---|---|
| CACCGCATCCTGAGGTGTGGAGGGCACGAAGTCTGGTTGACT | 7 |
| CACCGCATCCTGAGGCCGGTGTGAGGGCACGAAGTCTGGAAGACT | 5 |
| CACCGCATCCTGAGGCCGGTGTGGAGGGCACGAAGTCTGGTCGGACT | 4 |
| CACCGCATCCTGAGGCCGGTGGAGGGCACGAAGTCTGGAGGACT | 4 |
| CACCGCATCCTGAGGCCGGTGAGGGGCACGAAGTCTGGATGAAT | 4 |
| TGACTAGTACATGACCACTTGAACCCTCAGAGCACGCACTAAGGCACCTTT | 3 |
| CTAGCCATGGTGCCCTTACCCTCAGAGCGGAAGTACCTGATATGAAT | 3 |
| CCACCGCATCCATGACCACTTGACCACGCACGCACTGATTTGACT | 3 |
| TGACTAGTACATGACCACTTGACCCTCAGAGCCACGCACGGAAGTGGTAGACT | 3 |
| CACCGCATCCTGAGGCCGGTGTGAGGGCACGAAGTCTGGTTGACA | 3 |
| CACCGCATCCTGAGGCCGGTGTGAGGGCACGAAGTCTGGGAAT | 3 |
| CACCGCATCCTGAGGCCGGTGTGAGGGCACGAAGTCTGGAAGAAG | 3 |
| CTAGCCATGGTGCCCTTACCCTCAGAGCGGAAGTACCTGATAAGAAA | 2 |
| CTAGCCATGGTGCCCTTACCCTCAGAGCGGAAGTACCTACCTGATAAGAA | 2 |
| GGGTGAAGGTGCAACCCTATTTCATGAGGACCTACCATCTGGAGT | 2 |
| GTTACACGTGCGAGATCTTCGCATTGGACTTAACCTATAGACAAGAAT | 2 |
| ACGGATGTCGAGATCGGTACGGACGATGGTTTATCTAATGGGTTGGACT | 2 |
| GGCCATAGGCATCGGACGCGGGCGAAGGCCACGAAGTCTGGGGGACT | 2 |
| CACCGCATCCTGAGGCCGGTGTGGAGGGCACGAAGTCTGGGGACT | 2 |

Top 5 N40 Aptamer Sequences to N-terminal Amino Acid

N-Terminal Lysine

GCCGTAGGCGTAAGACCACACAACTTCGCTATCCACATGGCG

GCTAACAAGAGGACGTGGTGTACCATCATAGAGACGGTCA

AGATGCAGCAACGACATAGTACGATATGGTTCACATTGGT

ATCAAGTGATGCTCCAATAATCGTCTGGATGATCCCCCAT

ATGCACATTTCCCAGGCAGCTTTGCTGTCAGCCATCAGAG

N-Terminal Cysteine

CGGTGGGGGGAGGGAGTGGGCTTAAGGTCTTCGTTTGTGA

CGGTGGGGGGAGGGAAGGGAAGGGATATGTTAATTTCGTCGTGGC

GGACGGTGAGGAGGGTTGTTGATTTTGGTGTTATTTCT

GCAGTGGTGGGGGAAGGGGTGGTGGGCGTCTGATTGCG

CGTTGGGGGGAGGTGGGTGCGGAGTAGTTTATTTCGGTGG

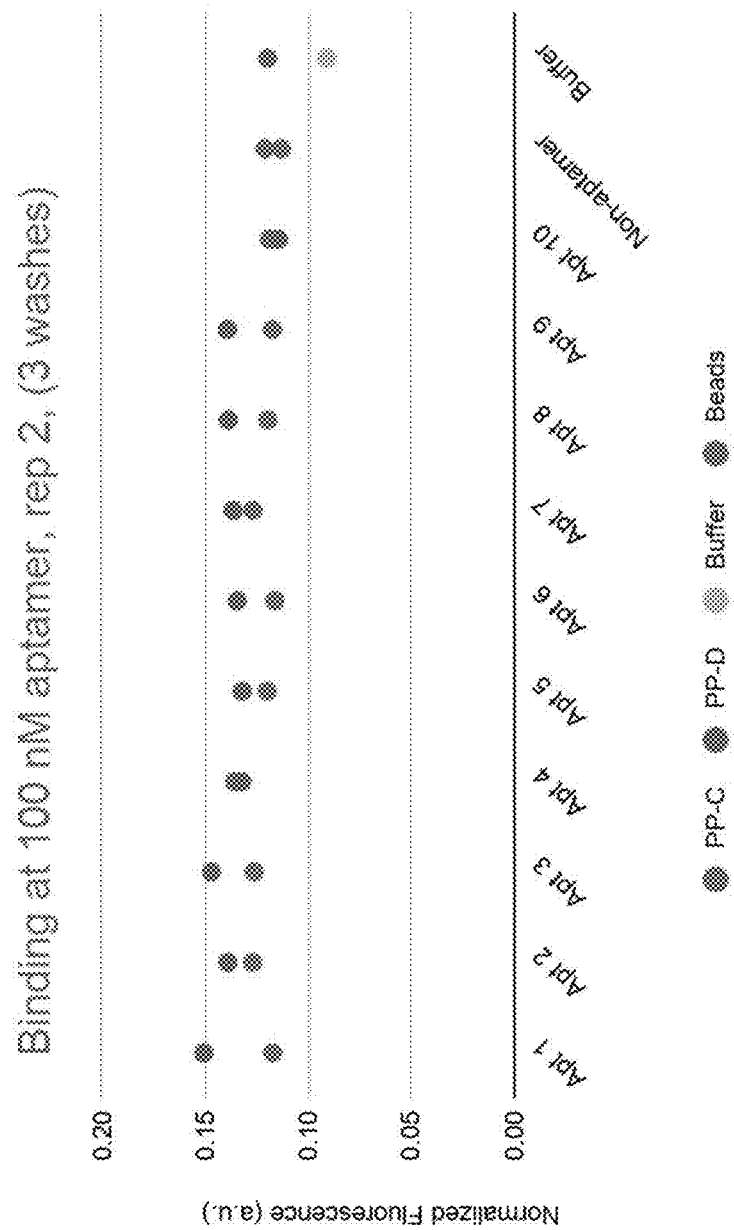

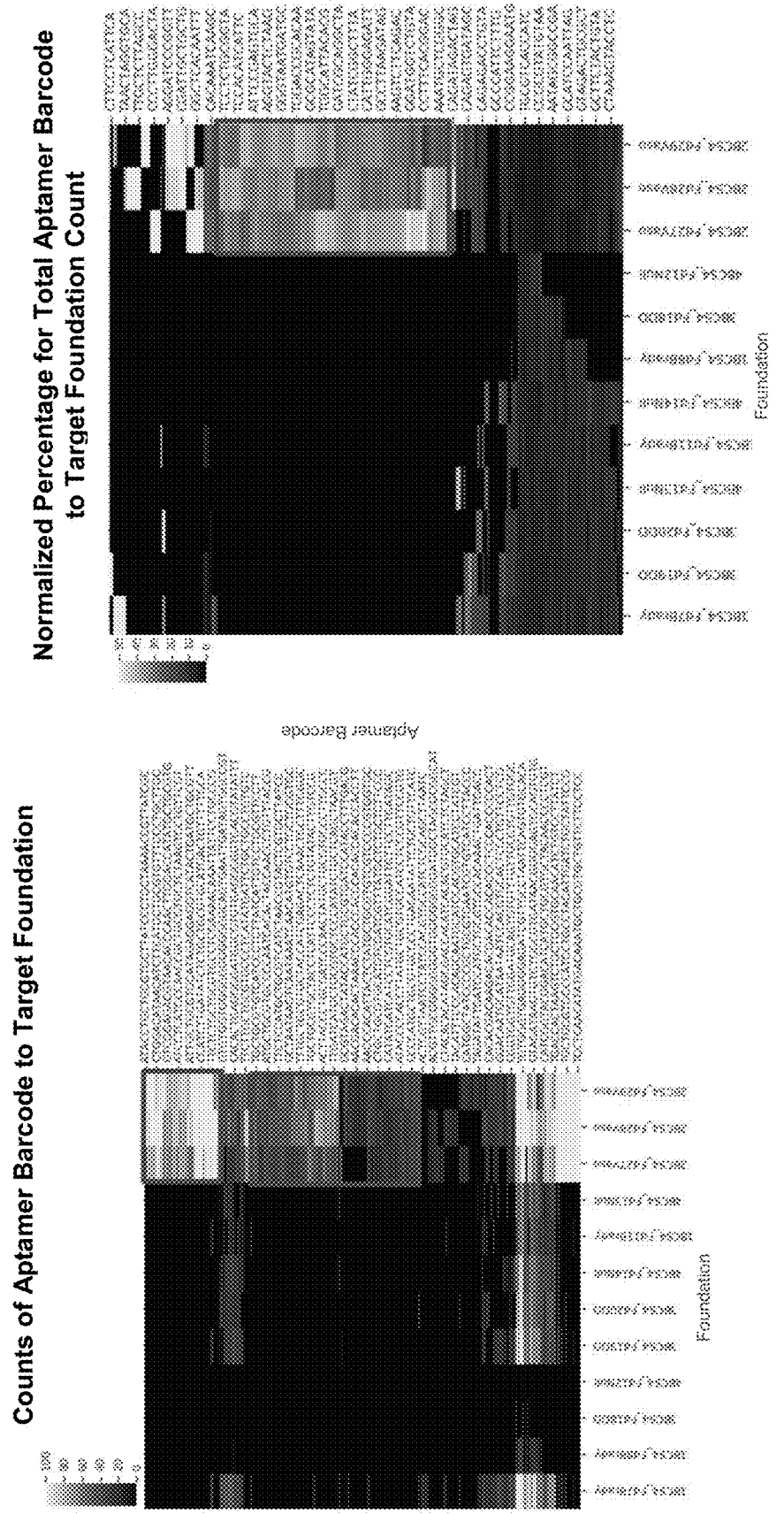

Multiplex Target sequences

```
Brady:        (N-terminus) - RPPGFSPFR      -Cys (C-terminus) -oligo
GnRH:         (N-terminus) - EHWSYGLRPG     -Cys (C-terminus) -oligo
Vaso:         (N-terminus) - YFQNCPRG       -Cys (C-terminus) -oligo
Target1:      (N-terminus) - YQNTSQNTS      -Cys (C-terminus) -oligo
Target1_NC2:  (N-terminus) - KQNTYQNTS      -Cys (C-terminus) -oligo
Target1_NC3:  (N-terminus) - QNTSYQNTS      -Cys (C-terminus) -oligo
```

FIG. 62

SDS-PAGE of dMS-EmGFP and dMS2 product

METHODS AND COMPOSITIONS FOR PROTEIN AND PEPTIDE SEQUENCING

CROSS REFERENCE TO RELATED APPLICATIONS

This application claims the benefit of priority under 35 U.S.C. § 119(e) to U.S. Application No. 62/900,440 filed on Sep. 13, 2019. This document is incorporated herein by reference in its entirety.

STATEMENT REGARDING SEQUENCE LISTING

The Sequence Listing associated with this application is provided in text form in lieu of a paper copy, and is hereby incorporated by reference into the specification. The name of the text file containing the Sequence Listing is sequencelisting.txt. The text file is 58 KB, and was submitted electronically via EFS-Web on Nov. 17, 2020.

TECHNICAL FIELD

This disclosure generally relates to methods and compositions for protein and peptide sequencing.

BACKGROUND

Rapid improvements in DNA sequencing technology in the last decade have yielded a wealth of molecular information. And while the ability to read genomes has revolutionized biological research, a significant amount of phenotypic and disease-state information cannot be deduced from the genome. RNA sequencing has provided a deeper understanding of the functional elements of the genome and their expression levels. However, efforts to correlate protein to mRNA expression levels are unreliable, and can provide a secondary measurement of protein expression levels only at the location of protein synthesis. RNA and DNA sequencing gives limited insight into antibody sequences as the diversity of antibody repertoire is generated by somatic hypermutation events. In order to capture information that occurs after DNA processing and secretion, such as post-translational protein modifications, translational fidelity, protein folding integrity, etc., scientists must be able to sequence proteins (i.e., read their amino acid sequences) directly from the sample of interest to infer correlations between protein levels and its enzymatic effect. De novo protein sequencing can lead to the discovery of rare and novel proteins from any organism (e.g. various tissues, pathogens, mutated cancer cells) from any protein-containing sample (e.g. blood, skin, cerebral spinal fluid, soil). Protein sequencing also can serve as a metric for therapeutic efficacy by allowing for extensive physiological monitoring through the course of disease treatment. Currently, however, there exists no cost and time-effective strategy for the large-scale and high-throughput sequencing of proteins and proteomes. Neither is there a robust method to sequence untargeted lowly expressed proteins. As a result, sequencing of antibodies and lowly expressed proteins remain wracked with obstacles with current technologies and practically inaccessible to all but the most specialized research efforts.

SUMMARY

This disclosure describes a collection of methods and compositions that form a pipeline of developing and using a protein sequencing platform which utilizes aptamers that bind specifically to N-terminal amino acids (FIG. 1). Amino acid-specific aptamers can be generated using the novel methods described herein (RCHT-SELEX). Such amino acid-specific aptamers can be used to recognize, identify and convert each amino acid of a protein or peptide into a DNA sequence (PROSEQ) or such amino acid-specific aptamers can be used to recognize and identify, based on a visual signal, each amino acid of a protein or peptide (PROSEQ-VIS). In addition, many different target-specific aptamers can be generated simultaneously, and used to produce and screen a large multitude of binders (MULTIPLEX). Simultaneous and specific aptamer selection relies on robust identification of targets. Nucleic acid barcoded target generation can be accomplished in vivo via a non-covalent bond between a peptide or protein using an RNA-binding protein and its corresponding recognition sequence (TUR-DUCKEN). Lastly, successful SELEX experiments require that aptamers with some specific binding preference and affinity for the molecular target be included in the original pool of $10^{14}$-$10^{15}$ candidate sequences, which is only a small fraction of all the DNA sequences possible. Machine learning (ML) can help to optimize experimental seed binders, so, unlike conventional SELEX experiments, optimal binders do not need to occur in the experimental dataset. The ability to construct computationally-derived, customizable DNA libraries to perform SELEX screens using a controlled input pool can significantly increase the exploratory space by systematically assaying aptamer candidates that include sequences with known binding properties (LEGO).

In one aspect, methods of sequencing a peptide are provided. Such methods typically include (a) incubating the peptide with a library of DNA aptamers exhibiting binding specificity toward at least one N-terminal amino acid under conditions where one or more aptamers bind specifically to at least one N-terminal amino acid of the peptide, wherein each aptamer in the library comprises a peptide binding ssDNA region and a unique barcode sequence indicative of the first binding round and the associated peptide binding ssDNA region; (b) ligating the DNA aptamer bound to the N-terminal of the peptide onto a proximal DNA barcode construct; (c) removing the peptide binding sequence from the DNA aptamer, thereby leaving the barcode of the DNA aptamer covalently attached to the DNA barcode construct: (d) removing the N-terminal amino acid from the peptide to produce an N-terminal amino acid-shortened peptide; (e) incubating the N-terminal amino acid-shortened peptide with the library of aptamers exhibiting binding specificity toward at least one N-terminal amino acid under conditions where one or more aptamers bind specifically to at least one N-terminal amino acid of the N-terminal amino acid-shortened peptide, wherein each aptamer in the library comprises a peptide binding ssDNA region and a unique barcode sequence indicative of the second binding round and the associated peptide binding ssDNA region; (f) ligating the DNA aptamer bound to the N-terminal of the peptide onto the proximal DNA barcode construct; (g) removing the peptide binding sequence from the DNA aptamer, thereby leaving the barcode of the DNA aptamer covalently attached to the DNA barcode construct; (h) removing the N-terminal amino acid from the N-terminal amino acid-shortened peptide; (i) repeating steps (a)-(d) a plurality of times to construct a chain of positional barcodes that correspond to sequential N-terminal amino acids in the peptide; and (j) sequencing the chain of positional barcodes to thereby obtain the sequence of the peptide.

In some embodiments, the peptide is from a synthetic sample, biological sample, or combinations thereof. In some embodiments, the biological sample is selected from the group consisting of blood, urine, saliva, tissue biopsy, sputum, stool, single cell, environmental samples, and bacterial swabs.

In some embodiments, the peptide is a full-length protein or a peptide comprised within a complex.

In some embodiments, the method further comprising, prior to step (a), fragmenting the peptide. In some embodiments, the fragmenting step comprises exposing the peptide with a fragmentation enzyme.

In some embodiments, the C-terminal end of the peptide is attached to a solid support. In some embodiments, the C-terminal end of the peptide is attached to an oligonucleotide tail.

In some embodiments, the removing the peptide binding sequence from the DNA aptamer step comprises cleaving the aptamer with a restriction enzyme. In some embodiments, the removing of the peptide binding sequence from the DNA aptamer is mediated by hydrogen bond disruption. In some embodiments, the removing the N-terminal amino acid step comprises Edman degradation of the peptide, cleaving the peptide with one or more aminopeptidases, heat, pH, or combinations thereof.

In some embodiments, the sequencing step uses a next generation sequencing (NGS) platform.

In another aspect, methods of identifying novel biomarkers are provided. Such methods typically include (a) providing protein samples from biological samples of interest and control or comparison biological samples; (b) optionally, removing proteins present in high concentrations; (c) performing the steps (a)-(j) of the method of claim 1; (d) performing a sup-diff to remove high concentration DNA barcode construct sequences associated with highly expressed proteins or contaminants such that a ratio of DNA barcode constructs associated with lowly expressed proteins to highly expressed proteins increases, thereby producing ratio-adjusted DNA barcodes; (e) amplifying the ratio-adjusted DNA barcodes; and (f) comparing the number of sequencing reads associated with each lowly expressed proteins from control samples to samples of interest; thereby identifying biomarkers that have different relative expression levels between the control samples and the biological samples of interest.

In still another aspect, methods of evaluating a disease state, evaluating a response to treating a disease, predicting a response to treating a disease, or combinations thereof, wherein the disease comprises aberrant expression levels of at least one known protein biomarker, are provided. Such methods typically include (a) providing protein samples from patient samples; (b) optionally depleting proteins present in high concentrations; (c) performing the steps (a)-(j) of the method of claim 1; (d) performing a sup-diff to remove high concentration DNA barcode construct sequences associated with highly expressed proteins or contaminants to increase the ratio of DNA barcode constructs associated with lowly expressed proteins to highly expressed proteins, thereby producing ratio-adjusted DNA barcodes; (e) amplifying the ratio-adjusted DNA barcodes; (f) analyzing the number of sequencing reads associated with known protein biomarkers to determine the relative quantity thereof (g) determining the presence or absence of expression level deviations of known protein biomarkers from one or more standard values, thereby evaluating the disease state, evaluating the response to treating the disease, predicting the response to treating a disease, or combinations thereof.

In some embodiments, the library of aptamers is produced using a RCHT-SELEX method.

In some embodiments, each aptamer in the library of aptamers exhibits binding specificity toward one N-terminal amino acid. In some embodiments, each aptamer in the library of aptamers exhibits binding specificity toward two or more N-terminal amino acids.

In some embodiments, the unique barcode sequence indicative of the aptamer's associated peptide binding ssDNA region and binding round comprises about 6 to about 20 nucleotides.

In some embodiments, each aptamer in the library of aptamers comprises a BCS compatible portion. In some embodiments, the BCS compatible portion of each aptamer comprises one or more DNA sequences complementary to the aptamer.

In some embodiments, the barcode sequence comprises a unique barcode that indicates the peptide or the sample from which the peptide was derived.

In yet another aspect, articles of manufacture for protein or peptide sequencing are provided. Such articles of manufacturing typically include a library of DNA aptamers, wherein each member of the library exhibits binding specificity toward at least one N-terminal amino acid.

In some embodiments, each member of the library further comprises common sequences indicative of the cycle number. In some embodiments, each member of the library further comprises a restriction site. In some embodiments, each member of the library further comprises at least one sequence for ligation, annealing, or combinations thereof.

In one aspect, methods of sequencing a protein or peptide are provided. Such methods typically include: (a) incubating the protein or peptide with a library of DNA aptamers exhibiting binding specificity toward at least one N-terminal amino acid under conditions where one or more aptamers bind specifically to at least one N-terminal amino acid of the protein or peptide, wherein each aptamer within the library comprises a peptide binding ssDNA region and a unique barcode sequence indicative of the first sequencing round and the associated peptide binding ssDNA region; (b) ligating the DNA aptamer bound to the N-terminal of the protein or peptide onto its proximal DNA barcode construct; (c) removing the peptide binding sequence from the DNA aptamer, thereby leaving only the barcode of the DNA aptamer and a short consensus sequence for subsequent ligation covalently attached to the DNA barcode construct, such that the identity of the binder and therefore the putative amino acid identity of the N-terminal of the peptide is recorded: (d) removing the N-terminal amino acid from the protein or peptide to produce an N-terminal amino acid-shortened protein or peptide; (e) incubating the N-terminal amino acid-shortened protein or peptide with the library of aptamers exhibiting binding specificity toward at least one amino acid under conditions where one or more aptamers bind specifically to at least one N-terminal amino acid of the N-terminal amino acid-shortened protein or peptide, wherein each aptamer within the library comprises a peptide binding ssDNA region and a unique barcode sequence indicative of the second sequencing round and the associated peptide binding ssDNA region; (f) ligating the DNA aptamer bound to the N-terminal of the protein or peptide onto its proximal DNA barcode construct; (g) removing the peptide binding sequence from the DNA aptamer, thereby leaving only the barcode of the DNA aptamer and a short consensus sequence for subsequent ligation covalently attached to the DNA barcode construct, such that the identity of the binder and therefore the putative amino acid identity of the N-terminal of the peptide is recorded; (h) removing the N-terminal amino acid from the N-terminal amino acid-shortened protein or peptide; (i) repeating steps (a)-(d) a plurality of times to construct a chain of positional barcodes that correspond to sequential N-terminal amino acids in the protein or peptide; and (j) sequencing the chain of positional barcodes, thereby obtaining the sequence of the protein or peptide.

In some embodiments, the protein or peptide is from a synthetic sample, biological sample, or combinations thereof. In some embodiments, the biological sample is selected from the group consisting of blood, urine, saliva, tissue biopsy, sputum, stool, single cell, environmental samples, bacterial swab, or any sample containing peptides or proteins.

In some embodiments, the protein or peptide is a full-length protein, a peptide fragment, or a protein or peptide comprised within a complex. In some embodiments, the method further includes, prior to step (a), fragmenting the protein or peptide. In some embodiments, the fragmenting step includes fragmenting the protein or peptide with trypsin, Lys-C, another fragmentation enzyme, alternative protein fragmentation or degradation methods, or combinations thereof.

In some embodiments, the C-terminal end of the protein or peptide is attached to a solid support. In some embodiments, the C-terminal end of the protein or peptide is attached to an oligonucleotide tail. In some embodiments, removing the aptamer includes cleaving the aptamer at the restriction site with a restriction enzyme. In some embodiments, the aptamer is attached to the barcode hydrostatically and removal of the peptide binding sequence is mediated by hydrogen bond disruption (rather than DNA cleavage by restriction enzyme).

In some embodiments, the removing the N-terminal amino acid step comprises Edman degradation of the protein or peptide, cleaving the protein or peptide with one or more aminopeptidases, heat, pH, or combinations thereof. In some embodiments, the sequencing step uses a next generation sequencing (NGS) platform. In some embodiments, the number of sequencing reads associated with amino acid sequences of known proteins is analyzed to determine the relative quantity of proteins in a sample.

In some aspects, methods of identifying novel biomarkers are provided. Such methods typically include: (a) providing protein samples from biological samples of interest and control or comparison biological samples according to the methods described herein; (b) optionally removing known proteins of very high concentrations; (c) performing the steps (a)-(j) of the methods described herein; (d) removing high concentration DNA barcode construct sequences associated with commonly highly expressed proteins or contaminants such that the ratio of DNA barcode constructs associated with lowly expressed proteins to highly expressed proteins increases, thereby producing ratio-adjusted DNA barcodes; (e) PCR amplifying the DNA barcode constructs post-sup-diff; and (f) comparing the number of sequencing reads associated with each lowly expressed proteins from control samples to samples of interest; thereby identifying putative biomarkers that have significantly different relative expression levels between control samples and samples of interest.

In some embodiments, methods of using the protein sequencing methods described herein are provided to evaluate disease state, evaluate response to treatment, predict treatment response, or combinations thereof, wherein one or more signs of those diseases is aberrant expression levels of known protein biomarkers. Such methods typically include: (a) providing protein samples from patient samples according to the methods described herein; (b) optionally depleting known proteins of very high concentrations; (c) performing the steps (a)-(j) of methods described herein; (d) removing high concentration DNA barcode construct sequences associated with commonly highly expressed proteins or contaminants to increase the ratio of DNA barcode constructs associated with lowly expressed proteins to highly expressed proteins, thereby producing ratio-adjusted DNA barcodes; (e) PCR amplifying the DNA barcode constructs post-sup-diff; (f) determining the relative quantity of known biomarkers by analyzing the number of sequencing reads associated with known protein biomarkers; (g) determining the presence or absence of expression level deviations of known biomarkers from standard values, thereby evaluating disease state, evaluating response to treatment, predicting treatment response, or combinations thereof.

In some embodiments, the library of aptamers is produced using the RCHT-SELEX method described herein. In some embodiments, the aptamer exhibits binding specificity toward one N-terminal amino acid. In some embodiments, the aptamer exhibits binding specificity toward two or more N-terminal amino acids. In some embodiments, the unique barcode sequence indicative of the aptamer's associated peptide binding ssDNA region and sequencing round includes about 6 to about 20 nucleotides. In some embodiments, a BCS Compatible portion of the aptamer construct may comprise one or more complementary DNA sequences hybridized to an aptamer as described herein. In some embodiments, a proximal DNA barcode foundation contains a unique barcode that indicates either the associated protein or peptide (if known) or the sample from which the protein or peptide was derived.

In another aspect, articles of manufacture for protein or peptide sequencing are provided. Such articles typically include a library of DNA aptamers, wherein each member of the library exhibits binding specificity toward at least one N-terminal amino acid.

In some embodiments, each member of the library further comprises a common sequence indicative of the cycle number (e.g., first, second, third, etc.) and a unique barcode sequence. In some embodiments, each member of the library further comprises a restriction site. In some embodiments, each member of the library further comprises at least one sequence for ligation, annealing, or combinations thereof.

The methods described herein also can be used for sequencing full-length proteins.

The methods described herein also can be used for sequencing the proteins within a protein complex.

The methods described herein also can be used for sequencing the proteins within a complex protein pool.

Definitions

Nucleic acids can be single stranded or double stranded, which usually depends upon its intended use. As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can be an engineered nucleic acid molecule such as a recombinant or a synthetic nucleic acid molecule.

Aptamers are single stranded nucleic acid sequences, which can be composed of RNA, DNA, TNA, modified nucleic acids, or other synthetic nucleic acid monologues. Aptamers are typically identified with a SELEX assay, which relies heavily on the evolution of a diverse pool of sequences amplified from round to round with PCR. Aptamer sequences are typically 20-45 base pairs (bp) plus additional flanking primer regions (typically 20-23 bp in length each for a forward and reverse primer). Capillary electrophoresis SELEX (CE-SELEX) does not rely on using aptamers with primer regions, however, CE-SELEX is limited to working with volumes in nL, thus limiting the initial starting pool of sequences from $10^{14}$-$10^{16}$ down to $10^8$-$10^9$.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate nucleic acids. Isolated nucleic acids also can be chemically synthesized, either as a single nucleic acid molecule or as a series of oligonucleotides via traditional methods such as bead purification, enzymatic digestion, column purification etc.

Polypeptides can be purified from natural sources (e.g., a biological sample) by known methods such as DEAE ion exchange, gel filtration, HIS-tag bead pull-down assays, affinity chromatography, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (e.g., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

As used herein, "specifically" recognizes or "specifically" binds refers to a molecule that exhibits high substrate specificity for a given target with very low to no substrate specificity for anything else within a known operating concentration range.

As used herein, "semi-specifically" recognizes or "semi-specifically" binds refers to a molecule exhibiting high substrate specificity for a known target, and medium to low binding specificity to a subset of other targets As used herein, "prefix" refers to at least the N-terminal amino acid and also may include the penultimate N-terminal amino acids at the N-terminal of a protein or peptide.

As used herein, "suffix" refers to one or more amino acids in the peptide C-terminal to the "prefix" amino acids as defined previously.

As used herein, "DNA barcode" refers to an oligo sequence with information indicative of at least molecule's identity.

As used herein, "DNA barcode construct" refers to the strand of DNA comprising of at least two DNA barcodes.

As used herein, "Barcode Sequencing (BCS) compatible" aptamer refers to a partially double stranded aptamer wherein one or more regions that do not participate in target binding can be hybridized with a complementary oligo, and may or may not contain an overhang.

As used herein, a "blocked aptamer" refers to a partially double stranded aptamer wherein at least the primer region of the aptamer but not the aptamer region itself can be hybridized with a protective complementary oligo.

As used herein, "sup-diff" refers to a method of removing DNA barcode constructs of highly expressed proteins.

As used herein, "optical barcode" or "optical signature" refers to detection of a fluorescently-tagged molecule either integrated into the oligo directly or attached via one or more binders.

As used herein, "optical barcode" refers to an ordered combination of optical signatures.

As used herein, "dsDNA lego piece" refers to a 5 or more base-pair-long DNA oligo with a 5' nucleotide overhang (e.g., of one or more nucleotides) at one or both ends, where the 5'-most nucleotide on at least one strand is phosphorylated.

As used herein, "ssDNA lego piece" refers to a 5 or more nucleotide long DNA oligo with a phosphorylated 3' or 5' end.

As used herein, "RNA lego piece" refers to a 5 or more nucleotide long RNA oligo with a phosphorylated 3' or 5' end.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

The patent or application file contains at least one drawing executed in color. Copies of this patent or patent application publication with color drawings will be provided by the Office upon request any payment of the necessary fee.

FIG. 4A is a schematic showing that conventional SELEX methods can undesirably enrich for aptamers that bind to components of the selection process ("non-specific high affinity binders") in addition to aptamers that bind to the desired target ("specific high affinity binders").

FIG. 4B is a schematic showing that the addition of a negative selection step in the SELEX methods described herein can reduce the ultimate enrichment of aptamers that bind non-specifically to selection components by first pulling out aptamers that bind to the beads, biotin, oligo, or other selection components prior to Bring-Up amplification or input into SELEX.

FIG. 14A is a schematic depicting a Barcode-Specific bridge wherein the bridge is entirely complementary to the aptamer tail, including barcode region, except for the 3' single stranded overhang region. FIG. 14B is a schematic depicting a Universal bridge wherein the bridge is complementary to the restriction site spacer and consensus sequence only, both of which are conserved across all aptamers and flank the barcode.

FIG. 32A-39C are schematics showing one embodiment of the LEGO methods described herein. Pools of first position, second position, third position, etc. LEGO pieces (A) are sequentially ligated (B) and PCR amplified to generate replicates. The resulting dsDNA is then digested into ssDNA to form a library of folded aptamers (C).

FIG. 32D is a schematic that indicates the steps of the SELEX procedure (from FIG. 3) into which the LEGO methods can be incorporated.

FIG. 33 is a schematic of the general workflow of all SELEX (RCHT-SELEX and NTAA-SELEX) experiments.

FIG. 34A is a schematic that depicts the 400 potential amino acid prefixes that the SELEX methods described herein is used to find aptamers for PROSEQ and PROSEQ VIS.

FIG. 34B is a schematic that depicts how the 400 potential amino acid prefixes are organized into 16 blocks.

FIG. 34C is a schematic that depicts how the suffix paired with the 2-mer prefix was alternated between odd and even rounds, with only the 2-mer prefix the constant peptide combination through all 4 rounds.

FIG. 34D is a specific example of how the suffixes ("backbone") are switched in alternating rounds while the prefix remains the same to find aptamers specific to the DD and DC prefix regardless of the suffix (DD/DD, SEQ ID NOs:124-127; DC/DC, SEQ ID NOs:128-131; DD/DC, SEQ ID NOs:132-135). The same bring up is also used to assay targets with alternating backbones and prefixes that are similar to tease out aptamers that are not specific to DD and DX.

FIG. 35 are embodiments of the three variations of SELEX aptamer incubation (Variant 1-3) with peptides compared to BCS conditions (BCS).

FIG. 36 is a graph displaying the log ratio of expression levels of every 12-mer combination from the sequencing runs of DNA pools after bringup divided by expression levels prior to the bringup for 96 conditions, two of which failed (two bottom right panels). The X and Y axes of each panel are every 6-mer DNA sequence possible. Panels with high ratios of red or blue demonstrate increased variance from a Gaussian distribution, indicating that the experimental conditions perturbed the random input pool further from it's input condition.

FIG. 37 are two tables displaying the sequences and read counts of the top 20 most common sequences from a random sampling of 100,000 reads in the aptamer pool after one round of Fake SELEX and SELEX. Sequences derived from Fake SELEX (SEQ ID NOs:136-155) are all different from the sequences from SELEX (SEQ ID NOs:156-175), suggesting that aptamers pulled down by peptide targets exhibit greater affinity than random sequences.

FIG. 38 is a table exhibiting the counts of replicate sequences between any of 9 experiments, 3 replicates experiments for 3 targets, performed with the same bringup pool. All replicates for a rounds were merged together and non-specific aptamers were filtered from the counts by bead control subtraction. Counts highlighted in red are counts of the same sequences that were found in experiments of differing targets. BRADY1r5 means target bradykinin, position 1, replicate 1 and SELEX round 5. GNRH4r5 is target GnRH, position 4, replicate 1, and SELEX round 5. Sequence contamination occurs across nearest neighbor replicates, indicated by the red regions, which was significantly reduced after altering automation protocols and target position on the plate.

FIG. 39 are two examples of aptamers selected using RCHT-SELEX methods herein to small peptides: one to vasopressin (SEQ ID NOs:176-179) and one to bradykinin (SEQ ID NOs:180-183). Aptamer structures are the lowest Gibbs free energy structures obtained by IDT's licensed UNAFold software.

FIG. 40 reports the top 5 aptamer sequences that are serially enriched specifically in the presence of peptides with an N-terminal lysine (SEQ ID NOs:184-188) or N-terminal cysteine (SEQ ID NOs:189-193) prefix identified in peptide Switch ML-SELEX experiments. These results indicate ML-SELEX's capability to find unique aptamers to individual amino acids.

FIG. 44 is a confusion matrix of top 10 enriched sequences for each replicate (rep) of each target (Backbone, Beads, Brady, PP-C, PP-CD). 0 indicates no sequence overlap between two selections, 1 indicates one sequence overlap, etc. −1 indicates the same selections. Within these selections, it is observed that there is some overlap of sequences (1-2 sequences). This information can be incorporated into final candidate selection. Candidate aptamers for PP-CD can be chosen to have no overlap with other control targets (Backbone, Beads, Brady) but it is permissible to choose candidates that may recognize PP-C and PP-CD switch, as these may recognize the PP on the N-terminal.

FIG. 45 is the results of a single point binding assay for 10 potential aptamer candidates. Binding, indicated by fluorescent signal (y axis) was measured for 10 aptamers at 100 nM. Apt 4 shows higher binding than the controls (non-aptamer and buffer) for target PP-C. Apt 1, 2, 3, 4, 7, 8, 9 show higher binding than controls for PP-D. Data was normalized to the positive control (FAM conjugated directly to beads).

FIGS. 51A and 51B are heatmaps reporting the instances of each target foundation sequenced with the aptamer barcode ligated to it. FIG. 51A reports total counts (SEQ ID NOs:204-243), while FIG. 51B reports the normalized percentage (SEQ ID NOs:244-279). Argipressin aptamers (highlighted in red) identified through RCTH-SELEX show specificity for argipressin over bradykinin targets and peptide targets with a DD N-terminal (DD targets), as their barcodes are ligated on all types of argipressin foundations, but to little to no empty controls, bradykinin, and DD target foundations.

FIG. 58A is an embodiment of a series of images generated by four iterations of probe incubation for a single peptide molecule at location (X,Y) on a chip. FIG. 58B is a table reporting the fluorescent signal observed by each channel (350, 433, 532, 555, 647) that reflect the results of FIG. 58A. Colored regions indicate signal above a noise threshold, which together make up the optical signature of the bound aptamer. FIG. 58C is an embodiment of a lookup table matching each aptamer identity to the optical signature observed through multiple iterations. FIG. 58D is an embodiment of the series of aptamers observed at location (X,Y) on a chip computed from 8 rounds of aptamer incubation. Overlapping N-terminal acid amino calls from the two amino acid identity-redundancy scheme are indicated in black while disagreeing calls are indicated in red. FIG. 58E is a schematic of a sequence calling strategy wherein the computed sequence generated by the peptide sequencing methods described herein is matched to a database of known peptides or a reference proteome.

FIG. 62 illustrates the peptide target sequences used in MULTIPLEX experiments (SEQ ID NOs:280-285).

DETAILED DESCRIPTION

Figure 1:
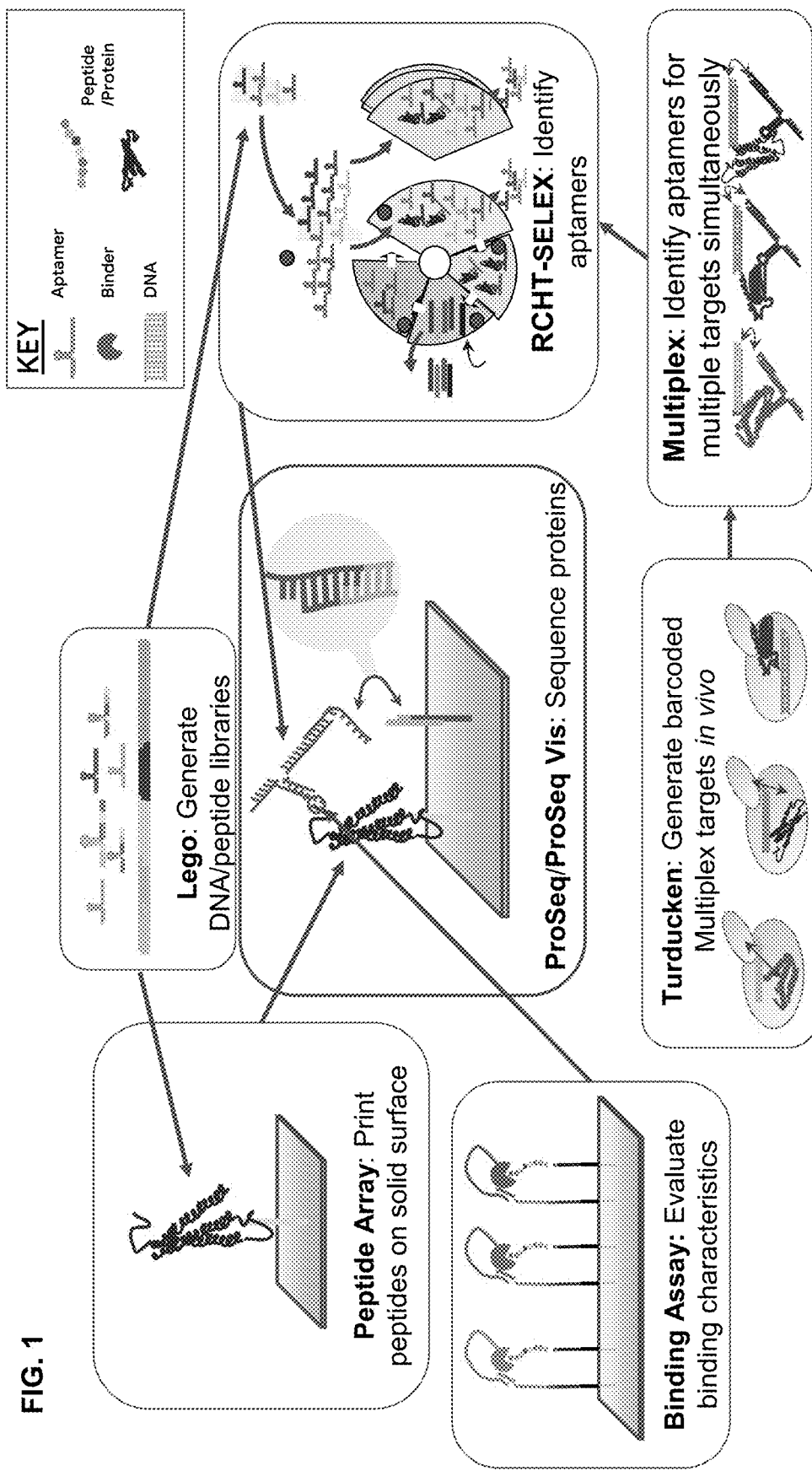
FIG. 1 is a schematic depicting how all the individual inventions described herein make up a pipeline of developing the PROSEQ platform.

This disclosure describes methods and compositions that form a pipeline of developing and using a protein sequencing platform which utilizes aptamers that bind specifically to N-terminal amino acids (FIG. 1). The protein sequencing methods described herein primarily rely upon aptamers having a variety of different features depending upon the particular application. For example, amino acid-specific aptamers can be generated using the novel methods described herein (RCHT-SELEX or NTAA-SELEX). Such amino acid-specific aptamers can be used to recognize, identify and via a nucleic barcoded region convert 1-2 amino acid residues of a protein or peptide into a DNA sequence (PROSEQ), or such amino acid-specific aptamers can be generated and used to recognize and identify, based on a visual signal, each amino acid of a protein or peptide (PROSEQ-VIS). In addition, many target-specific aptamers can be generated simultaneously, and used to produce and screen a large multitude of binders (MULTIPLEX). Simultaneous and specific aptamer selection relies on robust identification of targets. Nucleic acid barcoded target generation can be accomplished in vivo via a non-covalently bond between a peptide or protein using an RNA-binding protein and its corresponding recognition sequence (TURDUCKEN). Lastly, successful SELEX experiments require that aptamers with some specific binding preference and affinity for the molecular target be included in the original pool of $10^{14}$-$10^{15}$ candidate sequences, which is only a small fraction of all of the DNA sequences possible. Machine-learning (ML) can help to optimize experimental seed binders, so unlike conventional SELEX experiments, optimal binders do not need to occur in the experimental dataset. The ability to construct computationally-derived, customizable DNA libraries to perform SELEX screens using a controlled input pool can drastically customize the exploratory space by systematically assaying aptamer candidates that include sequences with known effective binding properties (LEGO).

Aptamers

Aptamers are short, single-stranded nucleic acid strands, which can be composed of RNA, DNA, modified nucleic acids, or other synthetic nucleic acid monologues, that fold into unique conformations that allow for binding specificity to biological targets such as proteins and peptides (Mckeague & Derosa, 2012). Aptamers are used to examine binding interactions involving molecular targets in a number of research areas including drug development, diagnostics, imaging, and basic science. Specifically, aptamers bind to targets with high specificity and affinity, can be generated and modified more quickly and at a lower-cost than antibodies, have a wider range of potential targets than antibodies (Zhou & Rossi, 2016), and are less likely to provoke immunologic side effects than antibodies (Bouchard, Hutabarat, & Thompson, 2010). However, aptamers have not experienced widespread success in clinical or industrial uses due, in large part, to the laborious nature of discovering and identifying aptamers with desired binding characteristics (Zhou & Rossi, 2016). Additionally, aptamers discovered in isolated environments (i.e. selected against purified targets) exhibit high binding affinity in the experimental conditions, but fail to bind to its intended target in in vivo conditions (Chen, et al., 2016). The present disclosure provides methods of making and using aptamers having very specific binding characteristics to amino acid residues at the N-terminal end of a peptide chain.

Figure 2:
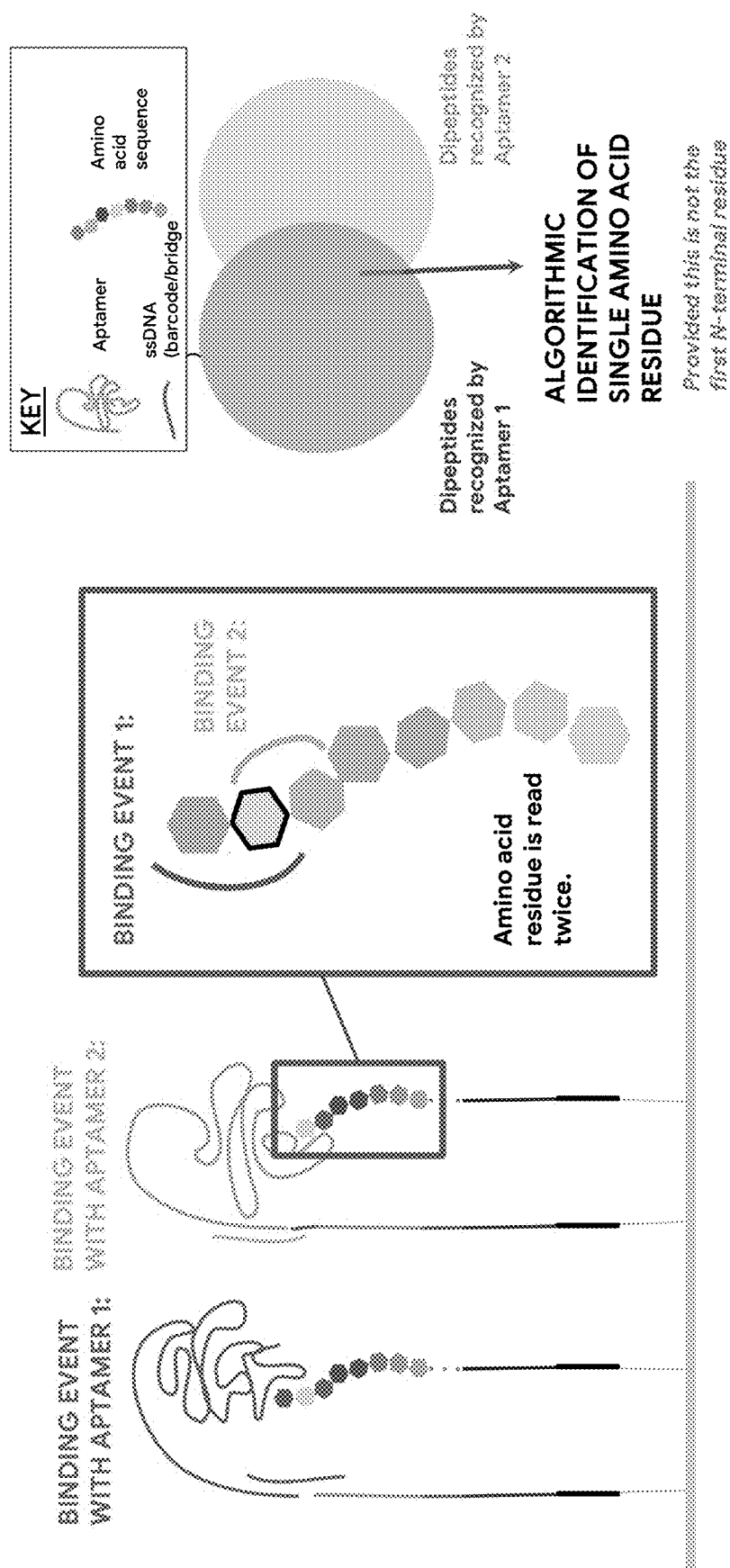
FIG. 2 is a schematic showing the two amino acid identity redundancy scheme, wherein each di-peptide aptamer binding event provides the putative identity of the two N-terminal amino acids, while each round of degradation only removes one amino acid, thus allowing each amino acid except the original N-terminal amino acid to be exposed to two rounds of aptamer binding.

Aptamers with a high peptide binding affinity have an increased chance of binding and of generating a binding event record over aptamers with lower binding affinities. Aptamers that are specific only bind to a small number of possible peptides and, as such, generate records that are informative about which molecules are present. Thus, aptamers with high affinity ($K_{dS}$<30 nM) and specificity (10× binding preference desired target over other targets) are desired for the protein sequencing technologies herein, however, sets of aptamers having various affinities can be used to retrieve information 'bits' about the protein sequence (i.e. PROSEQ AND PROSEQ-VIZ). In end-to-end simulations, results suggest that aptamers of only moderate binding affinity ($K_{dS}$>30 nM) and selectivity will enable us to accurately quantify mixtures of known proteins with relative ease. For non de novo applications, PROSEQ and PROSEQ-VIZ technologies can use a proteome map to resolve any resolution gaps in the data. Additionally, subsequent cycles can be repeated prior to removing the amino acid to allow for additional bits of information to be obtained before cleavage. Finally, if PROSEQ and PROSEQ-VIZ are restricted to aptamers that selectively bind to N-terminal dipeptide prefixes, highly specific aptamers are not necessary even for de novo sequencing. The noise from the reduction in specificity is offset by the additional observed binding events resulting from the two-amino acid identity-redundancy scheme, since it allows for the observation of two binding events per amino acid (except for the first N-terminal amino acid) to confirm its identity (FIG. 2). Each dipeptide aptamer binding event provides insight towards the identity of the two N-terminal amino acids, while each round of degradation only removes one amino acid, thus allowing each amino acid except the original N-terminal and C-terminal amino acids (which will only be read once) to be exposed to two rounds of aptamer binding. In the event of amino acid identification errors, downstream computation algorithms can be used to correct or detect inaccurate readbit results with a certain level of confidence.

Robust & Compressed High Throughput—Systematic Evolution of Ligands by Exponential Enrichment (RCHT-SELEX) and N-Terminal Amino Acid SELEX (NTAA-SELEX)

Systematic Evolution of Ligands by Exponential Enrichment (SELEX) is a known high-throughput screening (HTS) process that has been used to identify aptamers that bind to a specific target ligand in in vitro selection (Tuerk & Gold, 1990). Conventional SELEX protocols typically include screening a diverse and random oligonucleotide library against a single peptide or protein target by flowing aptamers onto bead-bound targets and eliminating weak binding aptamers through multiple rounds of selection where weak binding aptamers and non-binding aptamers are washed away (Blind & Blank, 2015).

Figure 3B:
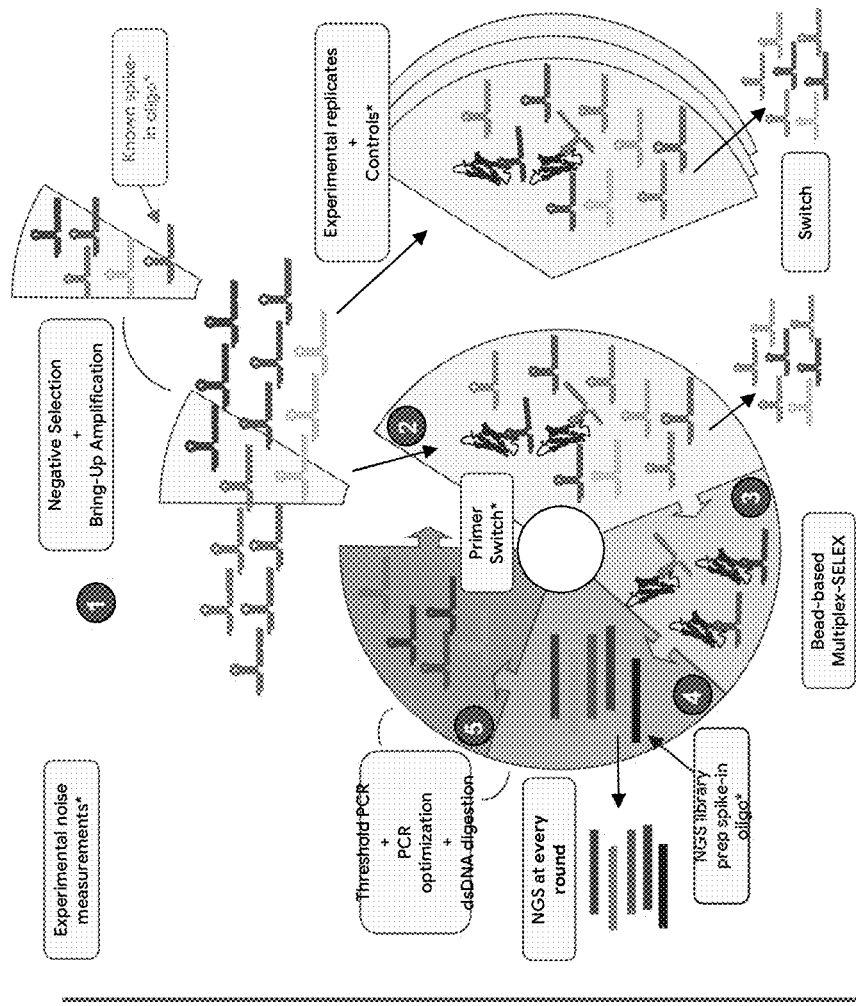
FIG. 3B is a schematic showing the steps in one embodiment of the ML-SELEX methods described herein.
Figure 3A:
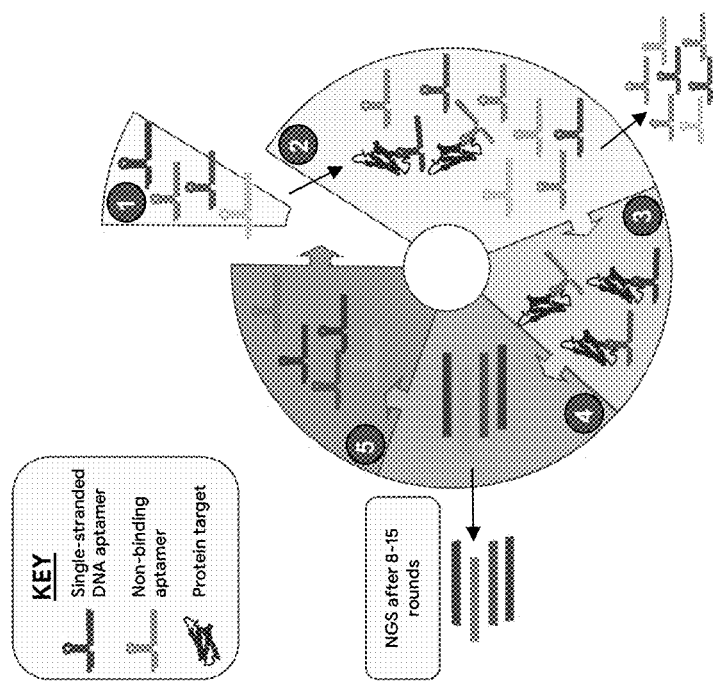
FIG. 3A is a schematic showing the steps in a representative conventional SELEX method.

Conventional SELEX methods begin with the synthesis of about $10^{14}$-$10^{15}$ unique sequences for oligonucleotide libraries, followed by 10-20 iterative rounds of a) single target incubation with a random pool of candidate aptamer sequences to promote aptamer/target binding, b) separation of target-bound oligonucleotides from unbound sequences, and c) amplification and characterization of bound aptamers (FIG. 3A). Several variations of the original SELEX method, such as capillary electrophoresis SELEX (CE-SELEX), microfluidic SELEX, and CELL SELEX, have been developed to fulfill different research needs.

The goal of conventional SELEX methods has been to increase the binding affinity of aptamers identified through experimental screening. Conventional SELEX methods for identifying aptamers suffer from two main problems that prohibit large-scale screening:

Conventional SELEX methods rely on a repeated screening process, in which experimental error can be compounded in every subsequent round of screening. For example, in each round, aptamers undergo PCR amplification, DNA cleanup, and conversion from double-stranded to single-stranded DNA via separation or enzymatic digestion. Variability in one or more of these processes across rounds and/or experiments can encourage the biased selection of an aptamer pool engineered to withstand the selection process of a specific experimental setup.

The lack of parallel selections with the same input library against controls and replicates prevents: (a) inter-experimental and intra-experimental comparison respectively, (b) signal-to-noise ratio analysis, and (c) ground truth measurements, all of which complicate downstream computational analysis, data cleaning and the application of predictive modeling such as ML. Models are attracted to the strongest signal, regardless of source. Often in the case of biology experiments, there exists operator error/noise, instrumentation noise, biological processes noise and noise due to the handling of physical reagents (i.e. contamination), and the combination of all of these different elements of noise can often drown out the experimental signal. As a result, models will often predict based on a very noisy signal, unless they are trained in advance to the different noise elements. To this end, several different features were designed (bringup, replicates, spike-in controls, Fake SELEX, etc.) to calculate and remove the noise during pre-model data processing, or to train the models on the elements of noise during the prediction stage. Additionally, there are several classes of models that have limited predictive capabilities outside of the linear range, and, often in biology, processes are nonlinear (e.g. such as PCR). Linear models have an advantage as they are well-studied, computationally inexpensive and often give robust predictions. However, when applied to non-linear datasets, linear models can often give improper predictions. On the other end of the spectrum, non-linear modeling approaches can be computationally more expensive and also are subject to overfitting (e.g., polynomial modeling on sparse data), but are often required to be utilized when linear models fail to describe data sets accurately. As a result, numerous unit tests were run to calculate the regions of linear and non-linear processes in order to best determine which type of modeling approaches can be applied.

Conventional SELEX methods allow for the screening of an aptamer pool against only one peptide or protein target at once. That is, each protein or peptide target must be screened in isolation to be able to identify the target. Therefore, screening against 1,000 peptide targets using conventional SELEX methods would require 1,000 individual SELEX experiments, each involving multiple rounds of screening.

In addition, for a 40-mer ssDNA oligo, for example, there are $10^{24}$ possible oligos that could be produced, and an exploration of $10^{12\text{-}15}$ of the total possible experimental space can result in difficulty finding a unique aptamer to a target. Currently, there are numerous barriers to efficiently screening such a large volume of candidates:

low hit rate: successful SELEX experiment requires that aptamers with a high affinity for the molecular target be included in the original pool of $10^{14}$-$10^{15}$ candidate sequences. For a $10^{14}$ sample, only $8.27\times10^{-11}$% of the experimental space of possible DNA sequences is being explored, such that in practice, even the most optimized experiment has a high probability of failure.

time-prohibitive: generally takes >6 months to a year to identify specific aptamer candidates.

non-specificity: traditional SELEX experiments incubate candidates with one target at a time, which only demonstrates the candidate aptamers' relative affinity, but not their specificity in a competitive environment.

inability for direct comparison: since most experiments start with a new random pool of input oligos, direct comparison across experiments is impossible.

difficulty in translating to environments differing from discovery conditions: translation of discovered aptamers can also be fraught with difficulties, due to their sensitive structural nature that is correlated with their discovery environment. Since structure informs function, aptamers selected in a particular environment may not fold and bind to their target in the same manner when conditions differ from experimental ones.

There are two significant gaps in current SELEX protocols. No existing method is tailored to accommodate large scale computational analysis for multiple targets between every round, for the purpose of using experimental data to supplement computationally-derived aptamers. If a working protocol existed, then empirical datasets could smoothly integrate with machine learning analysis and prediction pipelines, allowing for in silico prediction of aptamers to targets. Computationally predicted aptamers would allow for exploration across a wider range of sequences for optimal aptamer targets and also save resources and time in aptamer search queries. Also, SELEX protocols lack the precision and resolution to discover binders high-resolution for aptamer candidates that bind to a small portion of a larger target and can be used as N-terminal amino acid binders. Developed methods addressing both gaps are detailed below. A new SELEX method (referred to herein as RCHT-SELEX) is provided in Section A that optimizes the selection of high affinity and specificity aptamers in a time-efficient manner via an innovative combination of existing and novel techniques to address the gap in developing ML-compatible empirical datasets. In addition, another novel SELEX method developed with the priority of discovering N-terminal amino acid specific binders (referred to herein as NTAA-SELEX) is provided in Section B.

Section A RCHT-SELEX

FIG. 3 is a schematic showing how conventional SELEX methods (FIG. 3A) have been modified to produce RCHT-SELEX (FIG. 3B). The main differences between the two techniques are highlighted below:

Step #1 of conventional SELEX does not amplify the input pool; RCHT-SELEX amplifies input pool ("Bringup") after a negative selection step and spike-in addition such that: (a) there exists approximately 100 copies of each aptamer binder, and (b) the same input pool is used across experiments.

Step #2 of conventional SELEX is a single experiment of incubation of a single target to a library of aptamers; in contrast, RCHT-SELEX splits the Bringup pool across many experiments of several targets in triplicate (including 3 experimental bead-only controls) to be run in parallel, and assays the aptamers against targets with alternating region(s) in different rounds such that the only constant region driving the selection process is the region that the user desires a specific binder for, regardless of the targets' neighboring regions.

Step #4 of conventional SELEX sequences the evolved aptamer pool after 8-20 rounds of repeating Steps #2-#5, whereas Step #4 of RCHT-SELEX includes sequencing after every round of selection, and multiple techniques to maximize and standardize the amount of DNA input into the next rounds in each experiment.

Step #5 of conventional SELEX includes obtaining the aptamers that bound to target proteins in the previous round so that those aptamers can continue the selection process by repeating Steps #2, #3, #4 and #5 8-20 rounds; RCHT-SELEX can be performed in only 4 rounds and assays the aptamers against targets again after the primer regions are replaced with alternative primer sequences.

Since several experiments are run in parallel in RCHT-SELEX, and the goal is to reduce experimental bias across each experiment, several additional steps have been added to the RCHT-SELEX protocol to support running >36 experiments simultaneously. RCHT-SELEX can include techniques such as:

thresholding the same amount of DNA as inputs to subsequent rounds to reduce PCR bias ("Threshold PCR")

optimizing the PCR conditions for the specific candidate pool ("PCR Optimization")

performing unit tests before each digestion to determine optimal digestion conditions for each sample ("dsDNA Digestion").

Additional alterations of RCHT-SELEX can include:

assaying the same aptamer candidate pool with multiple targets pooled together in early rounds and demultiplexing by incubating the aptamers against each target individually in the final round ("Bead-Based Multiplex-SELEX")

alternating targets with varied local environment binding regions between alternating rounds of RCHT-SELEX for experiments where the desired aptamers are ones that bind specifically to a smaller region of a molecule rather than the whole molecule ("Switch")

switching primers mid-experiment to identify aptamers that are strong binders independent of the primer region ("Primer Switch").

Negative SELEX:

One technique that can be used to reduce the enrichment of aptamers to unwanted target(s) is to screen the initial pool of aptamer candidates for aptamers that bind to the selection components used in SELEX experiments (e.g., beads, streptavidin). Aptamers that express binding affinity to selection components are non-specific to the targets and can be removed from the candidate pool so that only aptamers that do not bind the selection components would be part of the aptamer candidate pool assayed against targets. See, for example, FIG. 4.

Single Bring-Up, Double Bring-Up and In-Experiment Replicates:

For example, a pool of $10^{12}$ DNA aptamers are selected from an original pool of $10^{15}$ and amplified through 13 cycles of PCR with unmodified primers resulting in approximately 2000 copies of each aptamer. Amplification is dependent on primer sequences and PCR conditions, and the bringup PCR protocol can be tuned to each individual library. The goal is to have at least 100 copies of most sequences present in each experiment with a minimum of 30 copies of each aptamer sequence present. Libraries are sequenced during protocol optimization stages to help approximate uniform amplification copy number across sequences.

Post amplification, about 2000 copies of each aptamer is distributed across 12 samples, resulting in approximately 166 copies of each aptamer in each initial starting library pool. The process of having multiple copies of the same aptamer present before initiating a selection allows for the direct comparison of results of the same initial bring-up to each other. Computationally, this feature allows for direct experimental replicates to occur side-by-side, and also provides the ability to train models to walk towards a particular target and away from another. Since it would take many sequencing runs to determine the precise amplification of $10^{12}$ sequences, a single NextSeq run of 400 million reads can be performed as an approximation of the amplification features of the library across the entire pool. Single Bring-Up stops at this step.

Figure 5B:
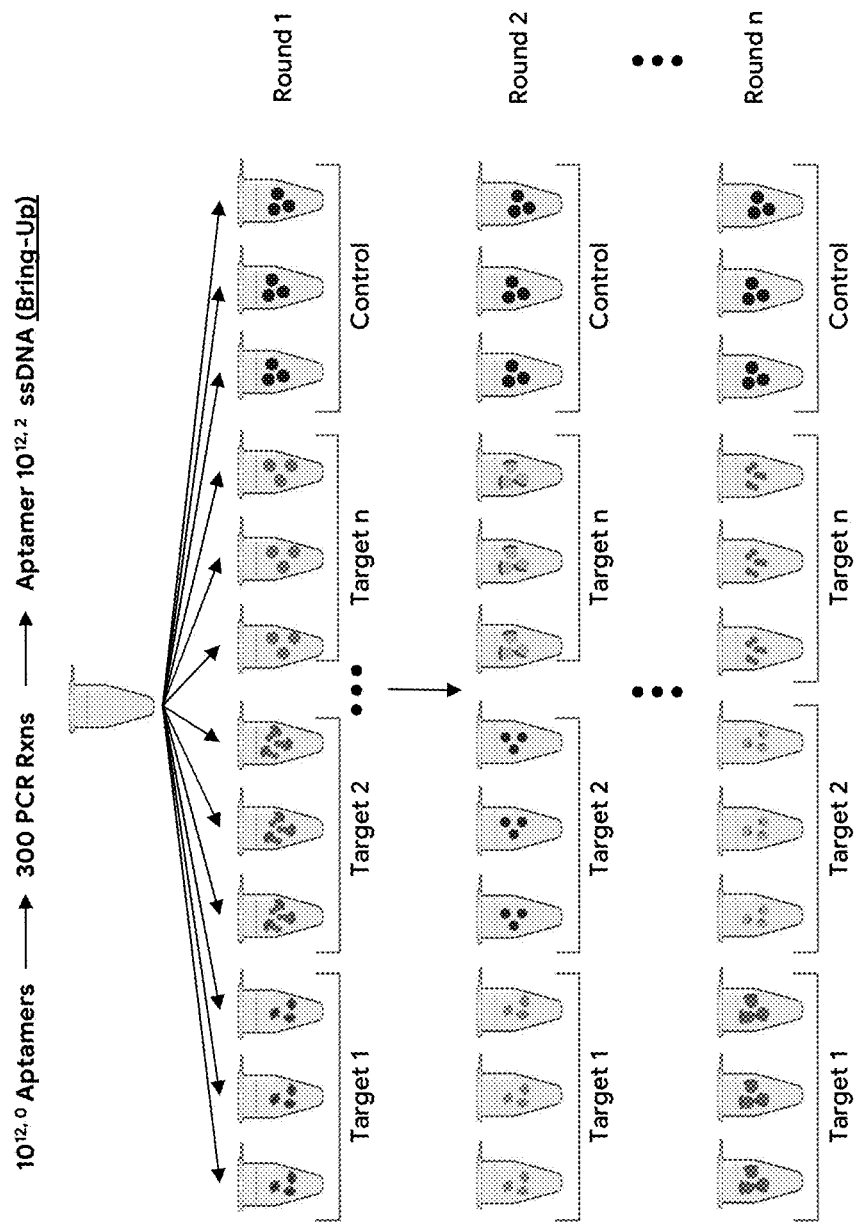
FIG. 5B is a schematic demonstrating the single bring-up experiments, double bring-up experiments, in-experiment replicates, and all-bead control experiments that can be used, in parallel or sequentially, during the RCHT-SELEX methods described herein.
Figure 5A:
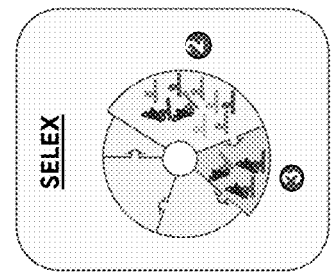
FIG. 5A is a schematic demonstrating the various steps within the RCHT-SELEX procedure (from FIG. 2) into which the single bring-up experiments, double bring-up experiments and/or in-experiment replicas can be incorporated.

For Double Bring-Up, a second bring-up is conducted by taking about 75 copies of each aptamer from the first bring up and amplifying it through 6 cycles with protected phosphorylated primers, which allows for comparison of results from the same initial bring-up across approximately 300 experiments (approximately 2000 copies of each aptamer from a single bring-up, 75 aptamers selected yield 26 possible pulls; each group of 75 aptamers will yield a double-bringup pool for 12 experiments, so 12*26=312 total experiments; NB there can be some loss in purification, digestion and other processes and amplification yield is highly correlative to the properties of primers and components of the PCR Mastermix). Amplification of aptamer candidates from each bring-up also increases the likelihood that strong and medium binders would carry through past early rounds. See, for example, FIG. 5B, which schematically demonstrates the single and double bring-ups and experimental replicates described herein, and FIG. 5A, which schematically demonstrates where in the RCHT-SELEX methods the single and double bring-ups and experimental replicates can be used.

Bead-Based Multiplex-SELEX

Figure 6:
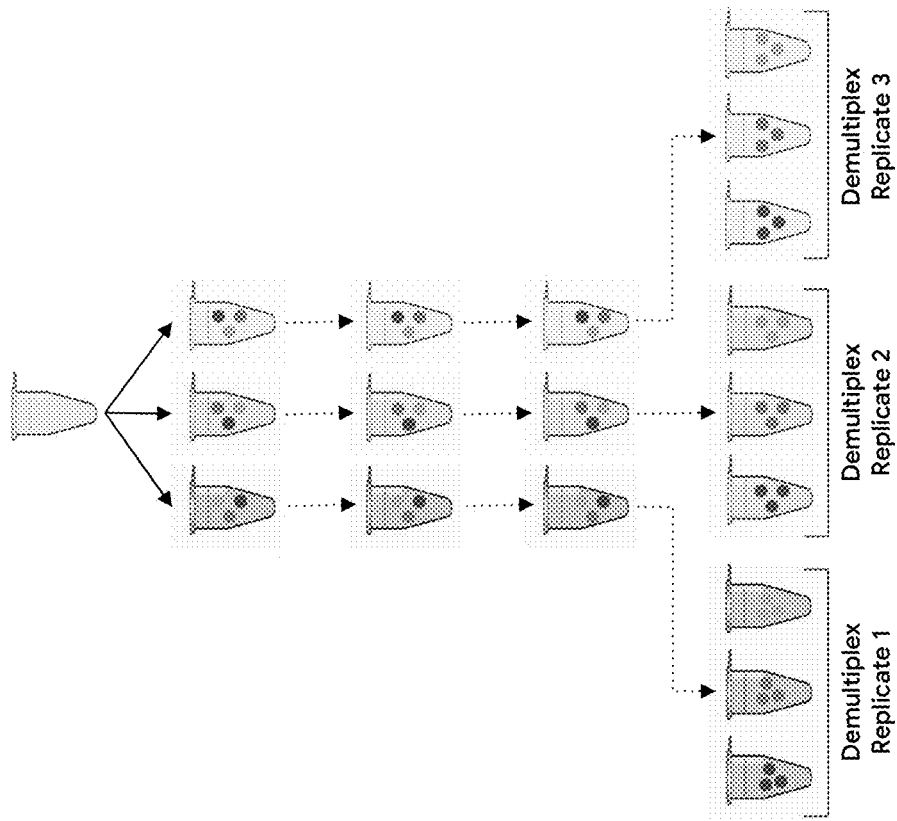
FIG. 6 is a schematic showing a bead-based multiplex version of RCHT-SELEX that allows for selection of aptamers to multiple targets per experiment. Aptamers identified in a bead-based multiplex version of RCHT-SELEX can be de-multiplexed in the final round by incubating those aptamers separately with beads that are conjugated to only one of the initial targets.

After, for example, four rounds of RCHT-SELEX is performed with multiple bead-bound targets pooled together, aptamers can be de-multiplexed in round 5 by incubating pools of amplified aptamers separately with beads that are conjugated to only one of the initial targets (see, for example, FIG. 6). Bead-based Multiplex-SELEX adds a competitive target environment, and scales the number of targets that can be explored within the same experiment.

Peptide Switch

Figure 7:
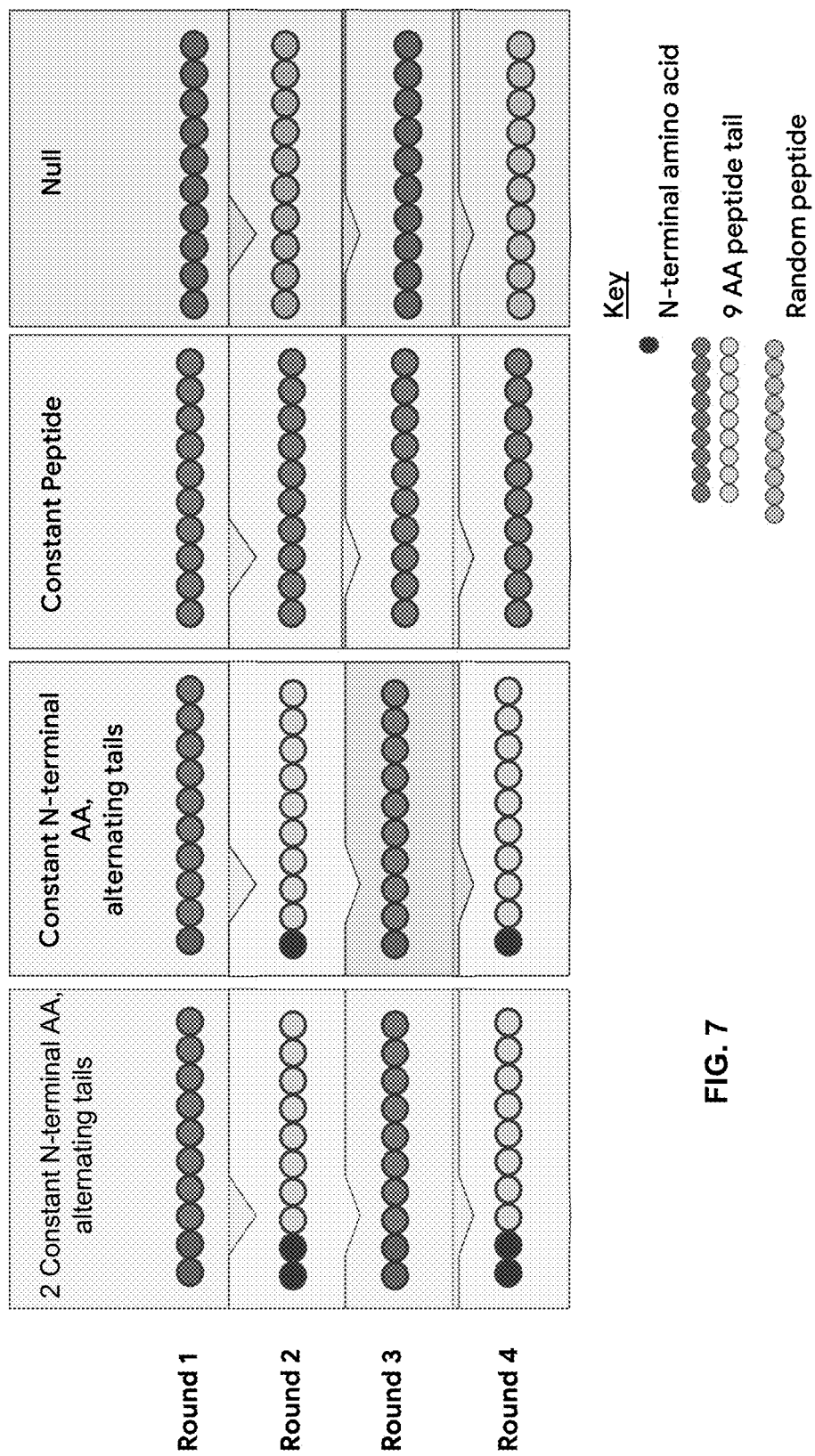
FIG. 7 is a schematic of a method of identifying aptamers that bind specifically to an N-terminal amino acid prefix independent of the composition of the peptide's suffix tail by assaying aptamers in iterative rounds where the peptide suffix is changed round to round while the desired N-terminal amino acid prefix remains the same. Four types of iterations are shown: dipeptide switch (Column 1), wherein the N-terminal amino acids remain the same while the suffix is switched; single amino acid switch (Column 2); consistent peptide target (Column 3); complete switch or null (Column 4), wherein peptide targets differ completely between alternating rounds.

When designing binders for protein sequencing, four goals must be accomplished: (1) target the specific amino acid, (2) target the specific amino acid in an N-terminal location, (3) do not bind to the same amino acid in non-N-terminal locations, and (4) bind robustly to the targeted N-terminal amino acid(s) regardless of the neighboring amino acids. The rationale for goal #4 is that local biochemical environments (e.g., neighboring amino acids) can influence the binding activity of aptamers, reducing their effective $K_d$. Since the goal in protein sequencing is to build binders that can be utilized in peptide strings across the entire proteome, binder design must account for local environmental impacts. In order to accomplish goal #4, altering changes in local environments were introduced during binder selection to develop binders agnostic to neighboring amino acids. This was conducted by fixing 1-2 amino acids in a precise location within a peptide string (typically the N-terminal position) and varying the connected or surrounding amino acids from round to round. FIG. 7 illustrates a method of identifying aptamers that bind specifically to an N-terminal amino acid prefix, independent of the composition of the peptide's suffix tail. This technique, labelled as 'peptide switch', evolves aptamers in iterative rounds where only the peptide suffix is changed while the desired N-terminal amino acid prefix remains the same, removing negative binders. Peptide switch experiments can include a null, scrambled or 'fake' target as well to define promiscuous binders to remove false positives.

PCR Optimization

PCR conditions can be optimized to maximize DNA output while minimizing unwanted products, such as concatemers. PCR optimization must be conducted for each individual library. In SELEX experiments, initial library primers must be replaced often between experiments to prevent PCR contamination in experiments. Mastermix and PCR optimization unit tests are conducted for each library after every change in library primers, which consist of tuning as many parameters as possible (buffer conditions, cycle number, enzyme, primer concentration, number of protected base pairs etc) before a SELEX library can be used in experiments. Results are analyzed with sequencing, Qubit, TapeStation, Bioanalyzer and digestion unit tests to choose the ideal optimization settings for the individual library. For example, amplification can be performed in a 50 μL reaction volume consisting of 38.49 μL nuclease free water, 0.30 μL 1 mM forward primer complementary to the first 6 nucleotides (referred to as 6XP), 0.30 μL 1 mM phosphorylated reverse primer (referred to as RP04), 0.50 μL Herculase® II Fusion DNA Polymerase, 10 μL Herc Buffer, 0.40 μL 25 mM dNTP, and 0.01 μL template. PCR can be performed using an Eppendorf Mastercycler nexus eco PCR machine. The thermal cycle can be programmed for 5 minutes at 95° C. for initial denaturation, followed by 13 cycles of 30 seconds of 95° C. for denaturation, 30 seconds at 55° C. for annealing, 30 seconds at 72° C. for extension, and 5 minutes at 72° C. for the final extension. The conditions for annealing are primer dependent and can be re-optimized for different primer sets used.

Digestion of dsDNA

Figure 8:
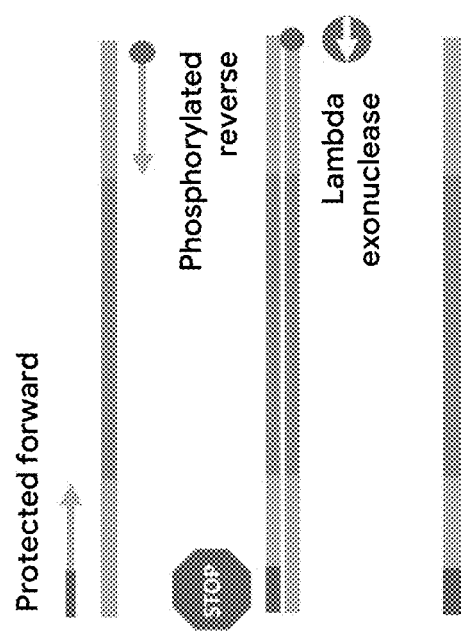
FIG. 8 is a schematic showing how lambda exonuclease can be used to convert double-stranded (ds) DNA into single-stranded (ss) DNA. Lambda exonuclease prefers to degrading targets at an approximate ratio of 20:1 that are phosphorylated on the 5' end. Aptamers must be single stranded to fold and bind to peptides, so bound aptamers are PCR-amplified with specific protected/phosphorylated primers which produces dsDNA, then digested with Lambda exonuclease to convert amplified products such that the forward ssDNA aptamer survives.

Lambda exonuclease is a highly processive exodeoxyribonuclease that prefers to digest the 5-phosphorylated strand(s) of dsDNA and has significantly lower activity on ssDNA and non-phosphorylated DNA (Little, 1967) (Mitsis & Kwagh, 1999). Lambda exonuclease can be used to efficiently digest PCR-amplified dsDNA into ssDNA in the following three steps: a) unit tests for optimal digestion conditions, b) segmenting pre-digested library into thirds, and c) bioanalyzer quality control (QC) assay to test amount of ssDNA vs dsDNA. Single-stranded PCR products can be produced by first performing PCR with two different primers (e.g., 3'-phosphorothioate protection primer complementary to the unwanted reverse strand and 5'-phosphorylated primer complementary to the desired forward strand) followed by PCR amplification, where the phosphorylated strand of the PCR product then can be removed by digestion with lambda exonuclease. RNA kits of the Bioanalyzer system can be repurposed to quantify ssDNA as the dyes in the RNA kits bind ssDNA as well. Although the measurement outputs are not calibrated for ssDNA, inferences from the bands and peaks can be made. See, for example, FIG. 8. RNA kits of the Bioanalyzer system can be hacked to quantify the amount of ssDNA relative to dsDNA in a sample as the dyes in the RNA kits bind to both ssDNA and dsDNA. When a sample with both ssDNA and dsDNA is processed through capillary electrophoresis on the Bioanalyzer, a unique non-overlapping peak is generated for ssDNA and dsDNA, where the relative area under each curve delineates the percentage of the sample that is attributed to ssDNA and dsDNA. The goal of utilizing the RNA Bioanalyzer kit analysis in a digestion assay is to confirm that all of the dsDNA has been converted into ssDNA without overdigestion of the ssDNA library. Although the measurement outputs are not calibrated for ssDNA, inferences about the nature of the DNA mixture can be made from the bands and peaks.

During experimentation, data demonstrated that quality and quantity of PCR yields influenced the ability to predict the digestion behaviors of lambda exonuclease. Libraries with additional concatemers products either digested very slowly or very quickly depending on the fraction of protected or phosphorated base pairs that were present in the concatemer sequences. Thus, unit tests can be performed when evaluating new libraries to prevent complete digestion of the sample. Before conducting digestion of all the PCR products, unit tests can be conducted to determine the optimal reaction time for efficient ssDNA production for each sample. Time course analysis of lambda exonuclease digestion can be performed on small samples of the purified PCR product following incubation at 37° C. for, for example, 2, 5, 10, 15, or 20 minutes, 75° C. for 10 minutes, and held at 4° C. An RNA bioanalyzer can be run on each of the samples to assess digestion and determine the optimal digestion conditions to apply to the rest of the PCR product sample.

Lambda exonuclease digestion of the entire sample can be performed by incubating at 37° C. for the optimal time determined by the time course analysis, followed by heat de-activation of the enzyme at 75° C. for 10 min and held at 4° C.

Figure 9:
FIG. 9A-9C are electropherograms displaying the extent of lambda endonuclease digestion of the random aptamer library was monitored using Small RNA kits on Agilent's Bioanalyzer Chip System. Representative bioanalyzer profiles are shown that correspond to (A) dsDNA, (B) partially digested DNA and (C) ssDNA aptamers. Data is represented on the right of each electropherogram in a gel-like image, with the green line representing the RNA marker. Confirmation of complete conversion to ssDNA occurred prior to the introduction of each aptamer library into each new RCHT-SELEX round.

Representative samples of the final lambda exonuclease digestion mixture can be run on another RNA bioanalyzer chip to ensure sufficient digestion of the PCR product to ssDNA prior to the next cycle of RCHT-SELEX (FIG. 9). If digestion is not complete, more lambda nuclease and ATP can be spiked in.

Figure 10A:
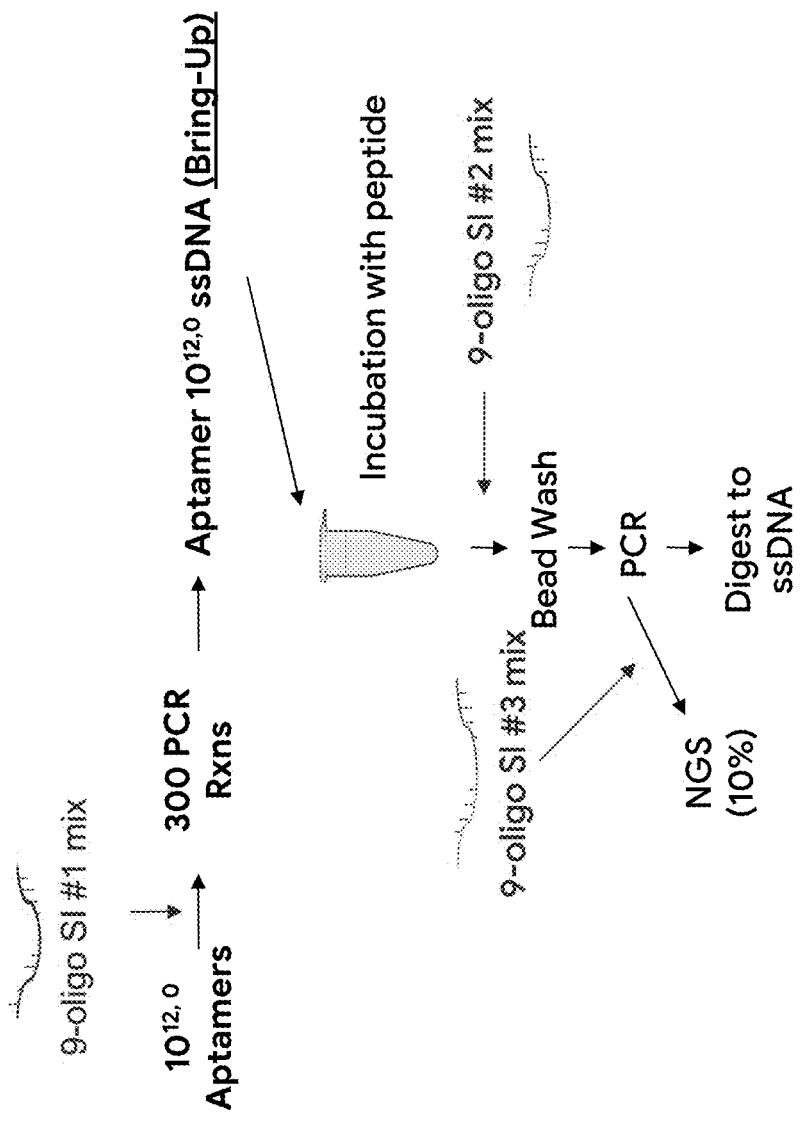
FIG. 10A-10C is a schematic showing that oligonucleotide spike-in controls and fake experiments can be used in the SELEX methods described herein. Positional spike-ins added in specific wells of a 96-well plate can be used to determine local contamination across wells (A). Different spike-ins are added at different stages of SELEX (i.e. prior to the Bring-Up, after each round of incubation before PCR amplification, and in each NGS sample) to determine PCR bias at each step (B). In Fake SELEX, a pull from the bring up is incubated in the absence of beads and targets and PCR amplified (C).
Figure 10B:
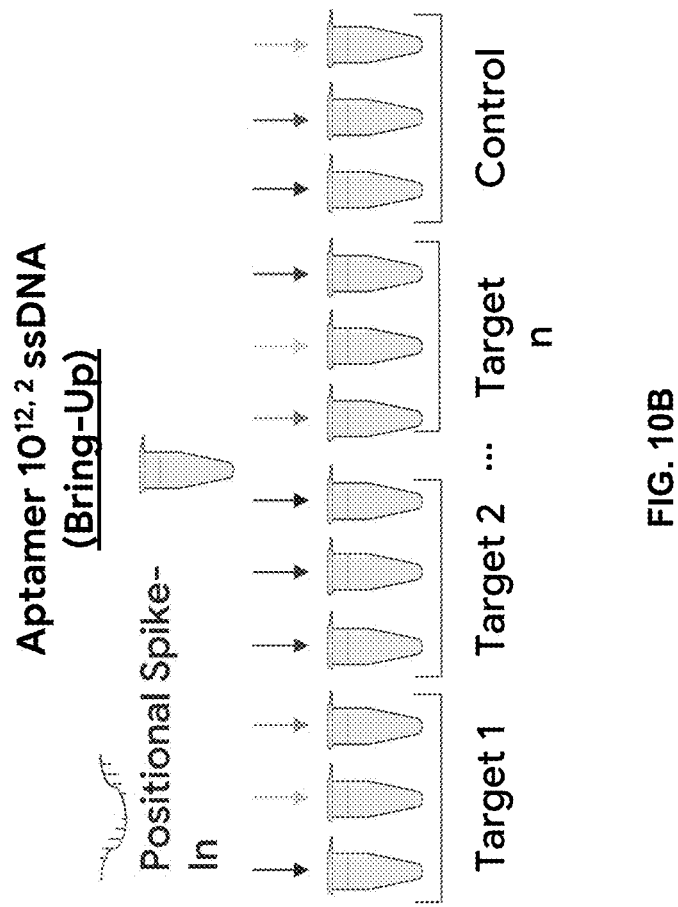
Figure 10C:
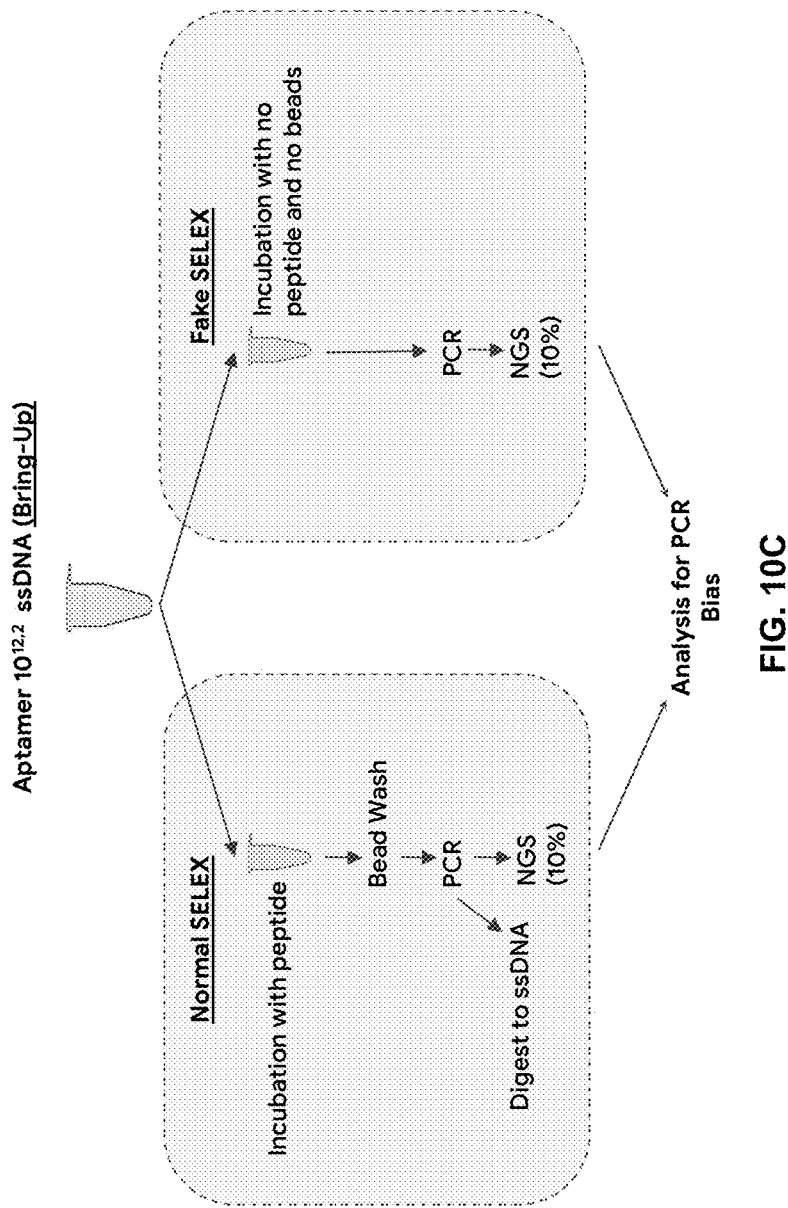

Additional Controls: Bead Controls, Spike-Ins and Fake SELEX
- spike-in oligonucleotides: small spike-ins of known aptamer mimics can be added as controls in various steps throughout RCHT-SELEX to detect experimental error. For example, a mixture of nine oligonucleotides with 3 representative sequences at three different levels of GC contents (e.g., 40%, 50%, 60%) of known sequences (i.e., "a 9-oligo mix") can be added before PCR to provide information regarding sample variability relating to PCR differences. See, for example, FIG. 10A. Alternatively or additionally, a known sequence can be added to each well (e.g., a positional spike-in) to provide information regarding spatial position on, for example, a 96-well plate. See, for example, FIG. 10B.
- all bead controls: all bead controls include in-parallel and sequential controls. See, for example, FIG. 10B. For in-parallel experiments, an all bead control (e.g., non-peptide conjugated bead sample) can be run in triplicate alongside experiments to determine the number of aptamers from the bring-up pool that bind to only the beads. In addition, these controls can be used to determine the level of well-to-well contamination or noise from each experiment. Sequential bead controls can be used after each round of RCHT-SELEX, where aptamers that bind to the peptide-conjugated beads are incubated with beads not conjugated to peptides. If desired, aptamers that bind to empty beads can be sequenced to identify common sequences among aptamers that are binding to the empty beads.
- fake SELEX: before each round of RCHT-SELEX, a small sample of the original input can be removed and kept at room temperature as a control to determine the effects of PCR bias since no target is present. See, for example, FIG. 10C.

Threshold PCR

Bound aptamers from bead-based RCHT-SELEX experiments can be amplified directly on magnetic beads. Thus, aptamers do not need to be denatured from the beads prior to running PCR, limiting the number of processing, handling and potential library loss steps at a sensitive stage in the SELEX assay (Hoon, Zhou, Janda, Brenner, & Scolnick, 2011). However, PCR reactions can reach a saturation point where reagents become limited or concentrations have become too high for uniform replication to continue. Since the concentration of aptamers bound are not known a priori to PCR amplification, and can only be estimated; it can not be determined precisely how many amplification cycles will be needed before amplification saturation will occur. Furthermore, PCR amplification can be impacted by some magnetic beads which are coated with bovine serum albumin (BSA), where, if the concentration of BSA is too high, then the total product produced by PCR is reduced. Additionally, in-house experimentation demonstrated that there was a non-uniform distribution of aptamers across beads, such that if the aptamer libraries on beads were physically split into separate solutions prior to amplification, different end-point amounts and variance in undesirable PCR products were seen across splits leading to unknown introduced variance across samples. In order to (a) resolve the complexity of introducing unquantifiable bias across samples, (b) amplify each library to the same concentration end-point, and (c) mitigate issues caused by PCR saturation and the presence of BSA, PCR amplification occurred in two stages: (1) PCR on beads and (2) threshold PCR. Conducting PCR amplification in two-stages provides the benefit of library redundancy if issues occur with digestion.

Figure 11C:
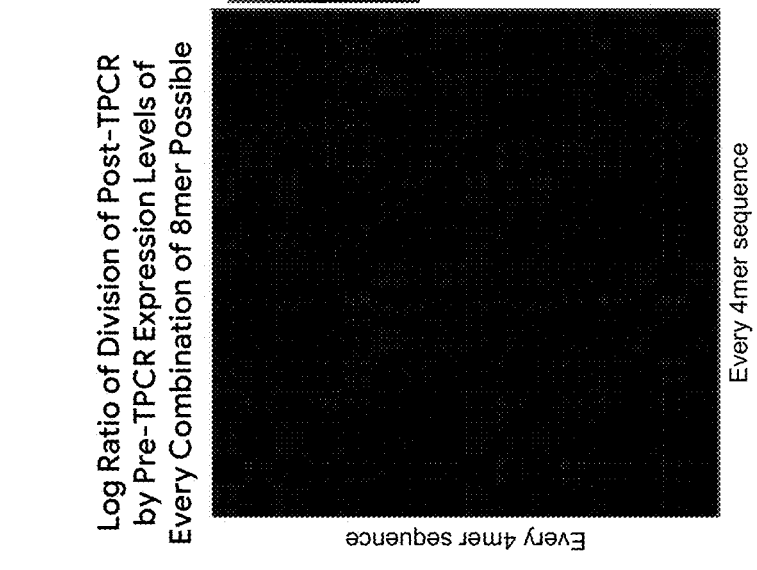
FIG. 11C is a heat map reporting the log ratio of the division of expression intensities of every 8mer combination from the sequencing runs of a DNA pool after and prior to threshold PCR in FIG. 11B. The minimal (black) signal demonstrates that threshold PCR can reduce the effects of compounding bias.
Figure 11B:
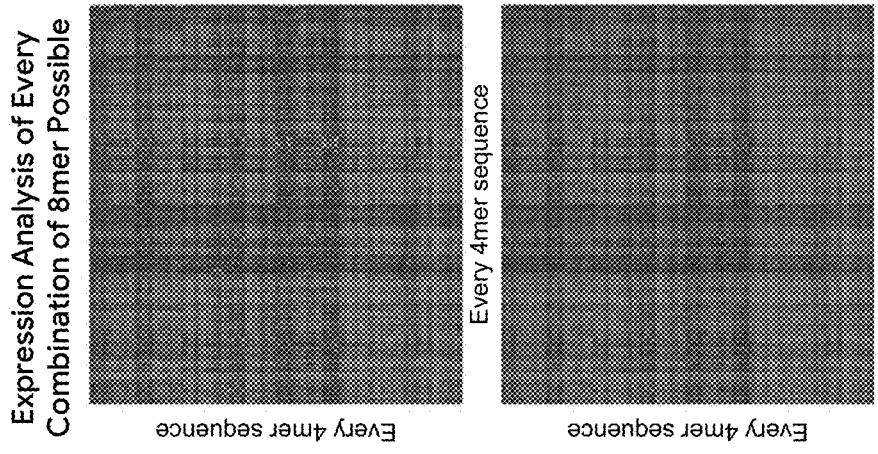
FIG. 11B is a graph displaying the expression intensities of every 8mer combination from the sequencing runs of a DNA pool prior (above) and after (below) threshold PCR. The X and Y axes are every 4mer DNA sequence possible. Comparison of the expression intensities between the pools are extremely similar, with a log variance of 0.132.
Figure 11A:
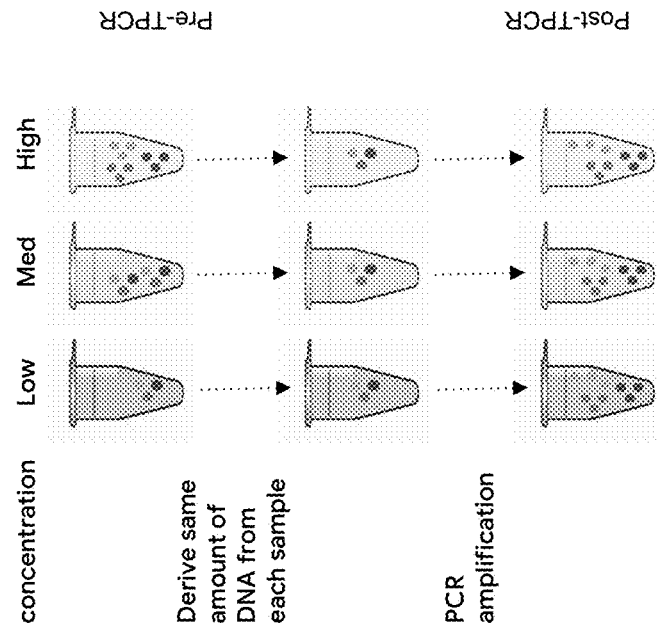
FIG. 11A is a schematic showing threshold PCR, wherein similar concentrations of DNA from different samples of varying concentrations are PCR-amplified to ensure similar amounts of input are introduced into each reaction in subsequent rounds of SELEX.

When running many experiments in parallel from the same bringup pool, PCR reactions can produce mixtures of aptamers with different end point concentrations based on the amount of DNA pulled down in each experiment (e.g., low, medium and high; FIG. 11). In order to conduct computational comparisons across many experiments, and to balance experimental requirements of the minimum amounts of material that automation can handle (e.g., pipetting volume minimums for magnetic beads), input library amounts are normalized prior to a second amplification step. Variance in input DNA template amount can impact the effects of PCR bias. The DNA concentration of each library after PCR on beads can be measured and the post-PCR library with the lowest concentration of DNA, or a standard amount, can be used as a standard for a threshold quantity. The rest of the samples are then subjected to the threshold quantity, and subsequent rounds of PCR follow before generating inputs to subsequent RCHT-SELEX rounds. See, for example, FIG. 11A. Numerous control experiments have demonstrated that the shape of the sequence distribution is not altered with this threshold PCR approach (FIGS. 11B and 11C).

Primer Switch

Figure 12:
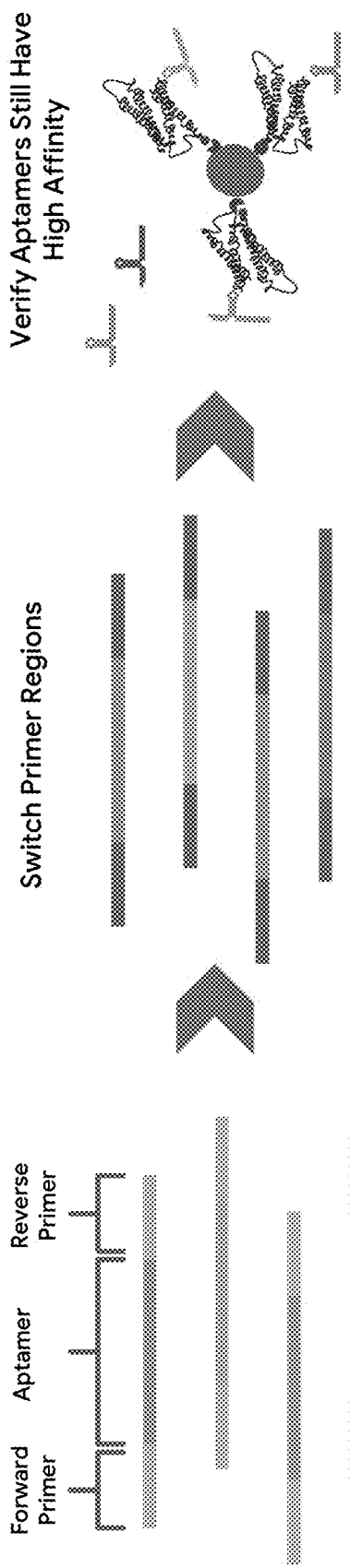
FIG. 12 is a schematic showing that primer switching can be used to select for aptamers with binding affinities independent of the primer region.

Constructs of the aptamer candidates can include a) random sequence of DNA which participates in or facilitates binding to a target and b) one or more regions to which DNA primers can hybridize so that the aptamer sequence can be PCR amplified. Primer regions can contribute to aptamer structure and binding affinity to a target molecule. The primer regions can be alternated to different primer sequences or removed entirely, and aptamers can be assayed again to isolate aptamers that have high affinity to the target molecule independent of the primer region. See, for example, FIG. 12

Sequencing Aptamer Pool after Every Round

A representative pull of dsDNA, prior to Threshold PCR, from every round of every selection were sequenced and analyzed for round-to-round enrichment of sequences. Unit tests have been conducted of sequencing pre- and post-Threshold PCR, which demonstrated that the distribution of sequences did not change during Threshold PCR. Since there wasn't a shift in sequence distribution, and for computational analysis a direct comparison point at each stage of SELEX is ideal, the pre-Threshold PCR stage was selected to: (1) reduce additional steps at the end of a SELEX experiment, and (2) allow for storage of DNA samples at higher concentrations and reduced volumes without additional manipulation (i.e. SpeedVac, etc).

As discussed herein, the RCHT-SELEX methods incorporate several novel modifications: (1) screening of up to 300 different targets simultaneously, (2) maintenance of high DNA concentrations between selection rounds with reduced PCR bias, (3) additional features for advanced post hoc computational analysis, including comparisons across every possible experiment regardless of the day it was conducted, and (4) increased binding specificity to small molecule targets, such as small peptides or amino acid targets. These capabilities can accelerate the large-scale identification of aptamers to biological targets for potential use in diagnostics, therapeutics, and basic science research. Novel features of the RCHT-SELEX methods described herein include, without limitation:

- single or double bring-up allows for direct comparison of results across targets, experiments and/or replicates from the same initial bring up;
- analysis of in-experiment replicates strengthens positive signal and saves time and money from testing undesirable aptamer candidates;
- threshold PCR generates robust aptamer library inputs for multiple parallel experiments with minimized PCR bias, provides an earlier recovery point if experimental issues with converting post-PCR dsDNA libraries into ssDNA libraries, and reduces library loss to concatemers;
- switch allows for the detection of aptamers that are specific to a desired sequence at a specific location of a target (e.g., small fragments of a larger molecule);
- bead-based multiplex SELEX increases targets within the same experiment, and reveals aptamer bind capabilities within a competitive environment;
- spike-in concentrations can be used to detect experimental error and PCR bias;
- Next Generation Sequencing (NGS) at every round combined with sensitive analysis can: (a) localize binders earlier and (b) generate input data for machine learning (ML) models. ML models can predict highly specific novel aptamers with fewer rounds of SELEX and explore a larger DNA input space than experimentally possible. The use of ML in aptamer prediction can increase the power of the SELEX methods described herein while saving precious research funds and time.

RCHT-SELEX methods described herein reduce labor and reagent costs while, more importantly, improving data quality, downstream analysis and broadening screening capabilities. In addition, the multiplex methods described herein can produce aptamers to targets that bind specifically in an environment with a multitude of available targets (e.g., cell surfaces, human blood), thus, vastly increasing the discovery to application pipeline for aptamers.

The RCHT-SELEX methods described herein can be used to examine substrate binding beyond DNA:peptide interaction. For example, binding between a number of biological targets can be examined provided both targets include oligonucleotides that can be ligated to each other. For example, a similar technique can be employed to screen for RNA aptamers that bind small molecule targets or protein complexes.

Additionally, many procedural modifications can be made to adapt this method to suit different applications. For example, and without limitation, other "input" nucleic acids, such as RNA or modified nucleic bases, can be screened for binding affinities with molecular targets of interest, or to screen for aptamers that bind to targets other than proteins or peptides (e.g., small molecules, intact proteins, other nucleic acids, specific cell lines). Another example of a modification is the replacement of Lambda exonuclease dsDNA digestion with asymmetric PCR to produce the ssDNA input into subsequent rounds of SELEX.

The RCHT-SELEX method described herein can be used to screen for aptamers with selective binding to specific peptide targets within a competitive multi-peptide environment. Like selective antibodies, the resulting aptamers can be used alone or in combinations with two or more aptamers to create a complex that exhibits multi-target binding distributions. For example, two aptamers, each highly selective for different targets, can be used sequentially, in-tandem, or joined together in order to create a single construct that binds to the two separate targets. Alternatively, two aptamers for the same primary target but with different off-target binding distributions can be joined together to increase the selectivity of binding to their common target through avidity while simultaneously decreasing off-target effects.

In addition to being used for measuring binding between aptamers and target, the RCHT-SELEX methods described herein can be used for measuring binding between different mixtures of any of the molecule classes previously described (e.g., by replacing the aptamer with a molecule that has been DNA barcoded and has a 3' C overhang arm), enabling bi-directional multi-way competitive measurements of any of the combinations of molecule classes including, without limitation, peptide vs protein, protein-protein, antibody-protein, small molecule-protein, peptide-cell surface marker, antibody-cell surface marker, etc. In some embodiments, both binding molecules (e.g., the binder and the target) can be drawn from a mixture of molecules from any of the above classes, allowing for measurement of cross binding in complex competitive environments.

Section B NTAA-SELEX

We have developed a new SELEX method to optimize the selection of high affinity and specific aptamers in a time-efficient manner via an innovative combination of existing and novel techniques:

1) Negative Selection

A common technique to reduce the enrichment of aptamers to unwanted targets (such as magnetic beads, PEG, reagents in binding buffers (such as BSA, etc) is to screen the initial pool of aptamer candidates aptamers that bind to the selection components used in the SELEX experiments, in our case, streptavidin beads in SELEX buffer (1×PBS, 0.025% Tween-20, 0.1 mg/mL BSA, 1 mM $MgCl_2$). Aptamers that express binding affinity to selection components are non-specific to the targets and are removed from the candidate pool so that only aptamers that do not bind the selection components would be part of the aptamer candidate pool assayed against targets. A single or multiple rounds of negative selection can take place for a library before initiating SELEX rounds. When choosing a target library size (e.g., $10^{14}$ molecules), a larger library needs to be used for negative selection to ensure that the supernatant includes enough molecules for the downstream SELEX experiments.

2) Peptide Backbone Switch

During each parallel selection, for each replicate of the target of interest, a peptide switch can be performed. Specifically, a "switch" target can be developed with a different backbone sequence, e.g., the amino acid sequences of the peptide target differs except for, e.g., the two amino acids at the N-terminus. By switching between at least two different backbones in rotating rounds, the chances of enriching aptamers that bound to anything that was not the dipeptide of interest were lowered.

3) Multiple Parallel Target Screening

In this technique, parallel selections of DNA aptamers for closely related, as well as unrelated targets can be used. The following metrics can be used across targets: 1) counts of each aptamer in each round, as determined by NGS sequencing and 2) the enrichment of each aptamer from round-to-round and 3) enrichment from the first round sequenced to the last round sequenced. By comparing these metrics across different target selections, one is able to determine what the binding signal looks like for a 'real binder', which is binding to a known target which has previously been shown to be 'aptagenic', and also what the binding signal looks like for a 'non-specific binder', which is non specifically binding to the surface on which the targets are immobilized (e.g., beads). These metrics across the parallel targets screening allows tracking the specificity of the aptamers and prevent unknown contamination effects.

4) Replicate Target Screening

In this technique, parallel selections of DNA aptamers can be used for the same target. Unique random DNA libraries can be used to perform SELEX for the same target either 2 or 3 times, at the same time. This allows the experimentalist to have confidence in the previously described metrics for each aptamer, especially if they fall within the same order of magnitude. In addition, it allows the experimenter to see if there are outliers within the aptamer pools. For example, if one random library has significantly lower enrichment than the other random library when looking for the final aptamer candidate, the experimentalist could choose to work with only the lead aptamer candidates from the library that showed higher enrichment.

5) Counter SELEX

Counter SELEX is a technique similar to negative selection, except that the aptamer library is incubated with molecules similar to the desired target on beads, the beads are pulled down with a magnet and the resulting supernatant contains the library of aptamers that do not bind to the similar targets. The supernatant then can be used for downstream experiments to assist with the enrichment of N-terminal binders. A counter SELEX can be conducted in parallel or sequentially to a negative selection at the start of an experiment, and can be run in single or multiple cycles. Counter SELEX can be run in between conventional SELEX rounds, or after the final SELEX round to enhance the signal of N-terminal aptamer binders in the library pool.

Many types of molecules can be used during counter SELEX. Counter SELEX can be used on targets that are similar in nature to the target but with slight modifications (e.g., to differentiate a post-translationally modified N-terminal amino acid from an unmodified N-terminal amino acid), peptide backbones (or suffices) used during a peptide switch or against a large pool of targets representing the proteome to ensure specific N-terminal aptamer binders towards the unique goal target.

If multiple backbones are used in a peptide switch experiment, then multiple peptide suffices can be used sequentially during a counter SELEX experiment. For instance, if two different backbones are used for a peptide switch, a parallel counter SELEX on a mixture of targets can be run in between SELEX rounds, where the 'target' pool for counter SELEX consisted of one half of one backbone bound to beads and one half of the other backbone bound to beads. Other embodiments could vary stringencies and/or introduce a combination of other molecules, such as random peptide libraries, various backbone designs, backbones with other N-terminal dipeptide suffixes.

6) PCR and Digestion Techniques

PCR Optimization, Threshold PCR, and Digestions of dsDNA techniques can be employed in NTAA-SELEX and are described in SECTION A RCHT-SELEX.

Novel features of the NTAA-SELEX methods described herein include, without limitation:

1) This protocol provides a path to discover aptamer binders to N-terminal amino acids, which can revolutionize approaches to enable high resolution identification of protein sequences and high throughput protein sequencing assays. The stability and flexibility of nucleic acids make aptamers a versatile tool for multiple approaches to protein sequencing and quantification technologies, including imaging and DNA barcoding methods described herein;
2) Multiple parallel SELEX experiments can allow for scaling aptamer discovery and the removal of aptamers that are non-specific binders to multiple peptide targets;
3) Sequencing of counter SELEX experiments can prompt the discovery of N-terminal binders and the removal of aptamer binders to other regions along the target;
4) Control targets can be run in each SELEX experiment to allow for the evaluation of inter-experiment comparison metrics;
5) Peptide Backbone Switch allows for the detection of aptamers that are specific to N-terminal amino acid(s) of a larger peptide, or, if desired, generation of aptamers to amino acid sequences internal to a peptide string or modified amino acids.

Protein or Peptide Sequencing (PROSEQ)

The PROSEQ methods described herein use barcoded amino acid-specific aptamers to convert a protein sequence into a readable DNA signal on a next generation sequencing (NGS) platform. Mass spectrometry (MS) is one of the common tools in identification and quantification of proteins, however the technology lacks the ability to cover the wide dynamic range necessary to detect lowly expressed proteins in complex samples (Schiess, Wollscheid, & Aebersold, 2008). Other existing specific protein quantification assays include antibody or aptamer binding assays where detectable antibodies, aptamers, or other small molecule binders bind specifically to known proteins, thus incapable of de novo sequencing or measuring proteins for which no specific binder has been found. The PROSEQ protein sequencing methods described herein can be used on small sample inputs (including single cells or small blood volumes) to identify the entire proteome, including low-expression proteins and single amino acid mutations to better understand diseases caused by aberrant or degenerative proteins. Additionally, the PROSEQ methods described herein allow for the ability to sequence heterogeneous samples or multiple samples in parallel since proteins can be barcoded with unique DNA tags, which can be incorporated into the DNA sequences that encode protein sequence information. Further, the methods described herein enable significantly deeper sequencing than existing methods such as mass spectrometry, since DNA sequences are derived from single peptides, amplified and read off from a sequencer (DR $10^0$-$10^9$), which is not subject to the same dynamic range constraints as mass spectrometry (DR>$10^5$) (Yates, Ruse, & Nakorchevsky, 2009). Additionally, samples can be processed to remove reads associated with high abundance proteins within a sample by 1) removing highly abundant proteins in the original input pool into PROSEQ or 2) separating out the DNA barcodes associated with highly abundant proteins to increase NGS read count of DNA sequences associated with low abundance proteins.

The PROSEQ methods described herein can be used in a clinical setting for quantifying protein expression levels or identifying novel protein fusions or mutations that are linked to disease from individual patient samples to assist with patient diagnosis and disease onset. In addition, the methods described herein can be broadly used for research areas of molecular and cellular biology, and protein engineering such as: sequencing proteins, discovering novel biomarkers, analyzing entire proteomes or metaproteomes, evaluating mechanisms associated with protein abundance and more.

1) Aptamers Provide the Capability to Perform De Novo Sequencing.

The methods described herein rely on a library of aptamers specific for unique combinations of one or two N-terminal amino acids, where each residue or residue pair has at least one or multiple possible aptamer binders. The ssDNA aptamers are designed to contain a 5' phosphate for ligation, a unique DNA barcode (which indicates the identity of the particular aptamer and the corresponding cycle number), a spacer/consensus region for subsequent barcode ligations (e.g., ligation consensus sequence), a restriction enzyme site with spacer, and an amino-acid recognition sequence (e.g., a single stranded DNA aptamer sequence). See, for example, FIG. 13. These aptamers may be incubated with the peptide targets either with or without a complementary DNA strand that covers some or all of the barcode sequence, the ligation consensus sequence, and the restriction enzyme site with spacer. In the case where these regions are uncovered, DNA complementary to the ligation and restriction sites can be hybridized after incubation to facilitate ligation and restriction, respectively.

The aptamers described herein can be used to sequence proteins or peptides in any of the following ways:

(A) Peptide Fragments from Proteins Processed in Solution or on a Solid Substrate Proteins from a sample (e.g., a blood sample, cell lysate or a single cell) can be obtained, denatured, conjugated to oligos and digested into peptide fragments. It would be understood that there are multiple methods of obtaining and digesting proteins, and conjugating peptide fragments to oligos prior to the sequencing steps. One such strategy includes denaturing proteins using a mild surfactant, and reducing and alkylating the denatured proteins to protect cysteine side chains. For example, amine groups on the side chain of lysine amino acids react with aldehyde-modified oligonucleotide through reductive amination reaction using sodium cyanoborohydride. The protein can be digested with Lys-C, which cleaves proteins on the C-terminal side of lysine. By using this approach, each digested peptide has a lysine residue that is attached to the oligonucleotide tail. Reductive amination reaction also can happen between the side chain of lysines and alkynes with an aldehyde functional group, preparing it for click chemistry reaction with azide modified DNA oligos. In another approach, side chains of the proteins can be protected, modified with an oligo or click chemistry linker, and then cleaved into peptide fragments using, for example, a conventional trypsin approach to cut at lysines and arginines, and/or other fragmentation enzymes that cleave at random amino acid sites (FIG. 13, step 2) or they can be processed in solution (see modifications below). At this point, the DNA-conjugated protein fragments can be ligated to DNA oligos on the surface of the sequencing substrate, where they will remain tethered throughout the DNA barcoding process and removed prior to DNA sequencing.

Aptamers can be taken directly from a SELEX experiment and applied to a BCS assay via the creation of a BCS Compatible aptamer pool, where one of the SELEX primer regions is converted into a BCS handle. The aptamer region of the binder will be sequenced and considered the 'barcode' of the binder. To generate the BCS Compatible aptamer pool, prior to incubating the peptide targets with the aptamers, a single stranded aptamer pool is incubated with bridge oligos that are partially complementary to the aptamer tail and partially complementary to the ligation region on the barcode sequence on the barcode foundation (BF) (single stranded overhang shown in FIG. 14) to (a) facilitate binding of the aptamer tail to the barcode sequence and (b) block the ssDNA region of the aptamer that is not involved in target binding from affecting proper aptamer folding. A DNA-barcoded library of BCS Compatible aptamers hybridized to bridges can be flowed across the peptides and incubated, allowing for the appropriate aptamers to bind specifically to the N-terminal amino acid residues (FIG. 13, step 3).

Figure 13:
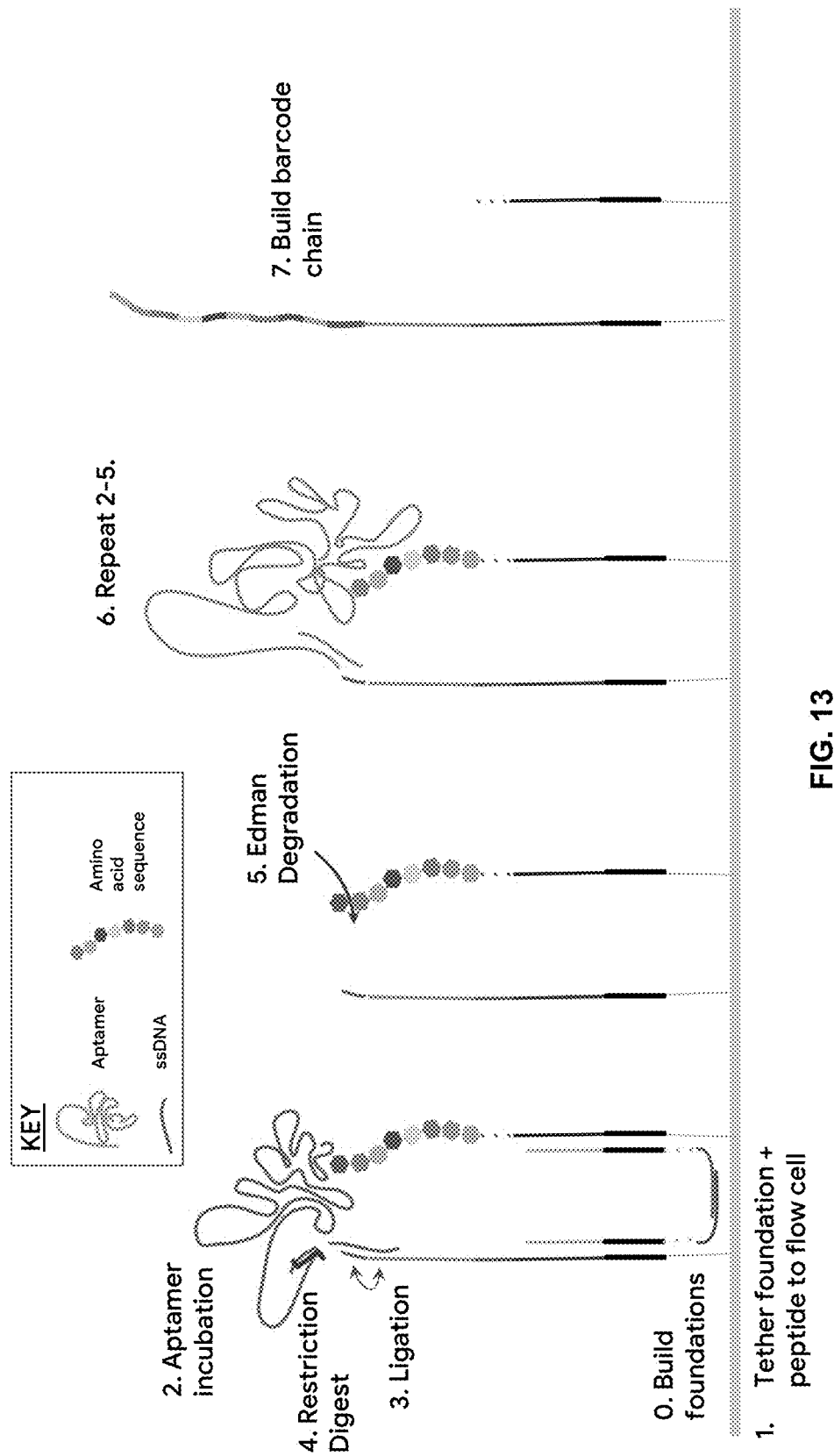
FIG. 13 is a schematic showing the peptide sequencing methods described herein. Step 0 includes building the foundation consisting of a 5' phosphorylated barcode foundation, a forward and reverse colocalization linker, and a protein or peptide target (PT) tagged with a C-terminal oligonucleotide sequence oriented with the 3' end connected to the protein or peptide and a free, phosphorylated 5' end; Step 1 includes the tethering of the peptide-foundation complex on a solid substrate; Step 2 includes incubating the bound proteins or peptides with a barcoded aptamer library under conditions that allow the appropriate aptamer to bind specifically to the appropriate N-terminal amino acid; Step 3 includes ligating the aptamer tail to a second oligonucleotide bound to the substrate; and Step 4 includes cleaving off the aptamer, leaving the DNA barcode associated with that particular amino acid bound to the second oligonucleotide. Upon removal of the N-terminal amino acid from the protein or peptide using Edman degradation and/or aminopeptidases, Steps 2-5 are repeated, generating a chain of DNA barcodes that can be used to identify each subsequent N-terminal amino acid.

After aptamer binding, unbound aptamers are washed away and the tail of the bound aptamer can be ligated to a second glass-immobilized DNA oligonucleotide colocalized with the peptide (FIG. 13, step 4). A restriction enzyme site included distal to the aptamer barcode can then be used to cleave the remainder of the aptamer, leaving the DNA barcode attached to the nearby oligonucleotide (FIG. 13, step 5). Then, Edman degradation and/or aminopeptidases can be used to remove the N-terminal amino acid from the fixed peptide. In Edman degradation, once a new N-terminal amino acid is exposed, another aptamer pool, with unique DNA barcodes indicating target recognition sequence and cycle number, can be introduced and another cycle of DNA barcode ligation can occur. After repeating this series of steps a plurality of times, a chain of DNA barcodes can be built that indicates the order of aptamer binding for a peptide that can be read using conventional NGS techniques. Using this information, the amino acid sequences of bound peptides can be obtained. In the case of aminopeptidases, more than one N-terminal acid amino acid may be cleaved at a time in a less controllable manner, which, although is not conducive for de novo sequencing, may reveal insight for non de novo sequencing methodologies.

(B) Full Length Proteins Processed in Solution

For full length proteins the protocol is similar to the above, but with some important differences. The following steps can be conducted: (a) lyse the cells (if the proteins are obtained from cells), isolate or purify, denature and protect the proteins, (b) protect reactive side chains of amino acid residues (such as thiol, carboxyl and amine groups), (c) conjugate a ssDNA oligonucleotide to the C-terminus of the protein, where the ssDNA oligonucleotide contains a primer region, a unique barcode and an initial ligation region, (d) deprotect all side chain protecting groups, (e) incubate proteins with aptamer pools, where the aptamers can contain a tail that includes a 5' phosphate for ligation, a unique DNA barcode (which provides information regarding aptamer binding sequence plus sequencing round), a spacer/consensus region for subsequent barcode ligations (e.g., ligation consensus sequence), a restriction enzyme site with spacer, and an N-terminal amino-acid recognition sequence (e.g., the single stranded DNA aptamer sequence), (f) ligate the bound aptamer to the DNA tail of the protein, (g) pull down the protein/aptamer complexes with a biotinylated reagent that has complementarity to the primer region of the protein/DNA conjugate molecule, (h) wash off unbound aptamer pool, (i) cleave the binding region of the aptamer off, leaving its DNA barcode attached to the protein's DNA tail, (j) cleave off the N-terminal amino acid, (k) denature the protein from its biotinylated oligo, (l) collect the supernatant of DNA barcoded proteins, (m) repeat steps (c)-(l) until the entire protein has been converted into a DNA strand, followed by PCR amplifying and sequencing the DNA barcode. If binders stay bound during the time and disruption during the protein-aptamer complex pull-down, then step (g) can also be performed prior to ligating the bound aptamer to the DNA tail of the protein [bind, pull-down, wash, ligate] (step f). It would also be understood that the biotinylated reagent that has complementarity to the primer region of the protein/DNA conjugate molecule (from step g) can be added during aptamer incubation (step e) to prevent aptamers from binding to DNA region of the peptide target instead of the N-terminal prefix.

Barcodes, including the overhangs, can be about 8 to about 26 nucleotides (nt) in length (e.g., about 9, 10, 12, 15, 16, 18, 20, 21, 22, 23, 24, or 26 nt in length). NGS technologies currently are optimized for short reads, or a maximum of about 300-600 cycles. For many proteins, long sequencing experiments (e.g., by PacBio) can be performed or the DNA strands can be fragmented into smaller regions and realigned post-sequencing.

(C) Protein Complexes Processed in Solution Followed by a Solid Substrate Step

For protein complexes, the proteins within protein complexes can be tagged with DNA oligonucleotides via an amino acid side chain and proximal side chains can be ligated together before the proteins are denatured, before proceeding with the protocol outlined above in the absence of peptide fragmentation (e.g., under section (B)). The protocol can be optimized such that only proteins in close proximity (e.g., bound complexes) are tagged with oligonucleotides that can be ligated to each other. The protein complexes can be pulled down and attached to a solid substrate, which can have DNA adaptors specifically placed so that protein complexes can be processed locally. The DNA adaptors on the chip can have a unique DNA starting barcode, which, when isolated and sequenced, can reveal insight into what the neighboring sequenced peptides fragments are, and therefore, of the protein complexes.

The PROSEQ methods described herein do not rely on previous knowledge of proteins or protein complexes (as is required when using, for example, mass spectroscopy), and provide an avenue for de novo sequencing. Once the protein or peptide molecule(s) have been converted into a DNA molecule, conventional tools such as PCR amplification, biotin pull-down assays and/or digestion can be used to amplify, enhance and modify the sequences to allow for pooling of many samples or to ascertain lowly expressed molecules within a sample. There are also many novel biological insights that can be obtained with the non-de novo applications of PROSEQ, such as high resolution protein quantification, that are not currently possible with conventional protein sequencing technologies.

Figure 15A:
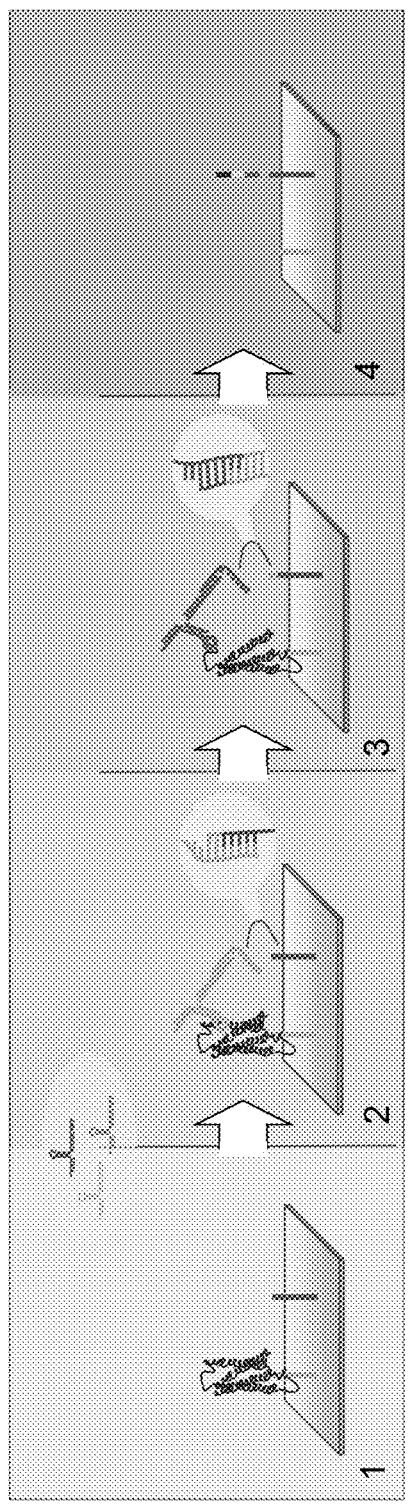
FIG. 15A is a schematic showing the peptide or protein sequencing methods described herein, where the peptide or protein sequence is determined based on a DNA sequence. Step 1 in this embodiment includes attaching the C-terminal end of a protein or peptide to a DNA primer oligonucleotide bound to a substrate; Step 2 includes incubating the bound proteins or peptides with a barcoded aptamer library under conditions that allow the appropriate aptamer to bind specifically to the appropriate N-terminal amino acid; Step 3 includes ligating the aptamer tail to a second oligonucleotide bound to the substrate; and Step 4 includes cleaving off the aptamer, leaving the DNA barcode associated with that particular amino acid bound to the second oligonucleotide. Upon removal of the N-terminal amino acid from the protein or peptide using Edman degradation and/or aminopeptidases, Steps 1-4 are repeated, generating a chain of DNA barcodes that can be used to identify each subsequent N-terminal amino acid.
Figure 15B:
FIG. 15B is a schematic showing an example of the correlation between individual amino acids and the corresponding aptamer barcodes.

FIG. 15A is another schematic showing an example of the aptamer-based peptide sequencing method described herein, with conjugating the C-terminal end of the peptides to an amine modified oligonucleotide bound to a substrate or using other strategies such as click chemistry or SMCC linker (succinimidyl 4-(N-maleimidomethyl)cyclohexane-1-carboxylate) to covalently bind the peptide to oligonucleotide (1), incubating the bound peptides with the DNA barcoded aptamer library (2), ligating aptamers that bound to a peptide to a second oligonucleotide immobilized on the solid substrate (3), and cleavage of the aptamer, leaving the DNA barcode attached to the second oligonucleotide (4). FIG. 15B is a schematic showing representative aptamers to different amino acids and the corresponding aptamer barcode, the sequence of which identifies the specific amino acid at that position.

2) The Protein Sequencing Methods Described Herein Overcome the Processivity Limits of Edman Degradation The methods described herein overcome the processivity limits of Edman degradation. For example, liquid chromatography (LC) typically is used to identify terminal amino acids after cleavage by Edman degradation. A putative drawback in standard Edman degradation is that, physically, there exists a maximum cycle number for accurate degradation and detection of N-terminal amino acids HO cycles). Since the present methods are not measuring the amino acid that is cleaved, limitations of detection of the cleaved amino acid is not an obstacle. Additionally, any processivity limitation in the PROSEQ methods described herein can be overcome by rotating between the use of Edman degradation and aminopeptidases (e.g., trypsin and pepsin) to cleave terminal amino acids. After approximately 30 cycles, for example, the methods described herein can use an exopeptidase to cleave the peptide at a specific amino acid site, which allows the sequencing to begin again from a new region of the peptide.

3) The Protein Sequencing Methods Described Herein Allow for Sequencing of a Heterogeneous Protein Pool One of the important features of the PROSEQ methods described herein is the ability to sequence large pools of proteins, where one or more of the proteins of interest (e.g., a target protein) are expressed at low levels or very low levels (e.g., a protein that is present in one part per 10 billion; potentially even lower with the "Sup-Diff" methods described herein). This is especially useful when processing samples such as plasma, which: (1) are easy to obtain from patients, (b) allow for longitudinal studies, and (c) can give insight to difficult to study diseases such as neurodegenerative diseases, due to the presence of biomarkers in the bloodstream. In plasma, 13 proteins plus albumin compose 96% of the protein sample, and some of the most interesting molecules, such as tissue leakage products and cytokines, make up the last 4% of the sample and found to be well under the instrument detection resolution limit for MS (Schiess, Wollscheid, & Aebersold, 2008). Thus, it can be extremely difficult to identify biomarkers or new proteins on plasma samples with MS. Unlike HPLC and MS, identifying amino acids based on aptamer binding is not limited to a detection limit of high individual protein concentrations within a sample. Since the final product actually being sequenced is DNA and not protein, there exist well developed tools to amplify, anneal, and pull down specific DNA populations of interest. After the DNA barcode chain is formed, the DNA sequencer platform can clonally amplify the sequences (e.g., using bridge amplification). Thousands of clusters of each individual DNA sequence produces a larger readable signal than its initial input signal from a lowly expressed protein, bypassing single molecule techniques. This ability to sequence large, non-uniform pools allows thousands of antigens spanning entire organism proteomes to be sequenced.

For samples that have a large dynamic range, a method referred to as "sup-diff" can be used to remove DNA barcode constructs of highly expressed proteins, leaving an enhanced ratio of DNA barcode constructs of lowly expressed peptide or protein clusters remaining in the pool of oligonucleotides to be sequenced. For example, there are two methods for enhancing the ratio of desired or lowly expressed peptides: an a priori and a non a priori method. The general strategy is to develop an ssDNA bait pool containing biotinylated RNA sequences complementary to certain sequences in the initial diverse pool of ssDNA (Diatchenko et al., 1996) (Gnirke et al., 2009). Said RNA bait pool is used to capture ssDNA targets via in solution hybridization and subsequent pulldown on streptavidin-coated magnetic beads.

Figure 16:
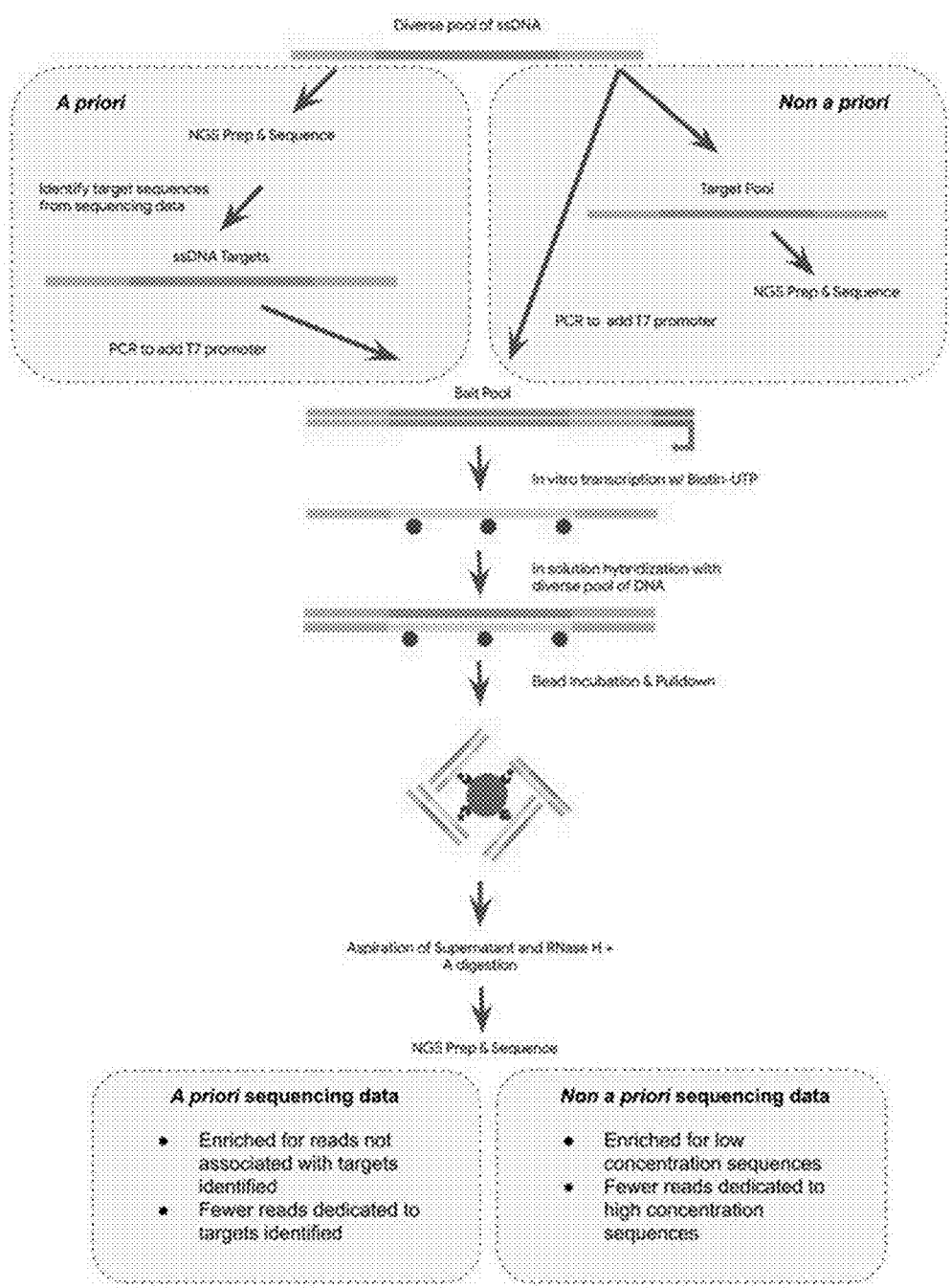
FIG. 16 is a schematic showing an a priori and a non a priori sup-diff strategy to pull out DNA constructs associated with known targets, or unknown but high concentration DNA constructs.

The chief difference between the a priori method and the non a priori method is that the a priori method pulls out only known sequences, while the non a priori method pulls out high abundance sequences in a pool of unknown distribution and constitution. In the a priori method, the diverse pool of ssDNA is first sequenced and then the user can design baits specific to what the user wants to pull out of the pool, which could include very high concentration sequences that might be contaminants. The a priori method enriches for sequences that were not pulled down by the designed baits, thus reducing NGS sequencing reads dedicated to the targets that were originally desired to be pulled out of the pool. In the non a priori method, the initial diverse pool of ssDNA is directly used to generate the RNA bait pool. The RNA bait pool could have the same fractionational distribution as the original target pool, or a distribution slightly skewed toward the initial high abundance sequences. By the assumption that the higher abundance target sequences will be more likely to find their RNA bait partners under optimized conditions of time, temperature, and ratio of overall bait to target, when the RNA baits are hybridized with the initial diverse pool of ssDNA, the high concentration sequences are more likely to be pulled out. See, for example, FIG. 16.

4) The Protein Sequencing Methods Described Herein Allows for Sequencing the DNA Barcode Using a Range of DNA Sequencing Technologies The methods described herein for sequencing proteins can be performed in conjunction with any existing DNA sequencing technology. With custom-built flow cells that have DNA printed on the glass in a specified manner and an automated fluidics system, the barcodes can be built as described in the preceding sections without the need for reprogramming or repurposing an existing DNA sequencing platform. These DNA barcodes that represent the protein/peptide sequence may then be sequenced on any existing DNA sequencing platform or technology.

5.) the Protein Sequencing Methods Described Herein Include Strategies to Ensure Robust Protein and DNA Sequencing Capabilities Despite the Harsh Chemistries of Edman Degradation The ProSeq methods described herein use barcoded amino acid-specific aptamers to convert a protein sequence into a readable DNA signal on a next generation sequencing (NGS) platform. The methods described herein overcomes the distortion of the protein sequencing platform components caused by Edman degradation, which prevents the clustering of DNA barcode constructs and, therefore, sequencing directly on the same chip. Trifluoroacetic acid (TFA) and the pH oscillations that occur during Edman degradation result in two main issues: (1) the loss of DNA cluster generation through the removal or modification of the P5 and P7 DNA adaptors on the chip, and (2) modifications of the constructed DNA barcodes resulting in sequence-information and amplification-capability loss.

(A) Off-Chip Sequencing of DNA Barcode

After building the DNA barcode construct containing a chain of DNA barcodes indicating the order of aptamer binding for a peptide, the constructs are amplified on the chip, or cleaved off the chip and amplified in solution. Amplification methods used include, without limitation, PCR, loop mediated isothermal amplification, nucleic acid sequence based amplification, strand displacement amplification, and multiple displacement amplification. Additionally, the original DNA barcode constructs could be transcribed on the chip into large amounts of RNA constructs, which could then be converted into a cDNA library consisting of many copies of the original DNA barcode. The amplification products, copies of the original DNA barcode constructs, can be removed from the microfluidic chamber and sequenced using standard DNA sequencing methods including, without limitation, Sanger sequencing, NGS, ion semiconductor sequencing, SOLiD technology, cPAS, etc. Numbers of reads are normalized to the number of PCR cycles used to estimate the quantity of each protein or peptide sequenced from the initial sample.

(B) XNA or Modified DNA/RNA Adaptors, Foundations and Barcodes

The methods described herein are a single-chip strategy to overcome the degradation of DNA components on the BCS platform by utilizing XNAs or modified DNA/RNAs that are (a) resistant to transformations due to Edman degradation or highly acidic conditions, (b) are able to be made into chimeras with conventional DNA nucleotides, and (c) compatible with existing polymerases that can amplify these non-natural nucleic acids or convert modified sequences into conventional DNA bps. Such modified nucleic acids may include a modification to the 2' carbon of the ribose sugar that enhances its hydrolytic stability or to the purine base itself (Watt, et al. 2009). Examples include, but are not limited to, 2'-O-methylated RNA, 2'-fluoro deoxyadenosine, 7-deaza-2'-deoxyadenosine, and 7-deaza-8-aza-deoxyguanosine.

Addition of XNA or modified DNA/RNA adaptors to degraded P7s: the methods herein can utilize the degraded P7 adaptors available on the chip as bases for custom XNA or modified DNA/RNA adaptors. After subjecting the P7 and P5 adaptors to acidic conditions, the P5 adaptors are at least partially removed and the P7s are degraded. Two methods of adding new adaptors for ligation and barcode generation handles, post-barcode cluster generation, are:

Approach 1: several cycles of Edman degradation can be conducted to remove P5 and depurinate P7 and XNA or modified DNA/RNA adaptor can be ligated to the remainder region of P7. A method of XNA adaptor ligation is to ligate an XNA or modified DNA/RNA adaptor with a phosphorylated 5' end to the 3' end of the P7. If the modified nucleic acid analogs lower the ligase efficiency, the adaptor sequence may be a chimeric XNA or modified DNA/RNA molecule with one or more standard cytosine or thymine nucleotides at its 5' end.

Approach 2: Conduct several cycles of Edman degradation to remove P5 and depurinate P7 and use click-chemistry to attach an XNA or modified DNA/RNA adaptor to the remainder region of P7. Another strategy to add an XNA adaptor is to chemically attach an XNA or modified DNA/RNA adaptor on P7s by ligating on the P7's 3' end an oligo linker with a reactive group at its 3' end. Chemistry reaction can attach a functional XNA or modified DNA/RNA adaptor to P7, optionally containing a cleavage site, with the corresponding reactive group at its 5' end to the oligo linker. Examples of reactive group pairs include, but are not limited to, NHS ester with amine (azide reaction), azide with alkyne (triazole reaction), maleimide with thiol (thioether reaction), and tetrazine with alkene. The P7 and linker can be blocked from unwanted annealing with an oligo that is partially complementary to both P7 and the extendor oligo during aptamer incubation.

XNA or modified DNA/RNA Foundations and Barcodes: the methods herein foundation pieces, binding regions of aptamers, BCS cassette components, aptamer barcode regions, or combinations thereof can comprise of XNAs or modified DNA/RNAs.

The Illumina sequencing protocol concludes sequencing runs once it no longer detects P5 adaptors, so additional steps may be needed to prevent premature sequencing cessation in embodiments wherein P5s are removed from the sequencing platform. These steps could include, individually or combined:

Enzymatic or chemical addition of multiple P5s to the chip after final round of Edman degradation Adapt sequencing instrumentation protocol code to continue sequencing run in the absence of P5

Enzymatically or chemically attach a custom primer sequence into the cleavage sites of the altered P7 strands and adapt sequencing protocol code to detect the custom primer sequence rather than P5 to determine whether to terminate sequencing run.

Figure 14A:
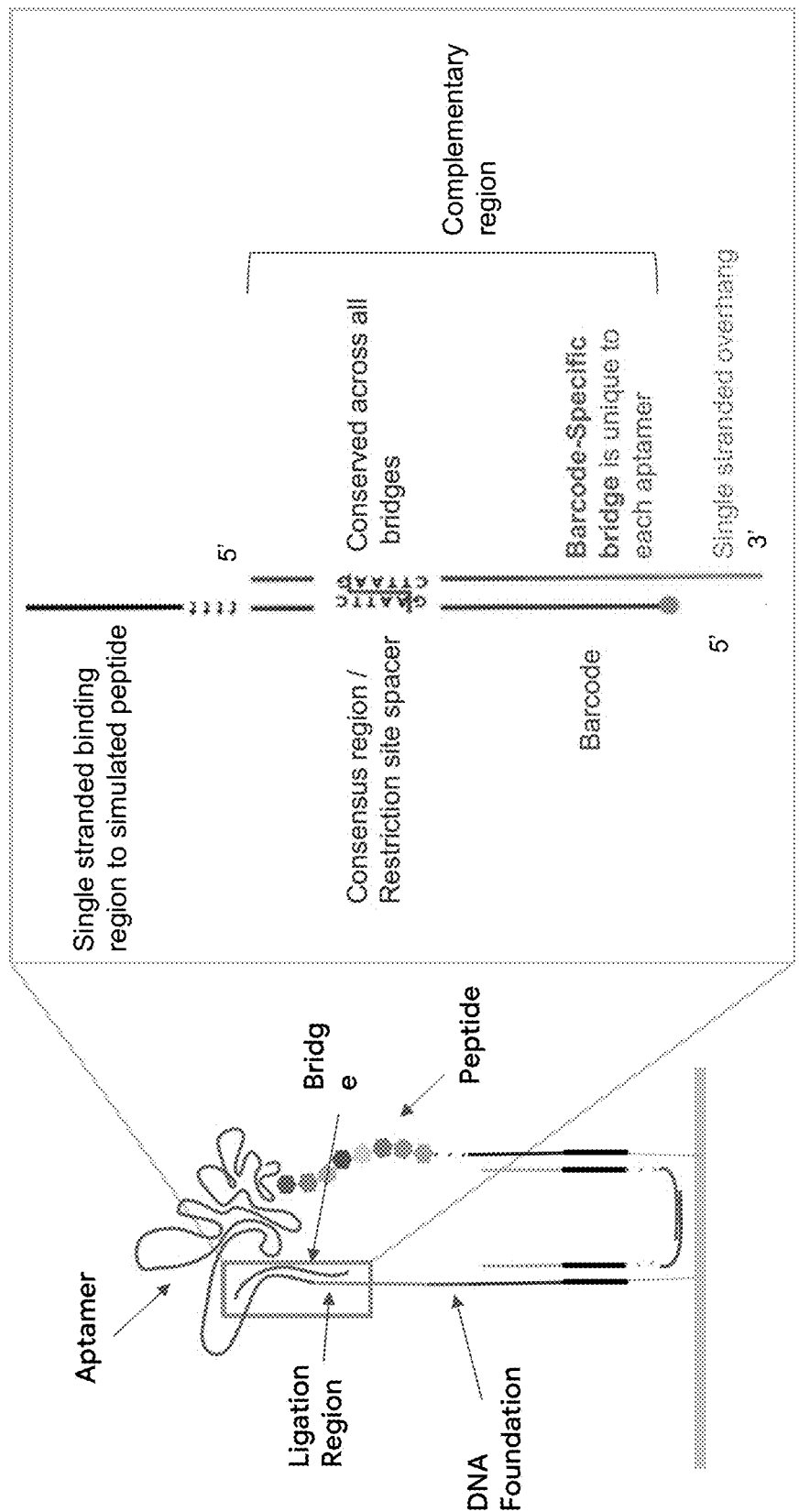
FIGS. 14A and 14B are schematics showing the construct of the aptamer tail and bridge oligo.
Figure 14B:
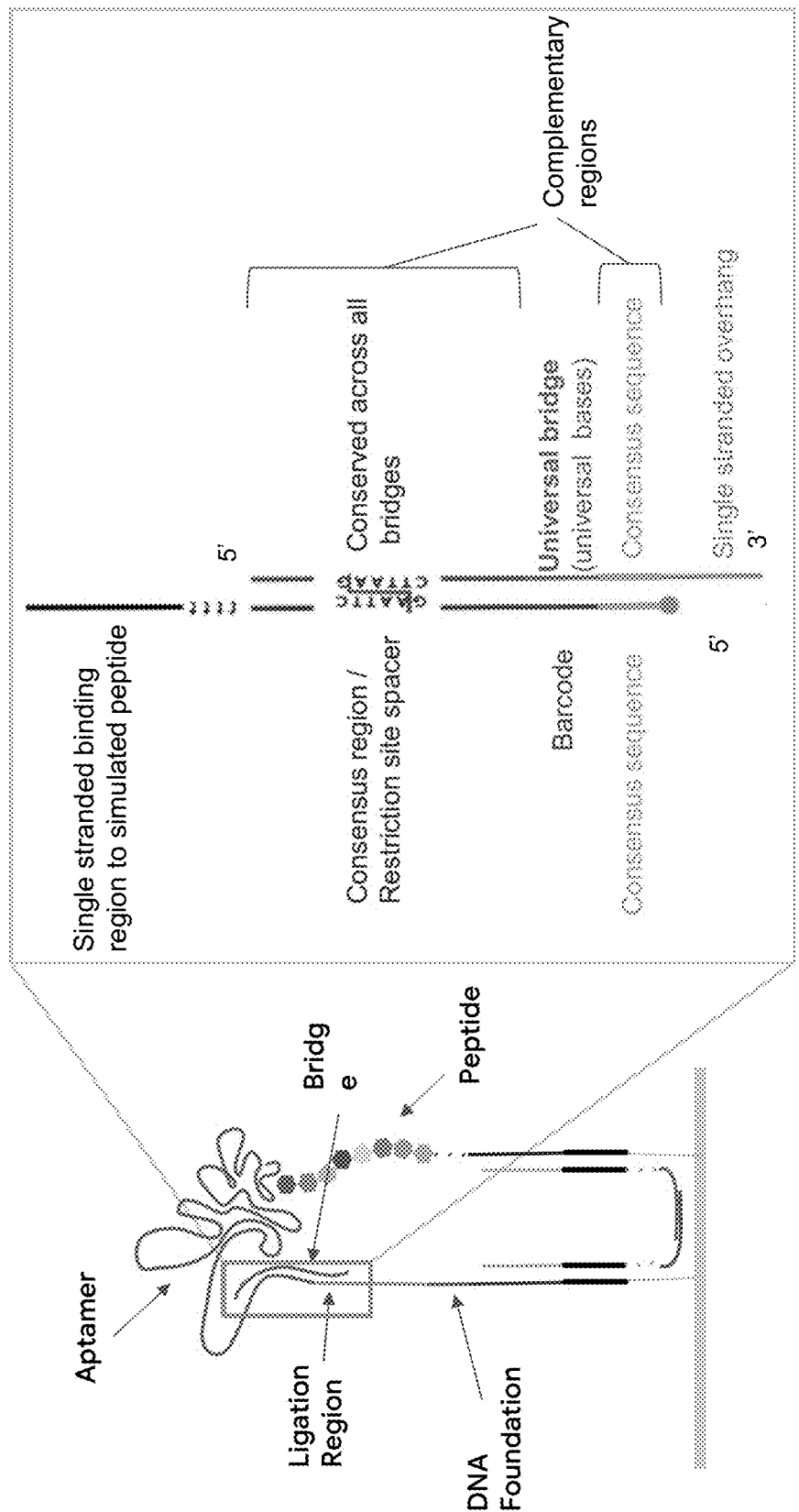
Figure 17:
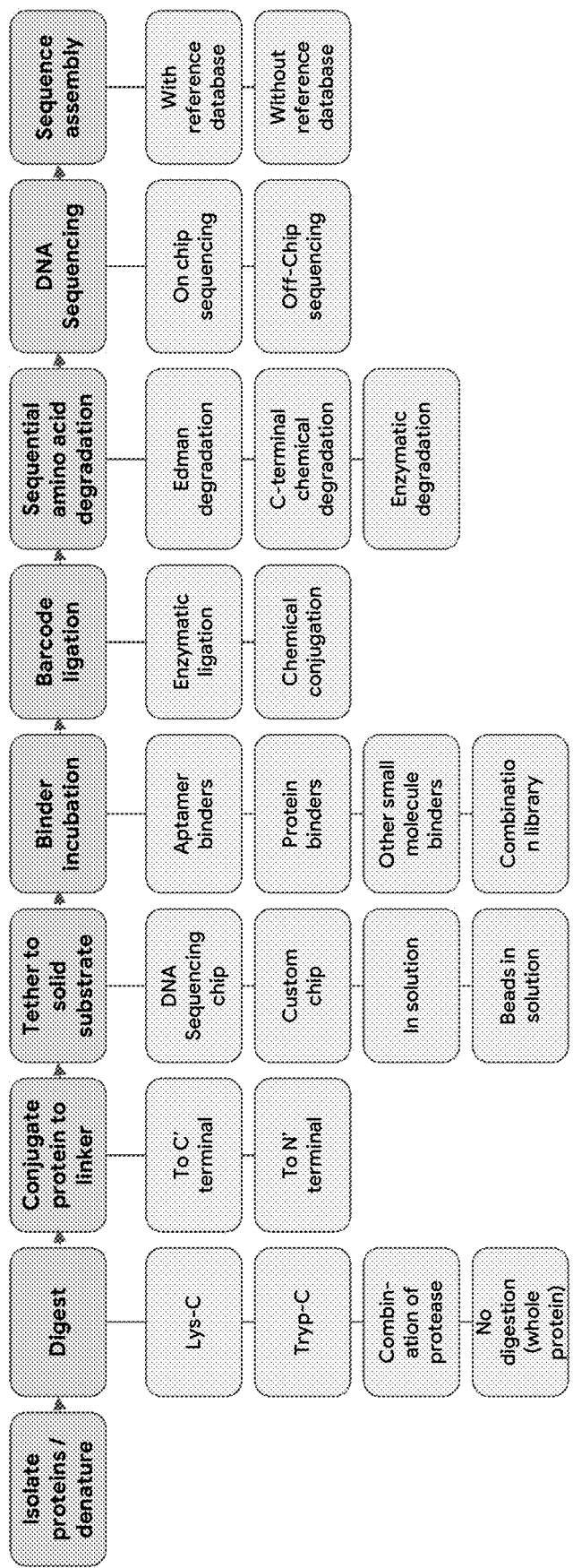
FIG. 17 shows examples of variations of steps within the PROSEQ platform.
Figure 18:
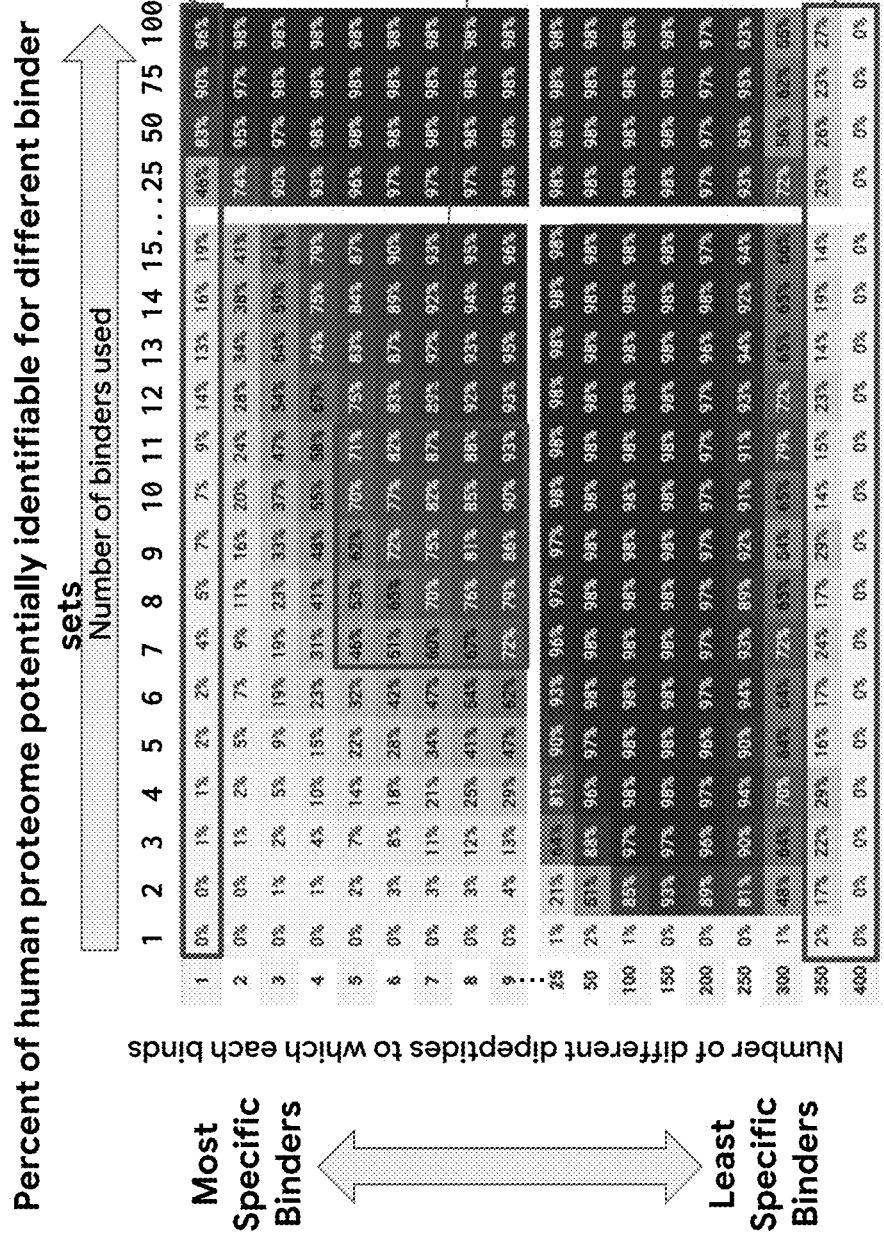
FIG. 18. is a heatmap showing the estimated percentage of human proteome potentially identifiable for each binder library with up to 100 binders that each bind to up to 400 different dipeptides on the ProSeq platform wherein proteins are digested at each lysine, resulting in peptides of 12mer or less. Details of simulation to get percent proteome coverage for hypothetical binder sets are as follows: (a) proteins are digested by LysC into fragments, (b) a protein is identified when one of its fragments has a matching barcode that is distinct among the proteome, then one of its fragments is uniquely identified, (c) the set of dipeptide (pair of amino acids) that a binder has affinity for is randomly chosen from the 400 possible, (d) 20 sets of binders is randomly chosen, (e) given the binder set and the dipeptides each binder has affinity for, the barcode read for each protein fragment is determined and the number of uniquely identified proteins is determined, (f) 12 cycles of Edman degradation, binding, and barcoding are performed on each fragment. The simulation does not model noise (binders failing to bind when they should or binding where they should not). In the real system some noise will be mitigated by the redundancy in dipeptide reads and by reading multiple copies of the same protein. Additionally, only 20 possible sets were evaluated to obtain a percentage match, so a smoother curve would be expected for binder sets of less specificity.

6) Exemplary Variations to the Protein Sequencing Methods Described Herein Include, without Limitation (FIG. 17):

multiple aptamer binding rounds: in some instances (e.g., if issues with aptamer specificity binding exist), several rounds of aptamer binding/DNA barcoding/aptamer denaturing can be performed before proceeding on to degrading the N-terminal amino acid for error correction. The additional data collection will allow for downstream computational analysis to reduce the noise for each individual measurement.

aptamers to two amino acids: in some instances (e.g., if aptamers to single amino acids do not have high enough affinity or are not specific enough for the methods), aptamers to two or more sequential amino acids can be generated (FIG. 18). The added benefit of aptamers binding and encoding for two amino acids is that there is improved signal-to-noise since each amino acid (aside from N- and C-terminal) will be read twice.

substrate: this barcode sequencing method also can be performed on glass, or quartz substrates with DNA oligos printed or chemically linked in random or patterned events. Such types of chips can be custom made or purchased; for example, academic labs make chips with clean rooms and DNA spotters, Agilent prints microarrays with known oligo sequences patterned in spots on glass, and Illumina's next generation sequencing chips are glass slides with randomly distributed DNA adaptors to the P5 and P7 sequence binding sites linked to a solid surface. In the case of custom glass slides, or substrates, DNA oligonucleotides can have specialized patterning to reduce off-target ligation noise.

different oligo orientation: the protein sequencing methods described herein orients the DNA barcode sequence such that the 5' end is attached to the DNA adaptors on the chip. With alternative or custom chips, the 3' end of the barcode sequence can be attached to the chip surface instead.

in solution: the need for a solid substrate can be eliminated entirely by ligating DNA barcodes directly to the C-terminus of the peptide. The peptide C-termini initially can contain a short oligonucleotide sequence that allows for ligation between the aptamer end and the peptide tail bridged by, for example, a 5-mer oligonucleotide. Following Edman degradation, subsequent DNA barcodes can be ligated onto the free end of the peptide tail. The resulting barcode sequence then can be PCR amplified and sequenced using standard NGS techniques.

beads in solution: peptides and oligonucleotides can be tethered to beads (either magnetic, glass, glass-covered magnetic bead, or other beads coated in acid-resistant materials), and serial peptide sequencing steps (e.g., aptamer binding, barcode incorporation, and peptide degradation) can be performed by immersion and separation of beads in solution. After the desired number of sequencing cycles, the DNA barcodes that provide the sequence of the peptide can be PCR amplified directly off the beads and sequenced using standard NGS techniques (Hoon, Zhou, Janda, Brenner, & Scolnick, 2011).

different binders: other than aptamers, barcoded-binders such as RNA, peptides, proteins, nanobodies, or other small molecules can be used to recognize amino acids.

different proteases: when processing protein samples, different proteases such as Lys-C as described above, trypsin, or a combination of multiple proteases can be applied. Additionally, a sample can be divided into multiple samples that are treated with multiple proteolysis strategies to build different proteome maps.

single platform versus separation of steps: it is possible for Edman degradation of the peptide and DNA barcode generation to occur off the sequencer platform, or build a complete end-to-end automated single platform. The DNA barcode chain can be fixed and sequenced in a separate step.

bridge design: bridges are oligos that are partially complementary to the aptamer tail with a 3' single stranded overhang, which anneals to the restriction site spacer and barcode (FIG. 14). Bridges can be designed such that they can be (a) a Barcode-Specific bridge wherein the bridge is entirely complementary to the aptamer tail, including barcode region, except for the 3' single stranded overhang region, such that each unique aptamer has a unique bridge associated with it (FIG. 14A), or (b) a Universal bridge wherein the bridge is complementary to the restriction site spacer and consensus sequence only, both of which are conserved across all aptamers and flank the barcode on the aptamer tail, such that all unique aptamers share the same bridge oligo (FIG. 14B). For the Universal bridge, the region that duplexes with the barcode on the aptamer tail can consist of (a) a sequence of universal base analogues, such as 5-nitroindole, 3-nitropyrrole, and 4-nitrobenzimidazol among others, or (b) a gap with no bases such that the Universal bridge consists of two separate oligos that anneal to the regions flanking the barcode.

ligation method: DNA barcodes can be chemically linked rather than enzymatically ligated together.

different readout: instead of using a DNA barcode to identify amino acid binders, one could use fluorescent dyes, beads, nanoparticles, etc. (see, also, the PROSEQ-VIS methods described herein).

sequential amino acid degradation: cleavage of single amino acids in between rounds can be performed either enzymatically or chemically, such as via Edman Degradation.

sequencing directionality: single amino acids can be cleaved from the N-terminal end or C-terminal end (Casagranda and Wilshire, 1994) (Cederlund et al., 2001). Protein sequencing from the N-terminal end is described in detail here. Based on this disclosure, it would be appreciated that similar methods can be applied to protein sequencing from the C-terminal end in conjunction with aptamers that have been designed to specifically recognize and bind to one or more C-terminal amino acids. For C-terminal sequencing, methods to remove the C-terminal amino acid and generate a C-terminal amino acid-shortened protein or peptide (instead of using, for example, Edman degradation to generate a N-terminal amino acid-shortened protein or peptide) are known in the art and include, without limitation, Bergman et al. (2001, Anal. Biochem., 290(1):74-82) and Casagranda and Wilshire (1994, Methods Mol. Biol., 32:335-49) can be used.

Figure 19:
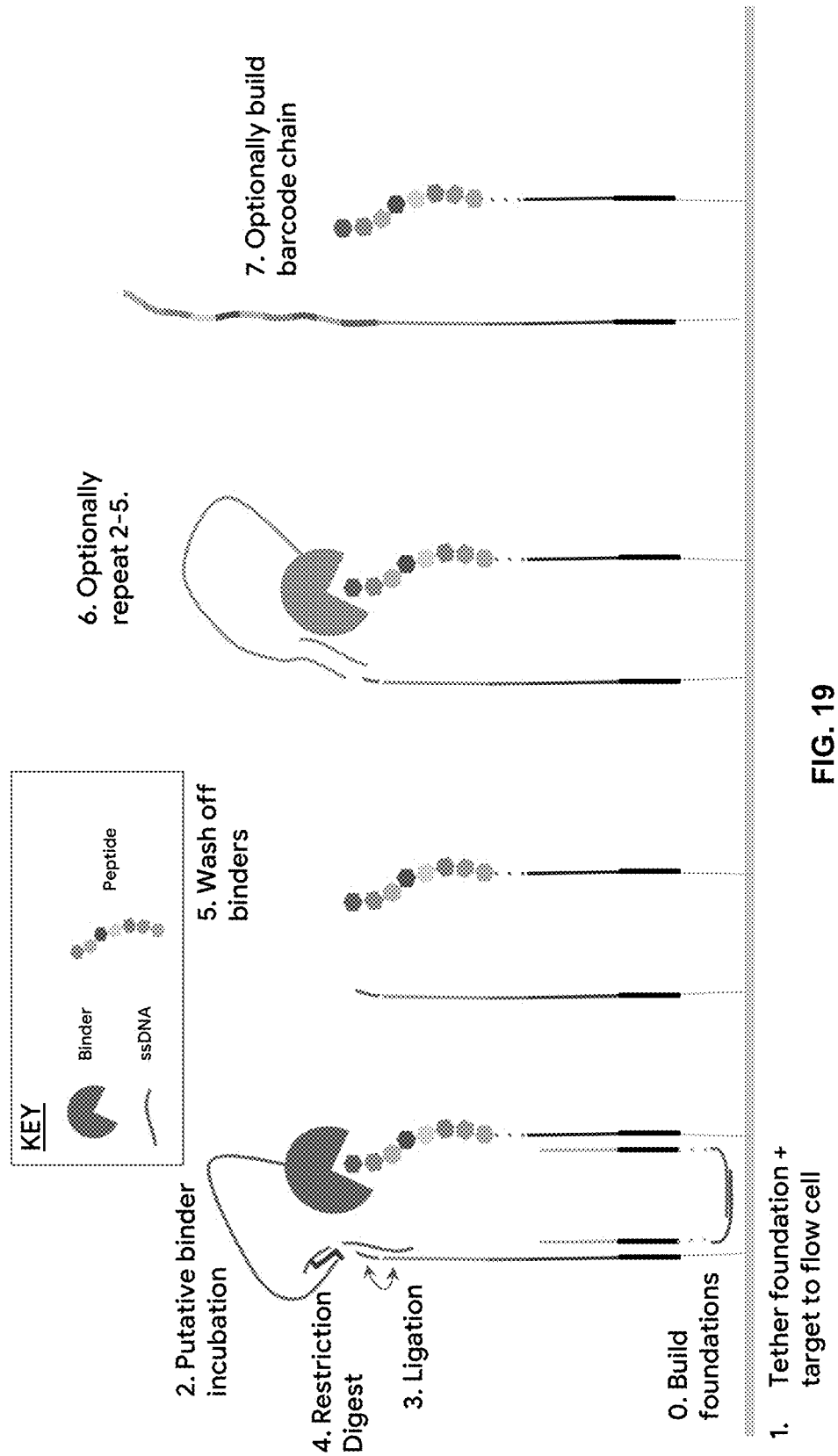
FIG. 19 is a schematic showing the binding validation methods described herein. Step 0 includes building the foundation consisting of a 5' phosphorylated barcode foundation, a forward and reverse colocalization linker, and a target tagged with a C-terminal oligonucleotide sequence oriented with the 3' end connected to the protein or peptide and a free, phosphorylated 5' end; Step 1 includes the tethering of the target-foundation complex on a solid substrate; Step 2 includes incubating the targets with a barcoded putative library under conditions that allow putative binders to targets; Step 3 includes ligating the oligonucleotide barcode tail to a second proximal foundation oligonucleotide barcode bound to the substrate; and Step 4 includes cleaving off the binder barcode tail, leaving the barcode associated with that particular putative binder ligated to the foundation oligonucleotide barcode. Optionally, upon removal of the putative binders from the tethered targets, Steps 2-5 are repeated, generating a chain of DNA barcodes that can be used to identify multiple binding events. Note that binding events are not restricted to N-terminal amino acids or attached target free end, and can occur at any exposed region of the target.

It would be understood that the PROSEQ methods described herein can also serve as large-scale, high-throughput binding specificity assay to characterize interactions in different substrate binding scenarios (BCS BINDING ASSAY). The key advantage of this assay is that it allows the recording of one or more binding events between many putative binders and many targets in one experiment. Once the desired targets are conjugated to co-localization foundations, the foundations can be tethered on a glass substrate, or processed in solution. Then, a diverse DNA-barcoded putative binder library (PBL) is incubated with the desired and unintended targets for incubation, allowing for binding. Each DNA-barcoded putative binder comprises of a binder molecule conjugated to a DNA sequence containing at least a a) restriction site, b) ligation site (e.g., a first ligation site), c) unique DNA barcode indicative of the identity of the putative binder and binding cycle, and d) another ligation site (e.g., a second ligation site). When a putative binder binds a tethered target, its DNA barcode tail is ligated to the proximal, target-barcoded DNA foundation that is colocalized with the target. The ligated barcode is cut with a restriction enzyme, exposing the DNA barcode construct to be ligated to another binder barcode in the next round. After repeating this series of steps on the chip, a chain of DNA barcodes containing information on the identity of the binder and target and order of binding events can be read off with conventional DNA NGS techniques (FIG. 19). Using this information, the probability distribution of a putative binder binding to the desired and unintended targets in various environments can be deduced.

The PRO SEQ methods described herein result in a number of advantages, including, without limitation, the ability to:

produce a probability distribution of binding events in one mixture by interrogating the same targets multiple times;

isolate binding events from unbound binder molecules via washing steps for the solid-state method. The separation of binding and ligation events decreases off-target ligation events;

assay a large library of putative binders in various environments (e.g. in the presence of unintended targets, other targets of interest, etc.). This is especially of importance to binders identified through a selection process wherein the binders were selected in isolation of other putative targets, but to be used in applications where various targets would be present;

detect rare binding events in a high-noise environment (due to high resolution data in NGS);

determine the dynamic range of the binder's functional buffer conditions;

simplify the process of separating bound and unbound ligands by simply flowing on wash buffer, if the reaction is not in solution.

Peptide or Protein Sequencing with Visualization (PROSEQ-VIS)

The PROSEQ-VIS methods described herein convert an amino acid sequence to an optical barcode. In the PROSEQ-VIS methods described herein, fluorophore-conjugated aptamers can be used to deconvolve an amino acid sequence, allowing for de novo protein sequencing. The PROSEQ-VIS methods described herein are capable of sequencing diverse samples, and particular samples in which one or more of the proteins of interest (e.g., target proteins) are present at low or very low concentrations (e.g., a protein present in one part per 10 billion). The PROSEQ-VIS methods described herein also provide for computational tools to determine the identity of the N-terminal amino acid based on the observed unique spectral signatures of binding events.

Figure 20:
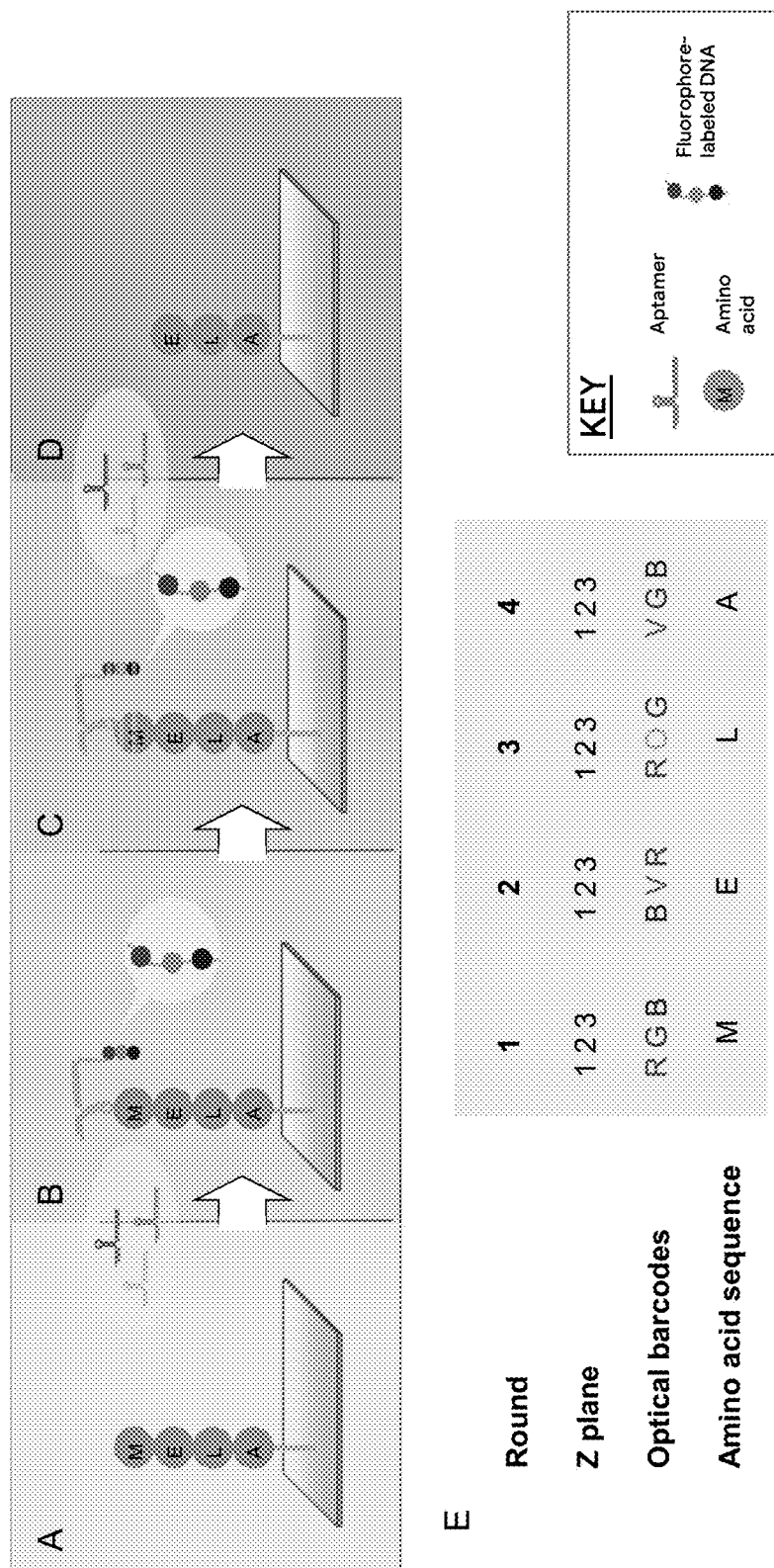
FIG. 20 is an overview of the peptide sequencing methods described herein, where the peptide or protein sequence is determined using fluorescence and microscopy. Peptide is tethered to known adaptor on chip (A). Library of fluorescent dye-conjugated aptamers, selected for specific N-terminal amino acid binding properties, is flowed across the peptides, incubated with targets and unbound aptamers are washed off the chip (B). The optical barcode of bound aptamers are imaged. For each round, a z-stack of images are taken in order to generate a spectral signature for the N-terminal amino acid (C). N-terminal amino acid on the fixed peptide is removed, the sample is washed and the same aptamer pool is flowed on to interrogate the newly exposed N-terminal amino acid (D). After repeating this series of steps on the slide, the identity of successive N-terminal amino acids at each round can be computationally deduce by comparing the optical barcodes for each peptide against the organism proteome (E).

The PROSEQ-VIS method described herein uses amino acid-specific aptamer binding to convert a protein sequence into a series of fluorescent images or an "optical barcode," which can be read via microscopy imaging. The optical fluorophores can be assigned to their aptamers, revealing the underlying protein sequence. See, for example, FIG. 20. This protein sequencing method can be used on small samples (including single cells or small blood volumes) to identify the entire proteome of expression, low-expression proteins and single amino acid mutations to better understand complex disease phenotypes. Additionally, the PROSEQ-VIS methods described herein can be performed on intact cells and tissues to visualize, not only the sequence of proteins, but also the location within a sample. See, for example, Table 1.

TABLE 1

| Biological Source of Proteins | Type of Protein | Approach for Peptide Sequencing |
| --- | --- | --- |
| Cell Lysate | Peptide | Fragmented; Solid Substrate |
| Blood | Full-length protein | Fragmented; In Solution |
| Saliva | Protein complex | Whole Proteins; Solid Substrate |
| Urine | Membrane protein | Full-length proteins; In Solution |

TABLE 1-continued

| Biological Source of Proteins | Type of Protein | Approach for Peptide Sequencing |
|---|---|---|
| Biopsy Tissue Single cells | Post-translational modified protein | Protein-Ligand Complex; Solid Substrate Protein-Ligand Complex; In Solution |

The PROSEQ-VIS methods described herein can be used in a clinical setting for identifying novel protein fusions or mutations that are linked to disease from individual patient samples, developing a diagnosis or prognosis, evaluating patient response to treatment, or predicting the likelihood of possible responses to certain treatments. In addition, the methods described herein can be broadly used for characterizing proteins, discovering novel biomarkers, analyzing whole proteomes or metaproteomes, building cell lines and evaluating mechanisms associated with protein abundance, sequence or function.

1) Aptamers Provide the Capability to Perform De Novo Sequencing

The PROSEQ-VIS methods described herein use a library of aptamers as described herein that are specific for unique combinations of one or two N-terminal amino acids, where each residue pair has at least one (e.g., or more than one; e.g., multiple) aptamer binders. The ssDNA aptamers are designed to contain a region that includes either a fluorophore or a region for annealing short dye-coupled ssDNA probes, such that the N-terminal amino acids can be identified by its unique spectral signature of binding events between the N-terminal amino acid and its corresponding aptamer(s).

Figure 21:
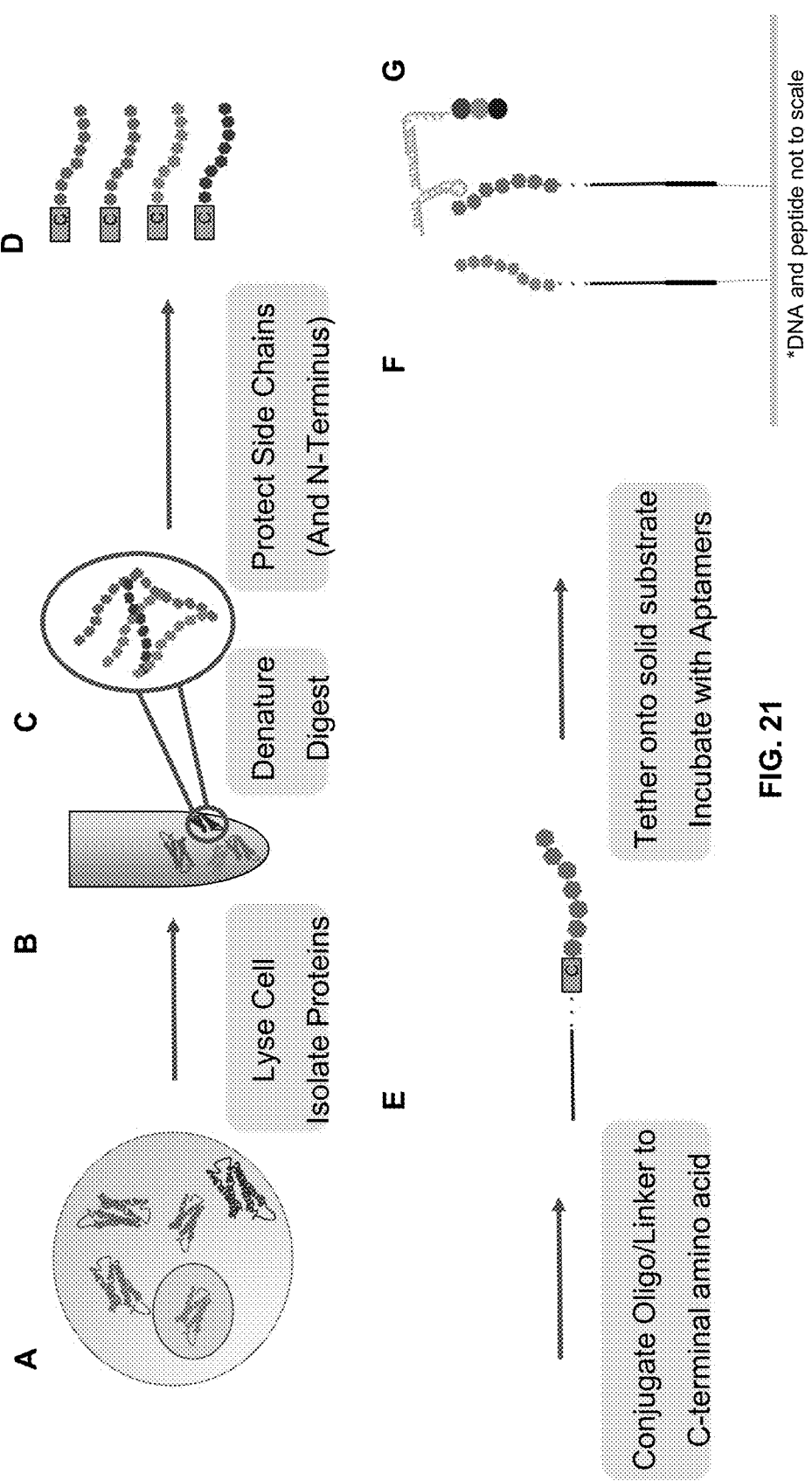
FIG. 21 is a schematic showing one embodiment of the method described herein in which proteins from cells are isolated and processed prior to tethering the protein to a solid substrate. For example, cells (A) can be lysed and the proteins isolated (B), and denatured and digested (C). The side chains and N-terminus of the peptides can be protected (D), the C-terminal amino acid modified with an oligo or a linker (E), and tethered to a solid substrate. (F). Opticallylabeled aptamers can be flowed onto the complex (G), an image captured, and the process repeated.

Proteins from a sample (e.g., a blood sample, cell lysis or a single cell) can be obtained, denatured, blocked and cleaved into peptide fragments. While denatured whole proteins can be analyzed without cleavage, proteins cleaved into smaller peptide fragments are optimal since: (1) rounds of Edman raise the noise-floor in imaging, and so fewer rounds of sequencing can be used to determine the sequence of a peptide fragment, and (2) certain imaging modalities (like TIRF) have a narrow focus window (10 s-100 s of nms) and signal detection is highly dependent on samples being fully contained within the optimal imaging window. Proteins can be cleaved into peptide fragments using, for example, a conventional trypsin approach to cut at lysines and arginines, and/or other fragmentation enzymes that cleave at random amino acid sites. The combination of both methods can help reduce error in post-sequencing computational alignment. Once the proteins are converted into short peptides, the free and unblocked C-terminal end can be conjugated to DNA primer oligonucleotides on a glass substrate or conjugated directly to the glass (FIG. 21). Then, a library of aptamers can be flowed across the peptides for incubation, allowing for aptamers to bind specifically to N-terminal amino acid residues. There are many ways to fluorescently label aptamer tails. Two potential imaging options are that the aptamer tail can have either: (a) an optical barcoded tail for imaging, or (b) a region where one or more short fluorescently-tagged DNA probes can anneal to an aptamer: amino acid complex.

1.1 Direct Aptamer-Dye Conjugation

After aptamer binding to N-terminal prefixes, the optical signature of the aptamer (a) can be imaged by a multichannel single-molecule epifluorescent or total internal reflection fluorescence (TIRF) imaging setup. For each N-terminal prefix read out ("round"), the unbound aptamers are washed off and a z-stack of images can be obtained during the incubation period in order to confirm the spectral signature for the N-terminal amino acid(s). The next round then begins by using Edman degradation and/or aminopeptidases to remove the N terminal amino acid on the fixed peptide. The same aptamer pool then can be used to interrogate the newly exposed N-terminal amino acid (FIG. 20A-20D). After repeating this series of steps, the identity of each N-terminal amino acid can be computationally deduced at each round by comparing the observed binding events for each peptide against the probability distribution of binding events for each aptamer-amino acid complex. Using this information, the amino acid sequence of each peptide can be deduced based on the series of amino acid signatures obtained in serial rounds of imaging and degradation. See, for example, FIG. 20E.

1.2 Oligo-Conjugated Dyes Hybridization to Aptamer

Figure 22:
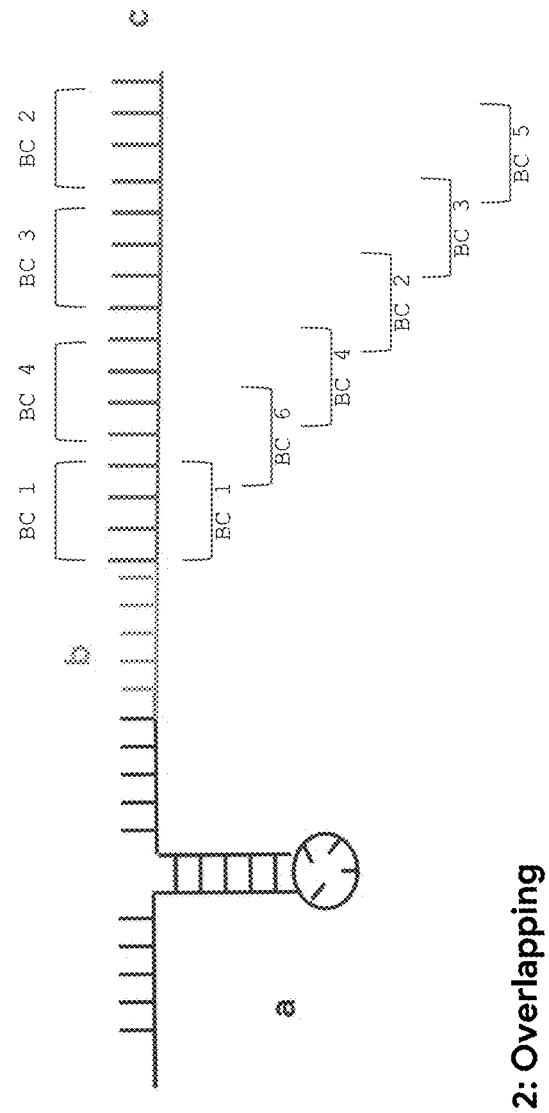
FIG. 22 is a schematic showing the construction of aptamers with regions to bind to complementary fluorescently-tagged oligos. The aptamers comprises of (a) the effective binding region, (b) an optional spacer, and (c) a barcode tail of one or more combinations of barcode units (BC) indicative of the probing iteration number and fluorescent tag, with each BC being complementary to a fluorescently-tagged oligo. There are two variations of barcode tail design: (1) BCs are spatially separate and can anneal with one or up to all unique complimentary probes at a time and (2) BCs are designed such that BC sequences overlap and can only anneal to probes complementary to non-overlapping BCs at a time. Note that BCs need not be spatially oriented in chronological order of probe incubation iterations (shown in picture) as the BC sequence itself contains the probing iteration number information.
Figure 23:
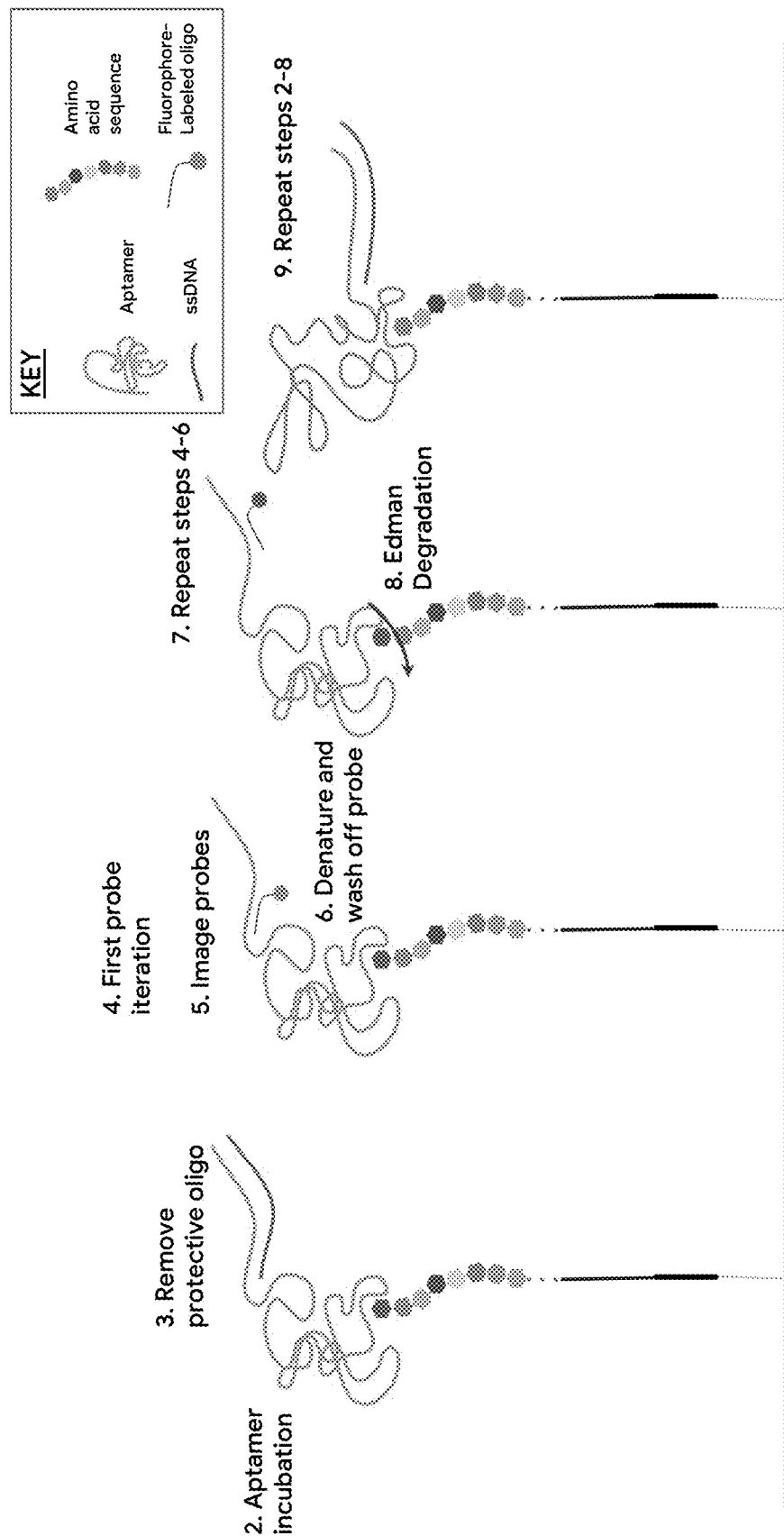
FIG. 23 is a schematic showing the peptide sequencing methods described herein. Step 1 includes the immobilization of the peptide-oligo target on a solid substrate; Step 2 includes incubating the bound proteins or peptides with a barcoded aptamer library under conditions that allow the appropriate aptamer to bind specifically to the appropriate N-terminal amino acid; Step 3 includes removing the protective complementary oligo, exposing the barcode region for probe annealing; Step 4 includes incubating the incubated with a library of probes that hybridize to barcode regions indicative of probe iteration 1; Step 5 includes washing off the unbound probes and imaging the bound probes; Step 6 includes denaturing the bound probes from the aptamer and washing off the probes off the substrate; Step 7 includes repeating steps 4-6 for all the probe iterations necessary for aptamer identification. Upon removal of the N-terminal amino acid from the protein or peptide using Edman degradation and/or aminopeptidases, Steps 2-8 are repeated, generating a series of optical barcodes that can be used to identify each subsequent N-terminal amino acid.

In the case of using aptamers with regions that bind to complementary fluorescently-tagged oligos, the assay includes multiple "iterations" of probe incubation and imaging per "round" of N-terminal prefix read out. The aptamers include 3 regions: (a) the effective binding region, (b) an optional spacer, and (c) a barcode tail of one or more combinations of barcode units indicative of the probing iteration number and fluorescent tag, with each barcode being complementary to a fluorescently-tagged oligo (FIG. 22). To prevent the barcode regions from affecting the folding of the aptamer's binding region, when the library of aptamers is flowed on, the oligo regions not related to N-terminal prefix binding can be partially or fully protected by hybridizing a complementary oligo to form aptamers that are partially double-stranded. The aptamer: amino acid complexes can be incubated with a library of probes that hybridize to barcode regions indicative of probe iteration 1. The number of unique fluorescent tags that can be employed per iteration is dependent on how many channels are in the imaging set-up, properties of the fluorescent dyes and emission filters, and sensitivity of the detector. During each iteration, each aptamer can hybridize to one or multiple oligo-bound probes for multiplexing as long as the complementary barcode units on the aptamers do not overlap for that iteration. The unbound probes then can be washed off and bound probes can be imaged to acquire the first section of the optical barcode. Thereafter, the bound aptamers can be incubated with the next set of probes that hybridize to barcode regions indicative of probe iteration 2. Iterations of probe incubation, imaging, and washing can be repeated until full optical barcodes are acquired. Lastly, Edman degradation can be performed to remove the N-terminal amino acid and the aptamer it is bound with to reveal the next N-terminal amino acid for the next round of sequencing (FIG. 23).

Figure 24:
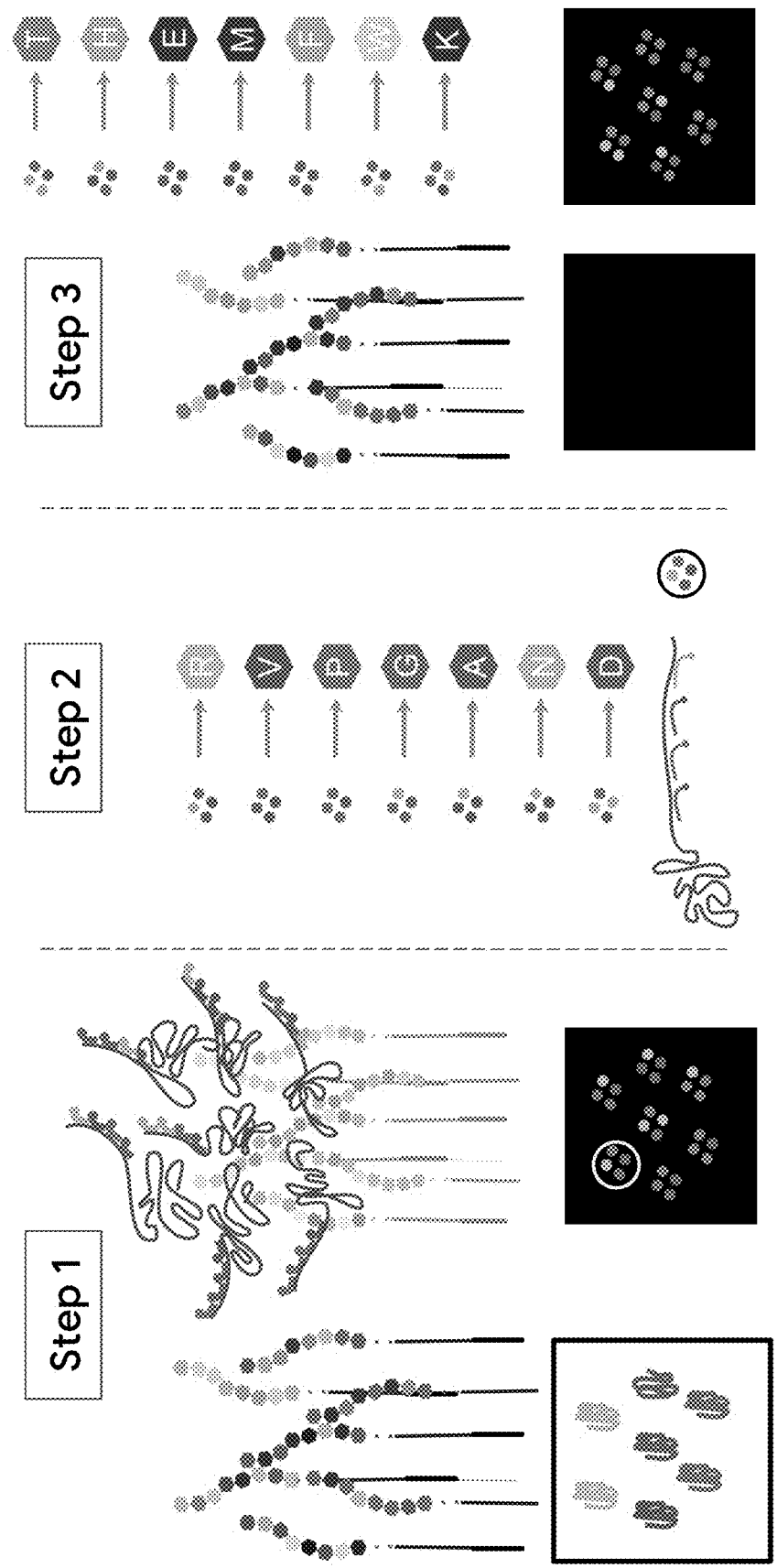
FIG. 24 is a schematic depicting the methods for PROSEQ VIS described herein when the library of aptamer probes consists of high affinity binders that bind specifically to a unique N-terminal amino acid prefixes. Single binding events that indicate the putative identity of the probed N-terminal amino acid prefix are observed by detecting aptamers that are directly conjugated to unique combination of dyes or a combination of dye-conjugated oligos hybridized to the aptamer. In Step 1, peptides are localized to the sequencing platform, and incubated with aptamers that recognize specific N-terminal dipeptides. In Step 2, each aptamer has multiple binding sites for dye-conjugated binders. These strong binders can simultaneously hybridize with the aptamer, and remain bound. The identity of the aptamer, and by extension that of the N-terminal amino acid (SEQ ID NO:121), is determined by evaluating the combination of colors detected at each location. In Step 3, aptamers are washed off and a new N-terminal amino acid exposed via degradation. The cycle is repeated for the remaining amino acids (SEQ ID NO:122).
Figure 25:
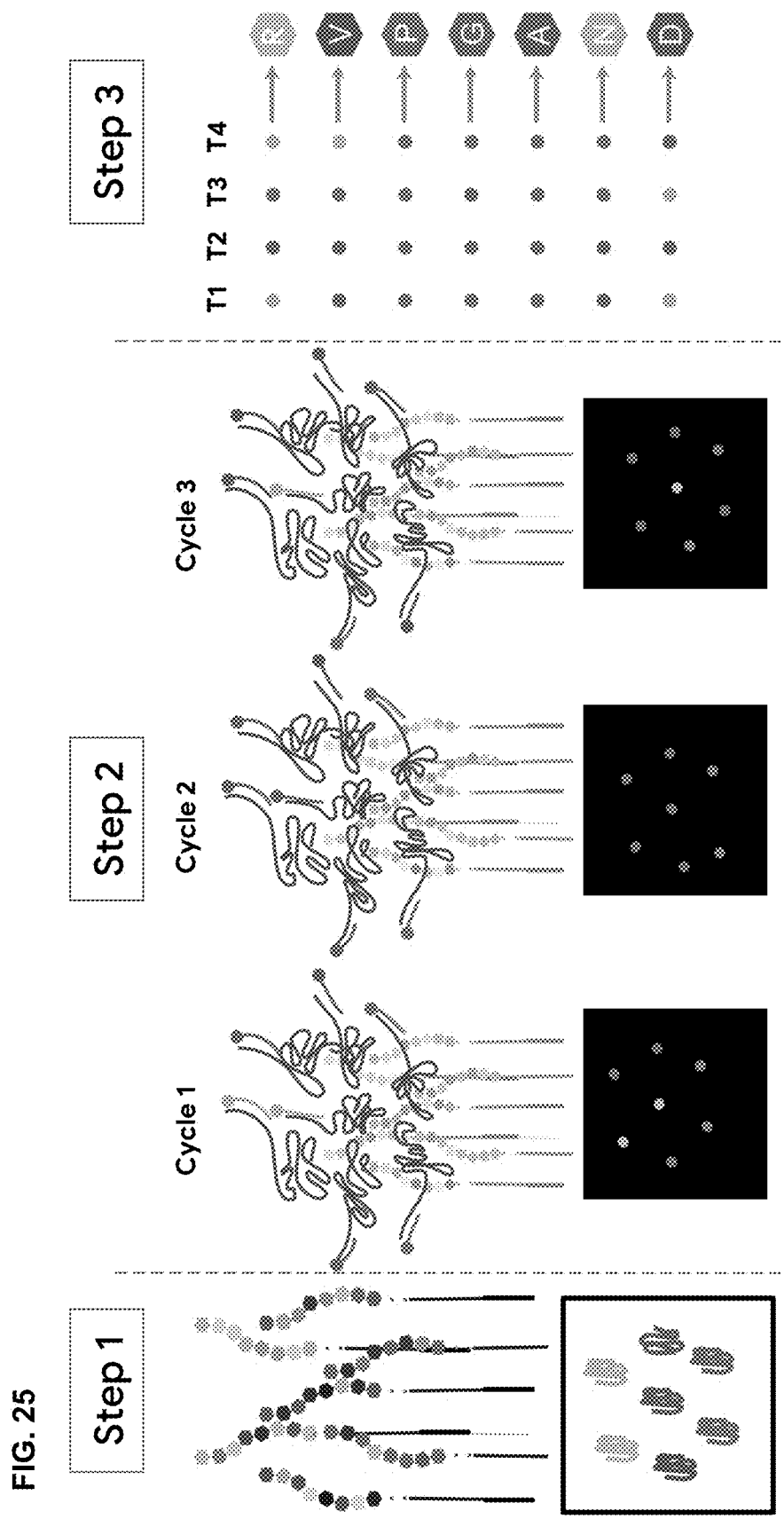
FIG. 25 is a schematic depicting the methods for PROSEQ VIS described herein when the library of aptamer probes consists of medium affinity binders that bind non-specifically to a set of N-terminal amino acid prefixes with variable probability distributions for each unique binding pair. Multiple binding events that indicate the putative identity of the probed N-terminal amino acid prefix are observed by detecting dye-modified aptamers over multiple cycles of incubation and wash off for each. In Step 1, peptides are localized to the sequencing platform, and incubated with aptamers that recognize a set of N-terminal dipeptides. In Step 2, Dye-conjugated binders hybridize to a single stranded portion of the aptamers, but because they are 'weak' binders, they lack specificity of a stronger binder. The dye-conjugated binders fluorescing at each peptide location is tracked over cycles to determine accuracy of call rate of amino acid. Can be used with either individual color or optical barcode. In Step 3, the identity of N-terminal amino acids at each round is computationally deduced by comparing the observed combination of fluorescent signals against probability distribution of binding events for each aptamer to each N-terminal amino acid prefix (SEQ ID NO:123).

It would be understood that procedural modifications, especially to the imaging and downstream signal deconvolution strategy, can be made to accommodate the affinity and specificity of the aptamers used to probe the N-terminal amino acids. In the case of utilizing highly specific binders, a library of aptamers specific to a unique N-terminal amino acid prefix and with low $K_d$ (tight binding) are flowed on, the unbound aptamers washed away, and the optical barcodes observed as described above (FIG. 24). In the case of aptamers with medium-to-low specificity, a library of fluorophore-conjugated aptamers can be flowed across the peptides for incubation, allowing for aptamers to bind semi-specifically to a set of N-terminal amino acid residues. Such aptamers preferentially bind to a given target, and may also bind to a subset of known N-terminal amino acids with a known probability distribution for each binding pair. For each round of sequencing, images can be taken before (for background), after (for specific binding) or during ($K_{on}$, $K_{off}$ measurements) cycles of aptamer incubations in order to generate a spectral signature for the N-terminal amino acid prefix composed of multiple binding events before the N-terminal amino acid is removed to reveal the next amino acid to be probed. Several rounds of incubation and detection can occur before removing the N-terminal amino acid via Edman in order to increase the confidence in the detected signal. After repeating multiple rounds of aptamer binding, the identity of N-terminal amino acids can be computationally deduced at each round by comparing the observed binding events for each peptide against a known probability distribution of binding events for each aptamer amino acid prefix, as each unique N-terminal amino acid is expected to have its own distinct binding signature given a pool of medium-strength binders (FIG. 25). Additionally, binders such as RNA or small molecules can be used, in addition to or as an alternative to aptamers, to recognize amino acids.

The methods described herein do not rely on previous knowledge of proteins (such as with a peptide database required in mass spectroscopy) and provide an avenue for de novo sequencing. If a database of proteins is available, however, it is likely, then, that only a subset of amino acids need to be identified in order to accurately map peptide fragments back to full-length proteins. Additionally, if purification or selection for (e.g. by molecular weight, charge, or affinity to a known molecule) proteins were performed prior to sequencing, it would further focus the list of candidates based on a subset amino acid sequence of a full-length protein identified.

The PROSEQ-VIS methods described herein result in a number of advantages and applications, including, without limitation, the ability to:
1) sequence peptides irrespective of peptide concentration;
2) convert a protein sequence to an optical sequence, which allows for isolation of the signal of lowly expressed proteins;
3) conduct de novo protein sequencing (e.g., to allow direct discovery of sequences in molecules such as cytokines);
4) process small volume samples, down to single cell protein sequencing; and
5) sequence peptides in situ for protein localization data in intact tissues.

Instead of using fluorophore-conjugated aptamers or oligo probes to identify amino acids, other optical methods such as quantum dots, dye-conjugated nanoparticles, or the like could be used. Instead of TIRF, other microscopy means can be used for imaging with varying degrees of resolution quality. Lastly, replacing the aptamer in the PROSEQ-VIS methods described herein with another type of N-terminal amino acid binding small molecule that has been barcoded with an optical barcode similarly allows for protein sequencing on the PROSEQ-VIS platform.

Concurrent Screening of Multiple Targets (MULTIPLEX)

Attempts by others to screen against multiple targets using SELEX have successfully multiplexed up to 30 biological similar targets in one SELEX experiment (e.g., VENNmultiplex SELEX by BasePair). Although the specific methods that achieve this are not known, it is likely that targets are bound to beads with different spectral content and incubated with aptamer candidates before being sorted by fluorescence activated cell sorting (FACS). This method limits the number of targets that one can multiplex at a time due to the optical limitations of the machinery.

The MULTIPLEX methods described herein allow for screening binders for multiple peptide or protein targets at once. In addition, the MULTIPLEX methods described herein allow for detecting rare binding events in a high-noise environment; increasing target specificity; and conducting specificity assays for multiple-target cross-validation matrix analysis and machine learning analysis. The MULTIPLEX methods described herein can be used to identify interactions between essentially any two biological molecules (e.g., two DNA or RNA barcoded molecules such as oligonucleotides and molecular targets, proteins and antibodies, small molecules and barcoded proteins) as long as both targets can be conjugated to oligonucleotides that can then be ligated to each other.

Figure 26:
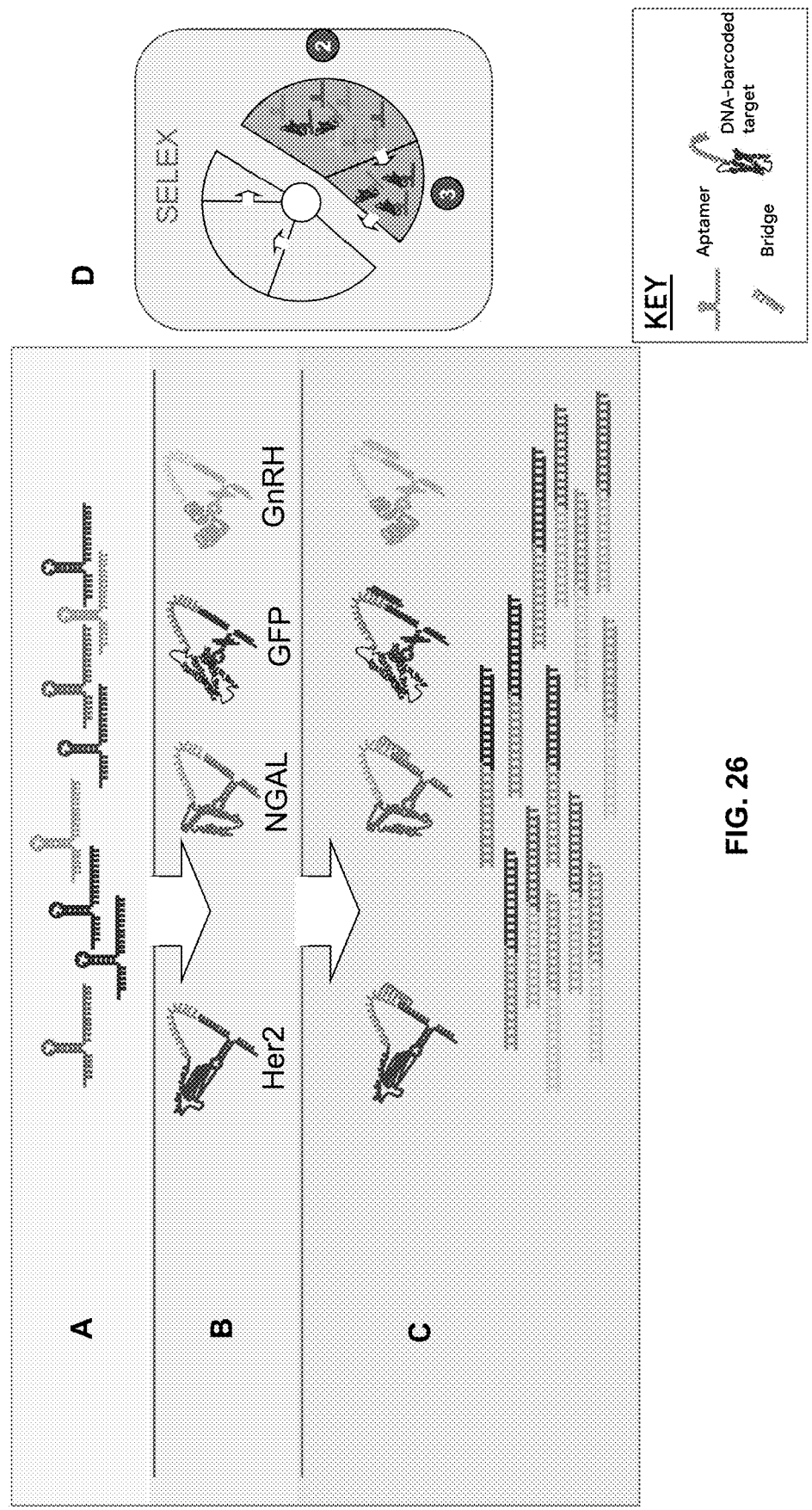
FIG. 26A-26C are schematics showing the MULTIPLEX methods described herein. An aptamer library (A) is incubated with a diverse pool of unbound DNA-barcoded protein or peptide targets (FIG. 18B). Upon aptamer binding to a barcoded target, the 3' end of the single stranded aptamer is joined to the ssDNA barcode that is specific to target identity by an ssDNA bridge that is half complementary to the 3' end of the aptamer and half complementary to the 5' end of the ssDNA barcode (C). The nick between the aptamer and ssDNA peptide barcode can be ligated and sequenced through to obtain the aptamer sequence and peptide barcode, which, in turn, provides the target to which the aptamer was bound.
FIG. 26D is a schematic that indicates the steps of the SELEX procedure (from FIG. 3) into which multiplexing can be incorporated.

The MULTIPLEX methods described herein involve incubating the aptamer candidates (FIG. 26A) with a diverse pool of unbound DNA-barcoded peptide targets (FIG. 26B). Upon aptamer binding, the 3' end of the single stranded aptamer is ligated to the peptide ssDNA barcode (FIG. 26C), and the DNA portion is amplified via PCR. Sequencing the aptamer and its covalently attached DNA barcode provides the aptamer sequence along with the unique identifier that indicates which target the aptamer was bound to, thus eliminating the obstacle of identifying which aptamers are bound to which targets. FIG. 26D is a schematic that indicates the steps of the SELEX procedure (from FIG. 3) into which multiplexing can be incorporated.

The MULTIPLEX methods described herein can reduce labor and reagent costs while improving data quality and broadening screening capabilities. In addition, the MULTIPLEX methods described herein can produce aptamers that specifically bind to their unique targets in an environment with a multitude of available targets (e.g., cell surfaces, human blood), thus, vastly increasing the pipeline for aptamer discovery to application.

1) Use of a DNA Barcode to Identify Peptide or Protein Targets

Figure 27:
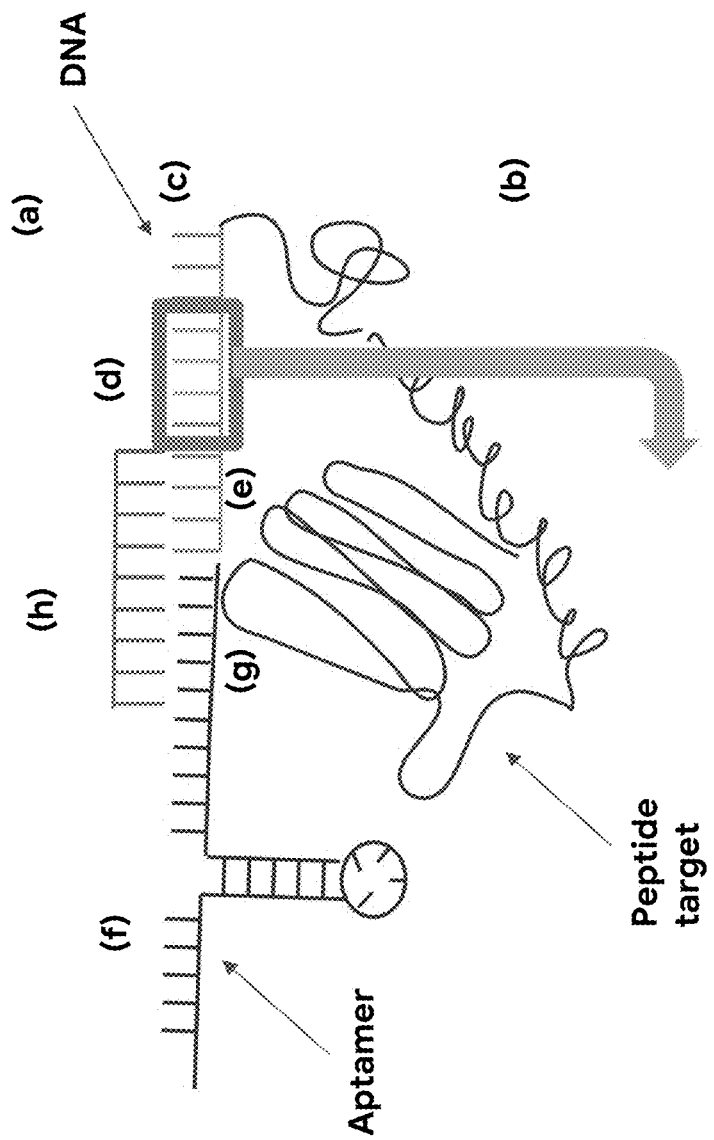
FIG. 27 is a schematic of a peptide-oligonucleotide conjugate (POC), which includes a single-stranded (ss) DNA tail (a) whose 3' end is covalently linked to the C-terminus of a peptide or protein target (b). The ssDNA tail (a) includes a 3' primer region (c), a unique DNA barcode (d), and a 5' bridge-binding sequence (e). An aptamer (f) includes a 3' bridge-binding sequence (g). A short oligonucleotide bridge (h) where half is complementary to the 3' bridge-binding sequence (g) at the 3' end of the aptamer (f) and the other half is complementary to the 5' bridge-binding sequence (e) of the ssDNA tail (a) can be used to ligate the aptamer (f) to the peptide (b).

As described herein, the targets in the MULTIPLEX methods described herein are peptide-oligonucleotide conjugates (POCs), which, with reference to FIG. 27, are single-stranded (ss) DNA tails (a) whose 3' ends are covalently linked to the C-termini of peptide or protein targets (b). A ssDNA tail (a) includes a 3' primer region (c), a unique DNA barcode (d), and a 5' bridge-binding sequence (e). An aptamer (f) includes a 3' bridge-binding sequence (g). After POC-aptamer binding in solution, a short oligonucleotide bridge (h) can be introduced, where half of the short oligonucleotide bridge (h) is complementary to the 3' bridge-binding sequence (g) at the 3' end of the aptamer (f) and the other half is complementary to the 5' bridge-binding sequence (e) of the ss DNA tail (a). After the bridge oligonucleotide binds both the aptamer and peptide tail, a ligase enzyme can be added to seal the nick, unused bridge oligonucleotides can be degraded and/or removed, and the ligase enzyme deactivated. This results in covalent linkage of the aptamer (f) to the peptide (b).

Following ligation, bead-bound POC targets can be obtained (e.g., pulled down using complementarity to biotinylated oligonucleotides), followed by removal of (e.g., washing) unbound aptamers. PCR can be performed on the beads through the ssDNA tail and the aptamer, and the resulting DNA construct can be sequenced to obtain the aptamer sequence along with the barcode identifier of its protein binding partner (boxed region in FIG. 27).

2) Use of Proximity-Dependent DNA Ligation to Identify Local Aptamer Binding Events from Global Noise One difficulty encountered in the MULTIPLEX methods disclosed herein is constraining the assay in a way that favors the ligation of bound partners over random available substrates in solution, since peptide tails and aptamers that are physically close together are more likely to ligate to each other than to free-floating DNA. Therefore, ligation reaction conditions can be developed and optimized to maximize local signal by optimizing several experimentally-tested parameters including, without limitation, reaction time, substrate concentration, temperature, and reaction solution. Additionally, tails of varying lengths and bridge regions of varying lengths can be designed and characterized to optimize local interaction in a high-noise environment.

3) Nested PCR for Additional Rounds of Multiplex-SELEX

Figure 28:
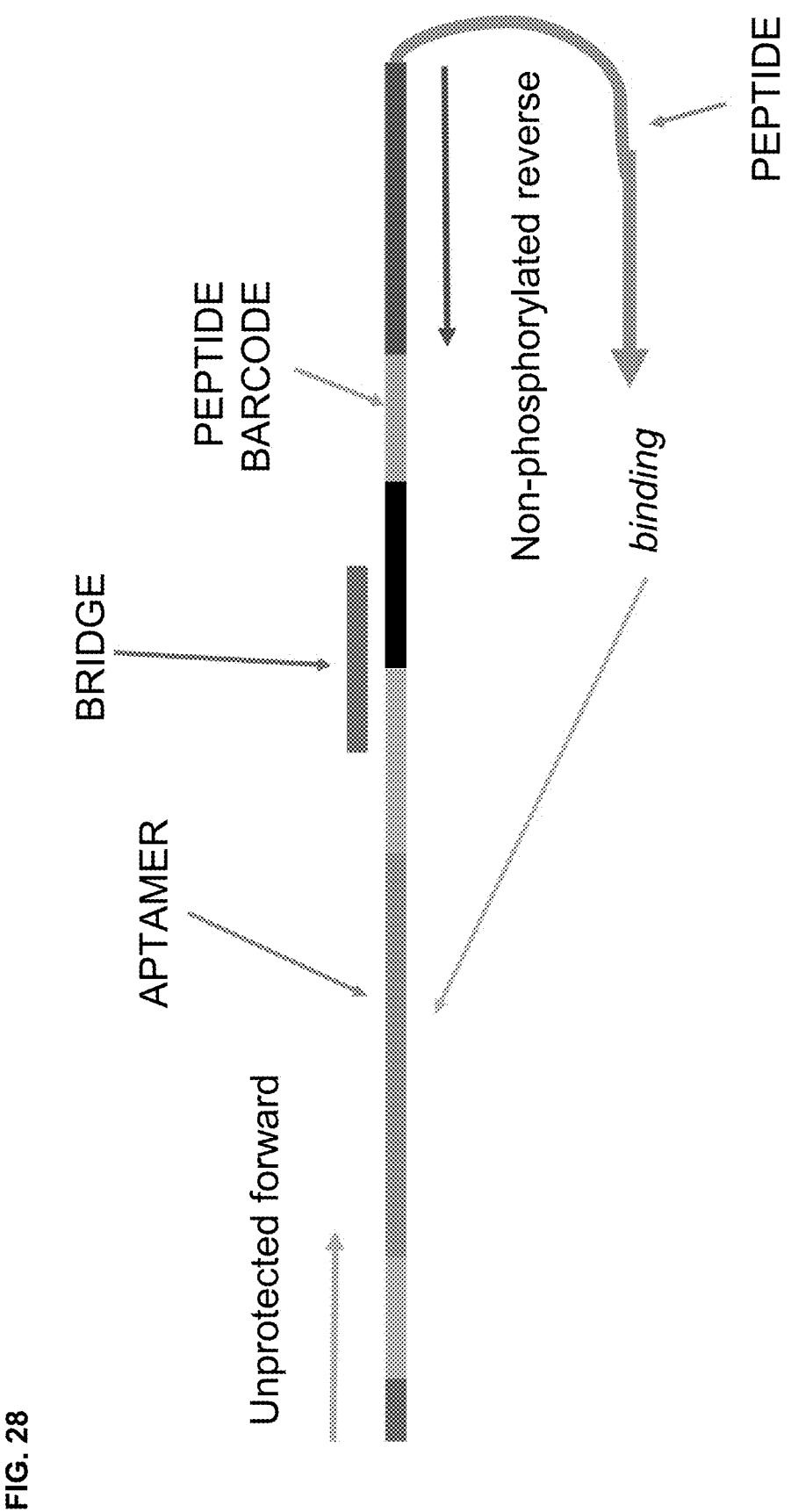
FIG. 28 is a schematic of the Nested PCR technique in MULTIPLEX.

To achieve multiple rounds in the MULTIPLEX methods described herein, the aptamer segment of the ligated aptamer-barcode product can be re-amplified (e.g., using nested PCR on the ligated complex with primers flanking the aptamer sequence) and processed (e.g., using purification via automated electrophoretic gel separation), followed by conversion to ssDNA (e.g., using enzymatic digestion). See FIG. 28.

4) Alternatives and Variations on the Multiplex Methods

Many procedural modifications can be made to adapt the multiplex methods described herein to suit different applications.

The MULTIPLEX methods described herein can be used to examine interactions in different substrate binding scenarios; for example, and without limitation: a) DNA-peptide binding, where the interacting region includes an aptamer bound to a peptide target; b) DNA-DNA binding, where the interacting region includes a region of base complementarity between two strands of DNA. With DNA-DNA interaction, the ability to identify local signals has been demonstrated when binding partners represent as low as 0.001% of the total pool in a 500 nM concentration solution, demonstrating the sensitivity of the MULTIPLEX methods described herein.

Additionally, the MULTIPLEX methods described herein can be used to examine substrate binding beyond DNA-DNA or DNA-peptide interactions. For example, the MULTIPLEX methods described herein can be used to examine binding between any number of biological targets provided both targets can be bound to each other (e.g., via ligation of oligonucleotides). For example, a MULTIPLEX method similar to that described herein can be employed to screen for RNA aptamers that bind small molecule targets or protein complexes.

An ssDNA tail can be attached to the C-terminus of a peptide or protein using any number of different techniques, including, without limitation, chemical linkers (e.g., click chemistry, SMCC linker, EMCS linker, etc.), biological linkers (e.g., biotin-streptavidin systems), cross-linking (e.g., using formaldehyde or UV), or the like.

In addition, it would be appreciated that a ssDNA tail can be attached to a different region of the protein or peptide (i.e., other than the C-terminus). For example, the ssDNA tails can be attached to the N-terminus, to a specific functional group, amino acid side chains, etc. Additionally or alternatively, multiple ssDNA tails can be attached to a single peptide or protein.

Ligation between the DNA ends can occur in multiple ways. Enzymatic ligation in aqueous solution can be used, but it is also possible to ligate the DNA ends chemically. In some embodiments, alternative ends of the bridge can be used for ligation. The overhangs and/or the bridge can also be modified to include base-pairing mismatches to introduce a gradient of binding interactions, such that the binding interaction between the binder and target takes precedence over the binding interaction of the bridge.

It would be understood that the MULTIPLEX methods described herein can be conducted in aqueous solutions or they can be tailored for use in a different system, such as on a fixed surface, on beads, in vivo, in a gel, or the like.

The MULTIPLEX methods described herein have been used to identify aptamers with selective binding to peptide targets in a competitive multi-peptide environment. Like selective antibodies, the resulting aptamers are suitable to be used alone or in combinations of two or more to create constructs that control their multi-target binding distributions. For example, two aptamers, each highly selective for different targets, can be joined together in order to create a construct that binds two separate targets; alternatively, two aptamers with the same primary target but with different off target binding distributions can be added to the pool in parallel or sequentially to increase the binding readout to their common target through analysis of regions of overlapping distributions.

Replacing the aptamer in the MULTIPLEX methods described herein with a molecule that has been DNA barcoded and has a 3' C overhang arm allows for measuring binding between different mixtures of any of the molecule classes previously described, enabling bi-directional multi-way competitive measurements of any of the combinations of molecule classes: including, peptide vs protein, protein-protein, antibody-protein, small molecule-protein, peptide-cell surface marker, antibody-cell surface marker, etc. In some embodiments, both the binder and the target molecules can be drawn from any mixture of molecules from any of the above classes, allowing for measurement of cross binding in complex competitive environments.

The MULTIPLEX methods described herein provide a high-sensitivity tool for detecting low-level binding events in a large substrate pool. The MULTIPLEX methods described herein reduce the need for a large number of rounds of SELEX (e.g., 8 to 20 rounds) and simultaneously allow for multiplexing several peptide targets in one solution. As a result of reduced rounds, the MULTIPLEX methods described herein minimizes the number of PCR amplifications that must be performed on the aptamer pool and, thus, minimizes the bias introduced with every round of amplification. Increased specificity and reduction of off-target binding is an added benefit in the MULTIPLEX methods described herein. For example, if a unique aptamer is isolated that binds to peptide target #1 in a mixture containing targets #1-10, it also is known that the aptamer, in addition to binding to target #1, does not bind to targets #2-10 (under those same conditions). This reduces the likelihood of selecting non-specific aptamers that may bind other targets in addition to the target of interest.

Target Protein and RNA-Binding Protein Fusion (TURDUCKEN)

The classification of binding interactions is highly desirable in a number of research areas including in drug development, diagnostics, and basic research. Protein and peptide libraries contain a bank of interesting biological targets against which binders (e.g., aptamers, small molecules, antibodies, etc.) can be screened. Presently, screening is typically performed in individual reactions where the identity of the protein or peptide target is known, making large-scale screening, particularly of unknown targets, cost and labor prohibitive. Pooling and screening several targets at once allows for scaling and greater binding specificity, however, there is currently no available method for creating target libraries where the identity of each target in a pool can be easily deduced.

Biological approaches for creating protein or peptide libraries rely on the cloning and purification of each protein individually into a model system such as yeast or *E. coli* (Jia & Jeon, 2016). To create a library of 1,000 unique proteins, researchers must perform 1,000 separate transformation reactions, protein purifications, and QC processes, before finally pooling the proteins together. Chemical synthesis can reliably produce peptide pools, but quickly can become cost-prohibitive and technically challenging for larger proteins and protein complexes.

Importantly, existing methods for creating libraries do not enable scientists to easily identify individual elements once the components are pooled. Common techniques for identifying proteins include mass spectrometry, antibody binding assays, and affinity tag binding assays (Miteva, Budayeva, & Cristea, 2012). Concentration thresholds of unique elements within a pool of proteins limit the use of mass spectrometry for the identification of lowly expressed individual proteins from a large pool; antibodies are often inconsistent, non-existent, or cost prohibitive for novel targets; and the affinity tag approach limits pool diversity to the number of unique affinity tags available.

The TURDUCKEN methods described herein allow a mixture of thousands of unique proteins to be made, tagged, screened and identified in one pool. The TURDUCKEN methods described herein allow for the production of a diverse protein pool and the screening of such a diverse protein pool.

1) Protein Expression

Figure 29:
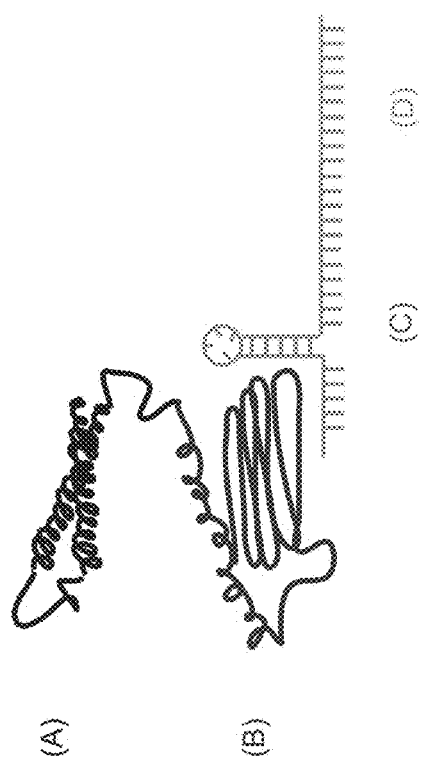
FIG. 29 is a schematic showing the barcoded (D) protein of interest (POI) (A) complex that is produced in vivo in the TURDUCKEN methods described herein. This approach exploits the non-covalent interactions between an RNA-binding protein (B) and its corresponding binding site (C).
Figure 30:
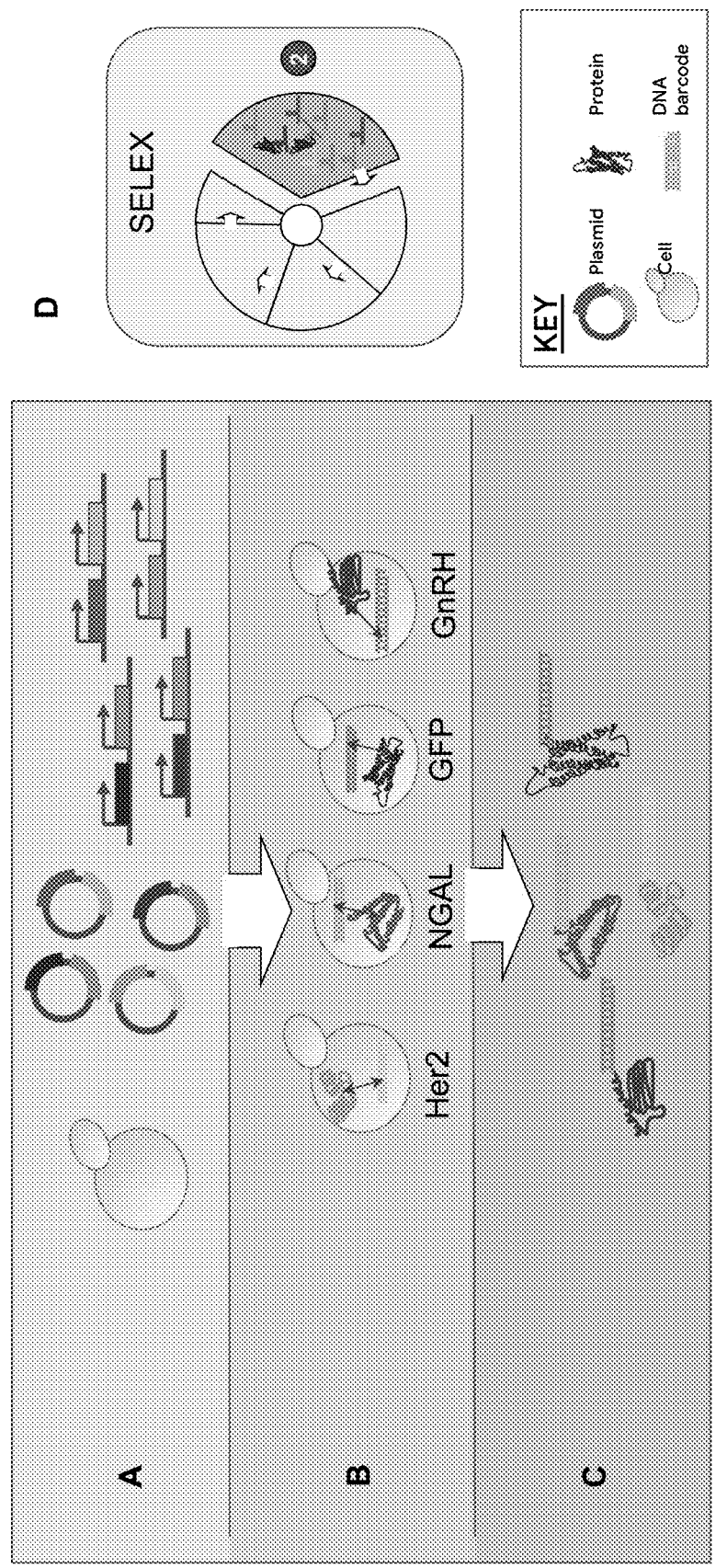
FIG. 30A-30C are schematics showing one embodiment of the TURDUCKEN methods described herein. A pool containing the plasmids of various protein of interest (POI)-RNA binding protein (RBP) fusion genes as well as their corresponding RNA barcode sequence are transformed into cells at an approximate dilution of 1 plasmid per cell (A), the POI-RBP fusions are expressed and bind their corresponding RNA barcodes (B), which then are purified (C).
FIG. 30D is a schematic that indicates the steps of the SELEX procedure (from FIG. 3) into which the TURDUCKEN methods can be incorporated.

An in vivo system in *S. cerevisiae* and *E. coli* is described in which each transformed cell is engineered to produce a different protein of interest (POI), which can be non-covalently linked to a RNA barcode whose sequence can be used to identify the POI; the non-covalent linkage relies on the natural interaction between an RNA binding site and its corresponding RNA-binding protein (RBP). See, for example, FIG. 29. Representative RNA binding sites and their corresponding RBPs that can be used in such constructs include, without limitation, the MS2 RNA hairpin bound by the MS2 phage coat protein and the boxB sequence bound by the bacteriophage anti-terminator protein N (lambdaN). Each POI (FIG. 29A) can be expressed as a fusion protein with a RNA-binding protein (part B of FIG. 29) in which the POI can be non-covalently linked to a specific RNA binding site (part C of FIG. 29), which is recognized by the RNA-binding protein and a unique barcode (part D of FIG. 29). Each construct in the pool typically contains a POI fused to a RBP, a DNA sequence that encodes the RNA sequence that is recognized by the RBP, a unique RNA barcode, and a promoter to drive expression. Representative promoters include, for example, the Gal 1, 10 bidirectional promoter, ADH1, GDS, TEF, CMV, EF1a, SV40, T7, lac, or any other promoter and promoter combinations compatible with the host organism. A pool containing the plasmids of various POI-RBP fusion genes as well as their corresponding RNA barcode sequence can be transformed into *S. cerevisiae* with an approximate dilution of 1 plasmid per cell (FIG. 30A). POI fusions made in vivo then bind their corresponding RNA barcodes inside the cell (FIG. 30B), which then can be purified (FIG. 30C). FIG. 30D is a schematic that demonstrates where, relative to the SELEX method (FIG. 3), the products of TURDUCKEN as described herein can be used.

2) Protein Purification

POI-RNA complexes can be obtained using any number of methods, resulting in only complexes containing both the POI fusion protein and the RNA barcode are collected. Simply by way of example, the complexes can be pulled down from a cell lysate via a His-tag or other purification tags, which can be included in the protein fusion component of the POI. POIs then can be washed and released from the anti-His beads or other pull-down assays compatible with the purification tag used, and further purified using a streptavidin-coated bead and a biotinylated oligo that is reverse complementary to a sequence in the RNA barcode. After this pull-down step, a mixture of beads are obtained that are bound to the POI-RNA complex, biotinylated oligonucleotides annealed to random RNA sequences, or nothing. The POI-RNA complex can be released from the streptavidin-coated beads and purified by heating and washing the mixture to denature the RNA and biotinylated oligonucleotide or by releasing the complex using restriction endonucleases.

3) Protein Pool for Use in Aptamer Binding Assays

The final product from this method is a diverse pool of proteins, each identifiable by an attached RNA barcode. This design allows for the use of this protein pool in multiplexed aptamer screening assays. For example, a pool of potential aptamers that also contain their own unique nucleic acid barcode can be incubated together with the protein pool and aptamers from the pool of potential aptamers are allowed to bind their targets. Through controlled enzymatic ligation (e.g., see the MULTIPLEX methods described herein), the non-covalently bound aptamer's barcode can be ligated (e.g., covalently) to the POI-RNA complex barcode. By sequencing through the ligated product, the aptamer sequence can be obtained, which provides the identity of its target.

The TURDUCKEN methods described herein allow for:

a) labeling of proteins in vivo using a nucleic acid barcode;

b) producing a large, diverse protein pool in a single transformation reaction;

c) identifying each component of the protein pool using NGS sequencing; and d) carrying out screening against multiple targets in one pooled reaction.

Other methods of generating DNA-barcoded proteins, such as chemical synthesis, are unable to operate on a large scale and must be performed in individual samples or wells. The TURDUCKEN methods described herein provide the ability to express and barcode thousands to millions of different proteins in the same pool in vivo with low rates of mislabeling proteins. This method saves significant time and money. Additionally, the TURDUCKEN methods described herein provide the advantage of being able to screen many targets at once simultaneously.

It would be understood that procedural modifications can be made to adapt the TURDUCKEN methods described herein to suit different applications. For example:

any number of organisms in addition to yeast (e.g., *E. coli*, mammalian CHO cells) can be engineered to produce protein-of-interest and nucleic acid (POI-NA) complexes.

the nucleic acids used in the TURDUCKEN methods described herein can be expressed from a variety of different constructs or vectors (e.g., circular plasmids, linear inserts, or chromosomally-integrated DNA).

alternate strategies for linking two substrates in vivo to create the POI-NA complexes (e.g., different RNA-binding proteins such as MS2 or BoxB/lambdaN systems, HUH-endonuclease domains, CRISPR associated protein).

DNA barcodes can be used instead of RNA barcodes using linker systems such as Spycatcher/Spytag, TALE, etc.

There are many potential uses for the in vivo protein labeling provided by the TURDUCKEN methods described herein. For example, the TURDUCKEN methods described herein can be used to study interactions between molecular targets (e.g., aptamers, small molecules, etc.) for basic or translational research. For example, fluorescent probes hybridized to the POI-DNA complex can be used to visualize proteins in vivo as a screening tool for drug discovery applications. For example, the TURDUCKEN methods described herein can be used to mine for aptamers that then can be used as an alternative to antibodies (e.g., as molecular probes, for targeted drug delivery, etc.).

Generating Large, Diverse, and Controlled DNA Libraries by Ligation (LEGO)

Systematic Evolution of Ligands by Exponential Enrichment (SELEX) is a biomolecular technique traditionally used to identify aptamers that is designed to isolate strong binders from a large pool of random aptamer candidates since it is extremely difficult and expensive to synthesize such a large pool of specific sequences. However, if one could generate their own initial SELEX starting aptamer pools, the landscape of SELEX experiments could allow for specialized adaptations, such as using ML-predicted sequences for a target as the starting aptamer pool. In order to accomplish the generation of such large, diverse, yet controlled or known libraries, a protocol referred to as LEGO was developed. For a 40-mer ssDNA oligo, there are $10^{24}$ possible oligos that could be explored, but each SELEX experiment only assays $10^8$-$10^{14}$ of the total possible experimental space. This represents only a small fraction of all the DNA sequences possible, such that, in practice, even the most optimized experiment has a low probability of finding the best aptamers for a particular target. Research has demonstrated that there are particular two dimensional structures, or secondary structures such as G-quadruplexes, that are often seen in aptamers (Tucker, Shum, & Tanner, 2012), and it is hypothesized that these secondary structures increase the aptamer's binding capabilities. The ability to generate an initial input library, rather than being restricted with the use of a random library, that biases towards popular secondary structures over unstructured aptamers would accelerate binder discoveries. Additionally, as artificial intelligence predictive algorithms, such as ML, increases their predictive capabilities; ML-guided input libraries for aptamer experiments would significantly increase the relative ratio of the potential aptamer candidates to non-candidates in the starting pool, and potentially reduce the number of rounds to find equally high affinity aptamers. As a result, with fewer SELEX rounds, aptamer candidates could be discovered faster, require less cost for discovery and discovered candidates would have reduced impacts from experimental noise such as PCR bias. In other words, fewer downstream quality control assays would need to be conducted to confirm that top aptamer candidates are true binders over aptamer candidates that happen to PCR extremely well and without specifically preference for the target of interest. Additionally, one could consider iterating an approach where a few rounds of SELEX are conducted from a random library, the library is sequenced, the resulting data is fed into an ML model, the model predicts what the next initial starting pool should look like (either features such as secondary structure or GC content, or direct sequences), and then a new library is generated for a new, more targeted SELEX experiment is started.

While random libraries can be synthesized cheaply, there is no current cost-effective method for generating large pools whose parameters (e.g., GC content, recurring motifs, fixed regions, length, etc.) can be easily determined and manipulated. Current methods for synthesizing short (>200 bp) DNA pools provide either:

a) high diversity with little control over sequence content: random DNA libraries with customizable primer regions can be chemically synthesized at low cost (e.g., under $300, TriLink Biotech). However, generating $10^{14}$ specified sequences by conventional microarray synthesis is prohibitively expensive (e.g., Integrated DNA Technologies: $2000 for 1 k sequences 200 bp long; Agilent: $13,000 for 244K sequences 90-bp max; Twist Biosciences $46 k for 1M sequences).

b) high control over sequence content with limited sequence diversity: groups have developed methods to construct DNA libraries by stitching together building blocks using 12-base fragments in a one-pot reaction (Fujishima et al., 2015) or 8-base fragments sequentially on an immobilized system (Horspool et al., 2010). Both of these methods possess constraints which restrict their use for aptamer library construction.

Figure 31:
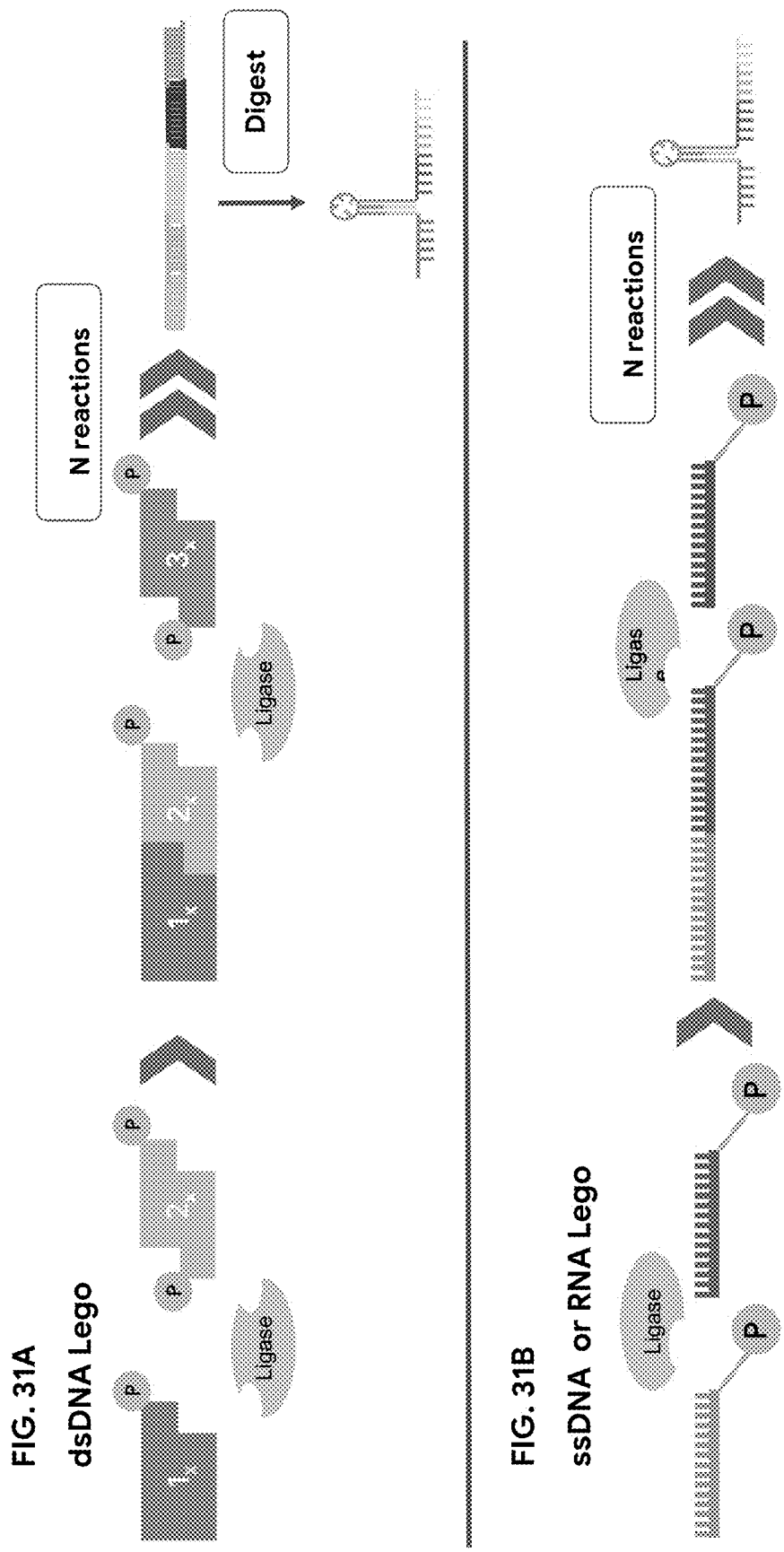
FIG. 31A-31B are schematics showing embodiments of LEGO methods described herein for dsDNA (A) ligation, and ssDNA and RNA ligation (B).
Figure 32:
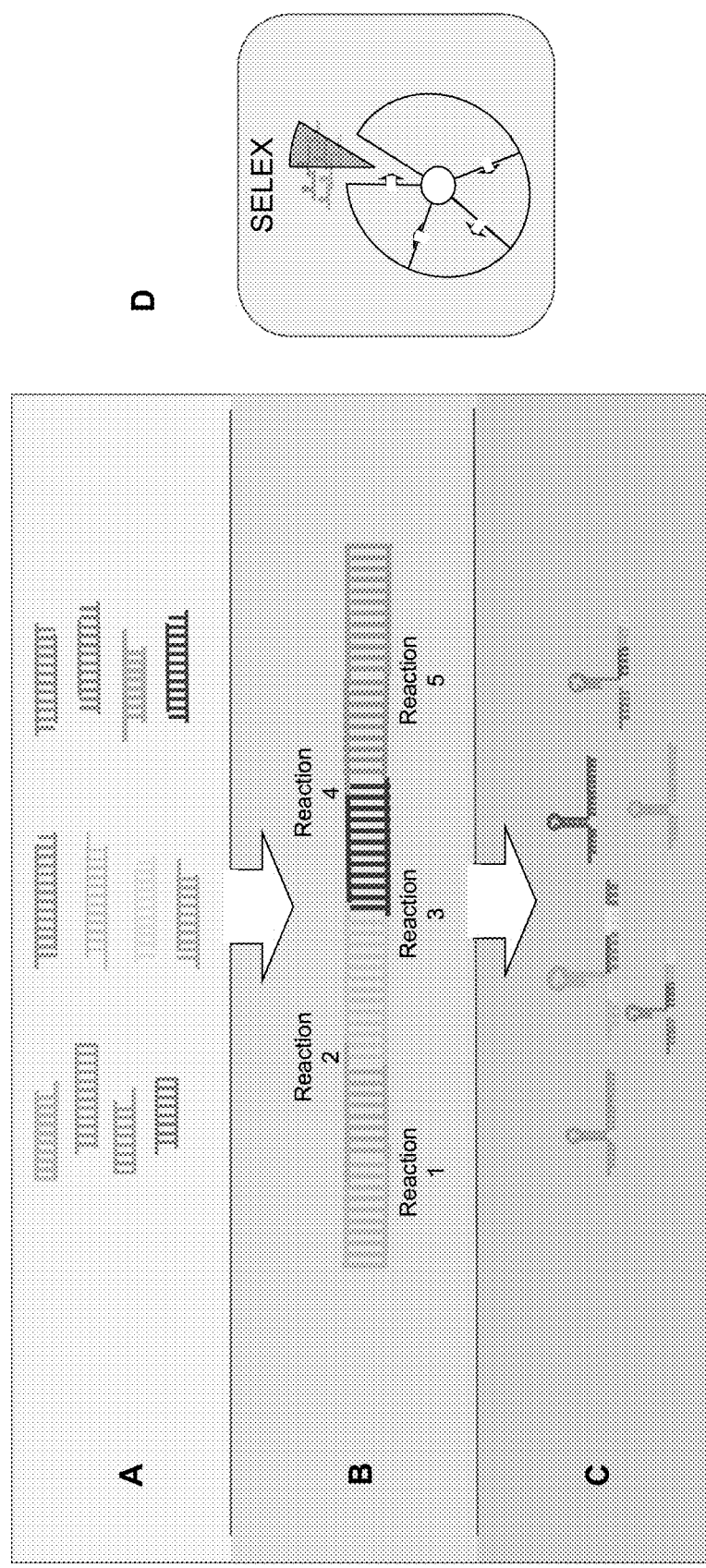

The LEGO methods described herein allows for the construction of computationally-derived, customizable DNA libraries that allow scientists to perform SELEX screens using a controlled input pool at a reasonable cost. It makes use of commercially available ligase enzymes to assemble a library of random 40-mers from sequential ligation of 5-mer or longer DNA LEGO pieces. There are at least two ways this can be done: by double-stranded ligation using a dsDNA ligase such as T4 DNA ligase (FIG. 31A) or by template-independent single-stranded ligation using a ssDNA or ssRNA ligase such as RNA ligase RtcB (FIG. 31B). In both strategies, ligation begins with the linkage of a forward PCR primer to the first LEGO piece, and continues by adding one LEGO piece at a time. The final ligation reaction takes place between the final LEGO piece and the reverse PCR primer (FIG. 32A-32B). Production of the primed 40-mer can be followed by amplification methods such as PCR using a protected forward primer and phosphorylated reverse primer. The PCR product can be cleaned using any preferred method and products of the correct base pair length can be selected using size selection methods such as the automated PippinHT program. The library can then be converted from double to single-stranded DNA, for example, using lambda exonuclease digestion, and the single-stranded product can be cleaned and concentrated (FIG. 32C). FIG. 32D is a schematic that demonstrates where, relative to the SELEX method (FIG. 3), the products of LEGO as described herein can be used.

The methods described herein have several several unique features that make it optimal for creating aptamer libraries:

1) Unique Overhang Design Allows for Positional Control for dsDNA Ligation

Successful ligation between two fragments of double-stranded DNA requires complementary single-base overhangs on both fragments. A pair of DNA blocks possessing compatible overhangs (e.g., A and T, G and C) preferentially ligate together. Blocks with incompatible overhangs (e.g., A and C, G and T, etc.) ligate together significantly less often. By using blocks with different combinations of A, T, C, and G overhangs, block positioning can be controlled. For example, blocks can be encouraged to assemble in the order 1-2-3 instead of 2-1-3, 3-1-2, etc. by designing them such that the overhangs of blocks 1 & 2 are compatible while those of 1 & 3 are not.

2) Short Building Blocks Allow the Whole DNA Space, Including Sequences which are Difficult to Synthesize to be Explored Libraries several magnitudes more diverse than those generated by other ligation methods can be created using shorter LEGO pieces. Using a bank of 1,024 5-mers, the entire space of 40-mer DNA libraries ($10^{24}$ unique sequences) can be generated. With the use of a single 1536 plate, any 40-mer aptamer or feature-spaced library that an experiment demands can be assembled. Additionally, certain sequences (e.g., long chains of G's) are difficult to synthesize accurately by conventional methods. Stitching together many shorter blocks provides a useful way to access these sequences.

It is understood that a number of modifications can be made to the methods described herein. For example:

Library design: while the methods described herein use 5-mers to construct 40-mers, libraries of a different length/multiple lengths from building blocks of a different length/multiple lengths can be built. During DNA synthesis, there is a low rate of 5' phosphorylation for oligonucleotides that are short (i.e. <6 nt) due to steric interactions from the glass substrate. Increasing the length of constructs used will increase the percentage of phosphorylated oligo reagents. However, increasing the lengths of the oligo pieces will require a larger number of different oligo pieces for assembling a library of the desired statistical distribution of sequences.

Building block design: the methods described herein with dsDNA use blocks that have phosphate group modifications on the 5' ends of both strands in order to facilitate ligation of the block to the growing strand and to the next piece in the sequence. Instead, pieces on which there is only one 5' phosphorylation can be used to reduce the potential for a flipped DNA block to be integrated/ligated into growing sequences. Alternatively, ligation-inhibiting modifications could be added onto 5' or 3' strands to discourage ligation of flipped pieces. For ssDNA ligation, the methods described herein use pieces that have 3' phosphorylation modifications, which is required for the RtcB enzyme to facilitate this reaction.

Starting material: XNAs, RNA, modified RNAs, single-stranded DNA or modified DNA, instead of unmodified double-stranded DNA, could be used to construct libraries with compatible ligases.

Linking method: there are multiple ways to connect strands of DNA together. The methods described herein uses T4 DNA ligase or RtcB ssRNA ligase to enzymatically link DNA building blocks together. Different ligase enzyme (ex. E. coli DNA ligase, CircLigase, thermostable ligases, etc.) or link building blocks chemically (e.g., click chemistry) could be used.

Ligation method: instead of doing a one-pot sequential ligation reaction, several smaller ligation reactions could be performed to create large blocks, and then pool the products to ligate the large blocks together. This can increase control over block position.

Medium: instead of doing the library construction in solution, the reaction can be performed on beads, on a solid support, in a gel, etc.

Size selection: in the ligation of these small pieces of DNA together, oftentimes the ligation products are not of the desired length. In order to purify the full-length products, manual and automated size selection methods such as the PippinHT automated DNA size selection system can be used.

Additionally, while the methods described herein can be used to generate random libraries for SELEX aptamer screens, the methods described herein also can be used to generate DNA libraries for different applications, such as:

building ML-derived DNA libraries for peptide/protein generation via translation. A priority in the SELEX aptamer screens described herein is to find aptamers that are specific to their amino acid targets. In order to do so, the same pool of random aptamers can be incubated with peptides of different sequences. Obtaining all the different peptide sequences that may be needed from vendors can be quite expensive, given that, oftentimes, many different variations of the same sequence need to be tested. In order to expand the space of random peptides that is available to use for SELEX, it would be helpful to be able to produce these peptides in-house. The methods described herein of random DNA library generation can produce these peptide libraries via cell-free translation kits or conventional DNA plasmid transformation experiments in cells. Promoter sequences can be included in the design of the adapter region blocks, or ligated on post library generation, and peptides could be generated from these sequences in vivo or in vitro.

building out sequences of DNA barcodes. The key to performing protein sequencing is the ability to encode and subsequently readout a sequence of amino acids. In a number of the protein sequencing methods described herein, DNA barcodes can be used to encode for identified regions of an amino acid sequence. In these methods, when an aptamer binds to the portion of the protein or peptide being sequenced, a DNA barcode region on the aptamer attaches, through any suitable linkage method, to a growing barcode chain. The enzymatic ligation methods described herein can be used to link together the barcodes to form the barcode chain or to attach a barcode to a universal adaptor.

modifying PROSEQ reagents. In a number of the protein sequencing methods described herein, functional aptamers and processed peptides contain regions of DNA such as spacers, barcodes, and ligation consensus regions. For peptides to be sequenced, a shorter oligo linker (e.g., 6 nt), can be conjugated to an amino acid residue to increase the rate of reaction before ligating the rest of the DNA elements in a LEGO-like manner. For aptamers found in SELEX, DNA tails that include a unique barcode for aptamer identity, cycle number, restriction site, etc. can be directly ligated onto the 5' end of the aptamer using a single stranded ligase such as RtcB. Additionally, asymmetric PCR can be employed to modify binders found in SELEX to be used directly on the PROSEQ platform.

The LEGO methods described herein allow for the creation of oligo libraries that can be customized to have certain properties (e.g., GC content, recurring motifs, etc.). These libraries are several magnitudes more diverse than those generated by other ligation methods and can be assembled at a reasonable cost.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Figure 33:
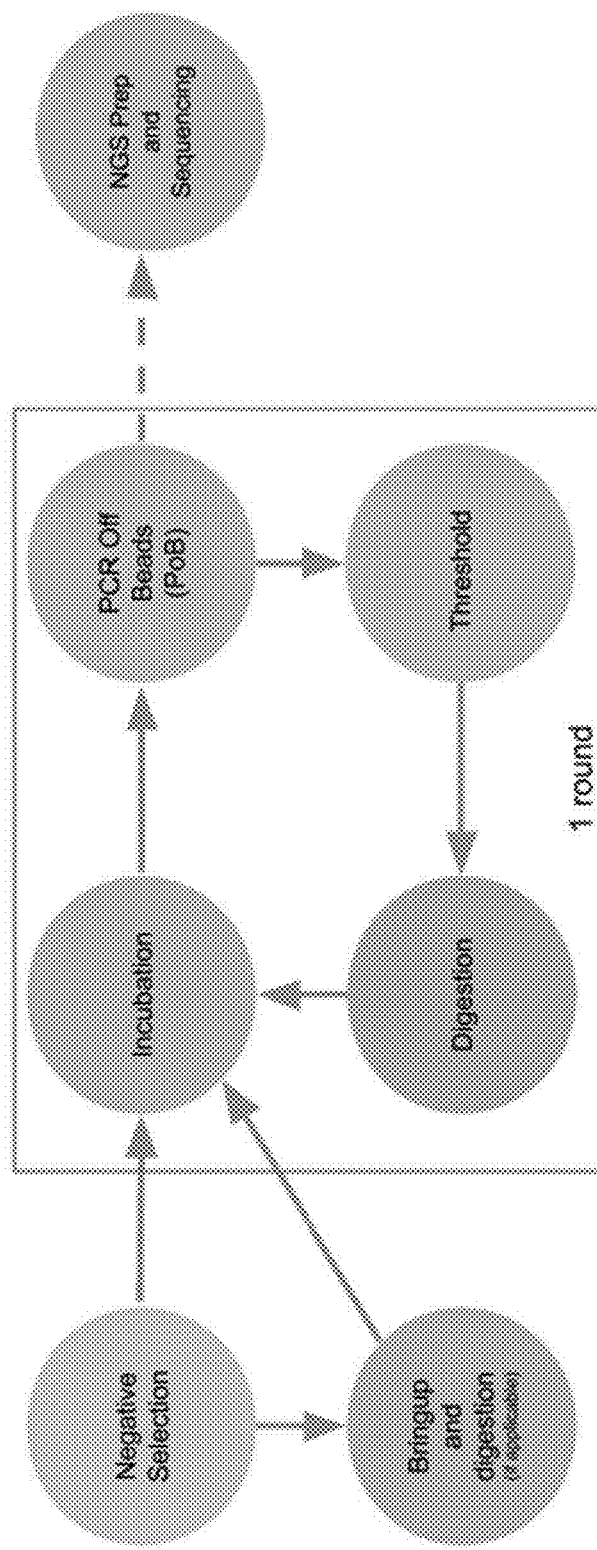

Relevant Information for Both RCHT and N-Terminal Amino Acid SELEX Experimentation
The following will be described below:
A. General methods for all SELEX Experimentation
B. RCHT-SELEX Experimentation
B.1 RCHT-SELEX General Experimentation Part I
B.2 RCHT-SELEX Incubation Variations
B.3 RCHT-SELEX General Experimentation Part II
B.4 RCHT-SELEX Additional Components
C. RCHT-SELEX Results
D. N-terminal Amino Acid SELEX Experimentation
E. N-terminal Amino Acid SELEX Results
F. Generalized SELEX protocol
General workflow for all SELEX (RCHT-SELEX and N-terminal Amino Acid SELEX) experiments is shown in FIG. 33.

Reagents
Aptamer libraries were purchased from TriLink Biotechnologies and IDT, with all other oligonucleotides purchased from IDT or synthesized in-house by K&A LABORGERATE H-8 DNA & RNA Synthesizer. All oligos were purified via HPLC (either IDT internal system or in-house Agilent 1290 Infinity II). All automated procedures were performed on the Agilent Bravo NGS Workstation or Opentrons OT-2. All SPRI purifications utilized Mag-Bind TotalPure NGS beads from Omega Biotek. All DNA quantifications were obtained using dsDNA and/or ssDNA High Sensitivity Qubit Fluorescence Quantification Assay (Thermofisher). A9932 All water used was Ambion™ Nuclease-Free water.

Libraries
Single-stranded N40 aptamer libraries consisted of 40 random bases, flanked by custom primer regions. In order to mitigate contamination by excessively enriched aptamers from past experiments, the primers on N40 libraries were switched every 2-3 months. The initial N40 library (TAGGGAAGAGAAGGACATATGAT TTGACTAGTACATGACCACTTGA (SEQ ID NO:1)) was ordered directly from TriLink Technologies. Subsequent custom primers were designed by using random sequence generator tools to generate putative sequences, cross-validated against in-house primer sets to avoid sequences that were too similar, and then using the IDT Oligo Analyzer to check for melting temperature as well as self and heterodimers. The custom primers were also quality checked using an abbreviated SELEX cycle before being used for the full SELEX process.
N40 libraries used:

Peptides
Biotinylated peptides were synthesized by Genscript. To facilitate attachment of the peptide to biotin, all C-terminal residues were lysines. The construct of each peptide was as follows: N-terminus-(2-mer prefix)-(8-mer suffix)-C-terminus-BIOTIN.

Figure 34:
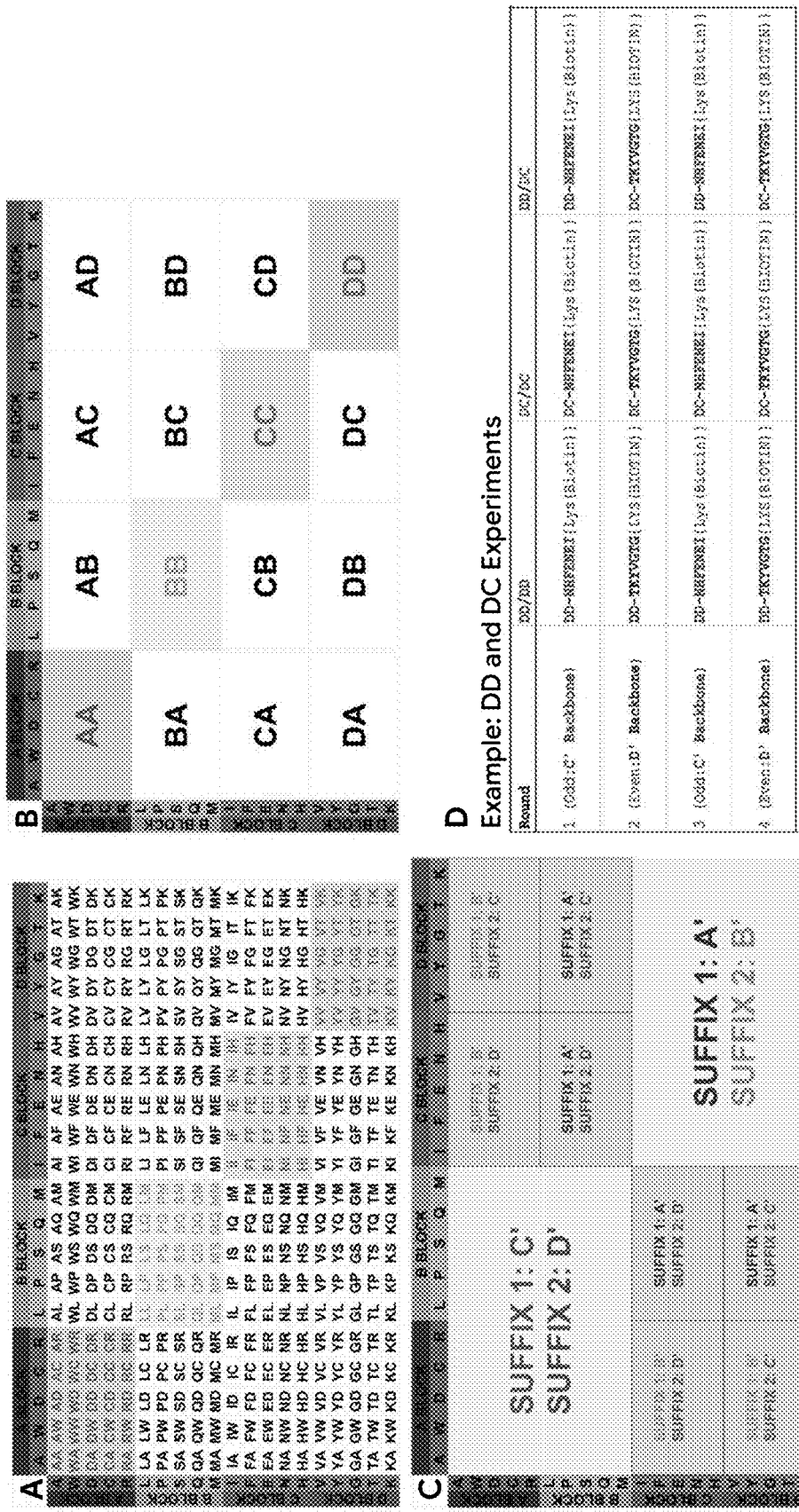

2-mer prefixes: The 20 naturally occurring amino acid prefixes were divided into 4 groups with 5 amino acids each. 2-mer prefixes were determined by pairing amino acids within a block with each other, and with amino acids from other groups. Each 2-mer prefix therefore belonged to one of 16 blocks (with 25 potential 2-mers to a block). In total, there are 400 possible 2-mer prefixes. For reference, the 400 potential prefixes have been depicted in FIG. 34A. The 16 blocks are depicted in FIG. 34B.

8-mer suffixes: For the dipeptide switch experiments, each 2-mer prefix was associated with 2 suffixes, out of four possible suffixes. Furthermore, whether there is a K or C on the end is dependent if the peptide is biotinylated (without DNA oligo attached) or made with a DNA oligo attached (PoC) respectively. These suffixes were:

```
A' suffix:
                             (SEQ ID NO: 5)
ADRWADR(K or C)

B' suffix:
                             (SEQ ID NO: 6)
MSQPLQP(K or C)

C' suffix:
                             (SEQ ID NO: 7)
NHFENEI(K or C)

D' suffix:
                             (SEQ ID NO: 8)
TKYVGTG(K or C)

E' suffix:
                             (SEQ ID NO: 9)
TAYVETE(K or C)

F' suffix:
                             (SEQ ID NO: 10)
QGHSIDN(K or C)
```

The two suffixes assigned to each 2-mer prefix were chosen to avoid similarity with the 2-mer prefix. For example, a 2-mer prefix from the AB block would be associated with the C' and D' suffixes, but not the A' and B' suffixes.

The suffix paired with the 2-mer prefix was alternated between odd and even rounds, with only the 2-mer prefix the constant peptide combination exerting selective pressure on the aptamers through all 4 rounds (FIG. 34C). Examples of

```
SELEX N40 Library1 (also referred to as the TriLink library):
                                                  (SEQ ID NO: 2)
TAGGGAAGAGAAGGACATATGATNNNNNNNNNNNNNNNNNNNNNNNNN
NNNNNNNNNNNNNNNNNTTGACTAGTACATGACCACTTGA SELEX N40 library2 (also referred to as OMB63):
(TTGACTAGTACATGACCACTTGANNNNNNNNNNNNNNNNNNNNNNNNN
NNNNNNNNNNNNNNNNNCACATCAGACTGGACGACAGAA (SEQ ID NO: 3))

SELEX N40 Library 3 (also referred to as OMB105 or Wolverine2):
                                                  (SEQ ID NO: 4)
TGATGCTATGCGACTTATTGTACNNNNNNNNNNNNNNNNNNNNNNNNN
NNNNNNNNNNNNNNNNTACTTGGCGTTCTTACCACCA
``` suffix and prefix combinations for DD and DC prefix experiments are depicted in FIG. 34D.

Section B RCHT-SELEX Experimentation

B.1 RCHT-SELEX General Experimentation Part I

Example 1—RCHT-SELEX Experimentation

Methods
Pre-SELEX Cycle Methods:
Bring Up

Depending on experimental needs, bring ups were performed via one of three variations. All bring ups were performed using 50 microliter PCR reactions, using Herculase II Fusion DNA Polymerase (Agilent Technologies). PCRs were SPRI-purified at a 0.6× ratio using Mag-Bind TotalPure NGS beads (Omega-Biotek) with the addition of 100% ethanol on a Bravo Automated Liquid Handling Platform (Agilent). The amplification conditions for this and all subsequent PCR reactions (with the exception of NGS preparation) were as follows: an initial denaturation at 95° C. for 5 minutes followed by 13 amplification cycles of 30 seconds of denaturation at 95° C., 30 seconds annealing at 55° C., 30 seconds elongation at 72° C., and a final elongation of 5 minutes at 72° C.

To facilitate regeneration of ssDNA libraries for aptamer incubation (detailed in the section on digestion), protected and phosphorylated primers were used. For the following primer constructs, * indicates the nucleotide was modified such that the sulfur atom in the phosphate backbone was substituted for a phosphorothioate bond substitutes a sulfur atom, which renders the sequence more resistant to nuclease digestion.

```
SELEX N40 Library1 (also referred to as the TriLink library):
Forward primer:
                                                    (SEQ ID NO: 11)
5'-T*A*G*G*G*A*AGAGAAGGACATATGAT-3'

(SEQ ID NO: 12)
Reverse primer:
/5Phos/-TCAAGTGGTCATGTACTAGTCAA-3'

SELEX N40 library2 (also referred to as OMB63):
Forward primer:
                                                    (SEQ ID NO: 13)
5'-T*T*G*A*C*T*AGTACATGACCACTTGA-3'

Reverse primer:
                                                    (SEQ ID NO: 14)
/5Phos/-TTCTGTCGTCCAGTCTGATGTG-3'

SELEX N40 Library 3 (also referred to as OMB105 or Wolverine2):
Forward primer:
                                                    (SEQ ID NO: 15)
5'-T*G*A* T*G*C* TAT GCG ACT TAT TGT AC-3'

Reverse primer:
                                                    (SEQ ID NO: 16)
/5phos/-TGG TGG TAA GAACGCCAAGTA-3'
```

Bring Up Variations
Option 1 (Primarily Used):

A sample of $10^{12}$ sequences (~48 ng) from the single-stranded N40 library were amplified across 288 reactions of 50 microliters each. The SPRI-purified product of all 288 reactions were pooled, to give us a final bring up with a diversity of $10^{12}$ sequences with approximately 1200 copies to be split across 12 SELEX reactions. This method was used to identify aptamers to the biological controls bradykinin, argipressin, and GnRH, as well as a subset of the dipeptide switch experiments.

Option 2:

Two samples of $10^{12}$ sequences (~48 ng each, ~96 ng total) from the single-stranded N40 library were amplified across 576 reactions of 50 microliters each. The SPRI-purified product of all 576 reactions were pooled, to give us a final bring up with a diversity of $2\times10^{12}$ sequences, to be split across 36 SELEX reactions. This method provided the input pools for the majority of the dipeptide switch experiments.

Option 3: Double Bring Up:

A bring up was performed in the style of variation 1, but with unmodified primers instead of the protected and phosphorylated versions. Aliquots of the purified bring up (with diversity of $10^{12}$ sequences) were used as a dsDNA input library for a second bring up (of either Variation 1 or 2) with the modified primers. A total of ~48 ng of each dsDNA aliquot was amplified across 288 reactions. The double bring up allows for the same input of $10^{12}$ sequences to be used across multiple sets of experiments, far exceeding the customary 12-18 SELEX reactions to which its distribution is usually limited.

Bring Ups: Spike-Ins

Depending on experimental needs, N40 constructs with known sequences were spiked into the bring up and carried through subsequent rounds of SELEX. These sequences were:

A6: high_gc_5:

(SEQ ID NO: 17)
TAGGGAAGAGAAGGACATATGATCACCGCATCCTGAGGCCGGTGTGGAG
GGCACGAAGTCTGGTTGACTAGTACATGACCACTTGA

C2: high_gc_5:

(SEQ ID NO: 18)
TAGGGAAGAGAAGGACATATGATCTAGCATGGTGCCCTTACCCTCAGAGC
GGAAGTACCTGATTTGACTAGTACATGACCACTTGA

~5.39 million molecules of each spike-in were present in each 50 ul reaction during the initial bring up, making each spike-in 53,947 times more abundant than the average random N40 sequence Refolding Aptamer libraries were heated to 95° C. for 5 minutes and then cooled on ice for 30 minutes to refold the DNA secondary structure into their lowest energy state.

Negative Selection

To remove aptamers that would otherwise bind to reagents consistently present across samples throughout the assay, oligo libraries underwent negative selection before they are used as input for SELEX. 166.62 pmol (4650 ng) of refolded ssDNA library are added to 500 ug of streptavidin coated beads (C1, T1, M270, or M280 depending on experimental needs) and brought to a final volume of 400 ul, at a concentration of 1×PBS, 0.025% Tween, and 10 mg/ml BSA. The reaction is incubated at room temperature (RT) of 22-24° C. with rotation for 30 minutes before the supernatant is collected.

When using peptide-oligo conjugates, the oligo-only tail is selected against. The oligo tail is incubated with a 5' biotinylated oligo with full length complementarity to the oligo tail at a 1:2 tail:complement ratio. Then, a sample containing 1.67 pmol of the oligo tail and 3.34 pmol of the complement are added to 166.62 pmol of the refolded ssDNA library previously negatively selected against beads. The reaction is incubated at room temperature RT with rotation for 30 minutes before adding 200 ug of streptavidin coated beads and incubating for a further 30 minutes. The supernatant from this incubation is then collected as the final negatively selected input.

Digestion

Amplified libraries were converted to single-stranded DNA (ssDNA) by enzymatic digestion using lambda exonuclease (New England BioLabs) and SPRI-purified by automated bead clean up. ssDNA digestion completion was qualified using the small RNA kit (Agilent) on the Bioanalyzer 2100 (Agilent), and the concentration quantified post-clean via a ssDNA Qubit Assay (Thermofisher).

SELEX cycle methods:

Refolding

Before each SELEX incubation, aptamer libraries were heated to 95° C. for 5 minutes and then cooled on ice for 30 minutes to refold the DNA secondary structure into their lowest energy state before every SELEX incubation.

B.2 RCHT-SELEX Incubation Variations

Figure 35:
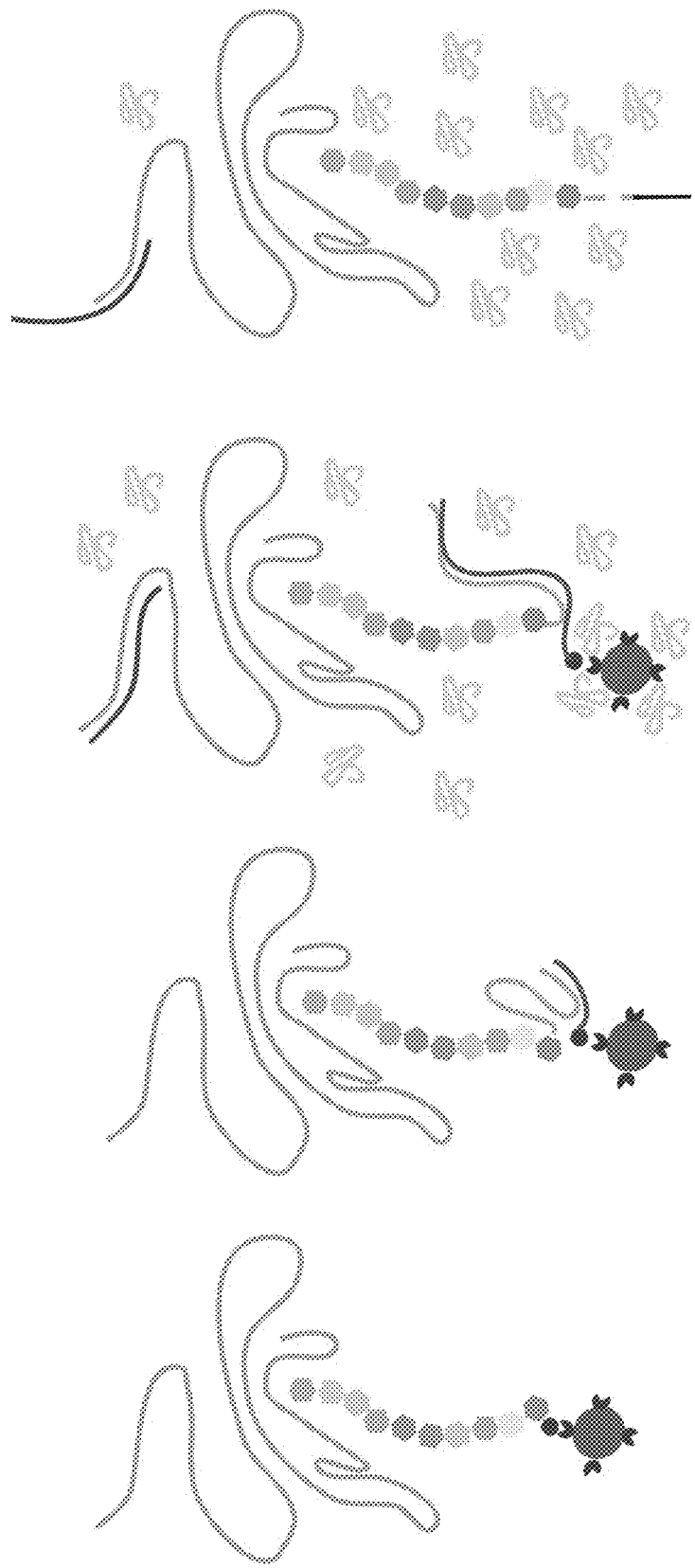

SELEX Incubation:

There are three variations on how the peptide may be incubated with the ssDNA aptamers. With variant 1, the initial SELEX incubation happens in the presence of streptavidin beads (Variation 1: SsDNA incubation with peptide-bead conjugate); with variant 2, streptavidin beads are added after the majority of the incubation is complete (Variation 2: SsDNA incubation with peptide-oligo target followed by bead pulldown). With variant 3, the peptide-oligo target is incubated with a biotinylated primer prior to addition of a partially double-stranded aptamers (Variation 3: (5) Blocked Aptamer incubation with peptide oligo-conjugate, with bead pulldown). See FIG. 35.

In all cases, ssDNA pools were heated to 95° C. for five minutes, then rapidly cooled on ice prior to incubation. For each reaction, up to 166.62 pmol (4650 ng) of folded aptamers were added to the peptide or peptide-bead conjugate and brought up to 400 ul total volume at a final concentration of 1×PBS and 0.025% TWEEN20. The final incubation buffer for variant 3 also incorporates BSA at a final concentration of 10 mg/ml. These buffer conditions can be distinguished as:

SELEX BUFFER V.1 (also referred to as SELEX buffer): 1×PBS and 0.025% TWEEN20

SELEX BUFFER V.2 (also referred to as SELEX buffer with BSA enrichment): 1×PBS, 0.025% TWEEN20, 10 mg/ml BSA These buffers are prepared from 10×PBS (Sigma-Aldrich), TWEEN20 (Sigma Aldrich), and powdered Bovine Serum Albumin (Sigma Aldrich).

Variation 1: SsDNA Incubation with Peptide-Bead Conjugate

Peptide Conjugation with Beads

After deciding on a concentration gradient for the SELEX experiment, the peptide targets on beads can be made in advance in one large batch to avoid round-to-round error caused by multiple conjugations. The beads can be frozen and thawed a single time without any experimental defects. Aliquots for each round were made and stored in either Eppendorf LoBind or Nunc plates in −20'C until taken out to thaw. Unit tests were performed on freshly conjugated beads vs frozen beads to ensure similar properties, and no discrepancies were found. The amount of target to produce should be based on the number of rounds, the starting concentration of the first round and a buffer stock in case there are experimental mishaps. In this example, 1:10 starting ratio of target:DNA aptamers is used. Using the Bravo Automated Liquid Handling Platform (Agilent), 18.5 pmol of peptide was incubated with 87.2 ug (8.72 ul of a 10 mg/ml stock) of MyOne Streptavidin C1 Beads (ThermoFisher) for 30 minutes with mixing. After 2 additional washes with SELEX buffer, each initial mixture of 18.5 pmol of peptide and 87.2 ug of beads was resuspended in 50 ul of SELEX buffer. These numbers were scaled up proportionately in order to create a large volume bead-conjugate stock that could be aliquoted and frozen at the beginning of each experiment. 50 ul of this stock could be added to 4650 ng of input ssDNA for a 1:10 target:ssDNA stringency experiment, and directly scaled down to a smaller volume for experiments with less than 4650 ng of input ssDNA. For experiments with the higher stringency of 1:25, the volume of peptide-bead conjugate added was further scaled down using a multiplier of 0.6×.

Depending on experimental needs, BSA-blocked M280 or T1 beads were used, or unblocked M270 or C1 beads. M280 and M270 beads had a diameter of 2.7 um, and C1 and T1 beads had a diameter of 1 um. Unit tests demonstrated that C1 beads, which manufacturers indicated were best for automation, pulled down different aptamer sequences from a bringup than M280, M270 and T1 beads. The mechanism for this result is unknown. As a result of the unit tests, M280 beads were selected for experiments moving forward since BSA-blocking was preferred to prevent for the selection of aptamers to the bead surface, and the larger surface area targets could provide a platform where individual peptides are placed further apart reducing selection for aptamers that prefer peptide dimerization.

Blank bead 'conjugates' were created by putting a mixture of beads and water through the same automated Bravo protocol, with the full 30 minute incubation and 2-3 wash cycles. Each initial input of 87.2 ug of beads was also resuspended in 50 ul of SELEX buffer, and later added to ssDNA at a ratio of 87.2 ug of beads for every 4650 ng of ssDNA (for 1:10 stringency reactions) or 34.88 ug of beads for every 4650 ng of ssDNA (1:25 stringency reactions).

SELEX Incubation

Up to 50 ul of the bead-conjugate was added to 166.62 pmol (4650 ng) of folded aptamer, and incubated with rotation at RT for 2 hours.

Streptavidin-Biotin Pulldown

Streptavidin M280 beads (Invitrogen) were added to the SELEX incubations at 83.33 ug for every 51.02 pmol of peptide present for 30 minutes under rotation.

Variation 2: SsDNA Incubation with Peptide-Oligo and Aptamer Incubation Followed by Bead Pulldown Peptide Conjugation No conjugation is required before incubation for this variation. Target is a peptide-oligo.

SELEX Incubation

Amount of added target depends on the desired stringency gradient. Often for small molecule targets a range of 1:1 to 1:10 (target:ssDNA) stringency conditions were used as starting conditions, held through target switch rounds and then the ratio between target:DNA was increased in subsequent rounds until sequencing data demonstrated enrichment for aptamers. Here, the methods used for an approach for a starting with a 1:10 target:ssDNA is described. For rounds 1 and 2, 166.62 pmol (4650 ng) of folded aptamers were directly added to 18.51 pmol of the peptide-oligo construct, for a stringency of 1:10 target:ssDNA. To account for the reduced 1:25 stringency in rounds 3 and 4, 166.62 pmol (4650 ng) of aptamer was directly added to 7.40 pmol of the peptide. The peptides and ssDNA were incubated for 2 hours with rotation at RT.

Streptavidin-Biotin Pulldown

In cases where targets had DNA oligo tails, a biotinylated primer (5' Biotin TAGGGAAGAGAAGGACATATGAT 3' (SEQ ID NO:19)) that anneals to part of the oligo tail was added to the SELEX incubations at a 1:2 peptide:biotinylated oligo ratio for every 51.02 pmol of peptide present for 30 minutes under rotation. The primer had two functions: (1) to prevent aptamers from binding to the DNA oligo tail, and (2) to allow for the target to be pulled down via a biotin-streptavidin reaction that would occur post-incubation. Streptavidin M280 beads (Invitrogen) were then added to the SELEX incubations at 83.33 ug for every 51.02 pmol of peptide present for 30 minutes under rotation. After the incubation with the beads allowing for the biotin-streptavidin reaction to come to completion, the beads were pulled down with a magnet (manually or with automation), washed and prepared for PCR.

Variation 3: (5) Blocked Aptamer Incubation with Peptide Oligo-Conjugate, with Bead Pulldown Incubation Solution Preparation (POC and Biotinylated Primer Incubation)

In addition to blocking a region of the tail portion of the peptide-oligo conjugates (POCs), a portion of the aptamer can also be blocked to prevent unnecessary binding between the primer region of the aptamer and the region of the DNA tail on the POC. POCs were added to a 5' biotinylated primer complementary to the length of the oligo tail at a 1:2 POC:biotinylated primer ratio. 10×PBS, TWEEN-20, BSA, and water were added to bring each reaction to a final 265 ul solution at 1×PBS, 0.025% TWEEN-20, and 0.1509 mg/ml BSA. The entire solution was incubated with rotation for 30 minutes at RT.

The POC input for each reaction was determined by the anticipated aptamer input. An example method is presented below for a 1:10 target:ssDNA stringency round. For rounds 1 and 2, 18.5 pmol of POC was prepared for an input of 166.62 pmol (4650 ng) of aptamers, culminating in a stringency of 1:10 target:ssDNA. In this particular gradient, after two rounds of 1:10 stringency, the next two rounds were accelerated to a 1:25 stringency to increase the signal of the enriched aptamers. It should be noted that increasing a stringency too quickly, or starting a stringency too high, will result in loss or no true aptamer signal. However, increasing a stringency too slowly, or starting at a stringency that does not generate competition between binders will result in time and resources lost to additional rounds of SELEX required before enrichment can be seen. In this example, to account for the reduced target needed for the 1:25 stringency in rounds 3 and 4, the amount of POC prepared for a 166.62 pmol (4650 ng) aptamer input reduced to 7.40 pmol.

SELEX Incubation

The peptides and ssDNA were incubated for 2 hours with rotation at RT. The final incubation buffer for the 400 ul reaction was 1×PBS, 0.025% TWEEN20, and BSA-matched concentration to the Hybridization Buffer used in BCS experiments (see below in Example 3—ProSeq Experimentation and Example 4—BCS Binding Assay Experimentation, variations ranged from 0.10 mg/ml-10 mg/ml).

POC Controls

For negative controls for Variation 3 of SELEX, aptamers are incubated with just the POC's oligo tail and no peptide.

Possible oligo tails for this purpose are as follows:

/5phos/cttagatgcacgtggataAT-
CATATGTCCTTCTCTTCCCTA (SEQ ID NO:20)

/5phos/cttagatgcacgcagcatAT-
CATATGTCCTTCTCTTCCCTA (SEQ ID NO:21)

Streptavidin-Biotin Pulldown

Streptavidin M280 beads (Invitrogen) were added to the SELEX incubations at 83.33 ug for every 51.02 pmol of peptide present for 30 minutes under rotation.

B.3 RCHT-SELEX General Experimentation Part II

Post-SELEX cycle methods:

Post-Incubation Wash (Applicable for all Variants)

The bead-peptide-aptamer conjugates were collected using an automated wash protocol on the Bravo. Each SELEX reaction was incubated on a magnetic plate for 2 minutes. Supernatant containing unbound aptamers was aspirated away and the beads were washed two times with SELEX buffer, followed by a final wash with 1×PBS. The 1×PBS was aspirated at the end of the protocol.

PCR on Beads

Immediately after the automated wash protocol finished, 50 ul of PCR solution was added to each well with beads. Unmodified variants of the bring up primers were used to amplify the 86 nt construct, except for the Wolverine2 library which is 84 nt long (full library constructs previously provided in the description of the libraries).

NGS Preparation

After PCR amplification on beads, DNA concentrations were measured via Qubit dsDNA assay and 10 ng samples of SPRI-purified PCRs on beads were taken for NGS preparation. Each aptamer identified from sequencing these samples were associated with the 6 bp barcode of the peptide they putatively bound to in solution. The P5 and P7 adapters required for Illumina sequencing were incorporated through PCR with custom NGS primers (5'-CAAGCAGAA- GACGGCATACGAGAT-(Forward primer)-3' (SEQ ID NO:22) and 5'-AATGATACGGCGACCACCGAGATCTA-CAC-(Reverse primer)-3') (SEQ ID NO:23). The forward and reverse primer regions are variable, depending on which N40 library was used for SELEX. The amplification conditions for these PCR reactions were as follows: an initial denaturation at 95° C. for 5 minutes followed by 10 amplification cycles of 30 seconds of denaturation at 95° C., 30 seconds annealing at 65° C., 30 seconds elongation at 72° C., and a final elongation of 5 minutes at 72° C. The final NGS library was SPRI-purified, pooled, and size-selected for 177 bp constructs via PippinHT (Sage Science).

Threshold PCR

For each SELEX reaction, 4.08 ng of the SPRI-purified product from the PCR on beads was amplified across twenty-four 50 ul PCR reactions using the custom modified primers for each library (sequences provided in the Bring Up section). The SPRI-purified dsDNA product of this library is an 86-bp (or 84-bp for Wolverine2 library) amplicon with the same construct as the original N40 library, with protected and phosphorylated ends that will facilitate enzymatic digestion of the reverse strand. The regenerated ssDNA library serves as the input for the next round of SELEX.

SELEX Cycles

The protocol steps between aptamer refolding, target selection, aptamer incubation, unbound separation, washing, amplification, NGS sample pull, threshold amplification, ssDNA library generation, and refolding can be repeated as a 'SELEX round' until enriched aptamers are discovered in the NGS sequencing data. Bring ups and initial negative selections are not repeated between rounds.

B.4 RCHT-SELEX Additional Components

Fake SELEX

During the first 2 hours of Variation 2 of SELEX, negative controls are incubated with just water and SELEX buffer. After each round of SELEX, samples from Fake SELEX were sequenced in order to determine the effects of PCR bias (since no enrichment should occur due to the lack of a target. Fake SELEX is useful in computational analysis and ML modeling of aptamers to train models to focus on the enrichment signal of the aptamer counts instead of the noise of operator error, contamination, PCR bias or other experimental or instrument noise.

BCS Compatible Aptamer Preparation

BCS, or the application of the DNA aptamers in ProSeq, requires a modification of the primer regions of the aptamers to include the correct ligation, restriction enzyme and spacer sequences to facilitate the binding and recording events in BCS. A unique barcode, however, is not required since sequencing can proceed through the entire aptamer sequence in order to record which aptamer bound to which target on the BCS chip. There are a few ways to convert the aptamer library into a BC S-compatible one, however the fastest, cheapest and most high-throughput method is to use PCR to modify the primer regions of the aptamers. To this end, ssDNA pools (up to 166.62 pmol for each reaction) were added to a 23 nt oligo "bridge mimic" complementary to the forward primer region of the aptamer at a 1:10 aptamer: bridge mimic ratio. The solution was brought up to a 135 ul solution at 1×PBS and 0.25% TWEEN 20. The mixture was heated to 95° C. for 5 minutes, rapidly cooled on ice, then added to the incubation solution.

For SELEX N40 Library 3 (aka OMB105, Wolverine2) which has the construct (SEQ ID NO: 24)
5'
TGATGCTATGCGACTTATTGTACNNNNNNNNNNNNNNNNNNNNNNNNN
NNNNNNNNNNNNNNNNNTACTTGGCGTTCTTACCACCA 3'

And the forward primer (SEQ ID NO: 25)
5' TGATGCTATGCGACTTATTGTAC 3'

The bridge mimic used was (SEQ ID NO: 26)
5' GTACAATAAGTCGCATAGCATCA 3'

Bead-Based Multiplex SELEX

This assay was almost identical to SELEX, with the exception that multiple peptides were added to each reaction. Peptides were separately conjugated with beads at the beginning of the experiment and aliquoted into individual stocks, to be mixed in equal molar proportions at the beginning of the SELEX incubation. The first four rounds were processed via the customary bring up/threshold PCR, digestion, incubation, automated wash, and PCR on beads cycles. To demultiplex in the final round, N*4.08 ng of each reaction resulting from PCR on beads was amplified across N*24 reactions, with N being the number of peptides that were concurrently incubated with the aptamer pool. SsDNA from this reaction was incubated in individual SELEX reactions at a stringency of 1:50, with only one peptide present in each reaction.

After using the Bravo's automated wash protocol to wash away unbound aptamers, 50 ul of PCR solution were added to each demultiplexed well. The SPRI-purified product of each of these PCR reactions was barcoded during NGS prep and sequenced to reveal the aptamers associated with each peptide in isolation.

Primer Switch

The custom primers flanking the N40 regions are excised and replaced with alternative primer sequences between rounds. The purpose of this primer switch is to mitigate contamination by excessively enriched aptamers from experiments using the same N40 library.

The current primer switch design was designed for the TriLink N40 library. By amplifying the original N40 construct (5'TAGGGAAGAGAAGGACATATGATNNNNNNNNNNNNNNNNNNNNNNNN
NNNNNNNNNNNNNNNNNNTTGACTAGTACATGACCACTTGA (SEQ ID
NO: 27)) with primers TriLinkFwd FokI
(5'TAGGGAAGAGGGATGAAGGACATATGAT (SEQ ID NO: 28))
and TriLinkRev FokI
(5'TCAAGTGGTCGGATGATGTACTAGTCAA (SEQ ID NO: 29)), a FokI restriction site is introduced to create
the new full length construct
TAGGGAAGAGGGATGAAGGACATATGATNNNNNNNNNNNNNNNNNNNN
NNNNNNNNNNNNNNNNNNTTGACTAGTACATCATCCGACCACTTGA (SEQ
ID NO: 30)).

By digesting this altered PCR product with Fok1 (NEB), a nuclease that cleaves 9 bp and 13 bp downstream of its restriction site (5' ... GGATG(N)$_9$/3' ... CCTAC(N)$_{13}$ (SEQ ID NO:31)), we cleaved off (5' TAGGGAAGAGGGAT-GAAGGACATA (SEQ ID NO:32) and 5' TTGACTAGTA-CATCATCCGACCACTTGA (SEQ ID NO:33)), leaving sticky ends. End-filling this construct with Klenow fragment (NEB) leads to the creation of blunt ends. Incubating this blunt-ended double-stranded library with new double-stranded primers and ligase completes the protocol, leaving us with our original N40 library with a new primer set swapped in. The success of each digestion and ligation event was analyzed via the Bioanalyzer Small RNA kit (Agilent).

Plate Layouts

In order to minimize the effects of local contamination between proximate wells, technical replicates (3 per experimental condition) were spatially randomized across different rows and/or different plates. For the dipeptide switch experiments, none of the technical replicates were adjacent to each other. This allowed computational filtering of noise during post-sequencing analysis.

Section C RCHT-SELEX Results

Bring Up

Figure 36:
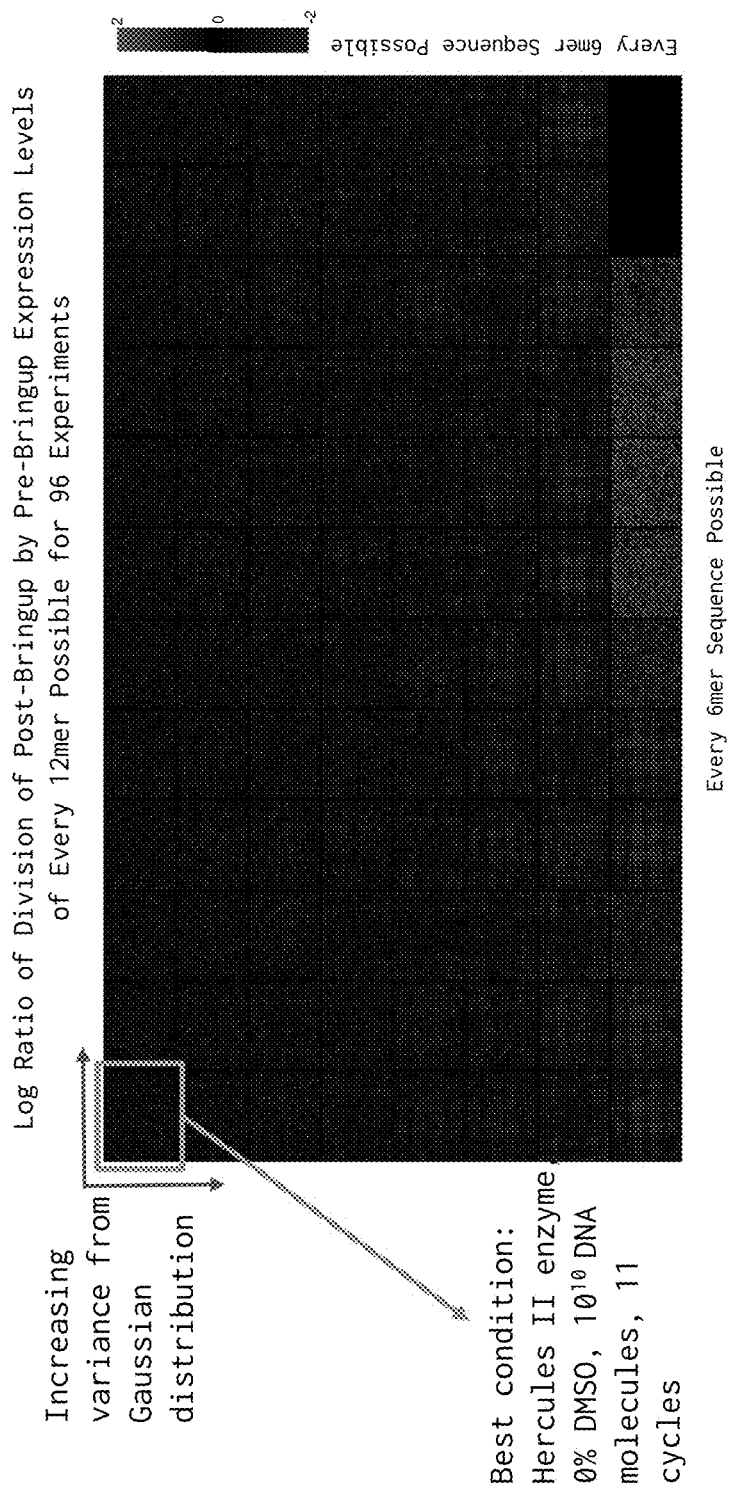

For the bringup, 96 unit tests were conducted to determine optimal bringup conditions for the each library, defined as the condition that introduces the least bias or variation in expression levels of all combinations of 6-mers possible after the bringup was performed. The expression intensities of every combination of 6-mer possible from the sequencing runs of DNA pools after the bringup divided by the expression intensities prior to the bringup. The best conditions for the OMB63 library resulting in the least variation in expression levels of every combination of 6-mers was 11 PCR amplification cycles, using Herculase II Fusion DNA Polymerase and 0% DMSA, with input of $10^{10}$ DNA molecules (FIG. 36).

Fake SELEX

Top 20 sequences from a random sampling of 100,000 sequences from Fake SELEX samples and real SELEX rounds were confirmed to be different, suggesting that DNA pools post-SELEX incubation were altered by the presence of bead-conjugated targets rather than a result of pulling down random sequences (FIG. 37). Fake SELEX analysis can be used to determine PCR bias elements during a SELEX experiment, and also be used to train models towards the ground truth of a positive aptamer signal.

Digestion

Bioanalyzer Small RNA kit traces show single clear peaks after digestion process at approximately 75 nt, which, considering the error of measurement in the technique, correlates to ssDNA product size desired (86 bp for most SELEX libraries) (FIG. 9C). Confirmation of complete conversion of dsDNA PCR product to ssDNA occurred prior to the introduction of each aptamer library into each new round of SELEX.

Threshold PCR

Unit tests have shown that threshold PCR introduced minimal bias. Comparing the sequencing data of the DNA prior to and after a threshold PCR run indicated that threshold PCR results in low variance (0.132 variance of log ratio) in the distribution of sequences between the pool prior to and after threshold PCR (FIG. 11B and FIG. 11C).

Replicate Experiments

Figure 38:
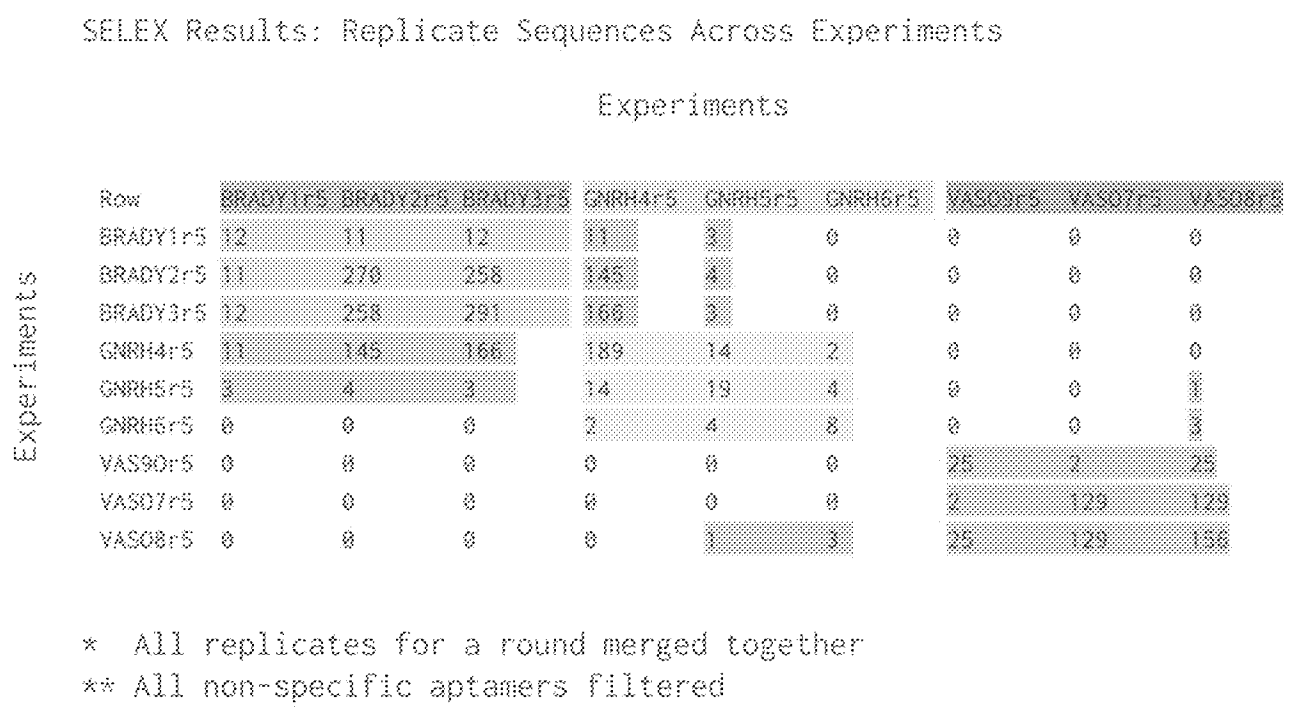

Aptamer sequences from the same bringup replicated across experiments of the same targets up to round 5, giving greater confidence in identified aptamers. Wells in which bradykinin and GNRH experiments were conducted were physically adjacent on the same plate. Within a biocontrols SELEX experiment, significant bleedthrough between targets bradykinin and GNRH were detected, allowing for detection of spatial contamination (FIG. 38). As a result, randomization of sample placement occurred on each plate, where different targets were positioned on the same row with no spaces inbetween each experiment and replicates of the same target were positioned with a distance of 2 columns between each replicate to reduce contamination. After significant evaluation, it was found that the contamination observed was a result of reagent carryover from automation.

Aptamers

Biocontrols

Figure 39:
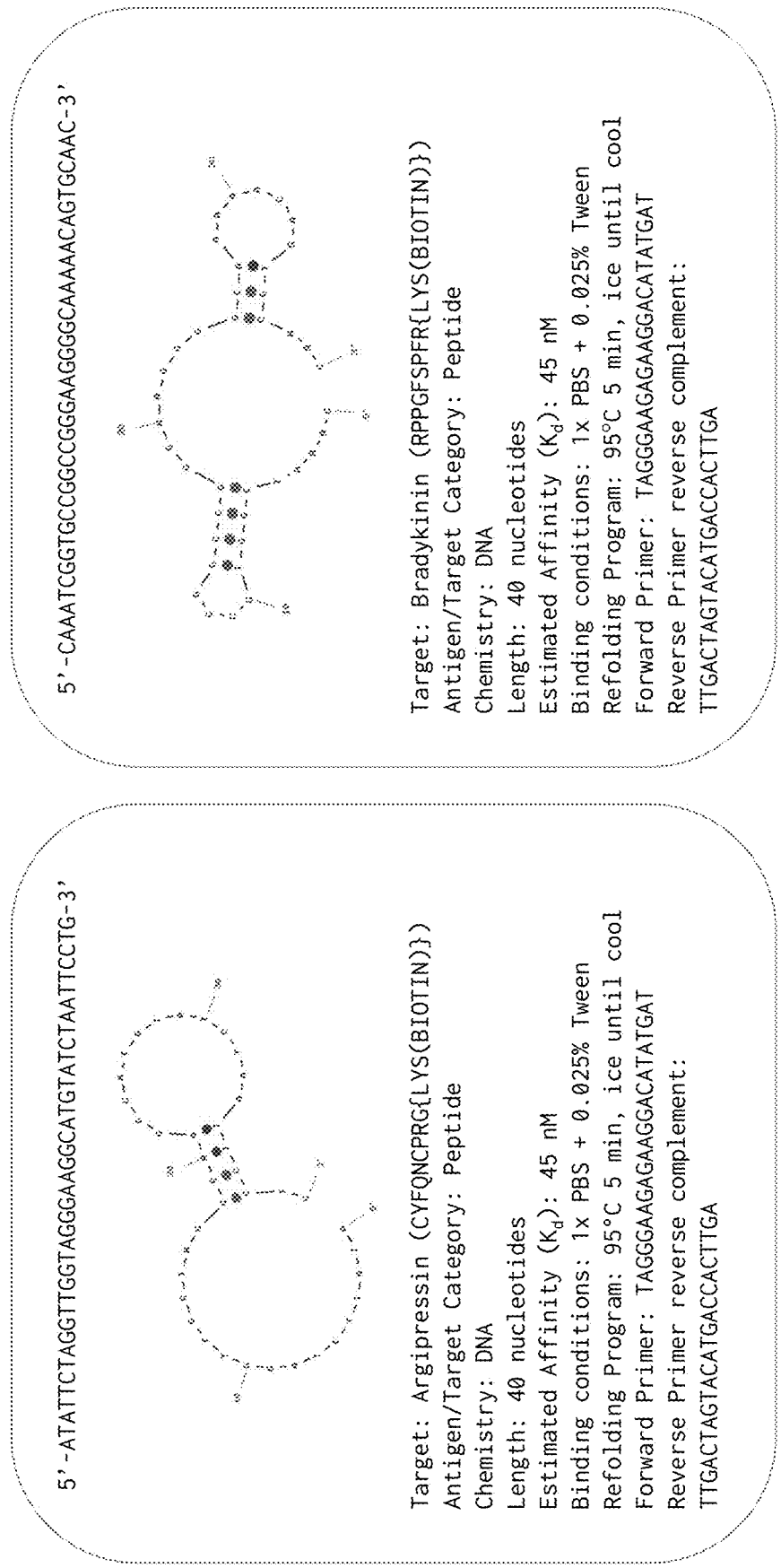

As proof-of-concept of the RCHT-SELEX process, DNA aptamers to argipressin (peptide sequence: CYFQNCPRG{LYS(BIOTIN)} (SEQ ID NO:34) and bradykinin (peptide sequence: RPPGFSPFR{LYS(BIOTIN)} (SEQ ID NO:35)) were identified to have high binding affinity with an estimated equilibrium dissociation constant ($K_d$) value of 45 nM based on the experimental conditions of SELEX incubation (FIG. 39). Further characterization of the aptamers can be performed to determine the $K_d$ with and without the primers. The N40 binding region sequences of the identified aptamers for each target are:

```
argipressin:
                                        (SEQ ID NO: 36)
5'-ATATTCTAGGTTGGTAGGGAAGGCATGTATCTAATTCCTG-3' bradykinin:
                                        (SEQ ID NO: 37)
5'-CAAATCGGTGCCGGCCGGGAAGGGGCAAAAACAGTGCAAC-3'
```

Both aptamers were flanked by the following primers during RCHT-SELEX:

```
Forward primer:
                                        (SEQ ID NO: 38)
TAGGGAAGAGAAGGACATATGAT Reverse primer reverse complement:
                                        (SEQ ID NO: 39)
TTGACTAGTACATGACCACTTGA
```

The same bringup was assayed against argipressin and bradykinin in 3 replicate experiments for each target; the identified sequences replicated in experiments of the same target, and did not replicate in experiments with different targets. The findings suggested that these aptamers may be specific aptamers for argipressin and bradykinin peptides, and useful for the detection of these targets in samples.

Peptide Switch

Within Block A peptide switch experiments, sequences serially enriched for specific N-terminal amino acids. Representative top aptamers for lysine and cysteine, defined as aptamers with the highest sequence counts after filtering for noise, are reported in FIG. 40. Both sets of aptamers were flanked by the following primers during RCHT-SELEX:

```
Forward primer:
                                        (SEQ ID NO: 40)
TAGGGAAGAGAAGGACATATGAT Reverse primer reverse complement:
                                        (SEQ ID NO: 41)
TTGACTAGTACATGACCACTTGA
```

Future experiments can be conducted to characterize and validate identified aptamers for protein sequencing.

SECTION D N-Terminal Amino Acid SELEX Experimentation

Example 2—N-terminal Amino Acid SELEX

Reagents

DNA libraries were purchased from TriLink Biotechnologies and all DNA primers were purchased from Integrated DNA Technologies with HPLC purification. All peptides were purchased from Genscript. 10×PBS and Tween-20 were purchased from Sigma-Aldrich. Lambda Exonuclease and buffer were purchased from New England Biolabs. Mag-Bind Total Pure NGS beads were purchased from Omega-Biotek. The bioanalyzer and all reagents, the Bravo liquid handler, and Herculase II Phusion polymerase and buffer were purchased from Agilent. Tubes, plates, and thermocyclers were purchased from Eppendorf. Nunc plates were purchased from VWR. Both 70% and 200 proof ethanol was purchased from Fisher Scientific. Nuclease-free water, $MgCl_2$, Bovine Serum Albumin, dNTP mix, Dynabeads M280 Streptavidin, and QuBit reagents were purchased from Thermo Scientific.

Methods

Figure 41:
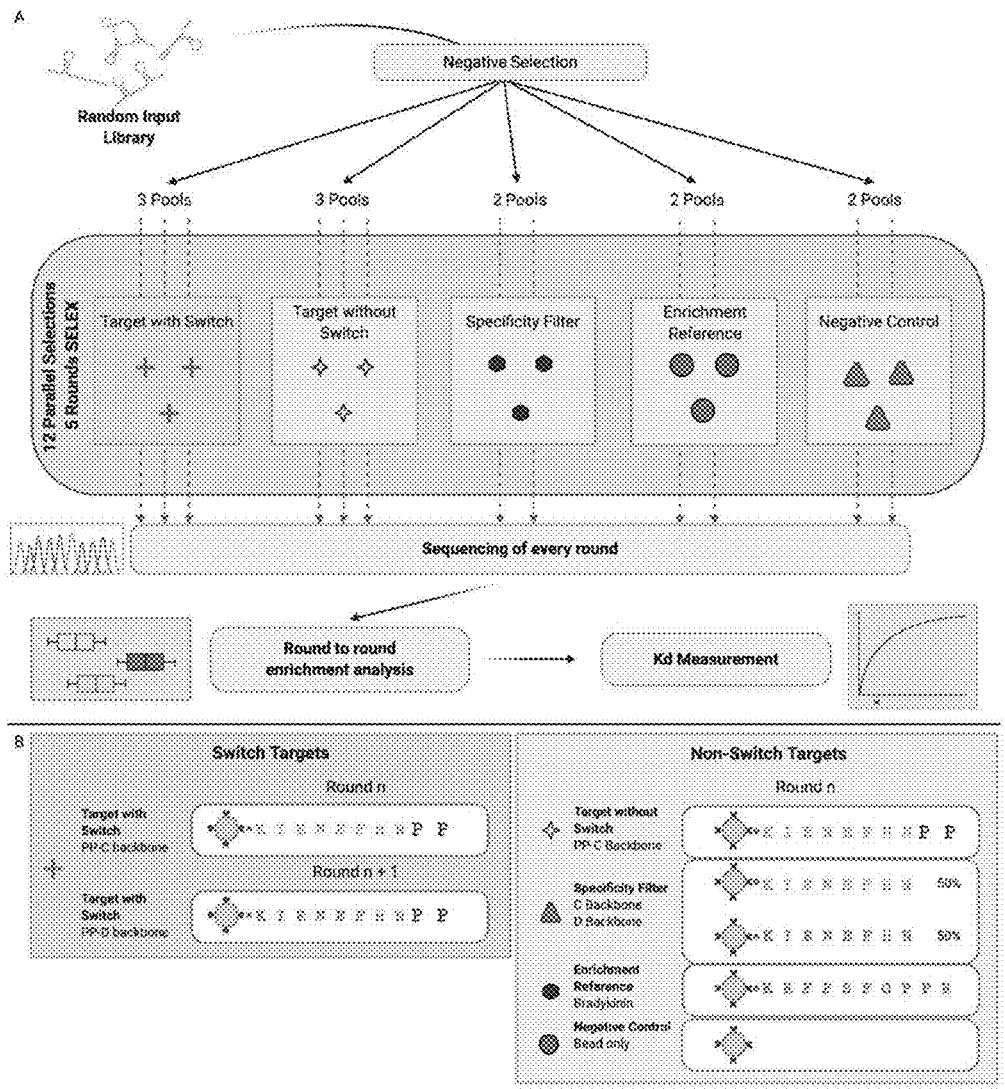
FIG. 41A. is a schematic diagram of the N-terminal Amino Acid SELEX experiment strategy of Example 2. 12 selections comprising replicates of each target mixtures were run for 5 rounds in parallel. The workflow begins with a negative selection against streptavidin beads on an initial pool of ssDNA and split across 12 random pools. 2 parallel selections were performed on each control reference target and 3 parallel selections on the target (Proline-Proline) with and without the switching of backbones (C and D backbones) in alternating rounds. A representative pool of ssDNA from every round of every selection was sequenced and analyzed for round-to-round enrichment of sequences.
FIG. 41B reports the target compositions and amino acid sequences (SEQ ID NOs:194-203) in Non-Switch and Switch SELEX.

In this example, aptamers specific to the dipeptide Proline-Proline (PP) were isolated using the N-terminal Amino Acid SELEX method (FIG. 41). 12 selections were run in parallel, against 5 total targets: 2 targets of interest and 3 control targets. 3 selections were run against each target of interest and 2 selections against each control target. All rounds of positive selection were sequenced and used for analysis of enrichment across rounds and targets. Additionally, automation was used in several steps to ensure minimization of potential errors across samples and to facilitate running parallel selections. For this experiment, the dipeptide, PP, was chosen as the N-terminal dipeptide of interest because it's bulky cyclic side chain allows multiple potential binding sites. PP targets were 10-mer peptides with two prolines at the N-terminal and an 8 additional amino acid region ("backbone"), followed by a C-terminal conjugated biotin (biotinylated targets) or DNA tail (PoC targets). To increase the chances of isolating an aptamer specific to the N-terminal PP dipeptide, both "switch" and "non-switch" targets were utilized, with multiple selections for each. Targets are referred to as PP-C for PP targets with the C backbone ("non-switch") or PP-D for PP targets with the D backbone ("non-switch"). If both targets were used in the selection ("switch"), they are referred to as PPCD Target-Bead Conjugation Target-bead conjugations were performed fresh before each round of incubation. Biotinylated peptide targets were conjugated to M280 streptavidin beads using the Agilent Bravo liquid handling platform. Beads were vortexed to homogeneity before 25 uL beads were added to the appropriate volume for 75 ng peptide target for each conjugation reaction. The beads and target incubated on a chilled plate (4° C.) for 2 minutes to allow the biotin and streptavidin to interact and form a tight bond before the beads were washed several times with SELEX buffer (1×PBS, 0.025% Tween-20, 0.1 mg/mL BSA, 1 mM $MgCl_2$). The final product of the bead conjugation reaction was resuspended in 50 uL of SELEX buffer.

Negative SELEX

DNA aptamer generation was carried out with a protocol involving aptamers in solution and biotinylated targets conjugated to streptavidin beads. The initial library of $10^{15}$ aptamers was pulled from the library stock and underwent 30 minutes of negative selection against 50 ul 10 mg/mL streptavidin beads in SELEX buffer. The supernatant was kept and put directly into a positive selection against the peptide targets. This positive selection was the first step of 5 rounds of SELEX with the following workflow: selection, amplification (small-scale PCR and large-scale PCR), and single strand generation.

Positive SELEX

Prior to every selection step, aptamers were annealed in Refold Buffer (1×PBS, 0.025% Tween-20, 1 mM $MgCl_2$) for 5 minutes at 95° C. and at least 30 minutes at room temperature (RT) of 22-24° C. Selections were carried out in SELEX Buffer for 30 minutes (negative selection) or 1 hour (positive selections) with rotation. Stringencies for each round for "Switch" and "Non-Switch" incubations are reported in Table 2.1.

TABLE 2.1

Stringencies by Round and Target Type

| Round | "Non-Switch" Stringency | "Switch" Stringency | "Switch" Backbone |
|---|---|---|---|
| 1 | 1:1 | 1:1 | C |
| 2 | 1:2 | 1:1 | D |
| 3 | 1:5 | 1:2 | C |
| 4 | 1:10 | 1:2 | D |
| 5 | 1:25 | 1:5 | C |

Amplification was performed in two steps: small scale PCR and large scale PCR. After washing off non-binders, the remaining target-aptamer conjugates were put directly into a small-scale PCR reaction of 1 reaction (50 uL) per sample. PCR reaction conditions consist of all of the DNA retained from the wash steps, 3 uM forward primer, 3 uM reverse primer, Herculase buffer, 0.2 mM DNTP, 0.0.5 units/L Herculase polymerase in a final volume of 50 uL.

After this PCR reaction was cleaned, an aliquot of the products was placed into a large-scale PCR with 24 reactions of 50 uL each. The purpose of this large-scale PCR was to amplify the DNA as much as possible without introducing excess PCR bias. PCR reaction conditions consist of 0.17 ng DNA, 6 uM forward primer, 6 uM reverse primer, 1× Herculase buffer, 0.2 mM DNTP, 0.5 units/uL Herculase polymerase in a final volume of 50 uL.

Both small scale and large scale PCR was performed using a Mastercycler Nexus with conditions as follows: 5 min at 95° C., 13 cycles of 95° C. for 30 seconds, 55 C for 30 seconds, 72° C. for 30 seconds, and 72° C. for 5 minutes. PCR reactions were purified using Mag-Bind® TotalPure NGS beads from Omega Bio-Tek and were performed using the Agilent Bravo liquid handling platform. ssDNA and Mag-Bind® TotalPure NGS beads were incubated at a 3:5 ratio and washed with 70% ethanol.

To generate single stranded DNA from the large scale PCR products, digestion with lambda exonuclease was performed at optimized times. Digestion was tracked qualitatively using a bioanalyzer. Cleaned digestions were quantified and used as input into the next selection.

NGS preparation and Sequencing

Samples after the SELEX rounds were prepared for sequencing. The samples were normalised to a concentration of 10 ng/ul. A 50 ul PCR reaction (2 ul of 6.25 uM forward and reverse primers, 10 ul of 10 ng/ul DNA sample, 36 ul Master Mix) was set up for each sample to amplify the DNA and the reaction was performed using the Mastercycler Nexus (PCR condition: 98° C. for 5 minutes, 10 cycles of 98° C. for 30 seconds, 65° C. for 30 seconds, 72° C. for 30 seconds and 72° C. for 5 min). After the reaction, the PCR product was cleaned (Agilent Bravo liquid handling platform). The Tapestation was then used to quantify the size of the PCR product to determine if the PCR reaction was successful. The samples should have DNA size of 170-190 bp. The concentration of the PCR product was determined using the qubit dsDNA assay. The PCR products were then pooled in a tube according to the concentrations of each product. The concentration of the pooled products were determined using the qubit dsDNA assay. PCR product was purified by selecting DNA size 177 bp (Pippin Prep system, Sage Science). The concentration of the purified product was determined using the qubit dsDNA assay. After purification, 10 uL of the purified product was finally sent for NGS sequencing.

Analysis

Figure 42:
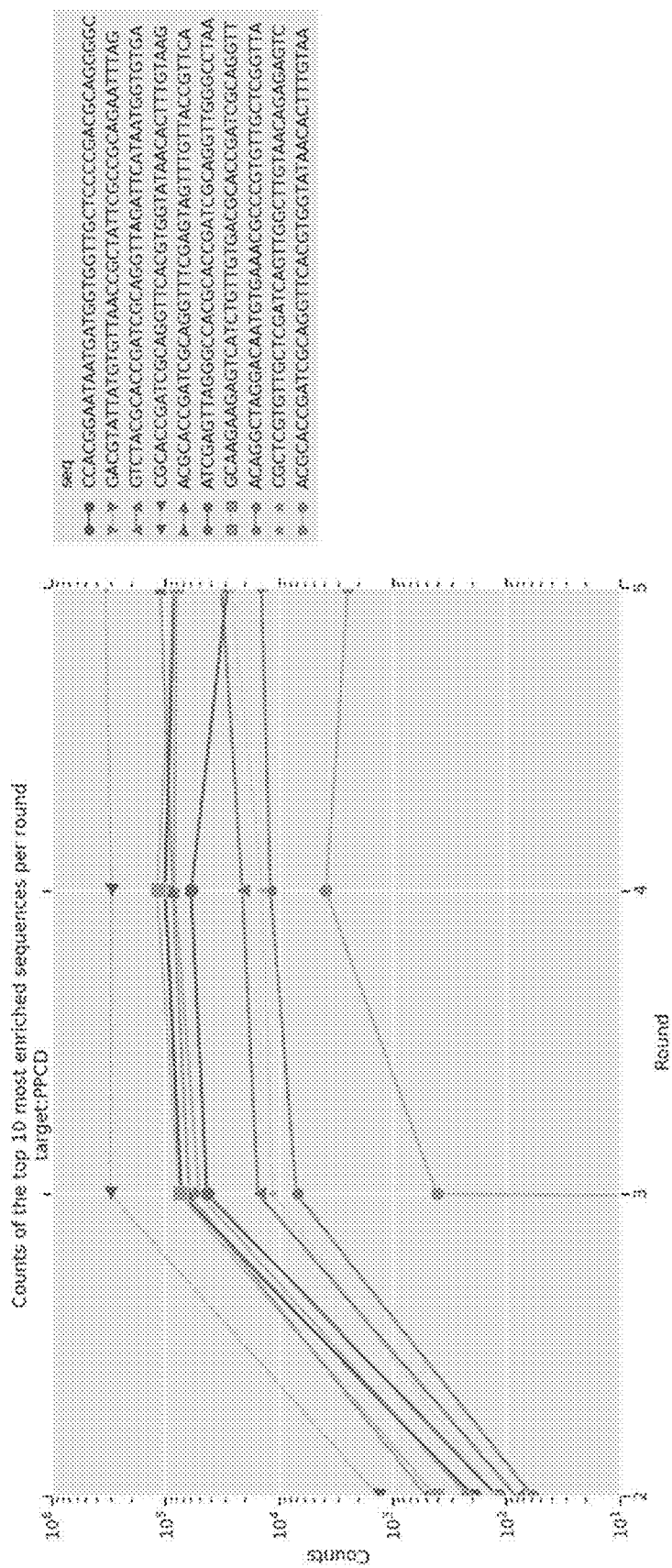
FIG. 42 reports the sequencing counts of the top 10 most enriched sequences per round. X axis is the round of SELEX, Y axis is the number of counts seen during sequencing for the 10 sequences. The 10 sequences displayed were chosen because their calculated enrichment values.
Figure 43:
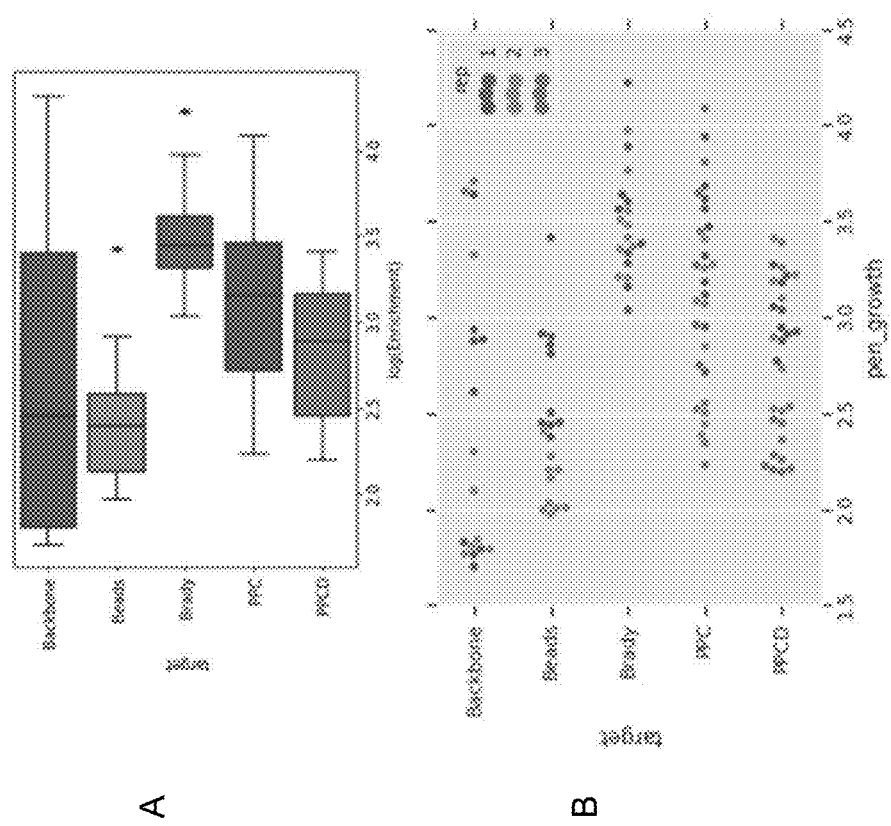
FIG. 43A is a box plot summarizing the enrichment of the top aptamers for each target. Specifically, enrichment was calculated from round 2 to round 5. Each boxplot shows the summary (minimum, first quartile, median, third quartile, and maximum) for the top ten aptamers from each selection performed for the given target. Total number of sequences for Backbone, Brady, Beads=20, Total number of sequences for PP-C and PPCD=30). X axis is in log scale and shows the enrichment. Y axis is the target of each selection. The median enrichment for PPCD switch is higher than the negative control (Beads), but lower than the positive control (Brady).
FIG. 43B is a categorical scatter plot reporting differences in enrichment among the top most enriched sequences for each selection for each target. Two selections were performed for Backbone, Beads and Brady each. Three selections were performed for PPC and PPCD. (Total number of sequences for Backbone, Brady, Beads=20, Total number of sequences for PPC and PPCD=30). Y axis is target, x axis is enrichment (pen_growth). For some selections/replicates (rep), higher enrichment was seen for the same target. For example, high enrichment (>3, equivalent to 1000-fold) was seen for 3 unique sequences in rep 2 while only 1 unique sequence in rep 1 in the selections performed for the target Backbone.
Figure 44:
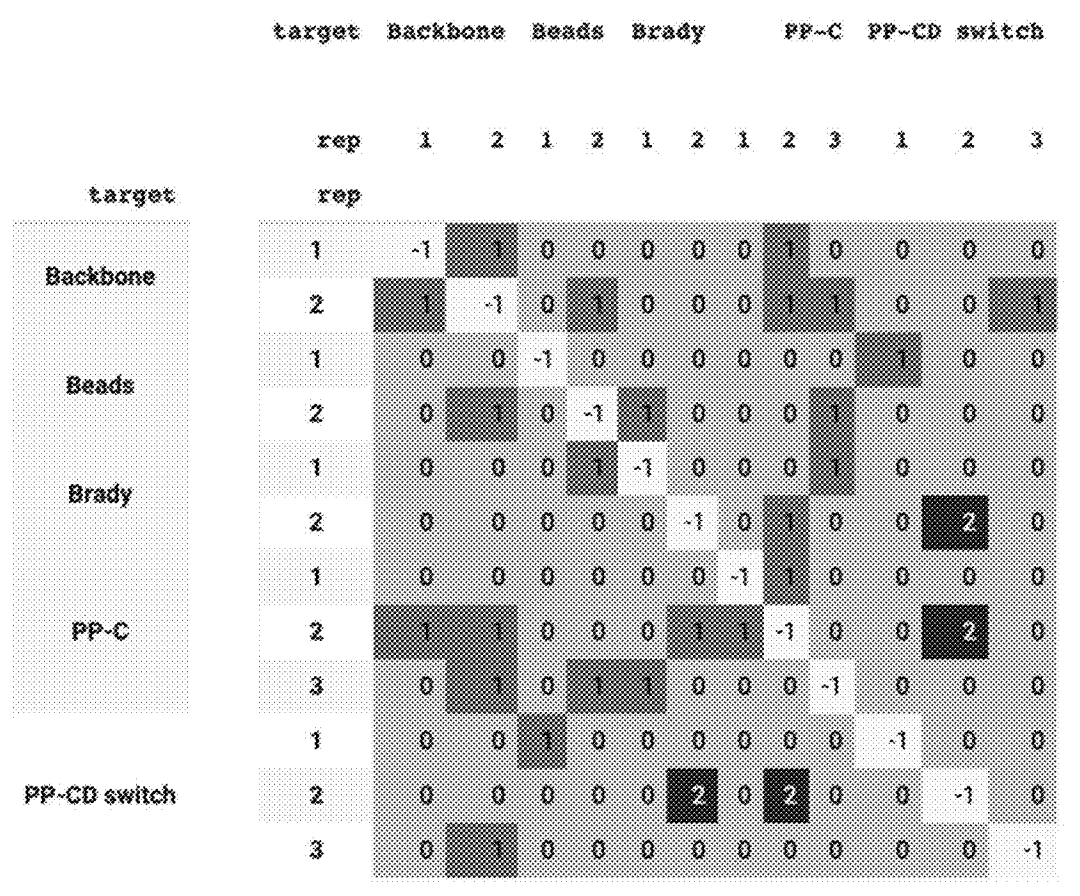

Rapid increase in enrichment for all targets was observed from round 2 to 3 and plateaued over rounds 3 to 5 (FIG. 42). Additionally log enrichment values around 3.5, 3.2, and 3.0 for aptamers bound to Brady, PP-C, and PP-CD targets respectively were observed, indicating that these targets had putative binders (FIG. 43A). To examine these binders further, the top 10 binders by enrichment per replicate for each target was pulled out (FIG. 43B). Enrichment for binders to each target clustered among experimental replicates, indicating that selections for these targets were isolating binders of interest. Further analysis of experimental replicates of binders to targets indicates that overall there is little overlap between binders in different replicates (FIG. 44). Due to the size of the initial random pools, there is little chance that identical sequences would be found in different experimental replicates or to different targets, suggesting that these are instead contaminant sequences, allowing for the filtering of these likely contaminant sequences prior to testing. These candidates were further filtered down to a short list of candidates to test binding characteristics in vitro.

To identify the final aptamer sequences to fully characterize, two filtering steps were performed. Candidate aptamers from PP-CD targets that had high enrichment (greater than 2, which correlates to at least 100-fold increase from R2 to R5) and which bound selectively to PP-CD (binders that did not bind other targets) were chosen. Filtering candidate sequences resulted in 26 candidates of which 10 were selected for final testing. These final ten candidates were chosen based on a variety of factors: highest enrichment ratio, total sequencing counts, representation within each selection replicate and zero sequence contamination in selection replicates.

Enrichment Calculation (Formulas Defining Growth and Pen_Growth:)

The number of times a given aptamer sequence appeared in the sequencing data set is the aptamer count. Two rounds of SELEX are defined, "before" and "after", as the subset of sequencing data to track the unique aptamer sequences. "Before" is the subset from round 2 and "after" is the subset from round 5. A logarithmic scaling factor was applied to each aptamer count to accommodate the wide range of aptamer counts, from 0 to $10^5$ $$before = \log_{10}(before_{ct}+1)$$

$$after = \log_{10}(after_{ct}+1)$$

Growth is defined as the enrichment of a given aptamer between the "before" round, round 2, and the "after" round, round 5.

$$growth = after - before = \log_{10}[(before_{at}+1)/(after_{at}+1)]$$

A raw_penalty value was calculated that penalizes sequences that have low count numbers in both round 2 and round 5, multiplied it by a factor γ and applied it to the growth factor by subtracting the product of γ and raw_penalty.

$$raw\_penalty = \sqrt[t]{10^{-after}/n_{after} + 10^{-before}/n_{before}}$$

$$\gamma = 1.26$$

$$pen\_growth = growth - \gamma \cdot raw\_penalty$$

Technicality: If efore<c, c can be used in the formulas instead, where:

$$c = 2\log_{10}\left(\frac{\gamma}{2}\log(10)\right) - \log_{10}(n_{before})$$

$K_d$ Measurement 200 pmol peptide (PP-C, PP-D) was conjugated to 100 uL Dynabeads™ M-280 Streptavidin (Thermo Scientific) following manufacturer's protocol and resuspended to original concentration in SELEX buffer. 5 mg fluorescein biotin (Biotinium, #80019) was resuspended in DMSO. 650 pmol fluorescein biotin was conjugated to 100 uL Dynabeads™ M-280 Streptavidin (Thermo Scientific) following manufacturer's protocol, as a positive control, and resuspended to original concentration. 5' end FAM labelled aptamer candidates #1-10 were purchased from IDT. Aptamers were synthesized with forward primer and reverse primer complements and tested with the full length. The full sequence of each aptamer is as follows: 5'-TTGACTAGTACATGAC-CACTTGA-N40-TTCTGTCGTCCAGTCTGATGTG-3' (SEQ ID NO:42). N40 sequences of aptamers tested is reported in Table 2.2

TABLE 2.2

Aptamer candidate sequences tested.

| | Random Region N40 only |
|---|---|
| Apt 1 | GACGGTACAGCTTAGTGAATTGCCCCCCGACGCAGGGGTT (SEQ ID NO: 43) |
| Apt 2 | TTTGCCGCTGTCTGACGCAAGACCACATCAACTTTATTTC (SEQ ID NO: 44) |
| Apt 3 | CGCTCGTGTTGCTCGATCAAGGGTCTGTGCGTCTAGCTGG (SEQ ID NO: 45) |
| Apt 4 | ACACCCAGACACCGCTGTCCGACGCAGGACTGACTGGGGC (SEQ ID NO: 46) |
| Apt 5 | AACGACCGGTTAGACTGTGACCGCTTATCGCCGCAGATAT (SEQ ID NO: 47) |

TABLE 2.2-continued

Aptamer candidate sequences tested.

Random Region N40 only

| Apt 6 | CGCATCCGGCGCAGGATTCAAGCGGGATTGTAAGGTAAGA (SEQ ID NO: 48) |
| --- | --- |
| Apt 7 | GACATTGCCCTTCGCCGCAGAAGTGATGAAAGGGTTTGTG (SEQ ID NO: 49) |
| Apt 8 | CGCTCGTGTTGCTCGATCAAGTGGACTAGAATTTGCTTCT (SEQ ID NO: 50) |
| Apt 9 | CCACGGAATAATGATGGTGGTTGCTCCCCGACGCAGGGGC (SEQ ID NO: 51) |
| Apt 10 | ACGCACCGATCGCAGGTTCACGTGGTATAACACTTTGTAA (SEQ ID NO: 52) |

Peptide conjugated beads were diluted to 0.03 mg/mL, or 1:320 of original concentration for the binding assay. 100 uL diluted peptide conjugated beads or fluorescein conjugated beads were aliquoted into individual wells of a 96 well plate. Plate was placed on a magnetic rack for 2 minutes and the supernatant was removed. 100 uL of 5' end FAM labelled aptamer candidates at varying concentrations (0, 100 nM, 250 nM, 500 nM, 750 nM, 1 uM, 2.5 uM, 5 uM, 10 uM, 20 uM), diluted in SELEX buffer, was added to the appropriate well. Plate was sealed with plate seal (AB 0558 Adhesive PCR film, ThermoFisher) and rotated in the dark at room temperature for 1 hour. After incubation, seal was removed and beads were washed 3 times with 100 uL SELEX buffer and resuspended in 100 uL SELEX buffer. Beads were transferred to a black plate and single endpoint fluorescent readout was measured using a plate reader (Biotek).

Note, this is one method of performing a binding assay to measure $K_d$. Other methods, which will produce even more accurate measurements include: microscale thermophoresis, biolayer interferometry, flow cytometry and surface plasmon resonance.

Section E N-Terminal SELEX Results

Figure 46B:
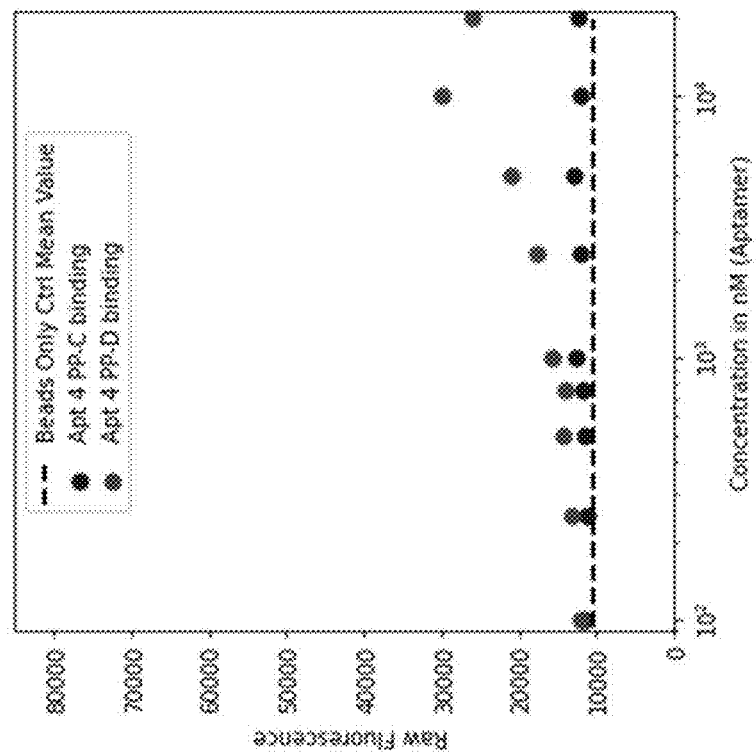
FIGS. 46A and 46B are binding curves for Apt 1 and Apt 4 respectively. Apt 1 (Panel A) shows increasing signal against PP-D, much greater than against PP-C. It looks to saturate against PP-C, while not saturating against PP-D, indicative of non-specific binding. Apt 4 (Panel B) shows saturation binding against PP-D and no binding against PP-C.
Figure 46A:
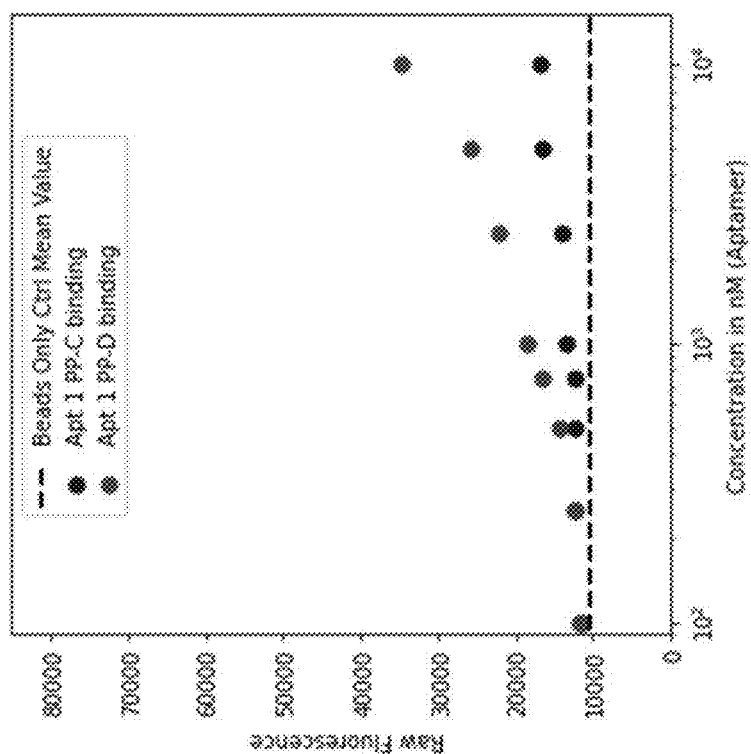

Aptamers were tested via plate-based $K_d$ measurement method described above. At a single concentration (100 nM), 7 aptamers showed higher fluorescent signal than the controls (non-aptamer and buffer only) towards the target PP-D. One aptamer showed higher fluorescent signal than controls towards the target PP-C(FIG. 45). Two aptamers were chosen for further testing, Apt 1 and 4. Apt 1 showed potential saturation binding towards PP-C but non specific binding towards PP-D (FIG. 46A). Apt 4 showed saturation binding towards PP-D but no binding towards PP-C (FIG. 46B).

Section F Generalized SELEX Protocol

Above are listed a wide variety of methods that were used, optimized and utilized in order to achieve aptamer binders from SELEX results, however for each application of SELEX described here: (1) RCHT-SELEX for ML-analysis or (2) N-terminal binder aptamers with NTAA-SELEX, there were different combinations of methods employed. Below is a template protocol that can be used to decipher the combination of methods required.

Overall Workflow:
1. Negative Selection
2. Bead conjugation
3. Amplification
4. Single Strand Generation/Antisense Digestion of Bringup
5. Incubation
6. Amplification off Incubation Beads
7. Threshold Amplification
8. Single Strand Generation/Antisense Digestion of Threshold
9. Counter Selection Equipment Protocols:
1. Qubit: Qubit was used to measure DNA concentration according to manufacturer protocols.
2. Bravo: Three types of protocols were run on the Bravo liquid handler: (1) PCR clean ups ("large volume" and "variable volume"), (2) Bead conjugations ("bead conjugation") and (3) Bead washing ("Wash no elute post SELEX"). For PCR clean ups, the Bravo was programmed to follow the manufacturer's guidelines for using Mag-Bind TotalPure NGS. For Bead conjugations, the Bravo was programmed to follow the manufacturer's guidelines for using Dynabeads™ M-280 Streptavidin. Incubation time and buffer was optimized for the peptide being conjugated. For bead washing, the Bravo was programmed to perform 3 washes of the peptide beads (after incubation with aptamer). The plate was incubated on a magnet for 2 minutes. The first two washes were performed with SELEX buffer, and the last wash was performed with 1×PBS. After the last wash, the beads were not resuspended but left in the plate for the next step of the SELEX protocol.
3. BioAnalyzer: Two types of protocols were run on the Agilent 2100 Bioanalyzer with 2100 Expert software. Library quality checks and post-PCR quality checks were performed using high sensitivity DNA chips with the high sensitivity DNA protocol according to the manufacturer's instructions. Post-digestion/single-strand generation quality checks were performed using small RNA chips with the Small RNA Series II protocol according to the manufacturer's instructions.

TABLE 2.3

| SELEX Stringency Gradients: | | | | | |
| --- | --- | --- | --- | --- | --- |
|  | R1 | R2 | R3 | R4 | R5 |
| Gradient 1 | 1:10 | 1:10 | 1:25 | 1:25 | n/a |
| Gradient 2 | 1:5 | 1:10 | 1:25 | 1:50 | 1:100 |

SELEX Buffer: 1X PBS, 0.025% tween-20, 1 mM $MgCl_2$, 0.1 mg/mL BSA, Nuclease-free $H_2O$ Technical Terms:

Fwd RC: forward reverse complement of the 5' end of the aptamer. This is a mimic of the bridge used in BCS because it makes the 5' end of the aptamer double stranded.

POC: Peptide-Oligo-Conjugate: this is the target of SELEX, i.e. what we are finding aptamer binders to. The POC is created from a 10-mer peptide and a 41 nt ssDNA tail.

bt peptide oligo comp: also known as peptide primer, biotinylated primer, DNA tail complement, blocking piece. This piece is the complement of the ssDNA "Tail" region of the Peptide-Oligo-Conjugate (POC). This piece has a biotin on the 3' side to bind to streptavidin beads, and is a full "block" of the oligo tail of the POC. It is incubated with the POC at a 2:1 ratio prior to incubating this target with aptamers.

Tail: Refers to the DNA tail that is conjugated to a peptide in the PoC (but may be used alone without peptide attached).

Backbone: also known as the suffix. This is the 8-mer region on dipeptide targets (both biotinylated and PoC) that is between the N-terminal dipeptide and the C-terminal conjugated biotin (biotinylated targets) or DNA tail (PoC targets). Backbones are named by the following convention: [letter]' (example: C' or D').

Stringency: this corresponds to the ratio of target:aptamer. For example: 1:10 stringency means there are 10 aptamers sequences for every 1 target, and vice versa 10:1 stringency means that there are 10 targets for every 1 aptamer. 10:1 is not very stringent, whereas 1:100 is extremely stringent.

Positive Selection: A selection where the aptamers are incubated with their targets, pulled down, and the supernatant is discarded (contains non-binders).

Negative Selection: A selection where the aptamers are incubated against random surfaces (tube sides, beads, etc), and the supernatant is kept (contains sequences that do not bind to random surfaces).

Counter Selection: A selection where the aptamers are incubated against things that closely resemble the target (example: different dipeptide or a backbone only), and the supernatant is kept Workflow Negative Selection (Beads Only or Beads+Tail)

Purpose: to eliminate aptamers from the library that have a high binding affinity for the beads.

1. Dilute input ssDNA ($10^{15}$ molecules) into refolding solution (1×PBS, 0.025% Tween-20, 1 mM $MgCl_2$, NF $H_2O$). Total volume is 150 uL.
2. Annealing (refolding aptamer): Heat to 95° C. for 5 minutes and cool on bench for 30 minutes.
3. Wash 55 uL of 10 mg/mL M280 beads in 500 uL of SELEX buffer 3 times. Resuspend in 55 uL of SELEX buffer
4. Incubate 50 uL of washed M280 beads in 200 uL of modified SELEX buffer (1×PBS, 0.025% Tween-20, 1 mM $MgCl_2$, 0.16 mg/mL BSA, NF $H_2O$) with cooled annealed library solution (150 uL) for 30 minutes with rotation in 1.5 mL lo-bind tube.
5. Place tube in magnetic rack and wait 1 minute for beads to fully aggregate next to the magnet.
6. Take supernatant (~200 uL) and transfer to new tube.
7. Measure DNA concentration using Qubit ssDNA kit. Typical expectation concentrations are in the range of 8-20 ng/uL.

Bead Conjugation

Purpose: Biotinylated peptide targets are conjugated to streptavidin beads that magnetically pull down aptamer binders during incubation.

Note: Peptide-bead conjugates can be made ahead of time and aliquoted in 96-well eppendorf plates for freezing (1 freeze/thaw cycle maximum), or made before each incubation to be used fresh.

1. Dilute stock peptide to appropriate concentration so that peptides and beads can be combined at the ratio of 200 pmol peptide target to 1 mg of Dynabeads M280 beads (according to the manufacturer's protocol).
2. Pipette in corresponding amounts of peptide and water to a volume of 50 uL per well into a 96-well eppendorf plate.
3. Pipette in corresponding amount of M280 Streptavidin beads into a NUNC plate, only filling wells that will be used.
4. Using a liquid handler, run protocol "bead conjugations". This performs the incubation, mixing and washing steps as defined by the manufacturer.
5. Dilute peptide beads to appropriate stringency, aliquot, and store at −20° C.

Amplification (Bring Up)

Purpose: create more copies of each aptamer of the negatively selected library.

1. Prepare a master mix using a 50 mL conical tube. Master Mix: 3 uM forward primer, 3 uM reverse primer, Herculase buffer, 0.2 mM dNTP, 0.5 units/uL Herculase polymerase in a final volume of 16000 uL (This is a total of 320 reactions of 50 uL per reaction). Each 50 uL reaction should have 0.17 ng DNA.
2. Aliquot master mix across 3 96 well plates, with 50 uL per reaction.
3. Seal 96 well plate and place in thermocycler using the following PCR protocol: 95° C. for 5 min, (95° C. for 30 sec, 55° C. for 30 sec, 72° C. for 30 sec)×13 cycles, 72° C. for 5 min, 4° C. Hold.
4. Pool 3 plates into one plate of 150 uL reactions.
5. Clean on liquid handler using protocol "large volume". This uses the manufacturer's protocol for Mag-Bind TotalPure NGS beads.
6. Pool bring-up into one 5 mL eppendorf lo-bind tube.
7. Measure the concentration of double stranded DNA using QuBit dsDNA kit to check concentration. Typically, concentrations are in the range: 40-90 ng/uL.

Single Strand Generation (Digestion of a Bringup)

Purpose: lambda exonuclease is used to digest the antisense strand of the double stranded DNA. ssDNA must be generated so that the aptamer can bind to the target.

1. Set up single strand generation reaction according to Lambda Exonuclease (M0262, NEB) manufacturer's specifications (For a 50 uL reaction, use up to 5 ug DNA, 5 uL 10× Reaction buffer, 1 uL lambda exonuclease and up to 50 uL $H_2O$). Add 10× reaction buffer to DNA first, vortex to mix. Add lambda next, pipet to mix.
2. Incubate reaction at 37° C. for 10-20 minutes depending on DNA input concentration.
3. Heat inactivate the exonuclease by incubating at 72° C. for 10 minutes, hold at 4° C.
4. Check the quality of DNA after digestion by running the DNA product on the Bioanalyzer small RNA kit according to manufacturer's protocol. If the traces show that there is still a double stranded product, add the same amount of lambda exonuclease as the original reaction and extend the incubation at 37° C. for 5-10 minutes. Check quality again.

5. Pool the DNA onto one plate and clean up on liquid handler using protocol "variable volume". This uses Mag-Bind TotalPure NGS beads according to the manufacturer protocol.
6. Check DNA concentration using the QuBit ssDNA kit. Normally the concentration is around or above 30 ng/ul.

PoC Target Incubation—No Bead Conjugation

Purpose: to incubate the aptamer library with the targets to see which aptamers bind to the targets.

This incubation is used for PoC targets ONLY, where the PoC is exposed to the aptamers prior to introduction of beads and pulldown. For any protocols using bead conjugation, use the biotinylated target incubation.

1. Dilute input ssDNA ($10^{15}$ molecules), with FWD RC/Bridge if using, into refolding solution (1×PBS, 0.025% Tween-20, 1 mM $MgCl_2$, NF $H_2O$). Total volume is 150 uL.
2. Annealing (refolding aptamer): Heat to 95° C. for 5 minutes and cool on bench for 30 minutes.
3. TARGET TAIL BLOCKING INCUBATION: Incubate target with bt peptide oligo comp primer at a ratio of 1:2 in modified SELEX buffer (1×PBS, 0.025% Tween-20, 1 mM $MgCl_2$, 0.16 mg/mL BSA, NF $H_2O$) at a total volume of 250 uL for 30 minutes with rotation in a sealed NUNC plate. Target concentration will vary depending on stringency gradient.
4. SELECTION INCUBATION: Combine 150 uL of cooled ssDNA in refolding solution with 250 uL of target and annealed biotinylated peptide oligo comp in modified SELEX buffer for a total volume of 400 uL in a sealed NUNC plate with rotation for 1 hour.
5. SEPARATION/PULL DOWN INCUBATION: Wash M280 beads beforehand 3× in SELEX buffer and resuspend in SELEX buffer at original concentration. Add beads to 400 uL selection incubation reaction after it has finished and incubate for 30 minutes.
6. Wash away non specifically binding or non binding DNA from target beads using liquid handler (Protocol: "wash no elute").

Biotinylated Target Incubation—Using Bead Conjugation

Purpose: to incubate our aptamer library with the targets to see which aptamers bind to the targets.

This incubation protocol should be used for any targets (biotinylated or PoC) that were conjugated to beads prior to the start of SELEX. Note that in this protocol, the aptamers are being exposed to targets with beads, as opposed to the "PoC Target Incubation" protocol where the PoC is exposed to the aptamers prior to introduction of beads and pulldown.

1. Dilute input ssDNA ($10^{15}$ molecules) in refolding solution (1×PBS, 0.025% Tween-20, 1 mM $MgCl_2$, NF $H_2O$). Total volume is 150 uL.
2. Annealing (refolding aptamer): Heat to 95° C. for 5 minutes and cool on bench for 30 minutes.
3. Thaw frozen bead conjugation plate, add modified SELEX buffer (1×PBS, 0.025% Tween-20, 1 mM $MgCl_2$, 0.16 mg/mL BSA, NF $H_2O$) to a total volume of 250 uL.
4. Combine 150 uL of cooled ssDNA in refolding solution with 250 uL of bead target conjugation in modified SELEX buffer for a total volume of 400 uL and incubate in a sealed NUNC plate with rotation for 1 hour.
5. Wash away non specifically binding or non binding DNA from target beads using liquid handler (Protocol: "wash no elute").

Amplification (PCR Off Beads [PoB])

Purpose: to amplify aptamers bound to target using PCR. Currently, the aptamers are still bound to the target and all non specific DNA has been washed away.

1. Add Master Mix (3 µM forward primer, 3 uM reverse primer, Herculase buffer, 0.2 mM DNTP, 0.5 units/µL Herculase polymerase in a final volume of 50 uL) to wells immediately after washing protocol ends to avoid beads drying out.
2. Transfer to Eppendorf lo-bind 96 well plate, seal, and place in thermocycler using the following PCR protocol: 95° C. for 5 min, (95° C. for 30 sec, 55° C. for 30 sec, 72° C. for 30 sec)×13 cycles, 72° C. for 5 min, 4° C. Hold.
3. Cleanup on liquid handler using protocol "variable volume".
4. Measure the concentration of double stranded DNA using QuBit dsDNA kit on a plate reader to check concentration. Typical concentrations are in the range: 4-20 ng/uL.

Threshold PCR

Purpose: to amplify aptamer library with protected primer and (Forward primer has 6 thiol sulfates, reverse primer has 5' Phosphate).

1. Prepare a master mix using a 50 mL conical tube. Master Mix: 3 µM forward primer, 3 uM reverse primer, Herculase buffer, 0.2 mM dNTP, 0.5 units/µL Herculase polymerase in a final volume of 16000 uL (This is a total of 320 reactions of 50 uL per reaction).
2. Make 1:10 dilution of PoB DNA and normalize input concentrations by pipetting 0.17 ng dsDNA per 50 uL reaction. Prepare a stock solution per sample by adding 4.3 ng dsDNA, 300 uL H2O, and 954 uL of master mix to each well. Aliquot each sample stock solution into 50 uL per reaction.
3. Seal plates and place in thermocycler using the following PCR protocol: 95° C. for 5 min, (95° C. for 30 sec, 55° C. for 30 sec, 72° C. for 30 sec)×13 cycles, 72° C. for 5 min, 4° C. Hold.
4. Cleanup DNA on liquid handler using protocol "large volume".
5. Measure the concentration of double stranded DNA using QuBit dsDNA kit on a plate reader to check concentration. Concentrations are typically in the range: 30-90 ng/uL.

Single Stranded Regeneration (Digestion of Threshold)

Purpose: to generate ssDNA for the next round of SELEX. This needs to be performed as multiple reactions because there are different concentrations of DNA for each selection.

1. Set up single strand generation reaction according to Lambda Exonuclease (M0262, NEB) manufacturer's specifications (For a 50 uL reaction, use up to 5 ug DNA, 5 uL 10× Reaction buffer, 1 uL lambda exonuclease and up to 50 uL $H_2O$). Add 10× reaction buffer to DNA first, vortex to mix. Add lambda next, pipet to mix.
2. Incubate reaction at 37° C. for 10-20 minutes depending on DNA input concentration. Group reactions on different plates depending on reaction times.
3. Heat inactivate the exonuclease by incubating at 72° C. for 10 minutes, hold at 4° C.
4. Check the quality of DNA after digestion by running the DNA product on the Bioanalyzer small RNA kit according to manufacturer's protocol. If the traces show that there is still a double stranded product, add the same amount of lambda exonuclease as the original reaction and extend the incubation at 37° C. for 5-10 minutes. Check quality again.

5. Pool the DNA onto one plate and clean up using protocol "variable volume". This uses Mag-Bind Total-Pure NGS beads according to the manufacturer protocol.
6. Check DNA concentration using the QuBit ssDNA kit. Normally the concentration is around or above 30 ng/uL.

Counter Selection

Purpose: to incubate targets against other targets that closely resemble one or more aspects of the target, in order to ensure aptamers being enriched are specific and actually binding to the target itself. This is very similar to a positive selection, except the targets are different and there is no "wash no elute" step.
1. Depending on the experiment, refold aptamers and set up incubation according to either the PoC or Biotinylated Incubation steps listed above.
2. After incubation, place the plate on the magnet for 2 minutes to allow all beads to aggregate by the magnet.
3. Remove the supernatant from each well and store into a clean eppendorf 96 well PCR plate.
4. Measure DNA concentration using Qubit ssDNA kit.

NGS Preparation

PoB DNA from round 2 onward is sequenced. Samples are prepared using NextSeq protocol (NGS preparation).

Additional Protocols:

Post-Digestion Bioanalyzer Check (Small RNA Kit):

The purpose of the Bioanalyzer test is to verify that dsDNA from the bringup/threshold has been effectively digested to ssDNA by lambda exonuclease. The Small RNA kit is used according to manufacturer's instructions.

Figure 47:
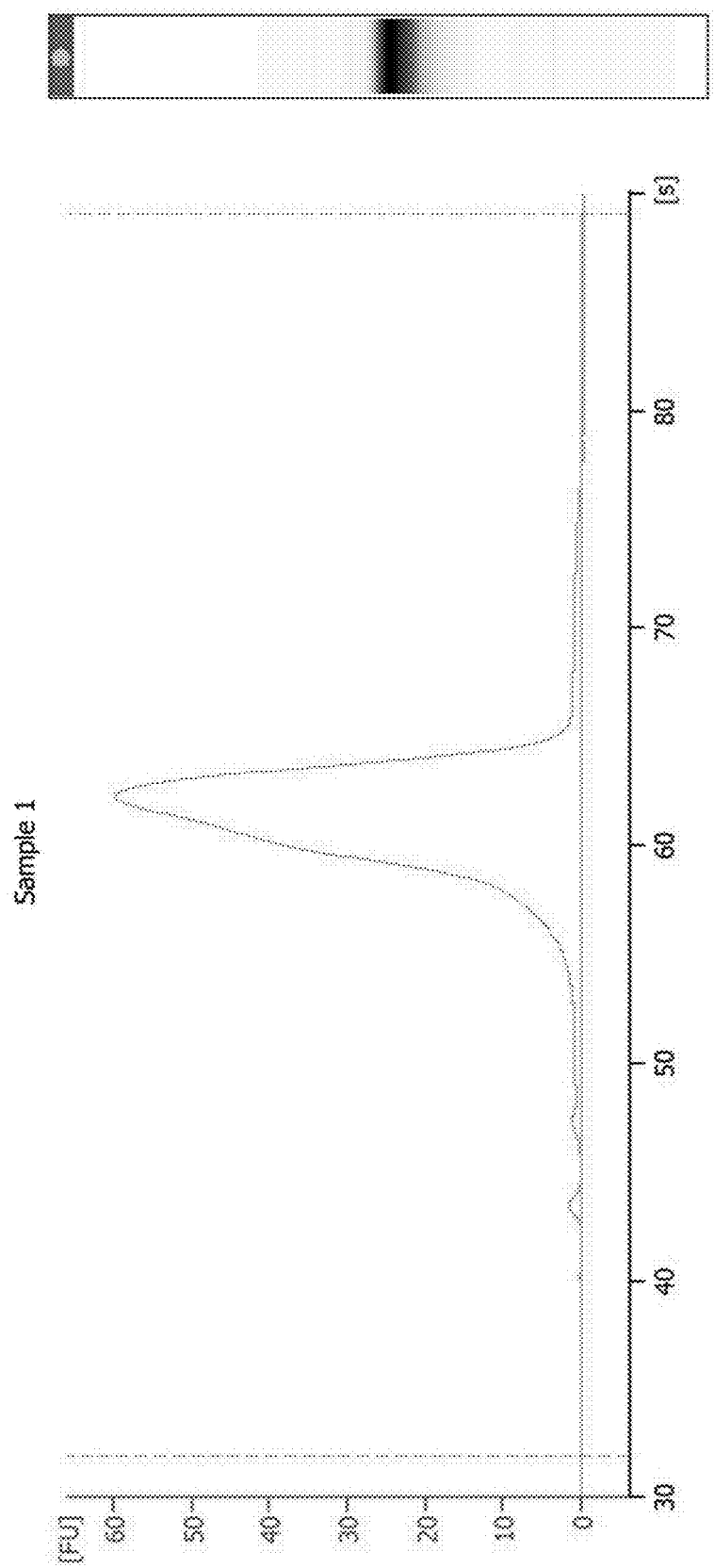
FIG. 47 is an example of an electropherogram from the Agilent Bioanalyzer assay with a desirable peak shape at 60 seconds, indicating proper digestion of PCR products into ssDNA.

To analyze results of the bioanalyzer assay, look for the locations of the ssDNA and dsDNA peaks. The ssDNA peak is at 60 seconds, dsDNA peak is at 40 seconds. If there are concatemers, they are observed at 55-65 seconds (wide, uneven peak). Digestions are complete when a sharp peak is seen at 60 seconds. See FIG. 47 for an example electropherogram.

dsDNA Bioanalyzer Check

The purpose of this Bioanalyzer test is to evaluate the quality of post-PCR/post-bringup+clean dsDNA in terms of size (basepairs). We use the High Sensitivity DNA kit according to manufacturer's instructions.

Figure 48:
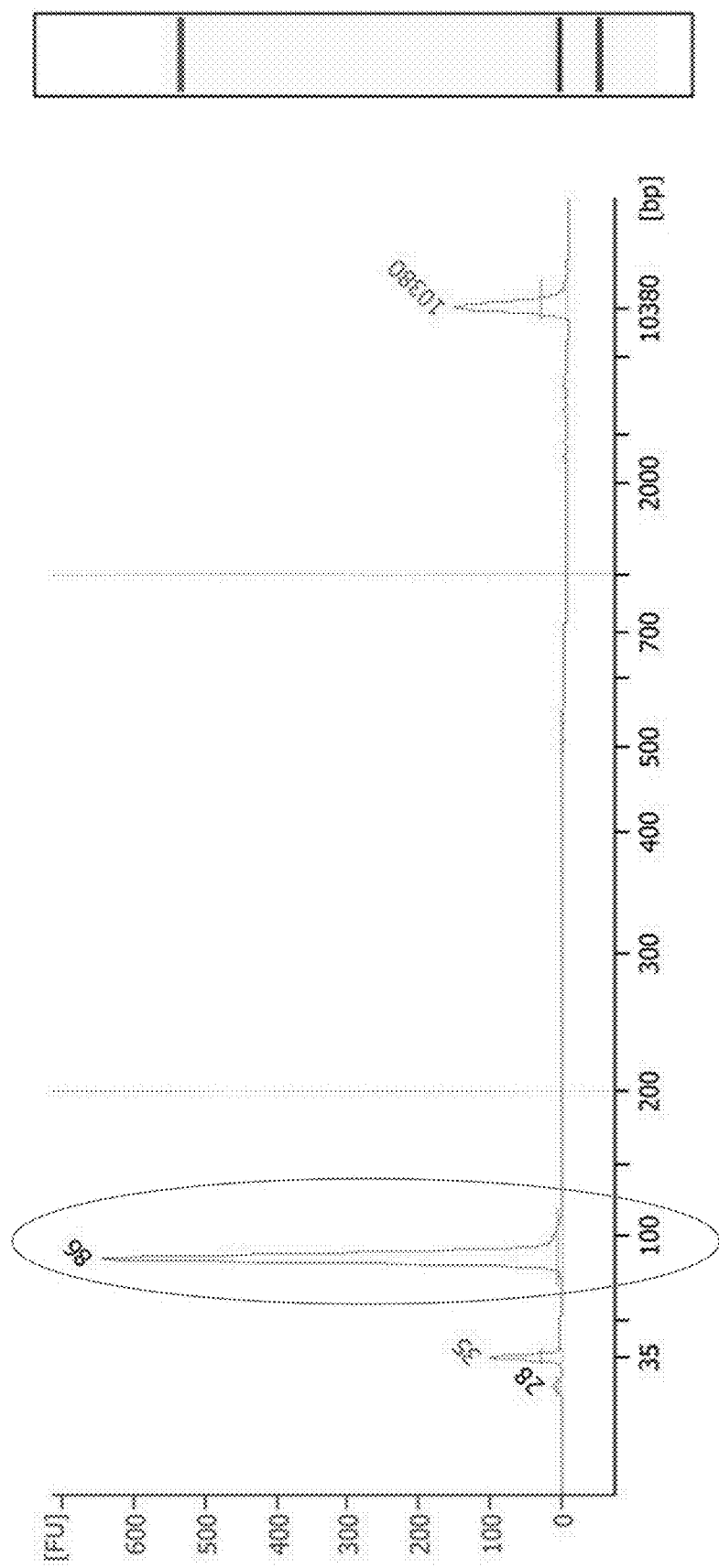
FIG. 48 is an example of an electropherogram from the Agilent Bioanalyzer assay with a desirable peak shape indicating most products are of the desired length (86 nt for the examples described herein).

To analyze the results of this assay, look for the lower marker at 35 bp, upper marker at 10380 bp. Check that the aptamer length matches up with the expected library length, in this example 86 bp. See FIG. 48 for an example of electropherogram.

Example 3—PROSEQ Experimentation

Below the following will be described:
SECTION A ProSeq Experimentation Methods
SECTION B ProSeq Results
SECTION C Generalized ProSeq protocol SECTION A ProSeq Experimentation Methods Reagents Aptamers and foundation oligos were either purchased from IDT, or synthesized in-house by K&A LABORGERATE H-8 DNA & RNA Synthesizer and purified via HPLC (Agilent 1290 Infinity II). Peptide-oligonucleotide constructs bradykinin, argipressin, and GNRH were commercially obtained from Genscript. Aptamer incubation and later DNA barcode sequencing was performed on NextSeq or MiSeq Reagent Kits, supplemented with PhiX Control v3, and sequenced on a MiSeq500 (Illumina). Bound aptamers were ligated to the barcode foundations using T4 ligase (blunt/TA Master mix formulation) and cleaved with EcoRI in Cutsmart® Buffer, all purchased from New England Biolabs. Excess aptamers and hybridization buffer were washed away with Cutsmart® buffer. For Edman degradation, peptides were coupled with phenyl isothiocyanate (PITC) in coupling buffer (0.4 M dimethyl allylamine in 3:2 (v/v) pyridine:water, pH 9.5), cleaved in trifluoroacetic acid (TFA), and dried under a stream of nitrogen gas. All reagents for Edman degradation were purchased from Sigma-Aldrich. All buffers were diluted with Ambion™ Nuclease-Free water. Analysis of NGS-data was accomplished with a custom analysis pipeline running on Colaboratory notebook environment.

Methods

Protein Sequencing

Build and Tether Foundations to Solid Substrate

Figure 49:
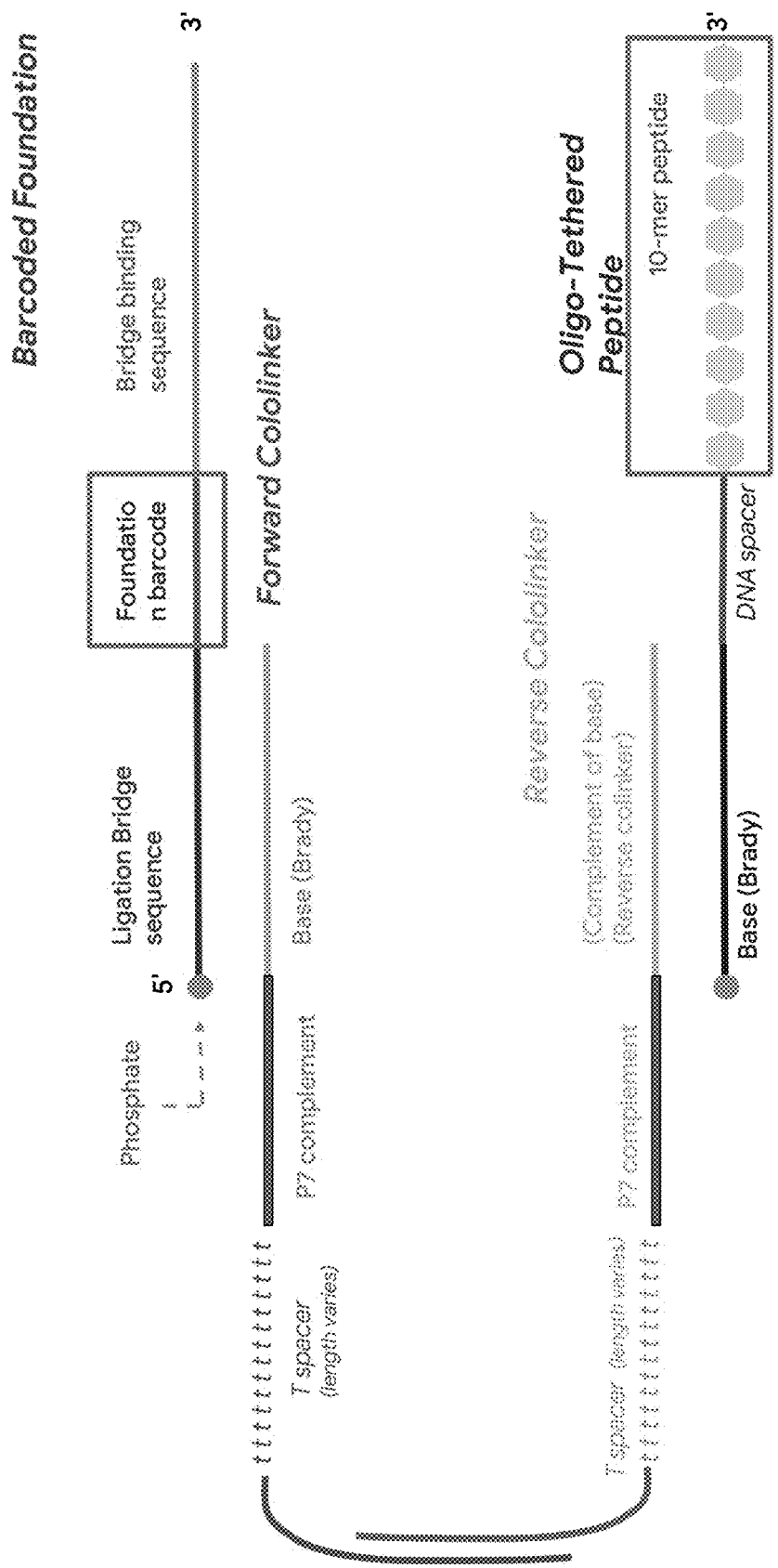
FIG. 49 is a schematic of the BCS core sequencing unit.

The core sequencing unit consists of four individual pieces of DNA: a 5' phosphorylated barcode foundation (BF), a forward and reverse colocalization linker (FC and RC), and a protein or peptide target (PT) tagged with a C-terminal oligonucleotide sequence oriented with the 3' end connected to the protein or peptide and a free, phosphorylated 5' end. The 5' end of the BF sequence is complementary to the 5' end of the FC to allow for hybridization, while the BF 3' end contains a unique barcode (for either sample multiplexing or associated PT identification) and a short consensus sequence complementary to a bridge sequence to facilitate aptamer ligation to the BF. The FC consists of the BF-complementary region at the 5' end, followed by sequence complementary to the glass-bound oligo, followed by a flexible T-spacer, with a short, high GC-content sequence at the 3' end complementary to the RC. In turn, the 3' end of the RC is complementary to the 3' end of the FC, followed by a long T-spacer, followed by a sequence complementary to the glass-bound oligo, followed by a sequence complementary to the PT-bound oligo. The 5' end of the PT oligo is similarly complementary to the 5' end of the RC, followed by a spacer before attachment of the PT at the 3' end (FIG. 49).

These four pieces were then combined and hybridized in solution such that PTs were connected to a unique BF via the FC and RC, which allows for either PT identification (in the case of validation and spike-in controls) or sample demultiplexing (in the case where multiple peptide pools are sequenced simultaneously). After hybridization, the four component complex was incubated on the oligo-seeded glass substrate. The FC and RC hybridized to the glass-bound oligo, and, with the addition of a DNA ligase, the BF and PT oligos were covalently connected to the glass bound oligos via ligation (in this case, a 'nick repair' ligation). In this way, BF-PT pairs were co-localized and spatially separated from all other BF-PT pairs to ensure that binding events on a given PT were confined to a single BF. Furthermore, the covalent attachment of the BF and PT to the glass promotes remaining colocalization of the BF and PT over multiple rounds of PT sequencing despite the harsh reagents required for PT degradation. Once the BF and PT are covalently attached to the glass bound oligos, the forward and reverse colocalization linker annealed to the BF and PT is washed away with formamide.

Aptamer Incubation

After the BF and PT are covalently attached to the substrate the sequencing process begins by incubating the first BCS Compatible aptamer pool, followed by washout of unbound aptamers and addition of a ligase to covalently connect the aptamer to the BF. This cycle of incubation and ligation is performed multiple times, where ligation is performed after each incubation or after all aptamer pools have been introduced. Prior to incubating the peptide targets with the aptamers, the single stranded aptamer pool is incubated with bridge oligos to form the library of BCS Compatible aptamers. It should be noted that only a single barcode is recorded between cycles of restriction digestion (described below). Following ligation, a restriction enzyme is introduced (along with an excess of the complementary sequence to the restriction site and spacers) to cleave the peptide-binding sequence of the aptamer from the aptamer barcode on the 5' end, leaving only the aptamer barcode and the short consensus sequence for subsequent ligation attached to the BF. After restriction, the PT is degraded processessively from the N-terminal using Edman degradation, aminopeptidases, or any other processessive degradation process. Significantly, the technique of building the sequence of aptamer-encoded barcodes can be applied equally to C-terminal to N-terminal peptide or protein sequencing, as the barcode sequence synthesis process is agnostic to PT orientation on its oligo tether. Furthermore, multiple cycles of aptamer incubation, ligation and restriction can be used to interrogate the same N-terminal amino acid sequence multiple times prior to PT degradation to more accurately identify the N-terminal composition.

Following degradation, another aptamer pool is incubated and the process is repeated. The aptamers in each round contain unique barcodes (even when the peptide binding sequences are the same), such that missed incorporation events (e.g., apparent deletions) may be easily identified and accounted for in subsequent data analysis steps.

DNA Barcode Construct Sequencing

The final step in the sequencing process is the addition of a PCR or next-generation sequencing (NGS) adapter. Using the same consensus and bridge sequences, the adapter is ligated to the 3' end of the sequence of aptamer barcodes that represent the series of aptamer binding events, which in turn is used to determine the sequence of the PT. Using the glass-bound oligo sequence and/or the BF 5' sequence as one primer and the PCR/NGS adapter as the other, the barcode construct is amplified off the chip and sequenced using standard NGS techniques, or, in the case of an NGS sequencing flow cell serving as the PT sequencing platform and the NGS adapter having the proper design, the barcode construct is amplified and sequenced directly on the NGS flow cell without further processing.

Sup-Diff

A Priori Sup-Diff

Biotinylated RNA bait generation

A priori Sup-Diff is performed on a pool of BCS barcode constructs. A preliminary NGS dataset reveals sequences of high readcount to be targets for depletion by Sup-Diff. The target is made in isolation of the other pool constituents by IDT or an in-house K&A H8 DNA Synthesizer. PCR is performed on the target sequence using a standard forward primer and a reverse primer containing a T7 RNA polymerase promoter sequence. The PCR product is cleaned on an automated Bravo wash protocol (~1-2 ug) and then used as a template to generate complementary biotinylated RNA bait via in vitro transcription in a 20 ul TranscriptAid T7 High Yield Transcription Kit (Thermo Scientific) reaction containing 10 mM ATP, CTP, and GTP, 7.5 mM UTP and 2.5 mM Biotin-16-UTP (Roche). After 4-6 hours at 37° C., the DNA template and unincorporated nucleotides are removed by DNase I (NEB) treatment and RNeasy Mini Kit column filtration (Qiagen).

In-Solution Hybridization and Bead Pulldown

A mix containing the target pool and nuclease-free water is heated for 5 minutes at 95° C., cooled on ice for 2 min and then mixed with biotinylated RNA bait with SUPERase In RNase Inhibitor (Invitrogen) in prewarmed (65° C.) 2× hybridization buffer (10×SSPE, 10×Denhardt's, 10 mM EDTA and 0.2% SDS). After 16 hours at 65° C., the hybridization mix is added to MyOne C1 streptavidin Dynabeads (Invitrogen), that are washed 3 times and resuspended in 2×B&W buffer (10 mM Tris-HCl (pH 7.5), 1 mM EDTA, 2 M NaCl). After 30 minutes at RT, the beads are pulled down and the supernatant retained.

"Soup" Processing and Sequencing

The supernatant ("soup") is treated with a mixture of two RNases, RNase H (NEB) and RNase A (Zymo), for 30 minutes at 37° C. The treated ssDNA is then amplified for 18 or more cycles. Initial denaturation is 5 min at 95° C. Each cycle is 30 seconds at 95° C., 30 s at 55° C. and 30 s at 72° C. Final extension is 5 min at 72° C. Bravo-washed PCR product is then NGS-prepped for sequencing with custom primers on an Illumina Miseq.

Non a Priori Sup-Diff

There also may be circumstances in which a non a priori version of Sup-Diff may be necessary. In such a case, a sample of the target pool may be used as a template for in vitro transcription (IVT). As a proof of concept, IVT optimizations were conducted in order to skew the representation of baits in the RNA bait pool toward the high abundance species.

RNA Bait Pool Generation

A gradient of SELEX spike-in sequences was created (% by mass): sequence 9 (0.000125%), sequence 13 (0.01%), sequence 11 (1%), sequence 12 (10%), sequence 10 (88.98%). This ssDNA gradient pool was used as a template in a 20 ul TranscriptAid T7 High Yield Transcription Kit (Thermo Scientific) reaction containing 0.1 mM, 0.25 mM, 1 mM, 2.5 mM, or 10 mM rNTPs (no biotinylated UTP). After 4-6 hours at 37° C., the DNA template and unincorporated nucleotides are removed by DNase I (NEB) treatment and RNeasy Mini Kit column filtration (Qiagen).

Reverse Transcription

The purified RNA bait pool was then reverse transcribed into cDNA using the Maxima Reverse Transcriptase kit (Thermo Fisher). A 28 ul initial reaction containing 500 ng of the RNA bait pool, 15-20 pmol of TriLink Forward primer, 0.5 mM of equimolar dNTP mix, and nuclease free water was incubated at 65° C. for 5 min. Then, 8 ul of 5× Reverse Transcriptase Buffer, 2 ul of SUPERase In RNase Inhibitor (Invitrogen), and 2 ul of Maxima Reverse Transcriptase enzyme were added and the reaction was incubated at 50° C. for 30 min followed by heat inactivation at 85° C. for 5 min. The resultant cDNA pool was treated with a mixture of two RNases, RNase H (NEB) and RNase A (Zymo), for 30 min at 37° C.

Amplification and Sequencing

The treated ssDNA was then amplified for 13 or more cycles. Initial denaturation was 5 minutes at 95° C. Each cycle was 30 seconds at 95° C., 30 seconds at 55° C. and 30 s at 72° C. Final extension was 5 min at 72° C. Bravo-washed PCR product was then NGS-prepped for sequencing with custom primers on an Illumina Miseq. A 41×8×6 read was conducted using a Miseq V2 Nano kit.

Section B ProSeq Results

Results—Barcode Sequence Synthesis Proof of Concept

As a proof-of-concept for synthesizing the DNA barcode representing the series of binding events that, in turn, represents the putative amino acid sequence of the protein or peptide being sequenced, the barcode synthesis process was performed using a 'simulated aptamer' DNA-DNA binding (e.g., hybridization) system. In this way, the uncertainty of the binding kinetics and binder-target specificity was reduced to create an 'ideal' binder-target system in which to demonstrate the serial barcode addition strategy. In addition, these DNA-DNA binders can be used as internal controls in future experiments to evaluate overall run quality.

Figures 50A, 50B:
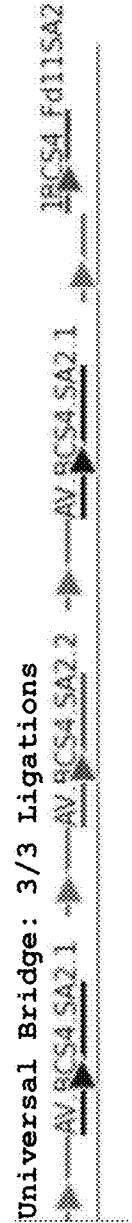
FIG. 50A is a heatmap reporting the counts of reads of barcodes added in each cycle, each with an expected position on the barcode construct, at each position on the barcode construct for 12 cycles of barcode ligation. In a ideal situation, barcodes added in the nth cycle should be in the nth position on the barcode construct. In the event of x failed ligations or no aptamer binding event, a barcode would be observed in the (n–x)th position. Results confirm it is possible to achieve serial ligation of 12 barcodes in the expected positions. Note, barcodes used in cycles 1-6 are repeated in the same order in cycles 7-12 and results were not de-multiplexed; thus a small fraction of counts from each boxed number from Expected Cycles 1-6 may be attributed to the cell five cells to its right (marked with *), meaning no barcodes were not ligated until at least after cycle 6 for those sequences.
FIG. 50B is an arrow plot depicting successful ligation of 3 barcodes in a row in 3 cycles of ligation mediated with a universal bridge design, confirming serial ligation is possible with universal bridges.

Using this idealized platform with Barcode-Specific bridges, up to 12 cycles of aptamer barcode ligation and restriction have been performed with as high as 63.8% efficiency based on the number of perfect 12/12 reads, with a per-cycle efficiency up to 75.5% for 3 cycles of barcode incorporation (FIG. 50A). This is consistent with current estimates of efficiency for each step, where the assumed efficiency of correct binder-target interaction is ~90%, the efficiency of ligation of the target-bound aptamer to its associated sequence of barcodes is >99%, and the efficiency of the restriction is estimated (conservatively) at 85%. In idealized conditions on the platform, the restriction enzyme efficiency has been measured at >95%, which means that given a moderate increase in binder specificity (to 95% accuracy) and idealization of restriction conditions in the context of the full sequencing cycle, it should be possible to achieve a per-cycle barcode incorporation efficiency above 90%.

With the Universal bridge design 5'CTGCGCC-TATACGAATTCGTTATC ############CTCTCCGT-TATC (SEQ ID NO:53), wherein each # is a 5-Nitroindole, three out of three serial barcode ligations of the correct order and orientation was achieved with an estimated per-round efficiency of 71% (FIG. 50B). In the same experiment, >36% of the reads associated with a unique foundation (Foundation 11) contained all three aptamer barcodes in the correct order, confirming that serial ligation and restriction is possible with Universal bridges.

Results—Peptide Target Identification Proof of Concept

Preliminary results using aptamers with binding sequences derived from RCHT-SELEX experiments against biologically relevant 10-mer peptides have shown that, within a given pool of SELEX-derived sequences, there are binders with affinities in the sub-nanomolar range.

Initial evidence of specific aptamer binding to 10-mer argipressin biopeptide has been shown in a combination of RCHT-SELEX and PROSEQ conditions. When a library of prospective aptamers for argipressin was incubated with foundations attached to either argipressin, bradykinin, DD, DNA, or no target (null control) in solution, barcodes of prospective bradykinin aptamer were ligated to all types of argipressin-linked barcode foundations and to no DD-linked barcode foundations (FIG. 51). The sequences for the top specific argipressin aptamers with its DNA barcode tail are:

(SEQ ID NO: 54)
/5Phos/GAGAGTAAAGCCGATAGGATAACGAATTCGTATAGGCGCAGGA
TGGACTTGATAACCTTCTGCTGCGTGCCTTGATGTGCTTACTTGGCGTTC
TTACCACCA (SEQ ID NO: 55)
/5Phos/GAGAGTTAGTCAGCAGGGATAACGAATTCGTATAGGCGCAGCA
TTTGATTCTGCTGCGTGCATACCCCTGTGTGTTATCCCTACTTGGCGTTC
TTACCACCA (SEQ ID NO: 56)
/5Phos/GAGAGTCCACGTGCACAGATAACGAATTCGTATAGGCGCAGCA
TACATCGGACATACATCCTGCGTGCATCCACCTTTGCATACTTGGCGTTC
TTACCACCA The barcodes of all three aptamers above have over 100 hits on all different argipressin foundations and no off-target hits. This data suggests that argipressin aptamers derived from the RCHT-SELEX methods preferentially bind to argipressin over DD peptides and bradykinin. They also do not bind to the oligo that is attached to all targets as shown by the lack of counts of argipressin aptamer barcodes to null foundations. Additionally, although the aptamers were isolated in RCHT-SELEX without the aptamer barcode necessary for compatibility with PROSEQ, specificity is still preserved after the aptamer tail sequences were added to the 5' end.

Results—Degradation

Figure 52:
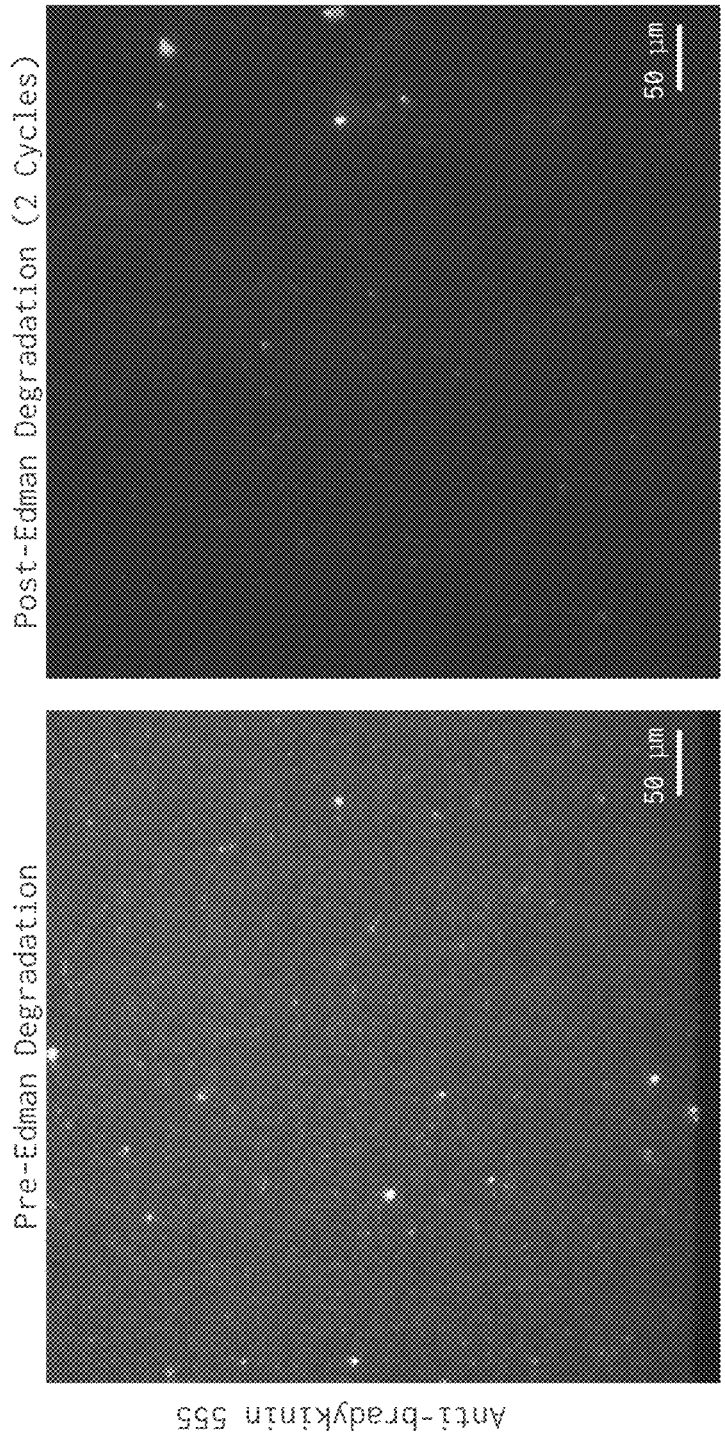
FIG. 52 are fluorescent images of a flow cell with bradykinin attached to its surface prior to Edman Degradation and after 2 cycles of Edman Degradation. Flow cells were probed with fluorescent bradykinin antibody and imaged through the 555 channel. Diminishing but not absent signal indicates decreased antibody binding, which may suggest peptides are partially degraded while still remaining attached to the flow cell surface.

Preliminary studies of Edman degradation on a biologically relevant peptide (Bradykinin) tethered to a glass substrate via an oligonucleotide suggest that the oligonucleotide tether is stable (e.g., antibody staining shows a strong signal both pre- and post-degradation). Furthermore, after multiple cycles of Edman degradation, the signal from the antibody staining is diminished but not entirely absent, suggesting that the peptide is in place post TFA exposure, and the degradation in signal is due to the loss of antibody binding due to the cleavage of amino acids (FIG. 52).

Results—Sup-Diff

Figures 53A, 53B:
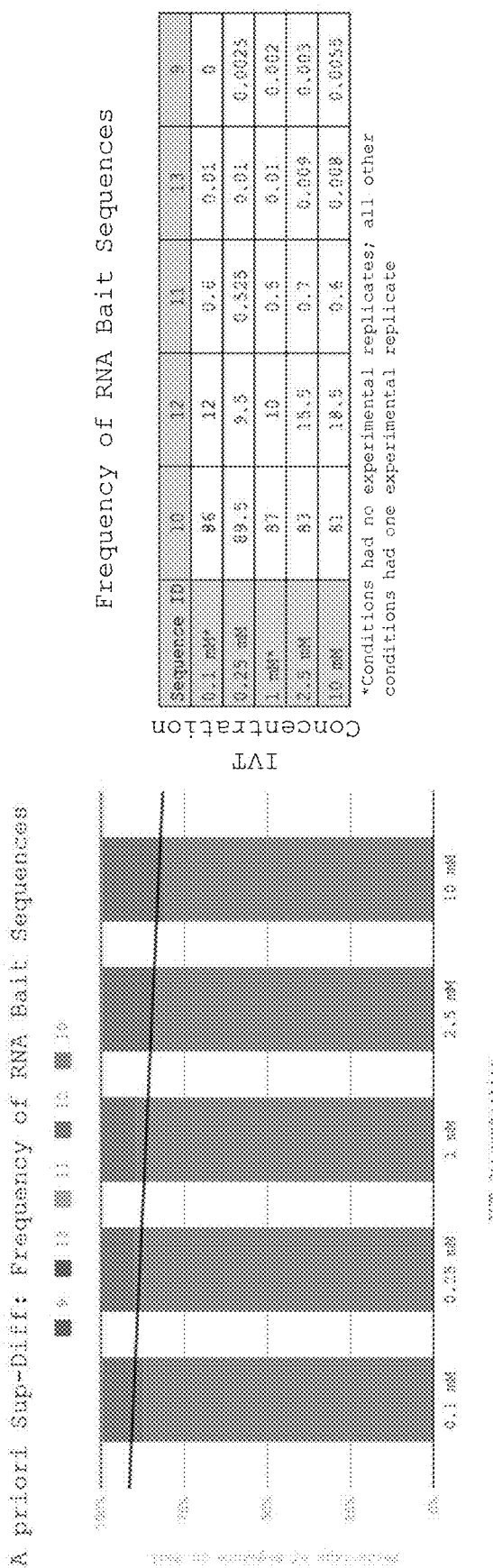
FIG. 53A is a 100% stacked column chart depicting the distribution of RNA baits complementary to 5 different sequences (9, 13, 11, 12, 19) generated from an original pool of 0.000125% sequence 9, 0.01% sequence 13, 0.1% sequence 11, 10% sequence 12, and 89% sequence 10 by weight with various concentrations of in vitro transcription enzyme (IVT). Changes in frequency of RNA bait sequences indicate that treatment with varying concentrations of IVT can generate different ratios of RNA bait sequences.
FIG. 53B is a table reporting the percentage of each RNA bait sequence by count generated with various concentrations of IVT.

Preliminary data on IVT optimization is promising for the method of non a priori Sup-Diff. Using the standard 10 mM rNTP IVT protocol to generate a pool of RNA baits from a target pool of the following distribution: 89% sequence 10, 10% sequence 12, 1% sequence 11, 0.01% sequence 13, and 0.000125% sequence 9, an RNA pool with the following composition was generated: 81% sequence 10, 18.5% sequence 12, 0.6% sequence 11, 0.008% sequence 13, and 0.0055% sequence 9. As the final concentration of each rNTP was reduced, a shift in the RNA bait distribution was achieved such that there is an increase in frequency of RNA baits to high abundance targets. From 10 mM final rNTP concentration to 0.25 mM final rNTP concentration there was an 8.5% average increase in frequency of RNA bait to the highest concentration target, sequence 10 (FIG. 53). It demonstrated that the distribution of an RNA bait pool generated from the target pool may be skewed toward a high abundance sequence, allowing for preferential pull-down of the high abundance species when the RNA bait pool is hybridized to the target sequence pool.

Section C Generalized ProSeq Protocol

Below is a template protocol used in developmental experiments.

Technical Terms

PoC (protein-oligo conjugate): Protein or peptide conjugated to the 3' end of an oligo containing a linker region, a region sequence complementary to 5' end of reverse cololinker and a 5' phosphate group.

RC (reverse cololinker): 3' end of the RC is complementary to the 3' end of the forward cololinker, followed by a flexible T-spacer, followed by a sequence complementary to the glass-bound oligo adaptor, followed by a sequence complementary to the oligo on the PoC.

FC (forward cololinker): The FC consists of the foundation-complementary region at the 5' end, followed by sequence complementary to the glass-bound oligo adaptor, followed by a flexible T-spacer, with a short, high GC-content sequence at the 3' end complementary to the RC.

Foundation: An oligo containing a barcode specific to a target and on which DNA barcodes bound to the target is built upon. 5' end of the foundation sequence is complementary to the 5' end of the FC to allow for hybridization, while the 3' end contains a unique barcode (for either sample multiplexing or associated PT identification) and a short consensus sequence complementary to a bridge sequence to facilitate binder DNA barcode ligation to the foundation.
Colocalized constructs: Complete core sequencing unit consisting of a PoC, RC, FC, and foundation piece hybridized together.
Restriction/Consensus Bridge: An oligo that is complementary to the restriction digest sequence in the BCS cassette. This sequence is added during the restriction digestion step to hybridize to the 5' end of aptamers that were ligated to the 3' end of the foundation/previous aptamer barcode in case the universal bridge has been washed away so that digestion can still occur. Improves efficiency of the digestion reaction.

TABLE 3.1

Buffer solutions

| Buffer | Formulation |
| --- | --- |
| Hybridization Buffer | 0.025% TWEEN20 in 1x PBS |
| Blocking Buffer | 0.025% TWEEN20 in 1x PBS + 10 mg/ml BSA |
| Chip Blocking Buffer | 10 uM of P5 Complementary oligo (5'-TCTCGGTGGTCGCCGTATCATT-3' (SEQ ID NO: 57))/P7 Complementary oligo (5'-ATCTCGTATGCCGTCTTCTGCTTG-3' (SEQ ID NO: 58)) sequences + 10 uM POC Tail blocking sequence (5'-TAGGGAAGAGAAGGACATATGATTA TCCACGTGCATCTAAG-3' (SEQ ID NO: 59)) |
| Aptamer Incubation Buffer | 0.025% TWEEN20 in 1x PBS + 0.1 mg/ml BSA |

Foundation Hybridization and Flow Cell Preparation
Foundation Hybridization
Purpose: to hybridize cololinkers, foundations, and targets at the correct ratios to form colocalized constructs.
Goal is to get final concentration of ~120 pM total foundation concentration, aim for a lower concentration if risk of sequencing failure of off-target ligation is high, i.e. first time using a new pool/set of aptamers
1. Thaw sequencing unit components on ice (FC/RC stock, foundations, and targets)
2. Hybridize sequencing unit components at 10 nM Forward Cololinker concentration (foundation, target, reverse cololinker in excess). In a 96 well plate combine sequencing unit components (1 well per target) in the order of:
   a. 91 uL Hybridization Buffer
   b. 1 uL Cololinker at 1 uM (1 uM stock has FC:RC 1:2)
   c. 5 uL Foundation at 1 uM stock (Multichannel from 96 well plate stock)
   d. 3 uL Target at 10 uM stock (Minimum final concentration of at least 50 nM)
   e. 100 uL Total
3. Denature/anneal foundations, cololinkers, and targets using the following cycling parameters on the thermocycler:
   a. 5 minutes at 95° C.
   b. 1 minutes at 85° C.
   c. 2 minutes at 75° C.
   d. 3 minutes at 65° C.
   e. 5 minutes at 55° C.
   f. 5 minutes at 45° C.
   g. 5 minutes at 35° C.
   h. 40 minutes at 25° C.→5 minutes in start step 5

4. Yields 10 nM colocalized constructs
5. With approximately 35 minutes remaining in denature/anneal thermocycling, start refolding for aptamers in round 1 (see below for dilutions)
Foundation Ligation
Purpose: to ligate the colocalized constructs to the flow cell to ensure targets and foundations are available for aptamer incubation.
1. Dilute 10 nM colocalized constructs 1:20 to get 500 pM working solution in Hybridization Buffer
   a. 95 uL Hybridization buffer+5 ul of 10 nM colocalized constructs mixture
2. In single Foundation Ligation Tube combine:
   a. Equal amounts of each target foundation (Final concentration of all foundations is 120 pM, i.e. 12 uL of 1 nM foundations—may need to dilute 1:20 in order to avoid small volume pipetting)
   b. 10 uL 2×Blunt/TA MINI (T4) Ligase
   c. Dilute in Hybridization Buffer for total volume of 100 uL
3. NOTE: Adjust Foundation Volume and NF H$_2$O Volume as needed to reduce loading concentration to avoid overclustering
4. Pipette mix GENTLY at least 15 seconds or until glycerol from Ligase is completely homogenized
5. Wash chip with 30 uL of Foundation Ligation mix
6. Add 30 uL Foundation mix to chip twice
7. Incubate for 15 minutes at 28° C.
8. Wash chip with 100 uL of 100% Formamide
9. Incubate for 90 seconds at 40° C.
Start of Barcoding Cycles (Repeated for Each Cycle)
Oligo Tail Block+BSA Block
Purpose: to reduce availability of flow cell surfaces and ssDNA ligated to the flow cell for non-specific binding of aptamers during aptamer incubation.
1. Wash chip with 500 uL of Binding Buffer
2. Wash chip with 30 uL of Chip Blocking Solution
   a. To prepare 100 uL of Chip Blocking Buffer:
      i. 60 uL of Blocking Buffer (0.025% TWEEN-20+10 mg/mL BSA in 1×PBS)
      ii. 10 uL of 100 uM P5 Complement (final conc. 10 uM) (sequence in Table 3.1)
      iii. 10 uL of 100 uM P7 Complement (final conc. 10 uM) (sequence in Table 3.1)

iv. 10 uL of 100 uM POC TailBlock (final conc. 10 uM) (sequence in Table 3.1)
v. 10 uL of 100 uM Foundation Base Block (final conc. 10 uM)
3. Add 30 uL of Chip Blocking Buffer to chip twice
4. Incubate 15 minutes at 37° C.

Aptamer Incubation
Purpose: to expose targets on the flow cell to aptamers to initiate binding between (1) target and binding region of aptamer and (2) foundation and BCS cassette of aptamer.
1. Aptamer Incubation Solution Prep:
   a. Aptamers+Bridge at 1:2 Ratio in Hybridization Buffer
   b. Heat aptamer mix to 95° C. for 5 minutes in PCR tube (keep in middle of strip to prevent melt compression of PCR tube)
   c. Cool aptamer tube at RT on benchtop for 1 hour
   d. Immediately prior to incubation of aptamers and bridges on chip, add 10 mg/mL BSA to achieve final BSA concentration of 100 ug/mL
      i. Example: Add 1 uL of 10 mg/mL BSA to 99 uL of aptamer mix
2. After 15 minutes Chip Blocking Buffer incubation, wash chip with 100 uL of Hybridization buffer for 60 seconds
3. Repeat 60 second Hybridization buffer wash
4. Wash 1× with 30 uL Aptamer Incubation Solution
5. Load 30 uL of Aptamer Incubation Solution to chip
6. Incubate for 30 minutes at 25° C.

Aptamer Ligation
Purpose: to ligate aptamers bound to targets to the colocalized foundations so the aptamer barcodes can be sequenced.
1. Wash 3×90 seconds with 100 uL Aptamer Incubation Buffer
2. Prepare Ligation Solution:
   a. 63 uL NF H$_2$O+7 uL 2× Blunt/TA MM Ligase
3. Wash 1× with 30 uL Ligation solution
4. Load 30 uL Ligation solution
5. Incubate for 3 minutes at 28° C.

Aptamer Restriction Digest
Purpose: To prepare the 3' end of the aptamer barcode ligated to the foundation for NGS ligation so it can be sequenced.
1. Wash 3× for 90 seconds in 1× Cutsmart buffer
2. Prepare Restriction Solution:
   a. 77 uL NF H2O
   b. 10 uL 10× Cutsmart
   c. 3 uL of 10 uM Restriction/Consensus Bridge
   d. 10 uL EcoRI HF (100,000 U/ml)
3. Wash 1× with 30 uL Restriction Solution
4. Load 30 uL Restriction Solution
5. Incubate for 30 minutes at 40° C.
6. Wash chip with 100 uL of 100% Formamide
7. Incubate for 90 seconds at 40° C.
8. Wash chip with 500 uL SELEX Buffer

[Repeat for Each Cycle]
End of Final Barcoding Cycle
NGS Adapter Ligation
Purpose: to ligate the P5 complement sequence to the 3' end of the barcode constructs so it will be read during sequencing.
1. Prepare NGS Ligation Mix:
   a. 63.5 uL NF H$_2$O
   b. 1.5 uL NGS Adapter+Bridge (1 uM NGS Adapter, 2 uM Bridge)
   c. 10 uL 10× Cutsmart buffer
   d. 25 uL Blunt/TA MM Ligase
2. Pipette mix solution until ligase is fully incorporated
3. Load 2×30 uL of NGS Ligation Mix
4. Incubate 165 seconds at 40° C.
5. Wash 2× with 500 uL NF H$_2$O, incubate each wash for 90 seconds Load Chip on Sequencer
Purpose: to prepare the flow cell and MiSeq for the sequencing run.
1. Change Sample Sheet to reflect read length, experiment/sample name
2. Load 20 uL of 20 pM denatured PhiX in 580 uL HT1 Buffer (supplied with sequencing cartridge) into the Sample port on the Miseq cartridge
3. Start Sequencer
   a. If a flow error arises during the pre-run check, exchange the plastic hinged piece that contains the gasket on the flow cell with the same piece from an old flow cell (after thoroughly rinsing with 70% Ethanol and NF H$_2$O)

Example 4—BCS Binding Assay

Reagents

Aptamers foundation oligos, and DNA targets were HPLC- or PAGE-purified by and purchased from IDT. Spot-Tag and bradykinin peptide-oligonucleotide constructs were commercially obtained from Genscript. The Spot-tag nanobody was purchased from Chromotek. Spot-tag nanobody-oligo conjugates were prepared using SoluLINK Protein—Oligonucleotide Conjugation Kit. Aptamer incubation and DNA barcode sequencing was performed on MiSeq Reagent Nano v2 Kits, supplemented with PhiX Control v3, and sequenced on a MiSeq500 (Illumina). Bound aptamers were ligated to the barcode foundations using T4 ligase (Blunt/TA Master mix formulation) and cleaved with EcoRI in CutSmart Buffer, all purchased from New England Biolabs. Excess aptamers and hybridization buffer were washed away with the 100% formamide purchased from Millipore Sigma. Analysis of NGS data was accomplished with a custom analysis pipeline running on a Colaboratory notebook environment.

Methods

Conjugate Spot-Tag Nanobody to DNA Tail

The commercially obtained Spot-tag nanobodies (Chromotek) were conjugated to the 3' end of a 5' phosphorylated oligo (3'ATCCCTTCTCTTCCTGTATACTAATAGG TGCACGTAGATTC/5Phos/(SEQ ID NO:60)) in a non-site directed manner using the SoluLINK Protein-Oligonucleotide Conjugation Kit according to manufacturer instructions.

Figure 54:
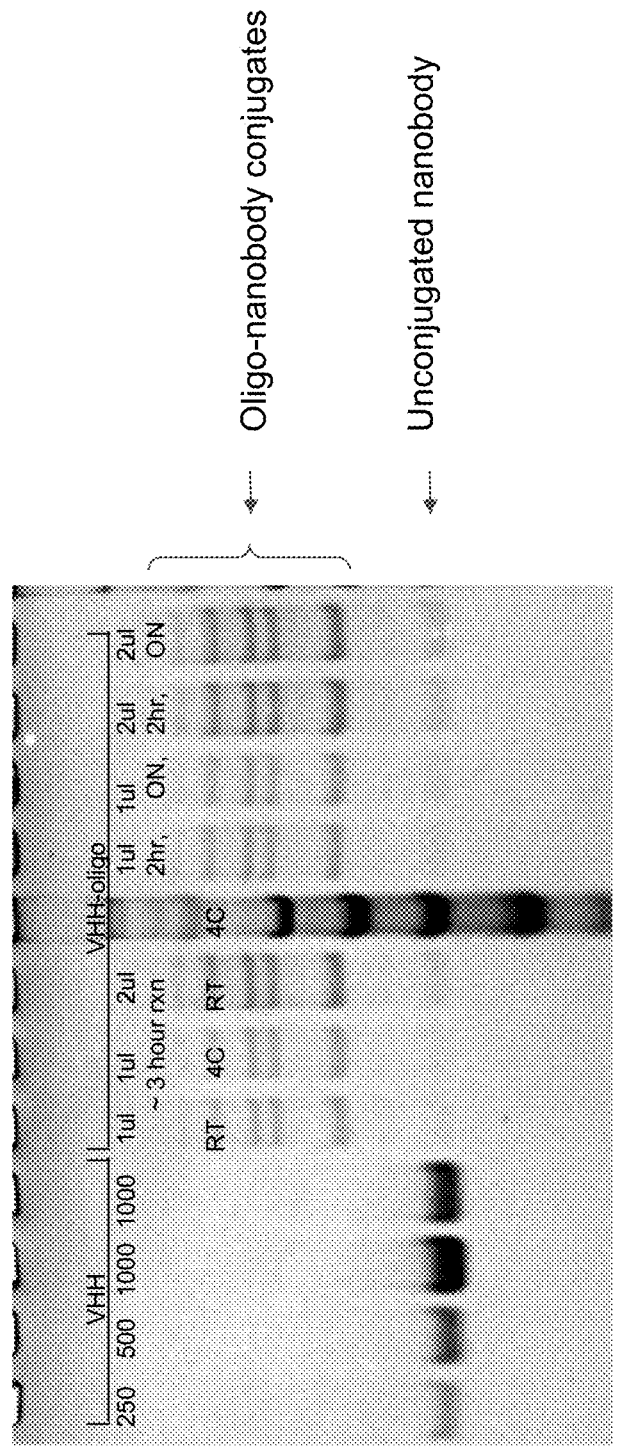
FIG. 54 is an image of an electrophoretic mobility shift assay (EMSA) gel demonstrating that Spot-tag nanobody was conjugated to oligos (VHH-oligo). The first four gel lanes show electrophoretic mobility of unconjugated Spot-tag nanobody by itself. In subsequent lanes, multiple higher molecular weight bands were observed on the gel, presumably corresponding to multiple oligos conjugated to a single nanobody.

Success of Spot-tag nanobody-oligo conjugation was confirmed by PAGE electrophoresis (FIG. 54). Labeling of the protein was not site-directed but could be achieved using the sortase-enzyme method. Multiple higher molecular weight bands were observed on the gel, presumably corresponding to multiple oligos conjugated to a single nanobody. Importantly, for BCS experiments these constructs are less of a concern because they will either 1) be non-functional, in which case they will not bind Spot-Tag and be washed away, or 2) will bind to the Spot-Tag, following which either of the multiple tails can then become ligated to the nearby foundation.

Build and Tether Foundations to Solid Substrate

Figure 55:
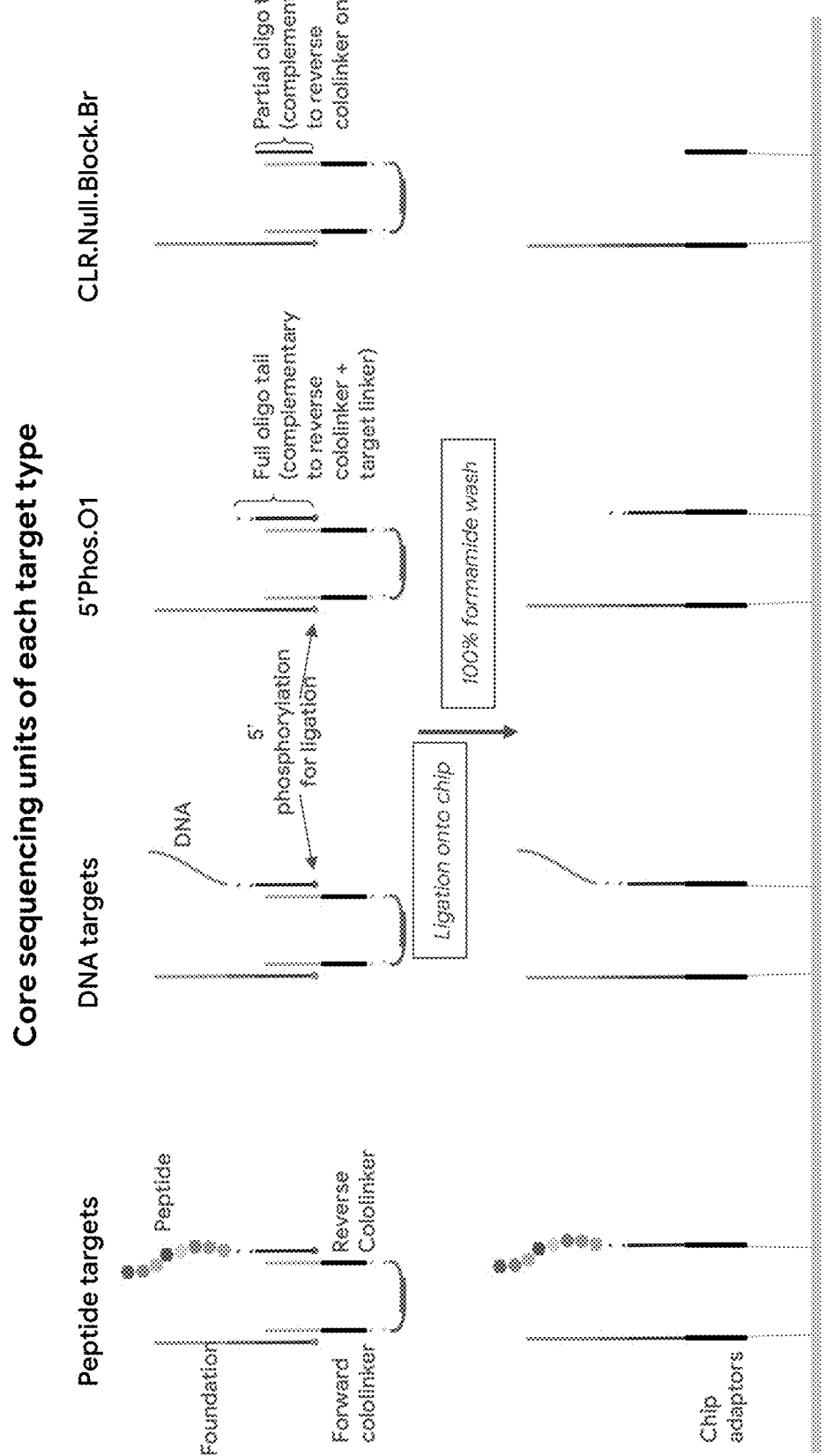
FIG. 55 is a schematic of the full core sequencing unit constructs of each target and their corresponding structures ligated onto the sequencing chip after ligation and formamide wash. The DNA targets serve as positive controls. 5'Phos.O1 control is for noise associated with the full oligo tail that is connected to all peptide targets, while the CLR.Null.Block.Br control is for noise associated with sequencing chip components.

As a proof-of-concept experiment to validate the ability of the BCS platform to record specific binding events in a complex environment, the Spot-Tag-oligo conjugates (Spot-Tag.O1) and 6 other control targets were seeded onto a MiSeq Nano v2 sequencing chip. The other peptide target was Bradykinin conjugated to a 5' phosphorylated DNA tail (Brady.O1). 2 null targets (oligo tails without target) comprised a 5' phosphorylated oligo (5'Phos.O1), and an oligo lacking a 5' phosphate, which therefore can not be attached to the chip (CLR.Null.Block). 2 DNA controls (SP6.O1 and SP4.O1), continuous oligo sequences that contained both a 5' phosphorylated linking region to tether to the P7 primers and a binding region to hybridize to a complementary strand, served as positive controls (FIG. 55). The binding region and DNA tail sequences of each target is reported in Table 4.1.

TABLE 4.1

Sequences of targets and oligo tail

| | Target Type | Target Name | Sequence |
|---|---|---|---|
| Peptide target | Spot-Tag* | Spot-Tag.O1 | (N-terminus)-PDRVRAVSHWSSGGG-Cys (SEQ ID NO: 61)<br>(C-terminus)-3'ATCCCTTCTCTTCCTGTATACTAATAGGT GCACGTAGATTC/5Phos/ (SEQ ID NO: 62) |
| Peptide target control for non-specific binding | Bradykinin* | Brady.O1 | (N-terminus)-RPPGFSPFR-Cys (SEQ ID NO: 63)<br>(C-terminus)-3'ATCCCTTCTCTTCCTGTATACTAATAGGT GCACGTAGATTC/5Phos/ (SEQ ID NO: 64) |
| Null control | DNA** | CLR.Null.Block | CTTAGATGCACGTGGATAAT (SEQ ID NO: 65) |
| | DNA** | 5'Phos.O1 | /5Phos/CTTAGATGCACGTGGATA (SEQ ID NO: 66) |
| Positive control | DNA** | SP6.O1 | /5Phos/CTTAGATGCACGTGGATAATCATAT GTCCTTCTCTTCCCTAATGAAGTACTAACC TGA (SEQ ID NO: 67) |
| | DNA** | SP4.O1 | /5Phos/CTTAGATGCACGTGGATAATCATAT GTCCTTCTCTTCCCTAATAGGATTCC (SEQ ID NO: 68) |

*The C-terminal of the peptide targets is directly conjugated to the 3' end of one DNA tail via a cysteine
**Binding sequences and DNA tails of DNA targets are continuous oligos rather than conjugated through another chemical conjugation method.

To tether a target-oligo conjugate and a DNA barcode foundation containing a sequence indicative of its associated target in proximity to each other to a solid substrate, it must be further assembled into a core sequencing unit. The core sequencing unit of the BCS platform consists of four individual pieces of DNA or oligo-conjugated molecules: a 5' phosphorylated barcode foundation (BF), a forward and reverse colocalization linker (FC and RC), and a target tagged with a C-terminal oligonucleotide sequence oriented with the 3' end connected to the target and a free phosphorylated 5' end. The 5' end of the BF sequence is complementary to the 5' end of the FC to allow for hybridization, while the BF 3' end contains a unique barcode (for either sample multiplexing or associated target identification) and a short consensus sequence complementary to a bridge sequence to facilitate aptamer ligation to the BF. The FC consists of the BF-complementary region at the 5' end, followed by sequence complementary to the glass-bound oligo, followed by a flexible T-spacer, with a short, high GC-content sequence at the 3' end complementary to the RC. In turn, the 3' end of the RC is complementary to the 3' end of the FC, followed by a long T-spacer, followed by a sequence complementary to the glass-bound oligo, followed by a sequence complementary to the target-conjugated oligo. The 5' end of the target oligo is similarly complementary to the 5' end of the RC, followed by a spacer before attachment of the target at the 3' end (FIG. 49).

Each control target was tested in triplicates and Spot-Tag in sextuplicate. Their respective FC, RC, and BF were thawed on ice before each set of sequencing units were combined in 91 uL of Hybridization Buffer (0.025% TWEEN20 in 1×PBS) in separate wells to generate solutions of 10 nM FC, with RCs, BFs and targets in excess. In this experiment, all targets employed the same FC sequence (5'CATCAGCTCGCAGTCGATCTCGTAT GCCGTCTTCTGTTTTTTTTTTTTTTTTTTT TTTTTTTTTTTTTTTTTTTTTCCAGCCACCGC-CAACCATCC-3' (SEQ ID NO:69)) and RC sequence (5'AT-TATCCACGTGCATCTAA-GATCTCGTATGCCGTCTTCTGTTTTTTTTTTTTTTTT TTTTTTTTTTTTTTTTTTTTTTTTG-GATGGTTGGCGGTGGCTGG-3' (SEQ ID NO:70)). FCs and RCs were kept in a stock solution with a ratio of 3:1 FC:RC in Hybridization Buffer. The components were added in the order of Hybridization Buffer, FC and RC stock, and BFs. Targets were added to the mixtures immediately prior to hybridization. Sequences and concentrations of each set of targets, FCs, RCs, and BFs are reported in Table 4.2. The final ratios of individual pieces are:

5:1 BF:FC

3:1 FC:RC

10:1 Target:RC

To assemble the sequencing units, the complete mixtures were mixed thoroughly, spun down for 30 seconds, sealed, and heated in a thermocycler with the following conditions: 5 minutes at 95° C., 1 minute at 85° C., 2 minutes at 75° C., 3 minutes at 65° C., 5 minutes at 55° C., 5 minutes at 45° C., 5 minutes at 35° C., 40 minutes at 25° C.

TABLE 4.2

Foundation sequence of each target replicate

| Target* | Foundation Name | Foundation (5'-3') |
| --- | --- | --- |
| Spot-Tag.01 | Fd31 | /5Phos/CGACTGCGAGCTGATGTGGCATCTGATAACG (SEQ ID NO: 71) |
| Spot-Tag.01 | Fd19 | /5Phos/CGACTGCGAGCTGATGAGGTACCAGATAACG (SEQ ID NO: 72) |
| Spot-Tag.01 | Fd20 | /5Phos/CGACTGCGAGCTGATGCACTTACGGATAACG (SEQ ID NO: 73) |
| Spot-Tag.01 | Fd27 | /5Phos/CGACTGCGAGCTGATGTCATGTGGGATAACG (SEQ ID NO: 74) |
| Spot-Tag.01 | Fd28 | /5Phos/CGACTGCGAGCTGATGCACCAAACGATAACG (SEQ ID NO: 75) |
| Spot-Tag.01 | Fd29 | /5Phos/CGACTGCGAGCTGATGATTGTCCCGATAACG (SEQ ID NO: 76) |
| Brady.01 | Fd12 | /5Phos/CGACTGCGAGCTGATGCGTTTGCAGATAACG (SEQ ID NO: 77) |
| Brady.01 | Fd13 | /5Phos/CGACTGCGAGCTGATGTCTTTCCGGATAACG (SEQ ID NO: 78) |
| Brady.01 | Fd14 | /5Phos/CGACTGCGAGCTGATGTTGCTCACGATAACG (SEQ ID NO: 79) |
| CLR.Null.Blk | Fd24 | /5Phos/CGACTGCGAGCTGATGAGGAGCAAGATAACG (SEQ ID NO: 80) |
| CLR.Null.Blk | Fd25 | /5Phos/CGACTGCGAGCTGATGTTCCCTTCGATAACG (SEQ ID NO: 81) |
| CLR.Null.Blk | Fd26 | /5Phos/CGACTGCGAGCTGATGTCTGAGGTGATAACG (SEQ ID NO: 82) |
| 5Phos.01 | Fd7 | /5Phos/CGACTGCGAGCTGATGGCCTTGATGATAACG (SEQ ID NO: 83) |
| 5Phos.01 | Fd8 | /5Phos/CGACTGCGAGCTGATGCGTACTAGGATAACG (SEQ ID NO: 84) |
| 5Phos.01 | Fd11 | /5Phos/CGACTGCGAGCTGATGTGTACGCAGATAACG (SEQ ID NO: 85) |
| SP6.01 | Fd21 | /5Phos/CGACTGCGAGCTGATGAGTACTGCGATAACG (SEQ ID NO: 86) |
| SP6.01 | Fd22 | /5Phos/CGACTGCGAGCTGATGTTGGGCAAGATAACG (SEQ ID NO: 87) |
| SP6.01 | Fd23 | /5Phos/CGACTGCGAGCTGATGTTCCACGTGATAACG (SEQ ID NO: 88) |
| SP4.01 | Fd15 | /5Phos/CGACTGCGAGCTGATGGAGTTACGGATAACG (SEQ ID NO: 89) |
| SP4.01 | Fd16 | /5Phos/CGACTGCGAGCTGATGTGATATAGGATAACG (SEQ ID NO: 90) |
| SP4.01 | Fd17 | /5Phos/CGACTGCGAGCTGATGACCTTAGAGATAACG (SEQ ID NO: 91) |

*See Table 4.1 for target sequences

Prior to seeding the colocalized constructs, the sequencing chip was washed with 100 uL Hybridization Buffer twice. Each mixture of colocalized constructs were diluted to 0.5 nM and and 1.14 uL of each mixture was combined with 10 uL of 2× Blunt/TA MM Ligase Master Mix and 44 uL of Hybridization Buffer, and gently mixed for a final concentration of 120 pM of colocalized constructs. To ligate the colocalized constructs onto the chip, the sequencing chip was washed with 30 uL of Foundation Mix twice and heated at 28° C. for 15 minutes on a hotplate. Then it was washed once with 100 uL of 100% formamide to remove unligated colocalized constructs. The chip was heated again at 40° C. for 90 seconds on a hotplate, washed with 500 uL of Blocking Buffer (0.025% TWEEN20 in 1×PBS+10 mg/ml BSA) once, washed with 30 uL of Chip Blocking Solution twice (10 uM of P5 Complementary oligo (5'-

TCTCGGTGGTCGCCGTATCATT-3' (SEQ ID NO:92))/P7 Complementary oligo (5'-ATCTCGTATGCCGTCTTCTGCTTG-3' (SEQ ID NO:93)) sequences+10 uM POC Tail blocking sequence (5'-TAGG-GAAGAGAAGGACATATGATTATCCACGTG-CATCTAAG-3' (SEQ ID NO:94))), incubated for 37° C. for 15 minutes on a hotplate, and washed with 100 uL Hybridization Buffer twice for 60 seconds one immediately before loading the prepared binder library (see Barcoded-Binder Library Preparation section below).

Barcoded-Binder Library Preparation

4 DNA barcoded "binders" were incubated with the targets, each consisting of a binder region, a DNA spacer region, a restriction site, DNA barcode indicative of the binder region identity, and ligation site. 2 DNA binders, U4.SA1.3 and U4.SA2.3, contained a binder region consisting of DNA that were complementary to SP4.O1 and SP6.O1 respectively. These binders were positive controls that should bind to SP4.O1 and SP6.O1 with high affinity and specificity. Another DNA binder, U4.SA4.2, contained a binder region consisting of a scramble DNA sequence that should bind to none of the targets present, serving as a negative control to measure noise. The last binder was the Spot-tag nanobody-oligo conjugate.

Prior to incubation each binder was hybridized to a universal bridge (5'-CTGCGCCTATAGGAATTCGTTATC/i5NitInd//i5NitInd//i5NitInd//i5NitInd//i5NitInd//i5 NitInd//i5NitInd//i5NitInd//i5NitInd//i5NitInd//i5NitInd/GGACACGGCCGTTATC-3' (SEQ ID NO:95)), an oligo that was partially complementary to the restriction site spacer and partially complementary to the consensus sequence (FIG. 14B). Each/i5NitInd/is a 5-Nitroindole, a universal base analogue that exhibits high duplex stability and hybridizes indiscriminately with each of the four natural bases (Loakes and Brown, 1994). The DNA binders and the Spot-tag nanobody target were hybridized with their respective bridges in separate reactions. The DNA binders were added to 2× excess bridge oligos per DNA binder in Hybridization Buffer to generate a 50 uL solution with an end concentration of 200 nM of each DNA binder (600 nM of all DNA binders combined). The solution was heated to 95° C. for 5 minutes at room temperature (RT) (22-24° C.) for an hour.

To hybridize the Spot-tag nanobody target to the universal bridge, it was added to 5× excess bridge per Spot-tag nanobody target in Hybridization Buffer to generate a 49 uL solution with an end concentration of approximately 400 nM Spot-tag nanobody target. In the preparations of nanobody-oligo conjugates, the DNA tails are added in excess and are not purified away. It is possible that the excess of unconjugated DNA tails present in the solution hybridize to the Spot-tag-oligo conjugates, preventing hybridization of the universal bridge needed for the subsequent ligation of the Spot-tag nanobody barcode to the nearby foundation. A ratio of 5:1 bridge: Spot-tag nanobody target was used such that any excess DNA tail that were in the solution but not conjugated to Spot-tag nanobody target from the protein-oligo conjugation reaction were hybridized to a bridge, promoting bridge hybridization with all oligo tails conjugated to Spot-tag nanobody targets. This solution was heated to 37° C. for 30 minutes and cooled at RT for 30 minutes. After cooling, the solutions containing the DNA binders and Spot-tag nanobody targets, both hybridized to universal bridges were combined and 1 uL of Blocking Buffer (0.025% TWEEN20 in 1×PBS+10 mg/ml BSA) was added. The final binder library solution had a concentration of 100 nM of each DNA binder (300 nM of all DNA binders combined) and 200 nM of Spot-tag nanobody target.

Barcoded-Binder Library Incubation, Binder Barcode Ligation, and Restriction Digest After the step of washing the sequencing chip with 100 uL Hybridization Buffer twice for 60 seconds (see Build and Tether Foundations to Solid Substrate section above), the chip was washed with Aptamer Incubation Buffer (0.025% TWEEN20 in 1×PBS+0.1 mg/ml BSA) for 60 seconds. The binder library was gently mixed and the sequencing chip was slowly loaded with 30 uL binder library solution twice. The sequencing chip was incubated with the binder library solution on a hotplate at 25° C. for 30 minutes. After incubation, the chip was washed with 100 uL of Aptamer Incubation Buffer for 90 seconds three times to wash away unbound and weakly bound binders.

To prepare the ligation reaction, 7 uL of 2× Blunt/TA MM Ligase solution was diluted in 63 uL of Hybridization buffer and gently mixed. 30 uL of the diluted ligase solution was loaded onto the chip twice before the chip was incubated for 5 minutes in a hotplate at 28° C. to ligate the DNA tail of the binders to its bound target's respective foundation oligo. The ligation reaction was terminated by washing the plate with 100 uL of 1× CutSmart solution for 60 seconds three times.

The rest of the binder besides the consensus region and binder barcode was removed from the barcode-foundation construct with a restriction digestion reaction. The restriction enzyme mix was prepared by adding 10 uL of 20 units/uL EcoRI to 30 uL 10 uM Restriction bridge (5'-CTGCGCCTATACGAATTCGTTATC-3' (SEQ ID NO:96)), 10 uL of 10× CutSmart solution, and 77 uL of Nuclease-Free $H_2O$ before the contents were gently mixed. 30 uL of the restriction enzyme mix was loaded onto the chip twice and incubated at 40° C. on a hotplate for 30 minutes. To terminate the ligation reaction and wash off any hybridized DNA, the chip was loaded with 100 uL of 100% formamide, incubated at 40° C. on a hotplate for 90 seconds, and washed with 500 uL of Hybridization Buffer.

Sequencing

The final step in the sequencing process was the addition of Next Generation Sequencing (NGS) adapters. 1.5 uL of 2:1 1 uM Universal NGS Adapter (/5Phos/AGATCG-GAAGAGCGTCGTGTAGGGAAAGAGTGTA-GATCTCGGTGGTCGC CGTATCATT (SEQ ID NO:97))+Universal NGS Adapter Bridge9/5 (5'-TTCCGATCTCGTTA-3' (SEQ ID NO:98)) was added to 10 uL of 10× CutSmart, 25 uL of 2× Blunt/TA MM Ligase, and diluted in 63.5 uL of Nuclease-Free $H_2O$. 30 uL of the NGS ligation mix was loaded onto the sequencing chip twice and the chip was incubated at 40° C. on a hotplate for 2 minutes and 45 seconds. The chip was washed with 500 uL of Nuclease-Free $H_2O$ twice with 90 seconds in between the washes. 20 uL of 20 pM denatured PhiX (Illumina) was diluted in 580 uL of HT1 buffer (Illumina) and loaded into the sample well of the sequencing cartridge. A 45 cycle read was conducted using MiSeq V2 chemistry.

Results

Conjugate Spot-Tag nanobody to DNA tail

Labeling of the protein was not site-directed as it was with the sortase-mediated method. Multiple higher molecular weight bands were observed on the gel, presumably corresponding to multiple oligos conjugated to a single nanobody. Importantly, for BCS experiments these constructs are less of a concern because they will either 1) be non-functional, in which case they will not bind Spot-Tag and be washed away, or 2) will bind to the Spot-Tag, following which either of the multiple tails can then become ligated to the nearby foundation.

Results—BCS Binding Assay Proof of Concept

Figure 56:
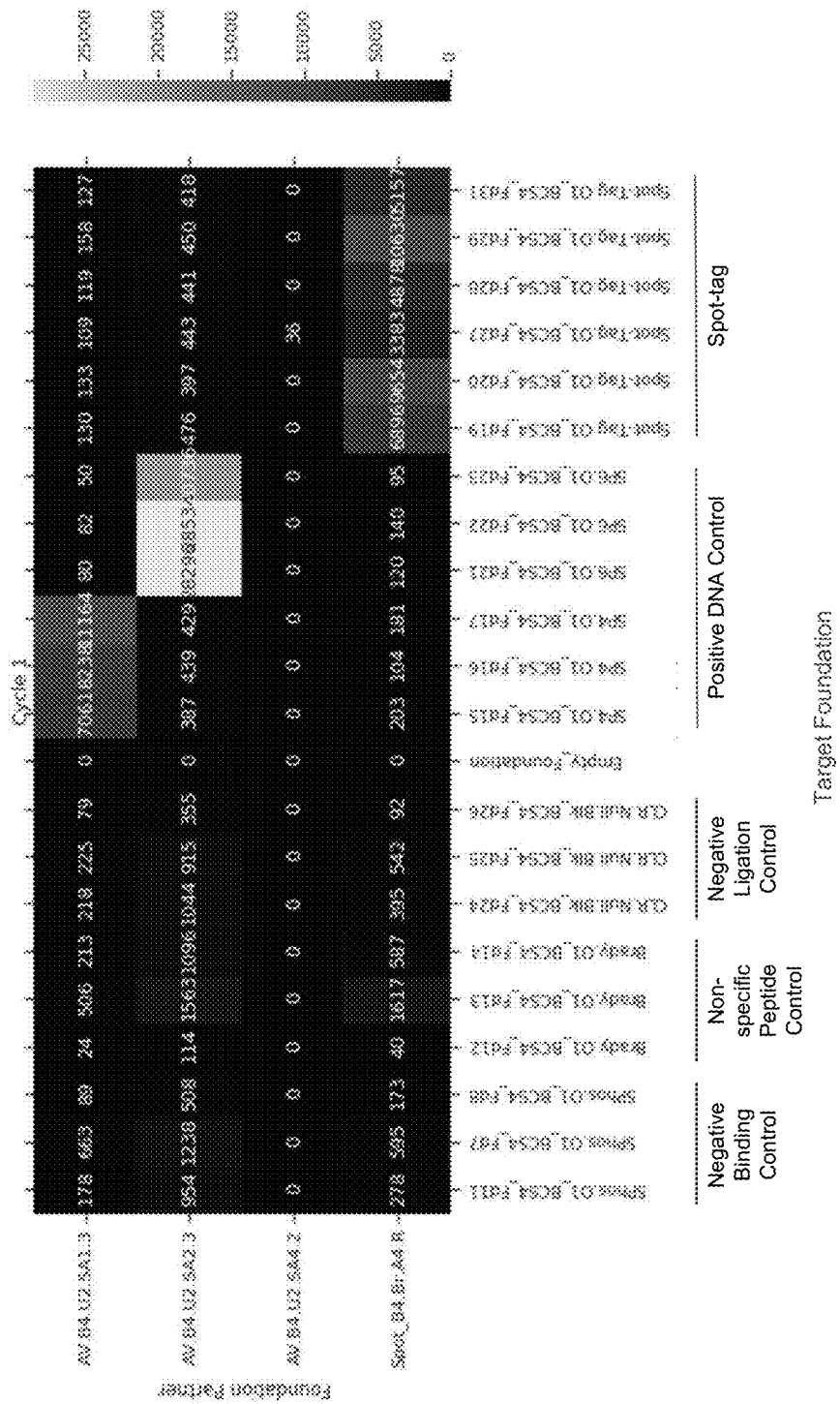
FIG. 56 is a heatmap reporting the instances of each target foundation sequenced with the binder barcodes ligated to foundations when Spot-tag nanobodies are conjugated to oligos. Controls are run in triplicate with different barcodes associated for each replicate, and DNA and Spot-tag experiments are run with 6 experimental replicates. DNA controls (Kd pM) bound and tagged complementary oligos with high fidelity (in terms of sequencing counts), and the Spot-tag nanobody bound and tagged the Spot-tag peptide (Kd 6 nM) with strong fidelity. Difference in sequencing counts between experimental replicates is thought to be due to the difference in barcode used for each replicate. The impact of barcode sequence was screened and analyzed to derive a set of barcodes used for downstream experimentation. No known variables (GC content, sequential basepairs, etc.) were found to be related to a barcode's impact on sequencing noise outside of target type (DNA vs Nanobody, etc). Experiments were repeated and validated, confirming the protocol utilization for a DNA:DNA binding system and peptide:nanobody binding system.

Preliminary results adapting a nanobody against its known peptide target on the BCS platform have shown that, within a complex environment, specific binding events with binders in the sub-micromolar range can be recorded into a DNA signal and deconvoluted. When a library of prospective binders was incubated with foundations attached to either bradykinin (Brady.O1), no target (CLR.Null.Blk and 5'Phos.O1 as null controls), DNA targets (SP4.O1 and SP6 as positive controls), or Spot-Tag protein (Spot-Tag.O1), barcodes of the Spot-Tag binder were ligated to all foundations associated with Spot-tag targets at a significantly higher rate than foundations corresponding to other targets. Sequencing counts of a Spot-tag binder barcode ligated to Spot-tag target foundations compared to other foundations was 3383-10630 vs 0-1617 counts (FIG. 56). Sequencing counts showed that 32-73% of Spot-tag target foundations were ligated to Spot-tag binder barcodes, while 0.3-10.7% of other foundations were ligated to Spot-tag binder barcodes. For positive target controls, SP4.O1 and SP6.O1, sequencing counts report a high number of DNA binder barcodes were ligated to its intended target foundation compared to foundations of other targets. Foundations of null control targets and the peptide target control for non-specific binding (Brady.O1) ligated to any binder barcodes were at or below the noise floor. No sequencing counts were observed for the negative control binder, AV.B4.U2. SA4.2.

Figure 57:
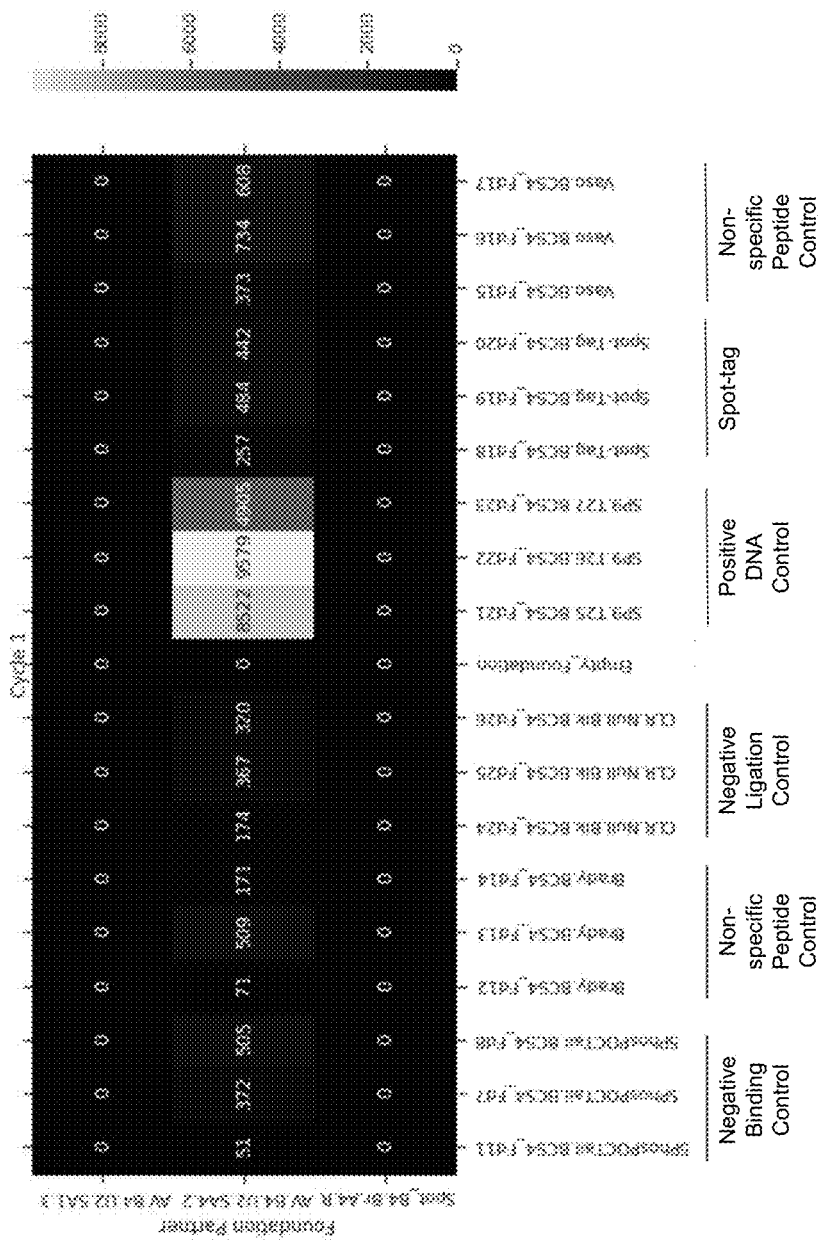
FIG. 57 is a heatmap reporting the instances of each target foundation sequenced with the binder barcode ligated to foundations when Spot-tag nanobodies were not conjugated to oligos. Experiments are run in triplicate with different barcodes associated for each replicate. Difference in sequencing counts between experimental replicates is thought to be due to the difference in barcode used for each replicate. The impact of barcode sequence was screened and analyzed to derive a set of barcodes used for downstream experimentation. No known variables (GC content, sequential basepairs, etc.) were found to be related to a barcode's impact on sequencing noise outside of target type (DNA vs Nanobody, etc.). For this experiment, only the DNA binder, AV.B4.U2.SA4.2, with its corresponding target (SP9) have high sequencing counts. Experiments were repeated and validated, confirming the protocol utilization for a DNA: DNA binding system and peptide:nanobody binding system.

To confirm that true signal was observed, in experiments where only unconjugated Spot nanobodies and oligos were loaded onto the sequencing chip, no Spot-tag nanobody barcodes were observed on respective foundations (FIG. 57). For further optimization experiments, it would be important to work with carefully purified protein-oligo conjugates, validate BCS process for oligo tails comprised of two parts to enable modularity of design, validate the BCS platform for protein-based binders with low affinity such as Myc-tag, and characterize BCS performance with binders across a different range of affinities and concentrations.

Example 5—PROSEQ-VIS Experimentation

Methods

Peptide Tethering

Proteins from cells are isolated, digested and processed prior to tethering peptide fragments to a solid substrate. Cells are first lysed and then proteins are isolated by precipitation. Isolated proteins are denatured using a surfactant, and then reduced and alkylated to protect Cysteine side chains. In order to attach oligo strands to the amino side chain of Lysines, the proteins are incubated in a reaction mixture of sodium phosphate buffer (pH 4-5), sodium cyanoborohydride, deionized water, and oligos modified with an aldehyde on their 3' end and a phosphate group at its 5' end. Afterwards. proteins are digested with Lys-C, resulting in peptide fragments with an oligo-modified lysine at each C-terminal. Then the 5' ends of the oligos are covalently attached to the 3' adaptor on a flow cell with a DNA ligase, tethering the peptide-oligo constructs to a solid substrate.

Aptamer Incubation and Imaging

After the oligo-peptide constructs are covalently attached to the substrate the sequencing process begins by incubating the first aptamer pool, followed by washout of unbound aptamers. On a single chip, 25 million to 5 billion peptide fragments can be immobilized across multiple fields of view. After target immobilization, a library of unique, aptamers with a unique tail of barcodes hybridized to a protective complementary oligo are incubated with the chip to allow for target binding. The unbound aptamers are washed off. The bound aptamers are treated with paraformaldehyde (PFA) before the dsDNA portion is denatured and the protective complementary oligo washed away to expose the barcode-containing region for probe hybridization. The aptamer: amino acid complexes are incubated with a library of probes that hybridize to barcode regions indicative of probe iteration 1. The unbound probes are then washed off and bound probes are imaged to acquire the first section of the optical barcode. After imaging, the bound probes are denatured from the aptamer barcode tail and washed off the chip. Thereafter, the bound aptamers are incubated with the next set of probes that hybridize to barcode regions indicative of probe iteration 2. Iterations of probe incubation, imaging, and washing are repeated until full optical barcodes are acquired. The peptides, along with the covalently bound aptamer, is degraded processessively from the N-terminal using Edman degradation, aminopeptidases, or any other processessive degradation process. Then, the cycle of aptamer incubation, iterations of probe incubation and single molecule imaging, and amino acid cleavage repeats for multiple rounds to obtain the sequence of the peptide molecule (FIG. 23).

As proof-of-concept that single molecule imaging can be achieved without TIRF microscopy, forward and reverse colocalization linkers (FC and RC) were tagged with fluorescent Streptavidin beads and imaged on a flow cell. The FC consisted of the barcode foundation-complementary region at the 5' end, followed by sequence complementary to the glass-bound oligo, followed by a flexible T-spacer, with a short, high GC-content sequence at the 3' end complementary to the RC. In turn, the 3' end of the RC was complementary to the 3' end of the FC, followed by a long T-spacer, followed by a sequence complementary to the glass-bound oligo, followed by a sequence complementary to another oligo. The FC and RC was biotinylated at the 5' end. The FC, LC, and Streptavidin beads, and flow cell surface were blocked separately with a BSA buffer (1×PBS, 0.05% Tween, 10 mg/ml BSA) for 1 hour at RT. In two separate reactions, the FC was incubated with Fluo-Spheres™ Streptavidin-Labeled Microspheres, 0.04 μm, yellow-green fluorescent (505/515), and the RC with TransFluoSpheres™ Streptavidin-Labeled Microspheres, 0.04 μm (488/645) in a 1:4 oligo to beads ratio such that each biotinylated oligo likely binding to at least one bead for 30 minutes at RT. The FC and RC were combined in a 1:2 ratio for 1 hour at RT. The solution was loaded onto a Illumina MiSeq v2 (50-cycles) chip and incubated for 30 minutes at 37° C. to allow for the FC and RCs to hybridize to the P7 adaptors in the chip. The imaging system is a wide-field upright fluorescence microscope with a 20× Nikon objective (NA=0.75). Glass piece of the chip was taken out from the MiSeq cassette and imaging was performed on the external top surface of the chip. The beads inside the chip were excited at 488 nm with SPECTRA X LED light engine and the emitted fluorescence signal was collected at 515 nm (with a 520/35 bandpass emission filter) and 645 nm (with a 676/29 nm bandpass emission filter). Images were acquired with an Andor EMCCD camera with 16 micron pixel size and 2 second exposure time.

Optical Barcode Deconvolution

After repeating this series of steps on the slide, the identity of successive N-terminal amino acids at each round is computationally deduced by colocalizing the optical barcodes and generating a peptide sequence. Once peptide sequences are generated they will be compared against the organism proteome for protein identification and quantification.

Results

Imaging Single Molecules

In each iteration of probe incubation and imaging, single peptide molecules at known locations on the chip (i.e. assigned coordinates (X,Y), generates spatially overlapping fluorescent signals (FIG. 58A) that can be detected by separate channels (FIG. 58B).

Figure 58:
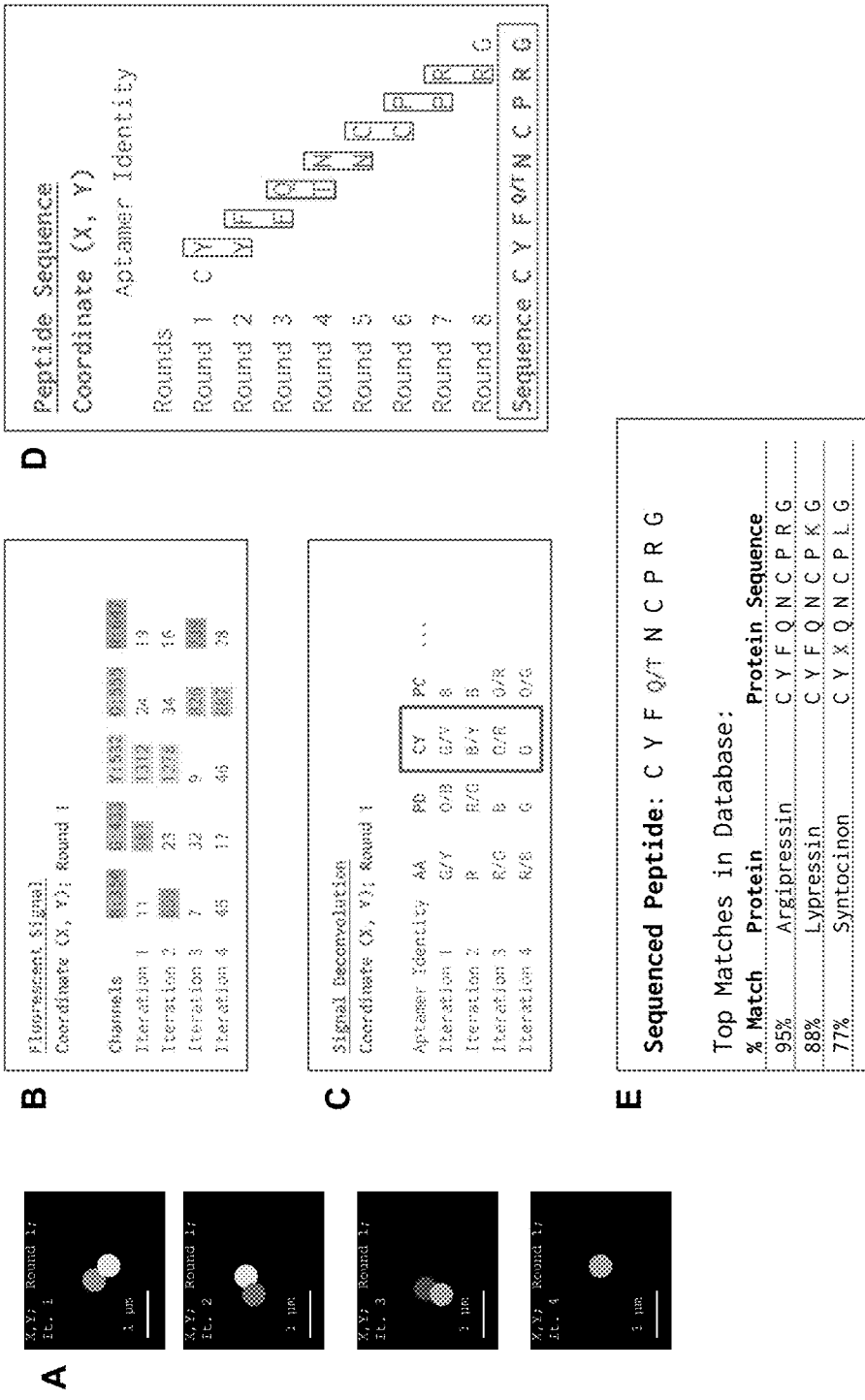
FIG. 58 are embodiments of results and computational deconvolution process from imaging to peptide identification for a single molecule peptide.
Figure 59:
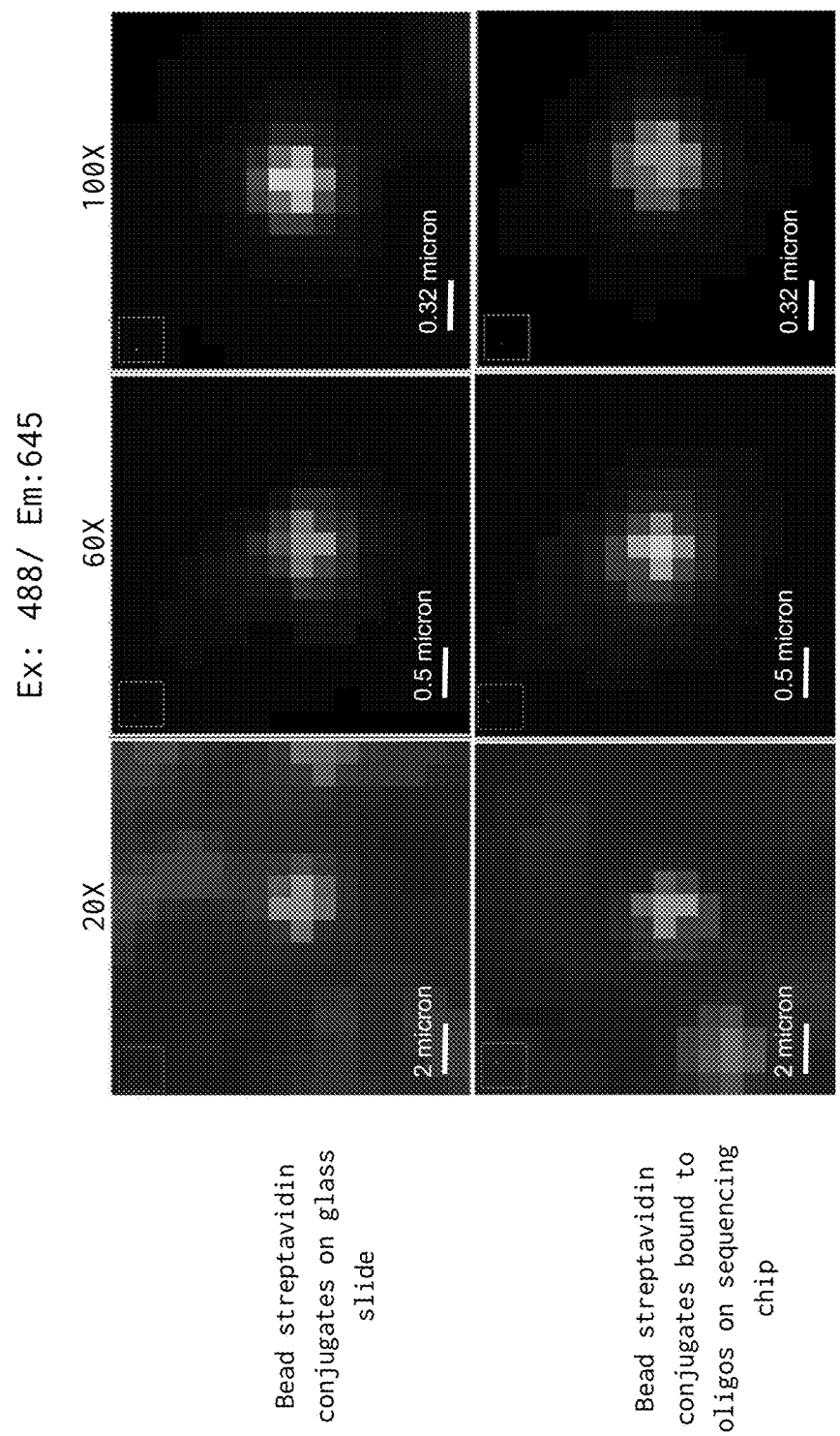
FIG. 59 are images of fluorescent bead-streptavidin conjugates on a glass slide (single molecule control) and bound to single oligos on a sequencing chip at 20×, 60×, and 100× magnification. The similarity of sizes of the observed spots between the fluorescent beads on the chip and sequencing chip suggests the observed spots on the sequencing chip are single molecules.
Figures 60A, 60B:
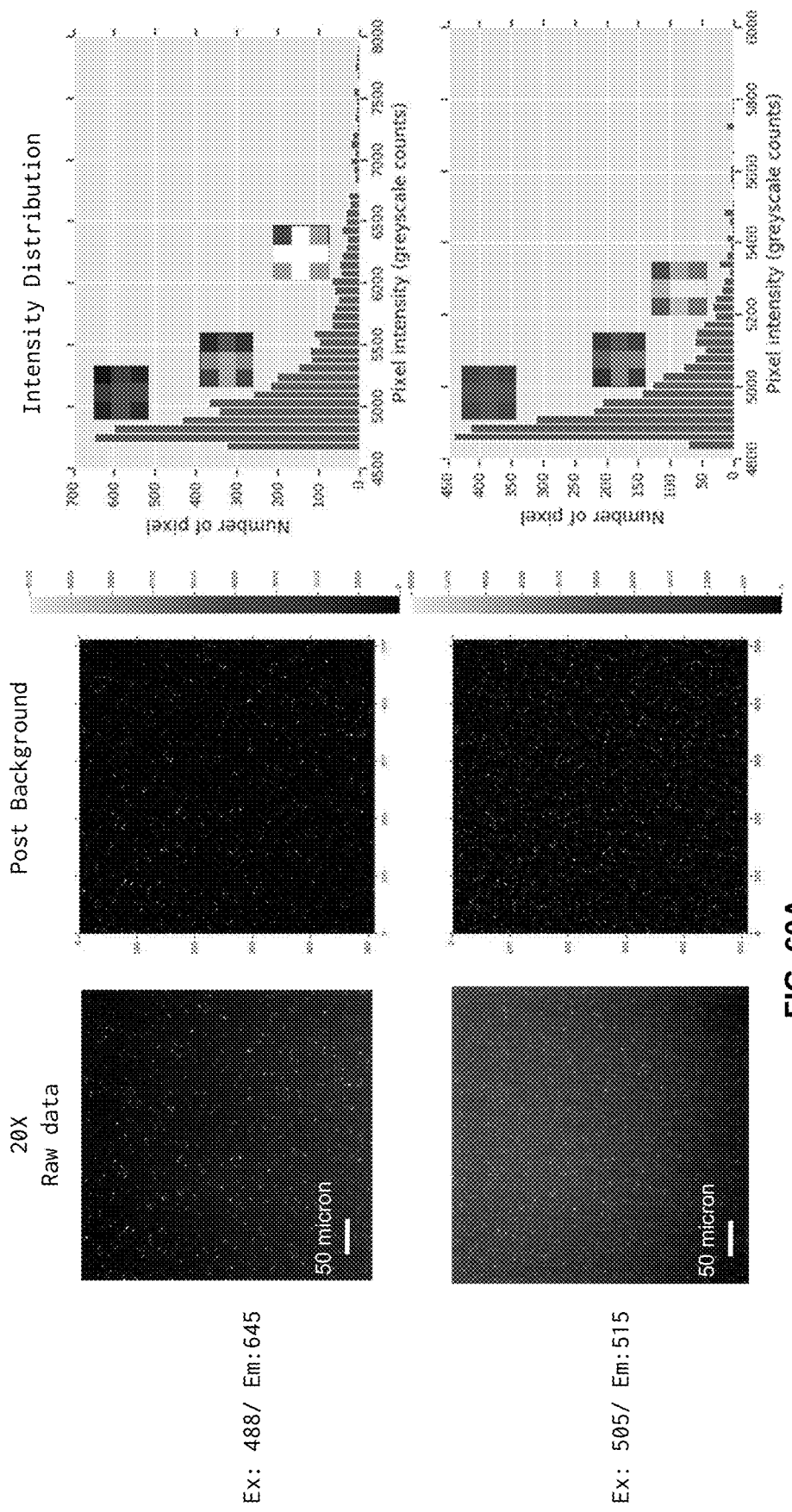
FIG. 60A are fluorescent images of fluorescent bead-streptavidin conjugates on a sequencing chip and the intensity measurement after background subtraction using a local threshold. The threshold value is the median intensity for the local neighborhood (30 by 30 pixel) of pixels.
FIG. 60B are thresholded intensity distribution of all the fluorescent spots in FIG. 60A.

Preliminary data has shown that single oligonucleotide imaging can be achieved with widefield fluorescence microscopy. Since each biotinylated oligo is binding to at least one streptavidin bead, each fluorescent spot represents at least one bead (FIG. 59). In the case where each biotinylated oligo is binding to a cluster of beads, spots will appear bigger, or brighter compared to spots with the same size. Streptavidin beads not bound to oligos were imaged on a glass as a control (FIG. 58). The similarity of sizes of the observed spots between the fluorescent beads on the chip and sequencing chip suggests the observed spots on the sequencing chip are single molecules. FIG. 60B shows the intensity distribution of all the fluorescent spots in an image snapshot. The local maxima of every 10,000 grayscale count (in the case of channel one: 488 nm excitation and 645 nm emission, FIG. 60B) can be used to distinguish spots with various peak intensities. For example, the first interval (grayscale count from 0-10,000 grayscale count) in FIG. 60B indicates only one streptavidin bead bound to one biotinylated oligo. The second or third interval suggests a cluster of (two or three) streptavidin beads were binding to one biotinylated oligo. Data from size comparison analysis and intensity distribution suggests that single oligo molecules were detected.

Fluorescent Signal Deconvolution Into Aptamer Identity

The fluorescent signature that combines fluorescent signal in each channel for each iteration of a round is compared against the known optical barcodes of each unique aptamer, thus deducing the likely identity of the bound N-terminal prefix based on probability distributions of binding events for each aptamer against each prefix (FIG. 58C).

Aptamer Identity to Protein Sequence

For each single peptide molecule at a known location on the chip, the N-terminal prefix calls from each round is used to computationally deduce the likely amino acid sequence of the peptide tethered at (X,Y). If the N-terminal prefix associated with the ssDNA binding regions of the recorded aptamers overlap such that the second amino acid of a round is the same as the first amino acid of the subsequent round, there is greater confidence in the computationally derived peptide sequence (FIG. 58D).

Protein Sequencing for Full Proteins

Contiguous peptide sequences are linked together in a series of non-contiguous assay-derived peptide sequences into a scaffold by stitching overlapping sequences to generate the sequence of the full-length protein. The sequences are mapped against a proteome map to identify known proteins in the sample, for example argipressin (FIG. 58E). Relative quantification of a unique protein/peptide in the sample is calculated from the number of derived peptide sequences associated with that protein/peptide.

Example 6—Multiplex Experimentation

Reagents

Aptamer libraries were purchased from TriLink Biotechnologies, and all other oligonucleotides were purchased from IDT. Peptide oligo conjugates were ordered from Genscript. All automated procedures were performed on the Agilent Bravo NGS Workstation. All DNA quantifications were obtained using dsDNA and/or ssDNA High Sensitivity Qubit Fluorescence Quantification Assay (Thermofisher). All water used was Ambion™ Nuclease-Free water.

Methods

Bring Up

N40 aptamer libraries consisted of 40 random bases, flanked by custom primer regions. Aliquots of these initial libraries (TTGACTAGTACATGACCACTTGA CACATCAGACTGGACGACAGAA (SEQ ID NO:99)) were ordered from TriLink. A sample of $10^{12}$ sequences (~48 ng) from this initial library were amplified across 288 reactions of 50 microliters each using Herculase II Fusion DNA Polymerase (Agilent Technologies) and SPRI-purified using Mag-Bind TotalPure NGS beads on a Bravo Automated Liquid Handling Platform (Agilent). The amplification conditions for this and all subsequent PCR reactions (with the exception of NGS preparation) were as follows: an initial denaturation at 95° C. for 5 minutes followed by 13 amplification cycles of 30 seconds of denaturation at 95° C., 30 seconds annealing at 55° C., 30 seconds elongation at 72° C., and a final elongation of 5 minutes at 72° C.

Digestion

Amplified libraries were converted to single-stranded DNA (ssDNA) by enzymatic digestion using lambda exonuclease (NEB) and purified by automated bead clean up. ssDNA digestion completion was qualified using the small RNA kit (Agilent) on the Bioanalyzer 2100 (Agilent), and the concentration quantified post-clean via a ssDNA Qubit Assay (Thermofisher).

Peptide-Oligo Constructs

Peptide-oligo constructs were synthesized by Genscript (full construct: (N-terminus)-NNNNNNNNN-Cys (SEQ ID NO:100) (C-terminus)-3'ATCCCTTCTCTTCCTGTATACTAGCACGTAGATTC 5' phosphate (SEQ ID NO:101)). The C-terminus of a 10-mer peptide (with the exception of GnRH, which was an 11-mer, and argipressin, which was a 9-mer) was attached to the 3' end of a 41-nucleotide oligo. All but the final amino acid residue of the peptides were derived from naturally occurring peptides (such as GnRH, bradykinin, and argipressin) or synthetic peptide designs, with the N-terminal residue reserved for a cysteine that facilitated peptide attachment to the oligo. The 41-nucleotide (nt) oligo featured a 9-nucleotide bridge-binding region at the 3' end, a 3 nt spacer, a 6 nt DNA barcode uniquely associated with the peptide, and a 23 nt primer region at the 5' end.

Incubation

SsDNA pools were heated to 95° C. for five minutes, then rapidly cooled on ice prior to incubation with peptide. For the ideal experimental condition in the first and second rounds of MULTIPLEX, 166.62 pmol (4650 ng) of folded aptamers were added to 18.51 pmol of the peptide-oligo construct (for a final stringency of 1:10 target:DNA). These numbers were scaled according to the amount of ssDNA available for incubation in each individual experiment. For rounds 3 and 4, the stringency was increased to 1:25. A final buffer solution was prepared from 10×PBS (Sigma-Aldrich), TWEEN20 (Sigma Aldrich), and HiFi Taq Ligase buffer (NEB) to bring the final incubation solution to 400 ul total volume, at a concentration of 1×PBS, 1× HiFi Taq Ligase Buffer, and 0.025% TWEEN20. The peptide-oligo constructs and aptamers were allowed to bind for 2 hours at RT under rotation.

Ligation

HiFi Taq Ligase (NEB) and a 18-mer DNA bridge (GCAUCUAAGUUCUGUCGU (SEQ ID NO:102)) were added to the 400 ul mixture of aptamers and peptide-oligo constructs, with 1 ul of HiFi Taq for every 50 ul of incubation solution and the 18-mer bridge at a final concentration of 100 nmol. Ligation happened at 25° C. for 30 minutes. The bridge was subsequently degraded by adding USER enzyme (NEB) and 10× cutsmart, and incubating the solution at 37° C. for 15 minutes.

Incubation with Biotin

A biotinylated oligo (/5Biosg/TAGGGAAGAGAAGGA-CATATGAT-3' (SEQ ID NO:103)) that hybridizes to the 5'-ATCATATGTCCTTCTCTTCCCTA-3' (SEQ ID NO:104) region of the peptide oligo construct was added to the reaction at an equimolar ratio to the peptide-oligo construct. The reaction was incubated for 30 minutes under rotation.

Streptavidin-Biotin Pulldown

Streptavidin C1 beads (Invitrogen) were incubated with the solution at 83.33 ug for every 51.02 pmol of peptide present for 30 minutes. Bead-bound peptide aptamer constructs were collected using an automated wash protocol on the Bravo. The MULTIPLEX reactions were incubated on a magnetic plate for 2 minutes. The supernatant containing unbound aptamers was aspirated away and the beads were washed two times with SELEX buffer, followed by a final wash with 1×PBS. The 1×PBS was aspirated at the end of the protocol.

PCR on Beads

Immediately after the automated wash protocol finishes, 50 ul of PCR Mastermix solution was added to the beads. The primers 5'-TAGGGAAGAGAAGGACATATGAT-3' (SEQ ID NO:105) and TTGACTAGTACATGAC-CACTTGA-3' (SEQ ID NO:106) were used to amplify the 126 nt construct (5' TTGACTAGTACATGACCACTT-GANNNNNNNNNNNNNNNNNNNNNNNNNNNNNN NNNNNNNNNNNNNCACATCA-GACTGGACGACAGAACTTAGATGCACGATC ATATGTCCTTCTCTTCCCTA 3' (SEQ ID NO:107)).

NGS Preparation 10 ng samples of SPRI-purified PCRs on beads were taken for NGS preparation. Each aptamer identified from sequencing these samples were associated with the 6 bp barcode of the peptide they putatively bound to in solution. The P5 and P7 adapters required for Illumina sequencing were incorporated through PCR with custom NGS primers (5'-CAAGCAGAAGACGGCAT-ACGAGATNNNNNNNNGTGCGTGCGTGCTTCTGTCG TC CAGTCTGATGTG-3' (SEQ ID NO:108) and 5'-AAT-GATACGGCGACCACCGAGATCTACACNNNNNNG-CATGCAGCCGGTTGACTA GTACATGACCACTTGA-3' (SEQ ID NO:109)). The amplification conditions for these PCR reactions were as follows: an initial denaturation at 95° C. for 5 minutes followed by 10 amplification cycles of 30 seconds of denaturation at 95° C., 30 seconds annealing at 65° C., 30 seconds elongation at 72° C., and a final elongation of 5 minutes at 72° C. The final NGS library was SPRI-purified, pooled, and cleaned via PippinHT (Sage Science).

Threshold PCR/Nested PCR

For each MULTIPLEX reaction, 4.08 ng of the SPRI-purified product was amplified across twenty-four 50 ul PCR reactions using 5'-T*A*G*G*G*A*AGAGAAGGAC ATATGAT-3' (SEQ ID NO:110) and/5Phos'/-TTGACTAGTACATGACCACTTGA-3' (SEQ ID NO:111)), wherein * indicates the nucleotide was modified such that the sulfur atom in the phosphate backbone was substituted for a phosphorothioate bond substitutes a sulfur atom, which renders the sequence more resistant to nuclease digestion. The end product of this nested PCR is a 86-bp amplicon that matches the original N40 library. It can be converted to ssDNA via enzymatic digestion, and used for another round of MULTIPLEX.

Results

The resulting data provided information about how aptamers preferentially bind to alternative targets in the same experiment. Presently, up to 6 targets have been concurrently evaluated via MULTIPLEX.

Figure 61:
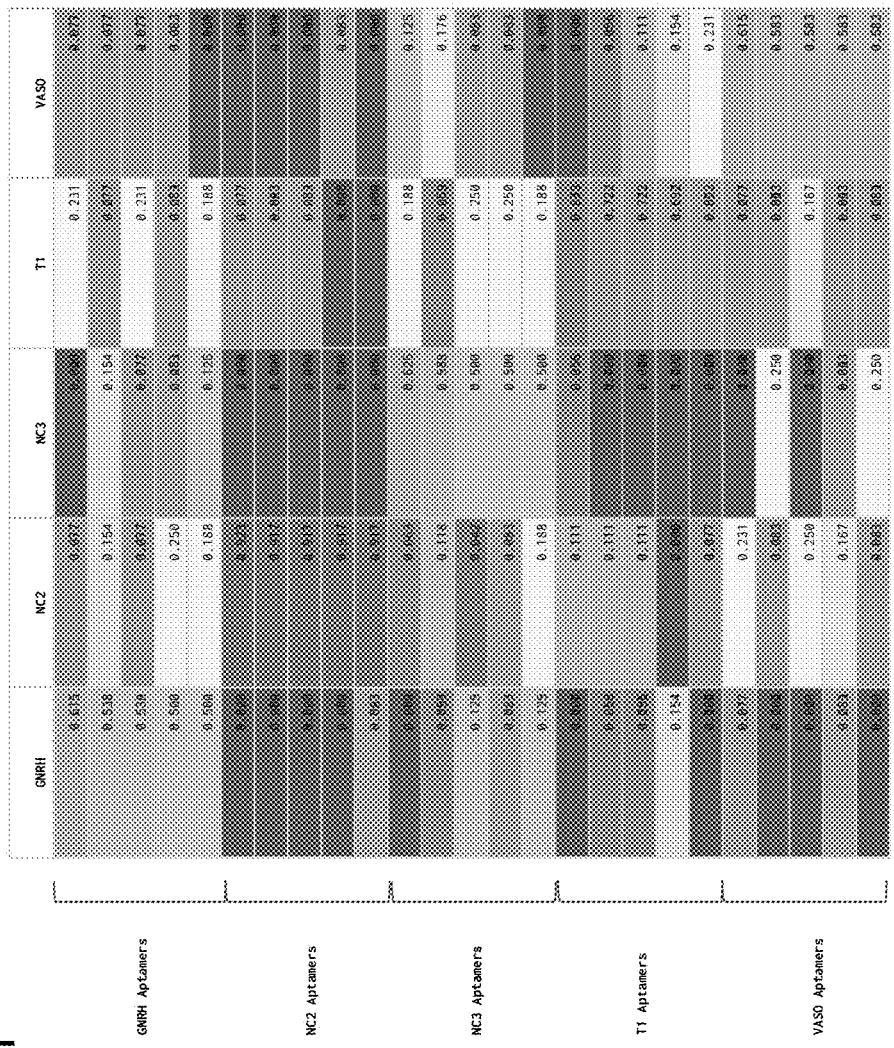
FIG. 61 is a heat map reporting MULTIPLEX selectivity performance. In a five target (GNRH, NC2, NC3, T1, Vaso) assay, aptamers were first filtered for abundance (at least 12 reads) and the top 5 sequences to each target were ranked based on selectivity (reads to the desired target/reads to all targets). Off-target hits are shown, with the selectivity highlighted by the red (low specificity) to blue (greater specificity) color gradient. The top 5 target-specific aptamers for each target exhibits 0.500 to 0.923 selectivity, indicating that at least half of the reads of each aptamer was bound to its intended target. In comparison, no more than 25.0% of the reads of the same aptamers were bound to any individual unintended target.

Within a given MULTIPLEX experiment, target-specific sequences showed selective binding behavior towards their associated targets (FIG. 61). Analysis measured selectivity as reads to the desired target divided by reads to all targets at round 4. The top 5 sequences of each target (GNRH, NC2, NC3, T1, Vaso) showed selectivity of 0.500 to 0.924 to their intended targets, and no more than 0.250 to any individual unintended target.

Within a MULTIPLEX experiment, there is significant bleedthrough between targets, with no aptamers that are exclusively identified with a single target (though there are round 4 aptamers identified with argipressin up to 58.3% of the time, GnRH 50% of the time, and Target1_NC2 up to 83.3% of the time). As three of the six targets had peptides of similar sequences (Target 1: (N-terminus)-YQNTSQNTS-Cys (C-terminus) (SEQ ID NO:112); Target1_NC2: (N-terminus)-KQNTYQNTS-Cys (C-terminus) (SEQ ID NO:113); Target1_NC3: (N-terminus)-QNT-SYQNTS-Cys (C-terminus) (SEQ ID NO:114)), it is not surprising that they may pull down the same aptamer (FIG. 62).

Example 7—Turducken Experimentation

Reagents

Constructs for expression of RNA-binding proteins and RNA sequences were assembled using the standard tools and methods of molecular biology, such as PCR amplification, restriction digest, infusion assembly or ligation. Genes of interest or the DNA sequences encoding RNA hairpins were ordered as geneblocs or assembled by PCR. All regions amplified by PCR were verified in the final bacterial clones by Sanger sequencing. Cloning of the expression construct for both RNA-binding protein and RNA was performed sequentially, with the gene encoding the RNA binding proteins inserted first, followed by restriction digest of these vectors and insertion of the DNA fragment encoding the RNA hairpin to produce vectors for expression of both the RBP and the RNA. Experiments were performed with a tandem fusion of the MS2 coat protein (dMS2) tagged with a 9×His motif for affinity purification, with or without a molecular fusion to Emerald GFP (EmGFP). MS2 binding site contains a U to C mutation, which improves the affinity of the RNA-protein interaction. For bacterial expression, dMS2-EmGFP or dMS2 were cloned into pRSFDuet1 vector under the control of T7 promoter using Infusion (Takara) cloning, and transformed into NEB Turbo cells for plasmid amplification. Plasmids were purified from NEB Turbo cells using standard miniprep kits (Zymo or Thermo) and sequence verified. All water used was Ambion™ Nuclease-Free water.

Methods

Transformation

For overexpression of proteins in bacteria, plasmids carrying dMS2-EmGFP or dMS2 were transformed into T7 Express lysY/Iq Competent *E. coli* from NEB, and plated on kanamycin antibiotic selection plates (50 ug/ml) overnight at 37° C.

Protein Expression

Single colonies were resuspended in 5 ml of LB liquid culture media with 50 ug/ml kanamycin and incubated with shaking at 37° C. until OD600 reached 0.4-0.8 to produce a starter culture. 50-500 ul of starter culture was used to inoculate 5 ml of fresh LB media with 50 ug/ml kanamycin, and protein production was induced by the addition of 0.1-1 mM IPTG, shaking either overnight at 22-27° C. or for 3-5 hours at 37° C.

Protein Isolation

Following protein induction, cells were pelleted by centrifugation at 3,000-5,000 g for 5 minutes, washed once with 1 ml of ice-cold PBS, pelleted again and re-suspended in 200-1000 ul of Y-PER Plus Dialyzable Yeast Protein Extraction Reagent supplemented with Halt Protease Inhibitor Cocktail. The weight of the cell pellet determined the volume of Y-PER reagent added per manufacturer's recommendation. The mixture was gently agitated at room temperature for 20 minutes, and soluble proteins were isolated from cell debris by centrifuging at 14,000×g for 10 minutes.

Supernatant containing soluble cell proteins was removed, analyzed by SDS-PAGE and Coomassie staining or BCA assays. dMS2 or dMS2-EmGFP were further isolated by Dynabeads™ His-Tag Isolation and Pulldown using manufacturer's protocol. Briefly, lysates from 5-ml liquid cultures were incubated with 100 ul of Dynabeads in final volume of 700-1400 ul, with the lysate volume adjusted using Binding/Wash buffer (50 mM Sodium Phosphate, pH 8.0, 300 mM NaCl, 0.01% Tween-20). After 5-10 minute incubation, the beads were washed 4× with 300-600 ul of Binding/Wash buffer, with the supernatant discarded after each wash and beads resuspended fully in-between.

To elute the protein, following the final wash beads were incubated for 10 minutes on a roller with 100-200 ul Binding/Wash buffer containing 300 mM imidazole. Eluted protein was exchanged into PBS and concentrated to ~1 mg/ml using 10 kDa Amicon Ultra-0.5 Devices. Purified protein was quantified using Pierce BCA Protein Assay Kit or SDS-PAGE gels stained with SimplyBlue SafeStain.

Binding Verification

Binding of dMS2-EmGFP and dMS2 to MS2 RNA was verified by electrophoretic mobility shift assays (EMSA).

Product Quantification

~350-nt long RNA containing MS2 binding site was produced by in vitro transcription using TranscriptAid T7 High Yield Transcription Kit, purified with Qiagen RNeasy Mini Kit and quantified using Nanodrop.

Product Identity Verification

The presence of the correct product was verified by agarose gel electrophoresis following purification. RNA was diluted in TE buffer to 1-10 uM final concentration and stored at −80 C. Prior to binding experiments, RNA was heated to 70-80° C. for 5 minutes and snap cooled on ice for 5 minutes. Electrophoretic mobility shift assays were performed by incubating 1-3 nM RNA with increasing protein concentrations (0-200 nM) in 80 mM KCl, 10 mM MgCl$_2$, 100 mM Hepes, pH 7.5 (20 ul final volume) for 30-60 min at room temperature. SUPERase RNase Inhibitor was added to all binding reactions. RNA and RNA-protein complexes were resolved by non-denaturing PAGE using Novex 4-12% Tris-Glycine Gels in Novex Tris-Glycine Native Running Buffer. RNA was stained using SYBR Green nucleic acid stain and gels imaged using E-Gel imager.

Results

Expression Verification

Figure 63:
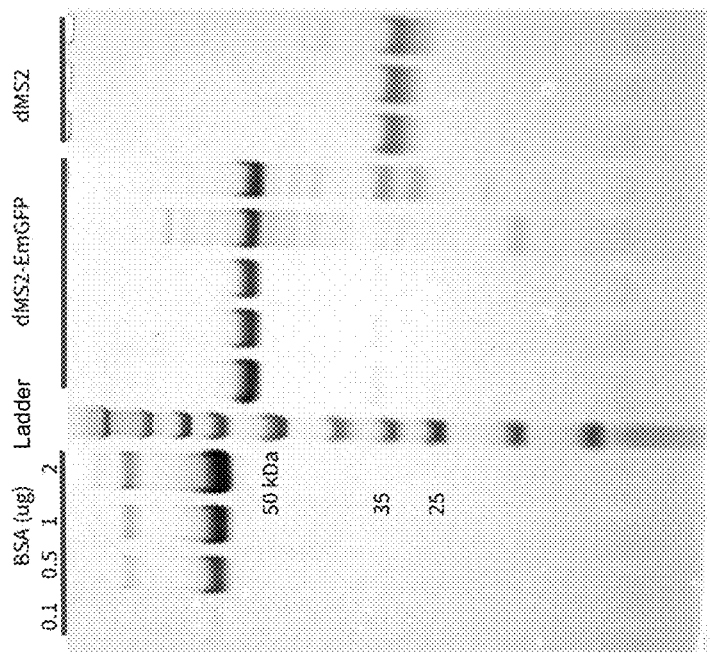
FIG. 63 is an image of an SDS-PAGE gel showing that denatured peptides purified using an Anti-His affinity pull down assay were of the expected size for dMS-EmGFP and dMS2, indicating that both dMS-EmGFP and dMS2 were expressed. BSA was included as a standard.

SDS-PAGE demonstrated that denatured peptides or proteins purified using an Anti-His affinity pull-down assay were of the expected size for dMS-EmGFP and dMS2, indicating that both dMS-EmGFP and dMS2 were expressed. BSA was included as a standard (FIG. 63).

Binding Verification

Figure 64:
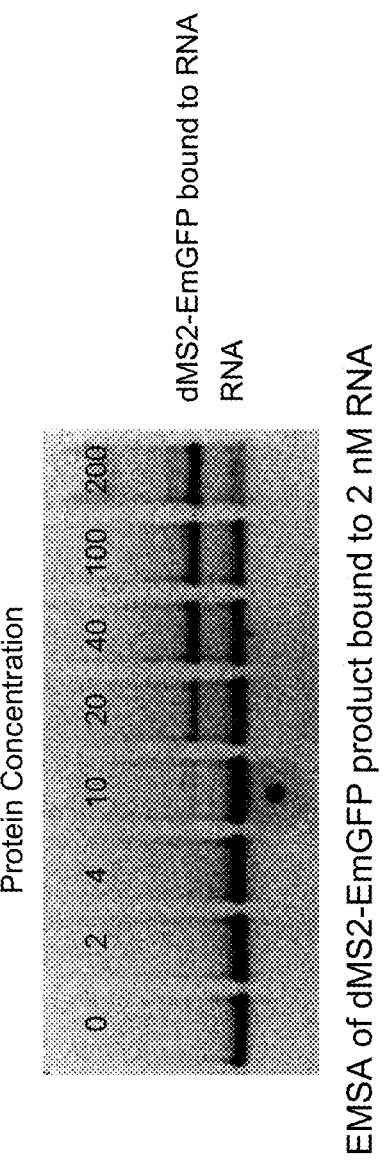
FIG. 64 is an image of an electrophoretic mobility shift assay (EMSA) gel demonstrating that dMS2-EmGFP fusion protein bound to 2 nM RNA (protein concentrations used in binding reaction indicated on the top, nM) containing the MS2 coat protein binding site.

EMSA demonstrated dMS2-EmGFP fusion protein bound to ~2 nM RNA containing the MS2 coat protein binding site (FIG. 64).

Product Verification

Figure 65:
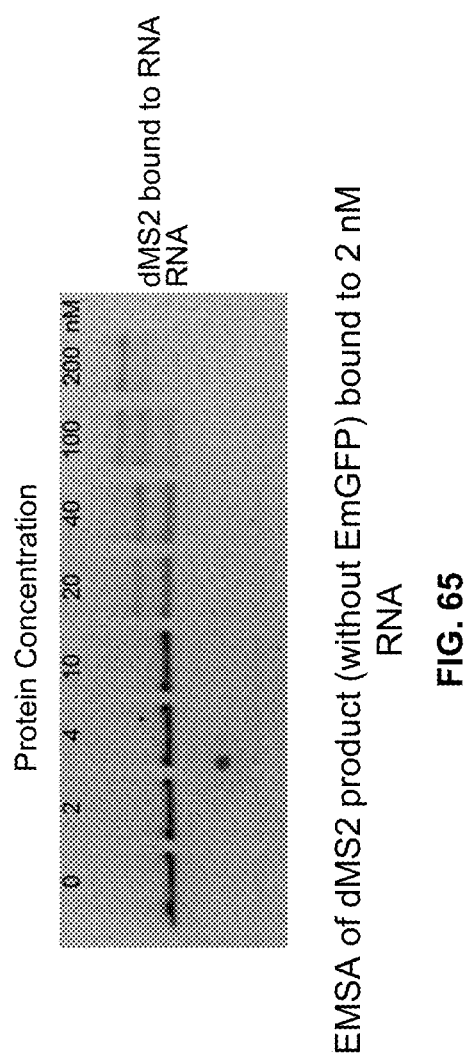
FIG. 65 is an image of an EMSA gel showing that the dMS2 proteins (without EmGFP) bound to ~2 nM RNA (protein concentrations used in binding reaction indicated on the top, nM) containing the MS2 coat protein binding site, verifying the identity of dMS2 proteins.

EMSA demonstrated that the dMS2 proteins (without EmGFP) bound to ~2 nM RNA containing the MS2 coat protein binding site, verifying the identity of the protein. (FIG. 65).

Example 8—LEGO Experimentation

Reagents

Double-stranded DNA primers (TriLink Forward: TAGGGAAGAGAAGGACATATGAT (SEQ ID NO:115); TriLink Reverse with Lego 4: GCTCTACAGTATTGACTAGTACATGACCACTTGA (SEQ ID NO:116)) and LEGO pieces (10-mers with 5' phosphorylated single base-pair overhangs) were obtained from IDT.

The LEGO sequences were:

```
Lego1:
                                    (SEQ ID NO: 117)
AATGCTGAGC

Lego2:
                                    (SEQ ID NO: 118)
CACTACAGCC

Lego3:
                                    (SEQ ID NO: 119)
TAGCACTGAG

Lego4 with TriLink Reverse:
                                    (SEQ ID NO: 120)
GCTCTACAGTATTGACTAGTACATGACCACTTGA
```

Methods

Ligation Reaction

An initial ligation reaction was performed at 25° C. (on a thermocycler) for 15 minutes using 2 ul of 2.5 uM TriLink Forward dsDNA primer, 2 ul of 2.5 uM initial dsDNA LEGO piece (LEGO1), 2 ul 10× CutSmart Buffer (NEB), 5 ul Blunt/TA Ligase Master Mix (NEB), 1 uL 2 mM ATP, and 10 uL of water. A subsequent LEGO piece was ligated to the extending product by adding 2 uL of 2.5 uM LEGO2 and 5 ul of Blunt/TA Ligase MM to the initial reaction and allowing it to incubate for 15 min at 25° C. This process was repeated two more times until the TriLink Reverse dsDNA primer with LEGO4 was added.

Post-Processing & Sequencing

Ligation product was collected with a cleanup assay run on a Bravo Automated Liquid Handling Platform (Agilent), PCR amplified, and then cleaned again with the same Bravo protocol. The cleaned PCR product was NGS-prepped for sequencing with custom primers. The NGS-prepped sample was size-selected for a 177-bp-long product using a PippinHT automated gel extraction system. A 40×8×6×38 (Read 1×i7×i5×Read2) read was conducted using NextSeq V2.5 chemistry.

Results

Figure 66:
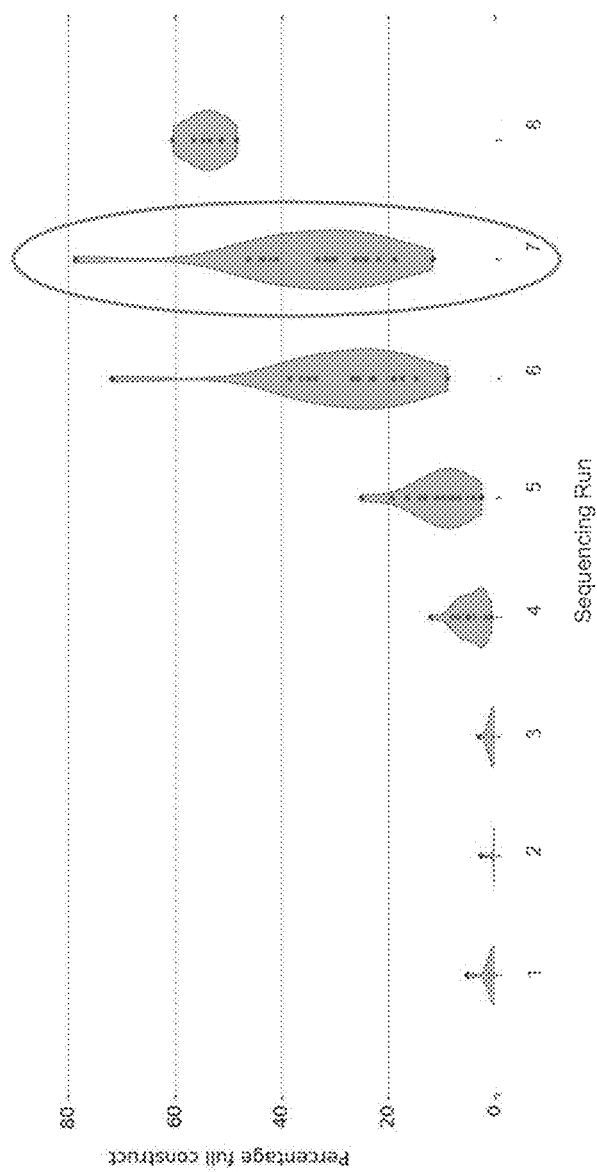
FIG. 66 is a violin plot displaying the percentage of sequences from each experiment that were the desired full length constructs using 10mer dsDNA pieces with 1 base pair overhangs, one of which reached 78.9% efficiency.
Figure 67:
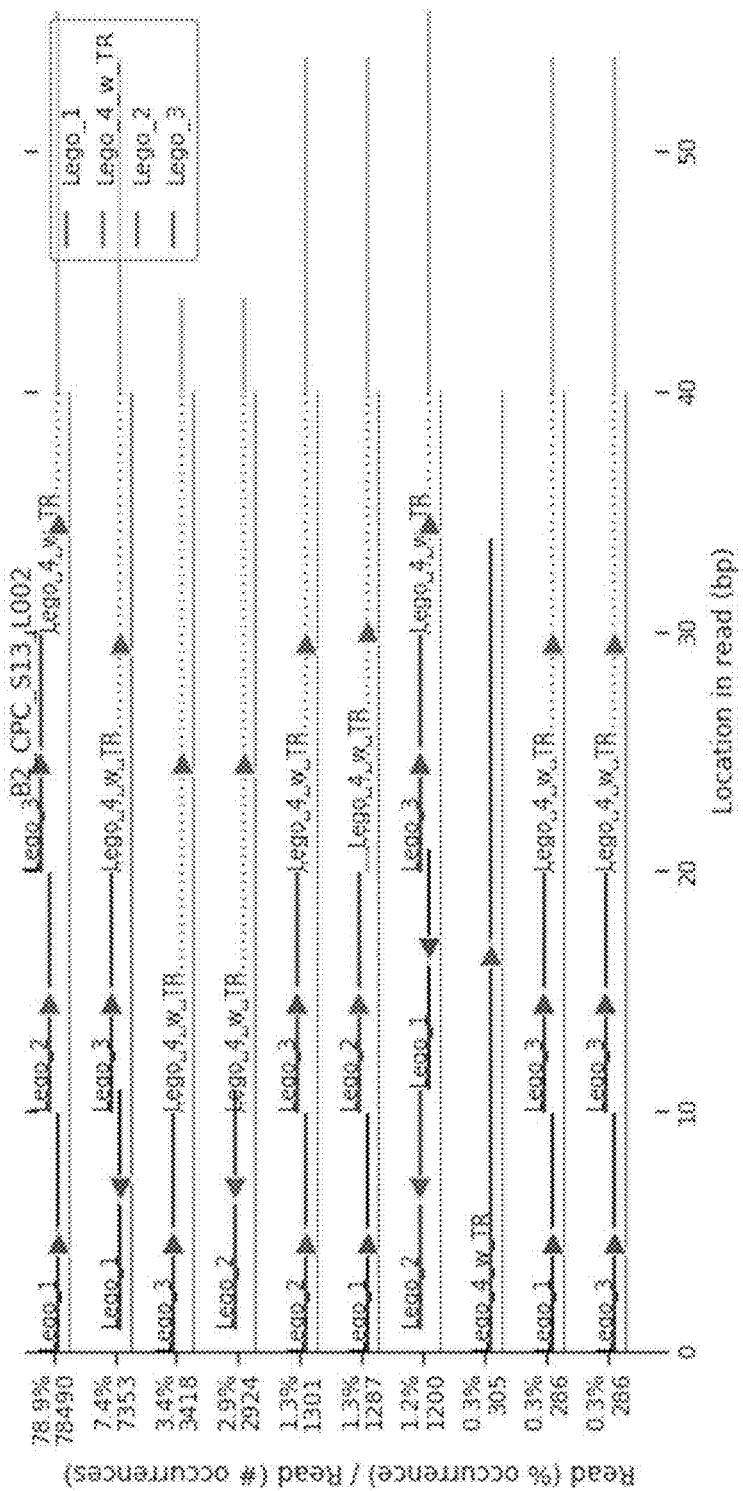
FIG. 67 reports the percentages of unique sequences produced in LEGO experiment 87P from FIG. 66, wherein 78.9% of the constructs were sequences of the desired length, order, and orientation of lego pieces.

Sequencing results demonstrated that with sequential ligations and unique single-base overhangs, 10-mers can be directed to assemble into a goal 40-mer sequence (with one 23 bp primer on each end) with ~80% efficiency (FIGS. 66 and 67). These results indicate that generating diverse pools with discrete sequences in various positions is feasible.

REFERENCES

Blind, M., & Blank, M. (2015). Aptamer Selection Technology and Recent Advances. *Molecular Therapy—Nucleic Acids*, 4. doi:10.1038/mtna.2014.74

Bergman, T., Cederlund, E., & Jornvall, H. (2001). Chemical C-Terminal Protein Sequence Analysis: Improved Sensitivity, Length of Degradation, Proline Passage, and Combination with Edman Degradation. *Analytical Biochemistry*, 290(1), 74-82. doi:10.1006/abio.2000.4922

Bouchard, P., Hutabarat, R., & Thompson, K. (2010). Discovery and Development of Therapeutic Aptamers. *Annual Review of Pharmacology and Toxicology*, 50(1), 237-257. doi:10.1146/annurev.pharmtox.010909.105547

Casagranda, F., & Wilshire, J. F. (1994). C-Terminal Sequencing of Peptides: The Thiocyanate Degradation Method. Basic Protein and Peptide Protocols, 335-350. doi:10.1385/0-89603-268-x:335

Chelsea K. L. Gordon, Diana Wu, Trevor A. Feagin, Anusha Pusuluri, Andrew T. Csordas, Michael Eisenstein, Craig J. Hawker, Jia Niu, H. Tom Soh. (2019). Click-PD: A Quantitative Method for Base-Modified Aptamer Discovery. *bioRxiv* 626572; doi: https://doi.org/10.1101/626572

Chen, M., Yu, Y., Jiang, F., Zhou, J., Li, Y., Liang, C., . . . Zhang, G. (2016). Development of Cell-SELEX Technology and Its Application in Cancer Diagnosis and Therapy. *International Journal of Molecular Sciences*, 17(12), 2079. doi:10.3390/ijms17122079 de Sousa Abreu, R. D., Penalva, L. O., Marcotte, E. M., & Vogel, C. (2009). Global signatures of protein and mRNA expression levels. *Molecular BioSystems*. doi:10.1039/b908315d Diatchenko, L., Lau, Y. F., Campbell, A. P., Chenchik, A., Moqadam, F., Huang, B., . . . Siebert, P. D. (1996). Suppression subtractive hybridization: A method for generating differentially regulated or tissue-specific cDNA probes and libraries. *Proceedings of the National Academy of Sciences*, 93(12), 6025-6030. doi:10.1073/pnas.93.12.6025

Fujishima, K., Venter, C., Wang, K., Ferreira, R., & Rothschild, L. J. (2015). An overhang-based DNA block shuffling method for creating a customized random library. *Scientific Reports*, 5(1). doi:10.1038/srep09740

Hoon, S., Zhou, B., Janda, K., Brenner, S., & Scolnick, J. (2011). Aptamer selection by high-throughput sequencing and informatic analysis. *BioTechniques*, 51(6). doi: 10.2144/000113786

Horspool, D. R., Coope, R. J., & Holt, R. A. (2010). Efficient assembly of very short oligonucleotides using T4 DNA Ligase. *BMC Research Notes*, 3(1), 291. doi:10.1186/1756-0500-3-291

Jia, B., & Jeon, C. O. (2016). High-throughput recombinant protein expression in *Escherichia coli*: Current status and future perspectives. *Open Biology*, 6(8), 160196. doi: 10.1098/rsob.160196

Little, J. W. (1967). An exonuclease induced by bacteriophage lambda. II. Nature of the enzymatic reaction. *J. Biol. Chem.* 1967; 242:679-686.

Loakes, D., & Brown, D. M. (1994). 5-Nitroindole as an universal base analogue. *Nucleic acids research*, 22(20), 4039-4043. https://doi.org/10.1093/nar/22.20.4039

Mckeague, M., & Derosa, M. C. (2012). Challenges and Opportunities for Small Molecule Aptamer Development. *Journal of Nucleic Acids*, 2012, 1-20. doi:10.1155/2012/748913

Miteva, Y. V., Budayeva, H. G., & Cristea, I. M. (2012). Proteomics-Based Methods for Discovery, Quantification, and Validation of Protein—Protein Interactions. *Analytical Chemistry*, 85(2), 749-768. doi:10.1021/ac3033257

Mitsis, P. G., & Kwagh, J. G. (1999). Characterization of the interaction of lambda exonuclease with the ends of DNA. *Nucleic acids research*, 27(15), 3057-3063. https://doi.org/10.1093/nar/27.15.3057

Pfeiffer, F., Rosenthal, M., Siegl, J., Ewers, J., & Mayer, G. (2017). Customised nucleic acid libraries for enhanced aptamer selection and performance. *Current opinion in biotechnology*, 48, 111-118

Schiess, R., Wollscheid, B., & Aebersold, R. (2008). Targeted proteomic strategy for clinical biomarker discovery. *Molecular Oncology*, 3(1), 33-44. doi:10.1016/j.molonc.2008.12.001

Tucker, W. O., Shum, K. T., & Tanner, J. A. (2012). G-quadruplex DNA Aptamers and their Ligands: Structure, Function and Application. *Current Pharmaceutical Design*, 18(14), 2014-2026. doi:10.2174/138161212799958477

Tuerk, C., & Gold, L. (1990). Systematic evolution of ligands by exponential enrichment: RNA ligands to bacteriophage T4 DNA polymerase. *Science*, 249(4968), 505-510. doi:10.1126/science.2200121

Vogel, C., & Marcotte, E. M. (2012). Insights into the regulation of protein abundance from proteomic and transcriptomic analyses. *Nature Reviews Genetics*, 13(4), 227-232. doi:10.1038/nrg3185

Yates, J. R., Ruse, C. I., & Nakorchevsky, A. (2009). Proteomics by Mass Spectrometry: Approaches, Advances, and Applications. *Annual Review of Biomedical Engineering*, 11(1), 49-79. doi:10.1146/annurev-bioeng-061008-1249 Zhou, J., & Rossi, J. (2016). Aptamers as targeted therapeutics: Current potential and challenges. *Nature Reviews Drug Discovery*, 16(3), 181-202. doi: 10.1038/nrd.2016.199

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of sequencing a peptide, comprising:
 (a) incubating the peptide with a library of DNA aptamers exhibiting binding specificity toward at least one N-terminal amino acid under conditions where one or more aptamers bind specifically to at least one N-terminal amino acid of the peptide, wherein each aptamer in the library comprises a peptide binding ssDNA region and a unique barcode sequence indicative of the first binding round and the associated peptide binding ssDNA region;
 (b) ligating the DNA aptamer bound to the N-terminal of the peptide onto a proximal DNA barcode construct;
 (c) removing the peptide binding sequence from the DNA aptamer, thereby leaving the barcode of the DNA aptamer covalently attached to the DNA barcode construct;
 (d) removing the N-terminal amino acid from the peptide to produce an N-terminal amino acid-shortened peptide;
 (e) incubating the N-terminal amino acid-shortened peptide with the library of aptamers exhibiting binding specificity toward at least one N-terminal amino acid under conditions where one or more aptamers bind specifically to at least one N-terminal amino acid of the N-terminal amino acid-shortened peptide, wherein each aptamer in the library comprises a peptide binding ssDNA region and a unique barcode sequence indicative of the second binding round and the associated peptide binding ssDNA region;
 (f) ligating the DNA aptamer bound to the N-terminal of the peptide onto the proximal DNA barcode construct;
 (g) removing the peptide binding sequence from the DNA aptamer, thereby leaving the barcode of the DNA aptamer covalently attached to the DNA barcode construct;
 (h) removing the N-terminal amino acid from the N-terminal amino acid-shortened peptide;
 (i) repeating steps (a)-(d) a plurality of times to construct a chain of positional barcodes that correspond to sequential N-terminal amino acids in the peptide; and
 (j) sequencing the chain of positional barcodes to thereby obtain the sequence of the peptide.

2. The method of claim 1, wherein the peptide is from a synthetic sample, biological sample, or combinations thereof.

3. The method of claim 2, wherein the biological sample is selected from the group consisting of blood, urine, saliva, tissue biopsy, sputum, stool, single cell, environmental samples, and bacterial swabs.

4. The method of claim 1, wherein the peptide is a full-length protein or a peptide comprised within a complex.

5. The method of claim 1, further comprising, prior to step (a), fragmenting the peptide.

6. The method of claim 5, wherein the fragmenting step comprises exposing the peptide with a fragmentation enzyme.

7. The method of claim 1, wherein the C-terminal end of the peptide is attached to a solid support.

8. The method of claim 1, wherein the C-terminal end of the peptide is attached to an oligonucleotide tail.

9. The method of claim 1, wherein the removing the peptide binding sequence from the DNA aptamer step comprises cleaving the aptamer with a restriction enzyme.

10. The method of claim 1, wherein the removing of the peptide binding sequence from the DNA aptamer is mediated by hydrogen bond disruption.

11. The method of claim 1, wherein the removing the N-terminal amino acid step comprises Edman degradation of the peptide, cleaving the peptide with one or more aminopeptidases, heat, pH, or combinations thereof.

12. The method of claim 1, wherein the sequencing step uses a next generation sequencing (NGS) platform.

13. A method of identifying novel biomarkers, comprising:
(a) providing protein samples from biological samples of interest and control or comparison biological samples;
(b) optionally, removing proteins present in high concentrations;
(c) performing the steps (a)-(j) of the method of claim 1;
(d) performing a sup-diff to remove high concentration DNA barcode construct sequences associated with highly expressed proteins or contaminants such that a ratio of DNA barcode constructs associated with lowly expressed proteins to highly expressed proteins increases, thereby producing ratio-adjusted DNA barcodes;
(e) amplifying the ratio-adjusted DNA barcodes; and
(f) comparing the number of sequencing reads associated with each lowly expressed proteins from control samples to samples of interest;
thereby identifying biomarkers that have different relative expression levels between the control samples and the biological samples of interest.

14. A method of evaluating a disease state, evaluating a response to treating a disease, predicting a response to treating a disease, or combinations thereof, wherein the disease comprises aberrant expression levels of at least one known protein biomarker, the method comprising:
(a) providing protein samples from patient samples;
(b) optionally depleting proteins present in high concentrations;
(c) performing the steps (a)-(j) of the method of claim 1;
(d) performing a sup-diff to remove high concentration DNA barcode construct sequences associated with highly expressed proteins or contaminants to increase the ratio of DNA barcode constructs associated with lowly expressed proteins to highly expressed proteins, thereby producing ratio-adjusted DNA barcodes;
(e) amplifying the ratio-adjusted DNA barcodes;
(f) analyzing the number of sequencing reads associated with known protein biomarkers to determine the relative quantity thereof;
(g) determining the presence or absence of expression level deviations of known protein biomarkers from one or more standard values,
thereby evaluating the disease state, evaluating the response to treating the disease, predicting the response to treating a disease, or combinations thereof.

15. The method of claim 1, wherein the library of aptamers is produced using a RCHT-SELEX method.

16. The method of claim 1, wherein each aptamer in the library of aptamers exhibits binding specificity toward one N-terminal amino acid.

17. The method of claim 1, wherein each aptamer in the library of aptamers exhibits binding specificity toward two or more N-terminal amino acids.

18. The method of claim 1, wherein the unique barcode sequence indicative of the aptamer's associated peptide binding ssDNA region and binding round comprises about 6 to about 20 nucleotides.

19. The method of claim 1, wherein each aptamer in the library of aptamers comprises a BCS compatible portion.

20. The method of claim 19, wherein the BCS compatible portion of each aptamer comprises one or more DNA sequences complementary to the aptamer.

21. The method of claim 1, wherein the barcode sequence comprises a unique barcode that indicates the peptide or the sample from which the peptide was derived.

* * * * *

SEQUENCE LISTING

<160> NUMBER OF SEQ ID NOS: 291

<210> SEQ ID NO 1
<211> LENGTH: 86
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 1
tagggaagag aaggacatat gatnnnnnnn nnnnnnnnnn nnnnnnnnnn nnnnnnnnnn    60
nnnttgacta gtacatgacc acttga                                        86

<210> SEQ ID NO 2
<211> LENGTH: 86
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 2
tagggaagag aaggacatat gatnnnnnnn nnnnnnnnnn nnnnnnnnnn nnnnnnnnnn    60
nnnttgacta gtacatgacc acttga                                        86

<210> SEQ ID NO 3
<211> LENGTH: 85
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 3
ttgactagta catgaccact gannnnnnnn nnnnnnnnnn nnnnnnnnnn nnnnnnnnnn    60
nnncacatca gactggacga cagaa                                         85

<210> SEQ ID NO 4
<211> LENGTH: 84
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 4
tgatgctatg cgacttattg tacnnnnnnn nnnnnnnnnn nnnnnnnnnn nnnnnnnnnn    60
nnntacttgg cgttcttacc acca                                          84

<210> SEQ ID NO 5
<211> LENGTH: 8
<212> TYPE: PRT
<213> ORGANISM: Artificial

```
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 5

Ala Asp Arg Trp Ala Asp Arg Xaa
1               5

<210> SEQ ID NO 6
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 6

Met Ser Gln Pro Leu Gln Pro Xaa
1               5

<210> SEQ ID NO 7
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 7

Asn His Phe Glu Asn Glu Ile Xaa
1               5

<210> SEQ ID NO 8
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 8

Thr Lys Tyr Val Gly Thr Gly Xaa
1               5

<210> SEQ ID NO 9
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 9

Thr Ala Tyr Val Glu Thr Glu Xaa
1               5
```

```
<210> SEQ ID NO 10
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa Lys or Cys

<400> SEQUENCE: 10

Gln Gly His Ser Ile Asp Asn Xaa
1               5

<210> SEQ ID NO 11
<211> LENGTH: 23
<212> TYPE: DNA
<213> ORGANISM: Artificial
<220> FEATURE:
<223> OTHER INFORMATION: Synthetic oligonucleotide

<400> SEQUENCE: 11
tagggaagag aaggacatat gat                                             23

<210> SEQ ID NO 12
<211> LENGTH: 23
<212> TYPE: DNA
<213> ORGANISM: Artificial
<220> FEATURE:
<223> OTHER INFORMATION: Synthetic oligonucleotide

<400> SEQUENCE: 12
tcaagtggtc atgtactagt caa                                             23

<210> SEQ ID NO 13
<211> LENGTH: 23
<212> TYPE: DNA
<213> ORGANISM: Artificial
<220> FEATURE:
<223> OTHER INFORMATION: Synthetic oligonucleotide

<400> SEQUENCE: 13
ttgactagta catgaccact tga                                             23

<210> SEQ ID NO 14
<211> LENGTH: 22
<212> TYPE: DNA
<213> ORGANISM: Artificial
<220> FEATURE:
<223> OTHER INFORMATION: Synthetic oligonucleotide

<400> SEQUENCE: 14
ttctgtcgtc cagtctgatg tg                                              22

<210> SEQ ID NO 15
<211> LENGTH: 23
<212> TYPE: DNA
<213> ORGANISM: Artificial
<220> FEATURE:
<223> OTHER INFORMATION: Synthetic oligonucleotide

<400> SEQUENCE: 15
tgatgctatg cgacttattg tac                                             23
```

```
<210> SEQ ID NO 16
<211> LENGTH: 21
<212> TYPE: DNA
<213> ORGANISM: Artificial
<220> FEATURE:
<223> OTHER INFORMATION: Synthetic oligonucleotide

<400> SEQUENCE: 16
tggtggtaag aacgccaagt a                                              21

<210> SEQ ID NO 17
<211> LENGTH: 86
<212> TYPE: DNA
<213> ORGANISM: Artificial
<220> FEATURE:
<223> OTHER INFORMATION: Synthetic oligonucleotide

<400> SEQUENCE: 17
tagggaagag aaggacatat gatcaccgca tcctgaggcc ggtgtggagg gcacgaagtc    60
tggttgacta gtacatgacc acttga                                         86

<210> SEQ ID NO 18
<211> LENGTH: 86
<212> TYPE: DNA
<213> ORGANISM: Artificial
<220> FEATURE:
<223> OTHER INFORMATION: Synthetic oligonucleotide

<400> SEQUENCE: 18
tagggaagag aaggacatat gatctagcat ggtgcccttg ccctcagagc ggaagtacct    60
gatttgacta gtacatgacc acttga                                         86

<210> SEQ ID NO 19
<211> LENGTH: 23
<212> TYPE: DNA
<213> ORGANISM: Artificial
<220> FEATURE:
<223> OTHER INFORMATION: Synthetic oligonucleotide

<400> SEQUENCE: 19
tagggaagag aaggacatat gat                                            23

<210> SEQ ID NO 20
<211> LENGTH: 41
<212> TYPE: DNA
<213> ORGANISM: Artificial
<220> FEATURE:
<223> OTHER INFORMATION: Synthetic oligonucleotide

<400> SEQUENCE: 20
cttagatgca cgtggataat catatgtcct tctcttccct a                        41

<210> SEQ ID NO 21
<211> LENGTH: 41
<212> TYPE: DNA
<213> ORGANISM: Artificial
<220> FEATURE:
<223> OTHER INFORMATION: Synthetic oligonucleotide

<400> SEQUENCE: 21
cttagatgca cgcagcatat catatgtcct tctcttccct a                        41

<210> SEQ ID NO 22
<211> LENGTH: 32
<212> TYPE: DNA
```

```
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (25)..(32)
<223> OTHER INFORMATION: n is a, c, g, or t

<400> SEQUENCE: 22
caagcagaag acggcatacg agatnnnnnn nn                                  32

<210> SEQ ID NO 23
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (30)..(35)
<223> OTHER INFORMATION: n is a, c, g, or t

<400> SEQUENCE: 23
aatgatacgg cgaccaccga gatctacacn nnnnn                               35

<210> SEQ ID NO 24
<211> LENGTH: 84
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 24
tgatgctatg cgacttattg tacnnnnnnn nnnnnnnnnn nnnnnnnnnn nnnnnnnnn     60 nnntacttgg cgttcttacc acca                                           84

<210> SEQ ID NO 25
<211> LENGTH: 23
<212> TYPE: DNA
<213> ORGANISM: Artificial
<220> FEATURE:
<223> OTHER INFORMATION: Synthetic oligonucleotide

<400> SEQUENCE: 25
tgatgctatg cgacttattg tac                                            23

<210> SEQ ID NO 26
<211> LENGTH: 23
<212> TYPE: DNA
<213> ORGANISM: Artificial
<220> FEATURE:
<223> OTHER INFORMATION: Synthetic oligonucleotide

<400> SEQUENCE: 26
gtacaataag tcgcatagca tca                                            23

<210> SEQ ID NO 27
<211> LENGTH: 86
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
```

```
<222> LOCATION: (24)..(63)
<223> OTHER INFORMATION: n is a, c, g, or t

<400> SEQUENCE: 27
tagggaagag aaggacatat gatnnnnnnn nnnnnnnnnn nnnnnnnnnn nnnnnnnnnn      60
nnnttgacta gtacatgacc acttga                                          86

<210> SEQ ID NO 28
<211> LENGTH: 28
<212> TYPE: DNA
<213> ORGANISM: Artificial
<220> FEATURE:
<223> OTHER INFORMATION: Synthetic oligonucleotide

<400> SEQUENCE: 28
tagggaagag ggatgaagga catatgat                                        28

<210> SEQ ID NO 29
<211> LENGTH: 28
<212> TYPE: DNA
<213> ORGANISM: Artificial
<220> FEATURE:
<223> OTHER INFORMATION: Synthetic oligonucleotide

<400> SEQUENCE: 29
tcaagtggtc ggatgatgta ctagtcaa                                        28

<210> SEQ ID NO 30
<211> LENGTH: 96
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (29)..(68)
<223> OTHER INFORMATION: n is a, c, g, or t

<400> SEQUENCE: 30
tagggaagag ggatgaagga catatgatnn nnnnnnnnnn nnnnnnnnnn nnnnnnnnnn      60
nnnnnnnntt gactagtaca tcatccgacc acttga                               96

<210> SEQ ID NO 31
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (6)..(14)
<223> OTHER INFORMATION: n is a, c, g, or t

<400> SEQUENCE: 31
ggatgnnnnn nnnn                                                       14

<210> SEQ ID NO 32
<211> LENGTH: 24
<212> TYPE: DNA
<213> ORGANISM: Artificial
<220> FEATURE:
<223> OTHER INFORMATION: Synthetic oligonucleotide

<400> SEQUENCE: 32
tagggaagag ggatgaagga cata                                            24
```

<210> SEQ ID NO 33
<211> LENGTH: 28
<212> TYPE: DNA
<213> ORGANISM: Artificial
<220> FEATURE:
<223> OTHER INFORMATION: Synthetic oligonucleotide

<400> SEQUENCE: 33
ttgactagta catcatccga ccacttga                                      28

<210> SEQ ID NO 34
<211> LENGTH: 10
<212> TYPE: PRT
<213> ORGANISM: Artificial
<220> FEATURE:
<223> OTHER INFORMATION: Synthetic peptide

<400> SEQUENCE: 34

Cys Tyr Phe Gln Asn Cys Pro Arg Gly Lys
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic peptide

<400> SEQUENCE: 35

Arg Pro Pro Gly Phe Ser Pro Phe Arg Lys
1               5                   10

<210> SEQ ID NO 36
<211> LENGTH: 40
<212> TYPE: DNA
<213> ORGANISM: Artificial
<220> FEATURE:
<223> OTHER INFORMATION: Synthetic oligonucleotide

<400> SEQUENCE: 36
atattctagg ttggtaggga aggcatgtat ctaattcctg                         40

<210> SEQ ID NO 37
<211> LENGTH: 40
<212> TYPE: DNA
<213> ORGANISM: Artificial
<220> FEATURE:
<223> OTHER INFORMATION: Synthetic oligonucleotide

<400> SEQUENCE: 37
caaatcggtg ccggccggga aggggcaaaa acagtgcaac                         40

<210> SEQ ID NO 38
<211> LENGTH: 23
<212> TYPE: DNA
<213> ORGANISM: Artificial
<220> FEATURE:
<223> OTHER INFORMATION: Synthetic oligonucleotide

<400> SEQUENCE: 38
tagggaagag aaggacatat gat                                           23

<210> SEQ ID NO 39
<211> LENGTH: 23
<212> TYPE: DNA
<213> ORGANISM: Artificial

```
<220> FEATURE:
<223> OTHER INFORMATION: Synthetic oligonucleotide

<400> SEQUENCE: 39
ttgactagta catgaccact tga                                             23

<210> SEQ ID NO 40
<211> LENGTH: 23
<212> TYPE: DNA
<213> ORGANISM: Artificial
<220> FEATURE:
<223> OTHER INFORMATION: Synthetic oligonucleotide

<400> SEQUENCE: 40
tagggaagag aaggacatat gat                                             23

<210> SEQ ID NO 41
<211> LENGTH: 23
<212> TYPE: DNA
<213> ORGANISM: Artificial
<220> FEATURE:
<223> OTHER INFORMATION: Synthetic oligonucleotide

<400> SEQUENCE: 41
ttgactagta catgaccact tga                                             23

<210> SEQ ID NO 42
<211> LENGTH: 85
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 42
ttgactagta catgaccact tgannnnnnn nnnnnnnnnn nnnnnnnnnn nnnnnnnnnn     60
nnnttctgtc gtccagtctg atgtg                                           85

<210> SEQ ID NO 43
<211> LENGTH: 40
<212> TYPE: DNA
<213> ORGANISM: Artificial
<220> FEATURE:
<223> OTHER INFORMATION: Synthetic oligonucleotide

<400> SEQUENCE: 43
gacggtacag cttagtgaat tgcccccga cgcagggggtt                           40

<210> SEQ ID NO 44
<211> LENGTH: 40
<212> TYPE: DNA
<213> ORGANISM: Artificial
<220> FEATURE:
<223> OTHER INFORMATION: Synthetic oligonucleotide

<400> SEQUENCE: 44
tttgccgctg tctgacgcaa gaccacatca actttatttc                           40

<210> SEQ ID NO 45
<211> LENGTH: 40
<212> TYPE: DNA
<213> ORGANISM: Artificial
<220> FEATURE:
```

<223> OTHER INFORMATION: Synthetic oligonucleotide

<400> SEQUENCE: 45
cgctcgtgtt gctcgatcaa gggtctgtgc gtctagctgg                                40

<210> SEQ ID NO 46
<211> LENGTH: 40
<212> TYPE: DNA
<213> ORGANISM: Artificial
<220> FEATURE:
<223> OTHER INFORMATION: Synthetic oligonucleotide

<400> SEQUENCE: 46
acacccagac accgctgtcc gacgcaggac tgactggggc                                40

<210> SEQ ID NO 47
<211> LENGTH: 40
<212> TYPE: DNA
<213> ORGANISM: Artificial
<220> FEATURE:
<223> OTHER INFORMATION: Synthetic oligonucleotide

<400> SEQUENCE: 47
aacgaccggt tagactgtga ccgcttatcg ccgcagatat                                40

<210> SEQ ID NO 48
<211> LENGTH: 40
<212> TYPE: DNA
<213> ORGANISM: Artificial
<220> FEATURE:
<223> OTHER INFORMATION: Synthetic oligonucleotide

<400> SEQUENCE: 48
cgcatccggc gcaggattca agcgggattg taaggtaaga                                40

<210> SEQ ID NO 49
<211> LENGTH: 40
<212> TYPE: DNA
<213> ORGANISM: Artificial
<220> FEATURE:
<223> OTHER INFORMATION: Synthetic oligonucleotide

<400> SEQUENCE: 49
gacattgccc ttcgccgcag aagtgatgaa agggtttgtg                                40

<210> SEQ ID NO 50
<211> LENGTH: 40
<212> TYPE: DNA
<213> ORGANISM: Artificial
<220> FEATURE:
<223> OTHER INFORMATION: Synthetic oligonucleotide

<400> SEQUENCE: 50
cgctcgtgtt gctcgatcaa gtggactaga atttgcttct                                40

<210> SEQ ID NO 51
<211> LENGTH: 40
<212> TYPE: DNA
<213> ORGANISM: Artificial
<220> FEATURE:
<223> OTHER INFORMATION: Synthetic oligonucleotide

<400> SEQUENCE: 51
ccacggaata atgatggtgg ttgctccccg acgcaggggc                                40

<210> SEQ ID NO 52
<211> LENGTH: 40
<212> TYPE: DNA
<213> ORGANISM: Artificial
<220> FEATURE:
<223> OTHER INFORMATION: Synthetic oligonucleotide

<400> SEQUENCE: 52
acgcaccgat cgcaggttca cgtggtataa cactttgtaa    40

<210> SEQ ID NO 53
<211> LENGTH: 48
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (25)..(36)
<223> OTHER INFORMATION: n is 5-nitroindole

<400> SEQUENCE: 53
ctgcgcctat acgaattcgt tatcnnnnnn nnnnnnctct ccgttatc    48

<210> SEQ ID NO 54
<211> LENGTH: 102
<212> TYPE: DNA
<213> ORGANISM: Artificial
<220> FEATURE:
<223> OTHER INFORMATION: Synthetic oligonucleotide

<400> SEQUENCE: 54
gagagtaaag ccgataggat aacgaattcg tataggcgca ggatggactt gataaccttc    60
tgctgcgtgc cttgatgtgc ttacttggcg ttcttaccac ca    102

<210> SEQ ID NO 55
<211> LENGTH: 102
<212> TYPE: DNA
<213> ORGANISM: Artificial
<220> FEATURE:
<223> OTHER INFORMATION: Synthetic oligonucleotide

<400> SEQUENCE: 55
gagagttagt cagcagggat aacgaattcg tataggcgca gcatttgatt ctgctgcgtg    60 cataccctg tgtgttatcc ctacttggcg ttcttaccac ca    102

<210> SEQ ID NO 56
<211> LENGTH: 102
<212> TYPE: DNA
<213> ORGANISM: Artificial
<220> FEATURE:
<223> OTHER INFORMATION: Synthetic oligonucleotide

<400> SEQUENCE: 56
gagagtccac gtgcacagat aacgaattcg tataggcgca gcatacatcg gacatacatc    60
ctgcgtgcat ccacctttgc atacttggcg ttcttaccac ca    102

<210> SEQ ID NO 57
<211> LENGTH: 22
<212> TYPE: DNA
<213> ORGANISM: Artificial
<220> FEATURE:
<223> OTHER INFORMATION: Synthetic oligonucleotide

<400> SEQUENCE: 57

```
tctcggtggt cgccgtatca tt                                              22
```

<210> SEQ ID NO 58
<211> LENGTH: 24
<212> TYPE: DNA
<213> ORGANISM: Artificial
<220> FEATURE:
<223> OTHER INFORMATION: Synthetic oligonucleotide

<400> SEQUENCE: 58

```
atctcgtatg ccgtcttctg cttg                                            24
```

<210> SEQ ID NO 59
<211> LENGTH: 41
<212> TYPE: DNA
<213> ORGANISM: Artificial
<220> FEATURE:
<223> OTHER INFORMATION: Synthetic oligonucleotide

<400> SEQUENCE: 59

```
tagggaagag aaggacatat gattatccac gtgcatctaa g                         41
```

<210> SEQ ID NO 60
<211> LENGTH: 41
<212> TYPE: DNA
<213> ORGANISM: Artificial
<220> FEATURE:
<223> OTHER INFORMATION: Synthetic oligonucleotide

<400> SEQUENCE: 60

```
atcccttctc ttcctgtata ctaataggtg cacgtagatt c                         41
```

<210> SEQ ID NO 61
<211> LENGTH: 16
<212> TYPE: PRT
<213> ORGANISM: Artificial
<220> FEATURE:
<223> OTHER INFORMATION: Synthetic peptide

<400> SEQUENCE: 61

Pro Asp Arg Val Arg Ala Val Ser His Trp Ser Ser Gly Gly Gly Cys
1               5                   10                  15

<210> SEQ ID NO 62
<211> LENGTH: 41
<212> TYPE: DNA
<213> ORGANISM: Artificial
<220> FEATURE:
<223> OTHER INFORMATION: Synthetic oligonucleotide

<400> SEQUENCE: 62

```
atcccttctc ttcctgtata ctaataggtg cacgtagatt c                         41
```

<210> SEQ ID NO 63
<211> LENGTH: 10
<212> TYPE: PRT
<213> ORGANISM: Artificial
<220> FEATURE:
<223> OTHER INFORMATION: Synthetic peptide

<400> SEQUENCE: 63

Arg Pro Pro Gly Phe Ser Pro Phe Arg Cys
1               5                   10

<210> SEQ ID NO 64
<211> LENGTH: 41

```
<212> TYPE: DNA
<213> ORGANISM: Artificial
<220> FEATURE:
<223> OTHER INFORMATION: Synthetic oligonucleotide

<400> SEQUENCE: 64
atcccttctc ttcctgtata ctaataggtg cacgtagatt c                    41

<210> SEQ ID NO 65
<211> LENGTH: 20
<212> TYPE: DNA
<213> ORGANISM: Artificial
<220> FEATURE:
<223> OTHER INFORMATION: Synthetic oligonucleotide

<400> SEQUENCE: 65
cttagatgca cgtggataat                                            20

<210> SEQ ID NO 66
<211> LENGTH: 18
<212> TYPE: DNA
<213> ORGANISM: Artificial
<220> FEATURE:
<223> OTHER INFORMATION: Synthetic oligonucleotide

<400> SEQUENCE: 66
cttagatgca cgtggata                                              18

<210> SEQ ID NO 67
<211> LENGTH: 58
<212> TYPE: DNA
<213> ORGANISM: Artificial
<220> FEATURE:
<223> OTHER INFORMATION: Synthetic oligonucleotide

<400> SEQUENCE: 67
cttagatgca cgtggataat catatgtcct tctcttccct aatgaagtac taacctga  58

<210> SEQ ID NO 68
<211> LENGTH: 51
<212> TYPE: DNA
<213> ORGANISM: Artificial
<220> FEATURE:
<223> OTHER INFORMATION: Synthetic oligonucleotide

<400> SEQUENCE: 68
cttagatgca cgtggataat catatgtcct tctcttccct aataggattc c         51

<210> SEQ ID NO 69
<211> LENGTH: 100
<212> TYPE: DNA
<213> ORGANISM: Artificial
<220> FEATURE:
<223> OTHER INFORMATION: Synthetic oligonucleotide

<400> SEQUENCE: 69
catcagctcg cagtcgatct cgtatgccgt cttctgtttt tttttttttt tttttttttt 60
tttttttttt tttttttttt ccagccaccg ccaaccatcc                     100

<210> SEQ ID NO 70
<211> LENGTH: 100
<212> TYPE: DNA
<213> ORGANISM: Artificial
<220> FEATURE:
<223> OTHER INFORMATION: Synthetic oligonucleotide
```

<400> SEQUENCE: 70
attatccacg tgcatctaag atctcgtatg ccgtcttctg tttttttttt tttttttttt            60
tttttttttt tttttttttt ggatggttgg cggtggctgg                                 100

<210> SEQ ID NO 71
<211> LENGTH: 31
<212> TYPE: DNA
<213> ORGANISM: Artificial
<220> FEATURE:
<223> OTHER INFORMATION: Synthetic oligonucleotide

<400> SEQUENCE: 71
cgactgcgag ctgatgtggc atctgataac g                                          31

<210> SEQ ID NO 72
<211> LENGTH: 31
<212> TYPE: DNA
<213> ORGANISM: Artificial
<220> FEATURE:
<223> OTHER INFORMATION: Synthetic oligonucleotide

<400> SEQUENCE: 72
cgactgcgag ctgatgaggt accagataac g                                          31

<210> SEQ ID NO 73
<211> LENGTH: 31
<212> TYPE: DNA
<213> ORGANISM: Artificial
<220> FEATURE:
<223> OTHER INFORMATION: Synthetic oligonucleotide

<400> SEQUENCE: 73
cgactgcgag ctgatgcact tacggataac g                                          31

<210> SEQ ID NO 74
<211> LENGTH: 31
<212> TYPE: DNA
<213> ORGANISM: Artificial
<220> FEATURE:
<223> OTHER INFORMATION: Synthetic oligonucleotide

<400> SEQUENCE: 74
cgactgcgag ctgatgtcat gtgggataac g                                          31

<210> SEQ ID NO 75
<211> LENGTH: 31
<212> TYPE: DNA
<213> ORGANISM: Artificial
<220> FEATURE:
<223> OTHER INFORMATION: Synthetic oligonucleotide

<400> SEQUENCE: 75
cgactgcgag ctgatgcacc aaacgataac g                                          31

<210> SEQ ID NO 76
<211> LENGTH: 31
<212> TYPE: DNA
<213> ORGANISM: Artificial
<220> FEATURE:
<223> OTHER INFORMATION: Synthetic oligonucleotide

<400> SEQUENCE: 76
cgactgcgag ctgatgattg tcccgataac g                                          31

<210> SEQ ID NO 77
<211> LENGTH: 31
<212> TYPE: DNA
<213> ORGANISM: Artificial
<220> FEATURE:
<223> OTHER INFORMATION: Synthetic oligonucleotide

<400> SEQUENCE: 77
cgactgcgag ctgatgcgtt tgcagataac g                          31

<210> SEQ ID NO 78
<211> LENGTH: 31
<212> TYPE: DNA
<213> ORGANISM: Artificial
<220> FEATURE:
<223> OTHER INFORMATION: Synthetic oligonucleotide

<400> SEQUENCE: 78
cgactgcgag ctgatgtctt tccggataac g                          31

<210> SEQ ID NO 79
<211> LENGTH: 31
<212> TYPE: DNA
<213> ORGANISM: Artificial
<220> FEATURE:
<223> OTHER INFORMATION: Synthetic oligonucleotide

<400> SEQUENCE: 79
cgactgcgag ctgatgttgc tcacgataac g                          31

<210> SEQ ID NO 80
<211> LENGTH: 30
<212> TYPE: DNA
<213> ORGANISM: Artificial
<220> FEATURE:
<223> OTHER INFORMATION: Synthetic oligonucleotide

<400> SEQUENCE: 80
cgactgcgag ctgatgagga gcaagataac                            30

<210> SEQ ID NO 81
<211> LENGTH: 31
<212> TYPE: DNA
<213> ORGANISM: Artificial
<220> FEATURE:
<223> OTHER INFORMATION: Synthetic oligonucleotide

<400> SEQUENCE: 81
cgactgcgag ctgatgttcc cttcgataac g                          31

<210> SEQ ID NO 82
<211> LENGTH: 31
<212> TYPE: DNA
<213> ORGANISM: Artificial
<220> FEATURE:
<223> OTHER INFORMATION: Synthetic oligonucleotide

<400> SEQUENCE: 82
cgactgcgag ctgatgtctg aggtgataac g                          31

<210> SEQ ID NO 83
<211> LENGTH: 31
<212> TYPE: DNA
<213> ORGANISM: Artificial
<220> FEATURE:
<223> OTHER INFORMATION: Synthetic oligonucleotide

<400> SEQUENCE: 83
cgactgcgag ctgatggcct tgatgataac g                                      31

<210> SEQ ID NO 84
<211> LENGTH: 31
<212> TYPE: DNA
<213> ORGANISM: Artificial
<220> FEATURE:
<223> OTHER INFORMATION: Synthetic oligonucleotide

<400> SEQUENCE: 84
cgactgcgag ctgatgcgta ctaggataac g                                      31

<210> SEQ ID NO 85
<211> LENGTH: 31
<212> TYPE: DNA
<213> ORGANISM: Artificial
<220> FEATURE:
<223> OTHER INFORMATION: Synthetic oligonucleotide

<400> SEQUENCE: 85
cgactgcgag ctgatgtgta cgcagataac g                                      31

<210> SEQ ID NO 86
<211> LENGTH: 31
<212> TYPE: DNA
<213> ORGANISM: Artificial
<220> FEATURE:
<223> OTHER INFORMATION: Synthetic oligonucleotide

<400> SEQUENCE: 86
cgactgcgag ctgatgagta ctgcgataac g                                      31

<210> SEQ ID NO 87
<211> LENGTH: 31
<212> TYPE: DNA
<213> ORGANISM: Artificial
<220> FEATURE:
<223> OTHER INFORMATION: Synthetic oligonucleotide

<400> SEQUENCE: 87
cgactgcgag ctgatgttgg gcaagataac g                                      31

<210> SEQ ID NO 88
<211> LENGTH: 31
<212> TYPE: DNA
<213> ORGANISM: Artificial
<220> FEATURE:
<223> OTHER INFORMATION: Synthetic oligonucleotide

<400> SEQUENCE: 88
cgactgcgag ctgatgttcc acgtgataac g                                      31

<210> SEQ ID NO 89
<211> LENGTH: 31
<212> TYPE: DNA
<213> ORGANISM: Artificial
<220> FEATURE:
<223> OTHER INFORMATION: Synthetic oligonucleotide

<400> SEQUENCE: 89
cgactgcgag ctgatggagt tacggataac g                                      31

<210> SEQ ID NO 90
<211> LENGTH: 31

```
<212> TYPE: DNA
<213> ORGANISM: Artificial
<220> FEATURE:
<223> OTHER INFORMATION: Synthetic oligonucleotide

<400> SEQUENCE: 90
cgactgcgag ctgatgtgat ataggataac g                              31

<210> SEQ ID NO 91
<211> LENGTH: 31
<212> TYPE: DNA
<213> ORGANISM: Artificial
<220> FEATURE:
<223> OTHER INFORMATION: Synthetic oligonucleotide

<400> SEQUENCE: 91
cgactgcgag ctgatgacct tagagataac g                              31

<210> SEQ ID NO 92
<211> LENGTH: 22
<212> TYPE: DNA
<213> ORGANISM: Artificial
<220> FEATURE:
<223> OTHER INFORMATION: Synthetic oligonucleotide

<400> SEQUENCE: 92
tctcggtggt cgccgtatca tt                                        22

<210> SEQ ID NO 93
<211> LENGTH: 24
<212> TYPE: DNA
<213> ORGANISM: Artificial
<220> FEATURE:
<223> OTHER INFORMATION: Synthetic oligonucleotide

<400> SEQUENCE: 93
atctcgtatg ccgtcttctg cttg                                      24

<210> SEQ ID NO 94
<211> LENGTH: 41
<212> TYPE: DNA
<213> ORGANISM: Artificial
<220> FEATURE:
<223> OTHER INFORMATION: Synthetic oligonucleotide

<400> SEQUENCE: 94
tagggaagag aaggacatat gattatccac gtgcatctaa g                   41

<210> SEQ ID NO 95
<211> LENGTH: 52
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (25)..(36)
<223> OTHER INFORMATION: n is 5-nitroindole

<400> SEQUENCE: 95
ctgcgcctat aggaattcgt tatcnnnnnn nnnnnnggac acggccgtta tc        52

<210> SEQ ID NO 96
<211> LENGTH: 24
<212> TYPE: DNA
<213> ORGANISM: Artificial
<220> FEATURE:
```

<223> OTHER INFORMATION: Synthetic oligonucleotide

<400> SEQUENCE: 96
ctgcgcctat acgaattcgt tatc                                          24

<210> SEQ ID NO 97
<211> LENGTH: 58
<212> TYPE: DNA
<213> ORGANISM: Artificial
<220> FEATURE:
<223> OTHER INFORMATION: Synthetic oligonucleotide

<400> SEQUENCE: 97
agatcggaag agcgtcgtgt agggaaagag tgtagatctc ggtggtcgcc gtatcatt    58

<210> SEQ ID NO 98
<211> LENGTH: 14
<212> TYPE: DNA
<213> ORGANISM: Artificial
<220> FEATURE:
<223> OTHER INFORMATION: Synthetic oligonucleotide

<400> SEQUENCE: 98
ttccgatctc gtta                                                    14

<210> SEQ ID NO 99
<211> LENGTH: 85
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t

<400> SEQUENCE: 99
ttgactagta catgaccact tgannnnnnn nnnnnnnnnn nnnnnnnnnn nnnnnnnnnn    60
nnncacatca gactggacga cagaa                                        85

<210> SEQ ID NO 100
<211> LENGTH: 10
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: n is a, c, g, or t

<400> SEQUENCE: 100 nnnnnnnnnc                                                         10

<210> SEQ ID NO 101
<211> LENGTH: 41
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(29)
<223> OTHER INFORMATION: n is a, c, g, or t

<400> SEQUENCE: 101
atcccttctc ttcctgtata ctannnnnng cacgtagatt c                      41

```
<210> SEQ ID NO 102
<211> LENGTH: 18
<212> TYPE: RNA
<213> ORGANISM: Artificial
<220> FEATURE:
<223> OTHER INFORMATION: Synthetic oligonucleotide

<400> SEQUENCE: 102
gcaucuaagu ucugucgu                                                    18

<210> SEQ ID NO 103
<211> LENGTH: 23
<212> TYPE: DNA
<213> ORGANISM: Artificial
<220> FEATURE:
<223> OTHER INFORMATION: Synthetic oligonucleotide

<400> SEQUENCE: 103
tagggaagag aaggacatat gat                                              23

<210> SEQ ID NO 104
<211> LENGTH: 23
<212> TYPE: DNA
<213> ORGANISM: Artificial
<220> FEATURE:
<223> OTHER INFORMATION: Synthetic oligonucleotide

<400> SEQUENCE: 104
atcatatgtc cttctcttcc cta                                              23

<210> SEQ ID NO 105
<211> LENGTH: 23
<212> TYPE: DNA
<213> ORGANISM: Artificial
<220> FEATURE:
<223> OTHER INFORMATION: Synthetic oligonucleotide

<400> SEQUENCE: 105
tagggaagag aaggacatat gat                                              23

<210> SEQ ID NO 106
<211> LENGTH: 23
<212> TYPE: DNA
<213> ORGANISM: Artificial
<220> FEATURE:
<223> OTHER INFORMATION: Synthetic oligonucleotide

<400> SEQUENCE: 106
ttgactagta catgaccact tga                                              23

<210> SEQ ID NO 107
<211> LENGTH: 126
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (24)..(63)
<223> OTHER INFORMATION: n is a, c, g, or t
<220> FEATURE:
<221> NAME/KEY: misc_feature
<222> LOCATION: (98)..(103)
<223> OTHER INFORMATION: n is a, c, g, or t

<400> SEQUENCE: 107
```

-continued

```
ttgactagta catgaccact tgannnnnnnn nnnnnnnnnn nnnnnnnnnn nnnnnnnnn      60 nnncacatca gactggacga cagaacttag atgcacgnnn nnnatcatat gtccttctct     120
tcccta                                                               126
```

<210> SEQ ID NO 108
<211> LENGTH: 66
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (25)..(32)
<223> OTHER INFORMATION: n is a, c, g, or t

<400> SEQUENCE: 108

```
caagcagaag acggcatacg agatnnnnnn nngtgcgtgc gtgcttctgt cgtccagtct      60
gatgtg                                                                66
```

<210> SEQ ID NO 109
<211> LENGTH: 70
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (30)..(35)
<223> OTHER INFORMATION: n is a, c, g, or t

<400> SEQUENCE: 109

```
aatgatacgg cgaccaccga gatctacacn nnnnngcatg cagccggttg actagtacat      60
gaccacttga                                                            70
```

<210> SEQ ID NO 110
<211> LENGTH: 23
<212> TYPE: DNA
<213> ORGANISM: Artificial
<220> FEATURE:
<223> OTHER INFORMATION: Synthetic oligonucleotide

<400> SEQUENCE: 110

```
tagggaagag aaggacatat gat                                             23
```

<210> SEQ ID NO 111
<211> LENGTH: 23
<212> TYPE: DNA
<213> ORGANISM: Artificial
<220> FEATURE:
<223> OTHER INFORMATION: Synthetic oligonucleotide

<400> SEQUENCE: 111

```
ttgactagta catgaccact tga                                             23
```

<210> SEQ ID NO 112
<211> LENGTH: 10
<212> TYPE: PRT
<213> ORGANISM: Artificial
<220> FEATURE:
<223> OTHER INFORMATION: Synthetic peptide

<400> SEQUENCE: 112

```
Tyr Gln Asn Thr Ser Gln Asn Thr Ser Cys
1               5                   10
```

```
<210> SEQ ID NO 113
<211> LENGTH: 10
<212> TYPE: PRT
<213> ORGANISM: Artificial
<220> FEATURE:
<223> OTHER INFORMATION: Synthetic peptide

<400> SEQUENCE: 113

Lys Gln Asn Thr Tyr Gln Asn Thr Ser Cys
1               5                   10

<210> SEQ ID NO 114
<211> LENGTH: 10
<212> TYPE: PRT
<213> ORGANISM: Artificial
<220> FEATURE:
<223> OTHER INFORMATION: Synthetic peptide

<400> SEQUENCE: 114

Gln Asn Thr Ser Tyr Gln Asn Thr Ser Cys
1               5                   10

<210> SEQ ID NO 115
<211> LENGTH: 23
<212> TYPE: DNA
<213> ORGANISM: Artificial
<220> FEATURE:
<223> OTHER INFORMATION: Synthetic oligonucleotide

<400> SEQUENCE: 115
tagggaagag aaggacatat gat                                             23

<210> SEQ ID NO 116
<211> LENGTH: 34
<212> TYPE: DNA
<213> ORGANISM: Artificial
<220> FEATURE:
<223> OTHER INFORMATION: Synthetic oligonucleotide

<400> SEQUENCE: 116
gctctacagt attgactagt acatgaccac ttga                                 34

<210> SEQ ID NO 117
<211> LENGTH: 10
<212> TYPE: DNA
<213> ORGANISM: Artificial
<220> FEATURE:
<223> OTHER INFORMATION: Synthetic oligonucleotide

<400> SEQUENCE: 117
aatgctgagc                                                            10

<210> SEQ ID NO 118
<211> LENGTH: 10
<212> TYPE: DNA
<213> ORGANISM: Artificial
<220> FEATURE:
<223> OTHER INFORMATION: Synthetic oligonucleotide

<400> SEQUENCE: 118
cactacagcc                                                            10

<210> SEQ ID NO 119
<211> LENGTH: 10
<212> TYPE: DNA
<213> ORGANISM: Artificial
```

```
<220> FEATURE:
<223> OTHER INFORMATION: Synthetic oligonucleotide

<400> SEQUENCE: 119
tagcactgag                                                              10

<210> SEQ ID NO 120
<211> LENGTH: 34
<212> TYPE: DNA
<213> ORGANISM: Artificial
<220> FEATURE:
<223> OTHER INFORMATION: Synthetic oligonucleotide

<400> SEQUENCE: 120
gctctacagt attgactagt acatgaccac ttga                                   34

<210> SEQ ID NO 121
<211> LENGTH: 7
<212> TYPE: PRT
<213> ORGANISM: Artificial
<220> FEATURE:
<223> OTHER INFORMATION: Synthetic peptide

<400> SEQUENCE: 121

Arg Val Pro Gly Ala Asn Asp
1               5

<210> SEQ ID NO 122
<211> LENGTH: 7
<212> TYPE: PRT
<213> ORGANISM: Artificial
<220> FEATURE:
<223> OTHER INFORMATION: Synthetic peptide

<400> SEQUENCE: 122

Thr His Glu Met Phe Trp Lys
1               5

<210> SEQ ID NO 123
<211> LENGTH: 7
<212> TYPE: PRT
<213> ORGANISM: Artificial
<220> FEATURE:
<223> OTHER INFORMATION: Synthetic peptide

<400> SEQUENCE: 123

Arg Val Pro Gly Ala Asn Asp
1               5

<210> SEQ ID NO 124
<211> LENGTH: 10
<212> TYPE: PRT
<213> ORGANISM: Artificial
<220> FEATURE:
<223> OTHER INFORMATION: Synthetic peptide

<400> SEQUENCE: 124

Asp Asp Asn His Phe Glu Asn Glu Ile Lys
1               5                   10

<210> SEQ ID NO 125
<211> LENGTH: 10
<212> TYPE: PRT
<213> ORGANISM: Artificial
<220> FEATURE:
<223> OTHER INFORMATION: Synthetic peptide
```

```
<400> SEQUENCE: 125

Asp Asp Thr Lys Tyr Val Gly Thr Gly Lys
1               5                   10

<210> SEQ ID NO 126
<211> LENGTH: 10
<212> TYPE: PRT
<213> ORGANISM: Artificial
<220> FEATURE:
<223> OTHER INFORMATION: Synthetic peptide

<400> SEQUENCE: 126

Asp Asp Asn His Phe Glu Asn Glu Ile Lys
1               5                   10

<210> SEQ ID NO 127
<211> LENGTH: 10
<212> TYPE: PRT
<213> ORGANISM: Artificial
<220> FEATURE:
<223> OTHER INFORMATION: Synthetic peptide

<400> SEQUENCE: 127

Asp Asp Thr Lys Tyr Val Gly Thr Gly Lys
1               5                   10

<210> SEQ ID NO 128
<211> LENGTH: 10
<212> TYPE: PRT
<213> ORGANISM: Artificial
<220> FEATURE:
<223> OTHER INFORMATION: Synthetic peptide

<400> SEQUENCE: 128

Asp Cys Asn His Phe Glu Asn Glu Ile Lys
1               5                   10

<210> SEQ ID NO 129
<211> LENGTH: 10
<212> TYPE: PRT
<213> ORGANISM: Artificial
<220> FEATURE:
<223> OTHER INFORMATION: Synthetic peptide

<400> SEQUENCE: 129

Asp Cys Thr Lys Tyr Val Gly Thr Gly Lys
1               5                   10

<210> SEQ ID NO 130
<211> LENGTH: 10
<212> TYPE: PRT
<213> ORGANISM: Artificial
<220> FEATURE:
<223> OTHER INFORMATION: Synthetic peptide

<400> SEQUENCE: 130

Asp Cys Asn His Phe Glu Asn Glu Ile Lys
1               5                   10

<210> SEQ ID NO 131
<211> LENGTH: 10
<212> TYPE: PRT
<213> ORGANISM: Artificial
<220> FEATURE:
<223> OTHER INFORMATION: Synthetic peptide

<400> SEQUENCE: 131
```

Asp Cys Thr Lys Tyr Val Gly Thr Gly Lys
1               5                   10

<210> SEQ ID NO 132
<211> LENGTH: 10
<212> TYPE: PRT
<213> ORGANISM: Artificial
<220> FEATURE:
<223> OTHER INFORMATION: Synthetic peptide

<400> SEQUENCE: 132

Asp Asp Asn His Phe Glu Asn Glu Ile Lys
1               5                   10

<210> SEQ ID NO 133
<211> LENGTH: 10
<212> TYPE: PRT
<213> ORGANISM: Artificial
<220> FEATURE:
<223> OTHER INFORMATION: Synthetic peptide

<400> SEQUENCE: 133

Asp Cys Thr Lys Tyr Val Gly Thr Gly Lys
1               5                   10

<210> SEQ ID NO 134
<211> LENGTH: 10
<212> TYPE: PRT
<213> ORGANISM: Artificial
<220> FEATURE:
<223> OTHER INFORMATION: Synthetic peptide

<400> SEQUENCE: 134

Asp Asp Asn His Phe Glu Asn Glu Ile Lys
1               5                   10

<210> SEQ ID NO 135
<211> LENGTH: 10
<212> TYPE: PRT
<213> ORGANISM: Artificial
<220> FEATURE:
<223> OTHER INFORMATION: Synthetic peptide

<400> SEQUENCE: 135

Asp Cys Thr Lys Tyr Val Gly Thr Gly Lys
1               5                   10

<210> SEQ ID NO 136
<211> LENGTH: 46
<212> TYPE: DNA
<213> ORGANISM: Artificial
<220> FEATURE:
<223> OTHER INFORMATION: Synthetic oligonucleotide

<400> SEQUENCE: 136
caccgcatcc tgaggccggt gtggagggca cgaagtctgg aagaat        46

<210> SEQ ID NO 137
<211> LENGTH: 46
<212> TYPE: DNA
<213> ORGANISM: Artificial
<220> FEATURE:
<223> OTHER INFORMATION: Synthetic oligonucleotide

<400> SEQUENCE: 137
tgactagtac atgaccactt gagcacgcac gcactaaggc cccaac        46

<210> SEQ ID NO 138
<211> LENGTH: 46
<212> TYPE: DNA
<213> ORGANISM: Artificial
<220> FEATURE:
<223> OTHER INFORMATION: Synthetic oligonucleotide

<400> SEQUENCE: 138
ctagcatggt gcccttaccc tcagagcgga agtacctgat atgaat        46

<210> SEQ ID NO 139
<211> LENGTH: 46
<212> TYPE: DNA
<213> ORGANISM: Artificial
<220> FEATURE:
<223> OTHER INFORMATION: Synthetic oligonucleotide

<400> SEQUENCE: 139
caccgcatcc tgaggccggt gtggagggca cgaagtctgg ttgaat        46

<210> SEQ ID NO 140
<211> LENGTH: 46
<212> TYPE: DNA
<213> ORGANISM: Artificial
<220> FEATURE:
<223> OTHER INFORMATION: Synthetic oligonucleotide

<400> SEQUENCE: 140
tgactagtac atgaccactt gagcacgcac gcactaaggc cccaag        46

<210> SEQ ID NO 141
<211> LENGTH: 46
<212> TYPE: DNA
<213> ORGANISM: Artificial
<220> FEATURE:
<223> OTHER INFORMATION: Synthetic oligonucleotide

<400> SEQUENCE: 141
ctagcatggt gcccttaccc tcagagcgga agtacctgat aagact        46

<210> SEQ ID NO 142
<211> LENGTH: 46
<212> TYPE: DNA
<213> ORGANISM: Artificial
<220> FEATURE:
<223> OTHER INFORMATION: Synthetic oligonucleotide

<400> SEQUENCE: 142
gaacccatgg ttcagtgctt catgttagta tgaaagctta aaaaaa        46

<210> SEQ ID NO 143
<211> LENGTH: 46
<212> TYPE: DNA
<213> ORGANISM: Artificial
<220> FEATURE:
<223> OTHER INFORMATION: Synthetic oligonucleotide

<400> SEQUENCE: 143
caccgcatcc tgaggccggt gtggagggca cgaagtctgg atgact        46

<210> SEQ ID NO 144
<211> LENGTH: 46
<212> TYPE: DNA
<213> ORGANISM: Artificial
<220> FEATURE:

<223> OTHER INFORMATION: Synthetic oligonucleotide

<400> SEQUENCE: 144
ctagcatggt gcccttaccc tcagagcgga agtacctgat ttgact        46

<210> SEQ ID NO 145
<211> LENGTH: 46
<212> TYPE: DNA
<213> ORGANISM: Artificial
<220> FEATURE:
<223> OTHER INFORMATION: Synthetic oligonucleotide

<400> SEQUENCE: 145
ctagcatggt gcccttaccc tcagagcgga agtacctgat aagaac        46

<210> SEQ ID NO 146
<211> LENGTH: 46
<212> TYPE: DNA
<213> ORGANISM: Artificial
<220> FEATURE:
<223> OTHER INFORMATION: Synthetic oligonucleotide

<400> SEQUENCE: 146
ccaaccggtc ctgggcgcta tcggctagct cttggagaaa atgact        46

<210> SEQ ID NO 147
<211> LENGTH: 46
<212> TYPE: DNA
<213> ORGANISM: Artificial
<220> FEATURE:
<223> OTHER INFORMATION: Synthetic oligonucleotide

<400> SEQUENCE: 147
ccaaccggtc ctgggcgcta tcggctagct cttggagaaa aagaat        46

<210> SEQ ID NO 148
<211> LENGTH: 46
<212> TYPE: DNA
<213> ORGANISM: Artificial
<220> FEATURE:
<223> OTHER INFORMATION: Synthetic oligonucleotide

<400> SEQUENCE: 148
ctagcatggt gcccttaccc tcagagcgga agtacctgat atgact        46

<210> SEQ ID NO 149
<211> LENGTH: 46
<212> TYPE: DNA
<213> ORGANISM: Artificial
<220> FEATURE:
<223> OTHER INFORMATION: Synthetic oligonucleotide

<400> SEQUENCE: 149
caccgcatcc tgaggccggt gtggagggca cgaagtctgg tagact        46

<210> SEQ ID NO 150
<211> LENGTH: 46
<212> TYPE: DNA
<213> ORGANISM: Artificial
<220> FEATURE:
<223> OTHER INFORMATION: Synthetic oligonucleotide

<400> SEQUENCE: 150
caccgcatcc tgaggccggt gtggagggca cgaagtctgg ttgaaa        46

```
<210> SEQ ID NO 151
<211> LENGTH: 46
<212> TYPE: DNA
<213> ORGANISM: Artificial
<220> FEATURE:
<223> OTHER INFORMATION: Synthetic oligonucleotide

<400> SEQUENCE: 151
caccgcatcc tgaggccggt gtggagggca cgaagtctgg tggaat          46

<210> SEQ ID NO 152
<211> LENGTH: 46
<212> TYPE: DNA
<213> ORGANISM: Artificial
<220> FEATURE:
<223> OTHER INFORMATION: Synthetic oligonucleotide

<400> SEQUENCE: 152
caccgcatcc tgaggccggt gtggagggca cgaagtctgg tggagt          46

<210> SEQ ID NO 153
<211> LENGTH: 46
<212> TYPE: DNA
<213> ORGANISM: Artificial
<220> FEATURE:
<223> OTHER INFORMATION: Synthetic oligonucleotide

<400> SEQUENCE: 153
gctagaacac gtccttcatt caaatagaaa ctttacagtc ttgact          46

<210> SEQ ID NO 154
<211> LENGTH: 46
<212> TYPE: DNA
<213> ORGANISM: Artificial
<220> FEATURE:
<223> OTHER INFORMATION: Synthetic oligonucleotide

<400> SEQUENCE: 154
gaacccatgg ttcagtgctt catgttagta tgaaagctta aaaaat          46

<210> SEQ ID NO 155
<211> LENGTH: 46
<212> TYPE: DNA
<213> ORGANISM: Artificial
<220> FEATURE:
<223> OTHER INFORMATION: Synthetic oligonucleotide

<400> SEQUENCE: 155
gaacccatgg ttcagtgctt catgttagta tgaaagctta ttgact          46

<210> SEQ ID NO 156
<211> LENGTH: 46
<212> TYPE: DNA
<213> ORGANISM: Artificial
<220> FEATURE:
<223> OTHER INFORMATION: Synthetic oligonucleotide

<400> SEQUENCE: 156
caccgcatcc tgaggccggt gtggagggca cgaagtctgg ttgact          46

<210> SEQ ID NO 157
<211> LENGTH: 46
<212> TYPE: DNA
<213> ORGANISM: Artificial
<220> FEATURE:
<223> OTHER INFORMATION: Synthetic oligonucleotide
```

<400> SEQUENCE: 157
caccgcatcc tgaggccggt gtggagggca cgaagtctgg aagact        46

<210> SEQ ID NO 158
<211> LENGTH: 46
<212> TYPE: DNA
<213> ORGANISM: Artificial
<220> FEATURE:
<223> OTHER INFORMATION: Synthetic oligonucleotide

<400> SEQUENCE: 158
caccgcatcc tgaggccggt gtggagggca cgaagtctgg tggact        46

<210> SEQ ID NO 159
<211> LENGTH: 46
<212> TYPE: DNA
<213> ORGANISM: Artificial
<220> FEATURE:
<223> OTHER INFORMATION: Synthetic oligonucleotide

<400> SEQUENCE: 159
caccgcatcc tgaggccggt gtggagggca cgaagtctgg aggact        46

<210> SEQ ID NO 160
<211> LENGTH: 46
<212> TYPE: DNA
<213> ORGANISM: Artificial
<220> FEATURE:
<223> OTHER INFORMATION: Synthetic oligonucleotide

<400> SEQUENCE: 160
caccgcatcc tgaggccggt gtggagggca cgaagtctgg atgaat        46

<210> SEQ ID NO 161
<211> LENGTH: 46
<212> TYPE: DNA
<213> ORGANISM: Artificial
<220> FEATURE:
<223> OTHER INFORMATION: Synthetic oligonucleotide

<400> SEQUENCE: 161
tgactagtac atgaccactt gagcacgcac gcactaaggc accttt        46

<210> SEQ ID NO 162
<211> LENGTH: 46
<212> TYPE: DNA
<213> ORGANISM: Artificial
<220> FEATURE:
<223> OTHER INFORMATION: Synthetic oligonucleotide

<400> SEQUENCE: 162
ctagcatggt gcccttaccc tcagagcgga agtacctgat atgaat        46

<210> SEQ ID NO 163
<211> LENGTH: 46
<212> TYPE: DNA
<213> ORGANISM: Artificial
<220> FEATURE:
<223> OTHER INFORMATION: Synthetic oligonucleotide

<400> SEQUENCE: 163
ctagcatggt gcccttaccc tcagagcgga agtacctgat ttgact        46

<210> SEQ ID NO 164
<211> LENGTH: 46

<212> TYPE: DNA
<213> ORGANISM: Artificial
<220> FEATURE:
<223> OTHER INFORMATION: Synthetic oligonucleotide

<400> SEQUENCE: 164
tgactagtac atgaccactt gagcacgcac gcactaaggc cccgtg                                46

<210> SEQ ID NO 165
<211> LENGTH: 46
<212> TYPE: DNA
<213> ORGANISM: Artificial
<220> FEATURE:
<223> OTHER INFORMATION: Synthetic oligonucleotide

<400> SEQUENCE: 165
caccgcatcc tgaggccggt gtggagggca cgaagtctgg tagact                                46

<210> SEQ ID NO 166
<211> LENGTH: 46
<212> TYPE: DNA
<213> ORGANISM: Artificial
<220> FEATURE:
<223> OTHER INFORMATION: Synthetic oligonucleotide

<400> SEQUENCE: 166
caccgcatcc tgaggccggt gtggagggca cgaagtctgg ttgaca                                46

<210> SEQ ID NO 167
<211> LENGTH: 46
<212> TYPE: DNA
<213> ORGANISM: Artificial
<220> FEATURE:
<223> OTHER INFORMATION: Synthetic oligonucleotide

<400> SEQUENCE: 167
caccgcatcc tgaggccggt gtggagggca cgaagtctgg aggaat                                46

<210> SEQ ID NO 168
<211> LENGTH: 46
<212> TYPE: DNA
<213> ORGANISM: Artificial
<220> FEATURE:
<223> OTHER INFORMATION: Synthetic oligonucleotide

<400> SEQUENCE: 168
caccgcatcc tgaggccggt gtggagggca cgaagtctgg aagaat                                46

<210> SEQ ID NO 169
<211> LENGTH: 46
<212> TYPE: DNA
<213> ORGANISM: Artificial
<220> FEATURE:
<223> OTHER INFORMATION: Synthetic oligonucleotide

<400> SEQUENCE: 169
ctagcatggt gcccttaccc tcagagcgga agtacctgat aagaag                                46

<210> SEQ ID NO 170
<211> LENGTH: 46
<212> TYPE: DNA
<213> ORGANISM: Artificial
<220> FEATURE:
<223> OTHER INFORMATION: Synthetic oligonucleotide

<400> SEQUENCE: 170
ctagcatggt gcccttaccc tcagagcgga agtacctgat aagaaa　　　　　　　　　46

<210> SEQ ID NO 171
<211> LENGTH: 46
<212> TYPE: DNA
<213> ORGANISM: Artificial
<220> FEATURE:
<223> OTHER INFORMATION: Synthetic oligonucleotide

<400> SEQUENCE: 171
gggtcgaagg tgcaacccta tttcatgagg acctaccatc tggagt　　　　　　　　　46

<210> SEQ ID NO 172
<211> LENGTH: 46
<212> TYPE: DNA
<213> ORGANISM: Artificial
<220> FEATURE:
<223> OTHER INFORMATION: Synthetic oligonucleotide

<400> SEQUENCE: 172
gttacacgtg cgaacatatg ctttagcggc cacccggaat aagaaa　　　　　　　　　46

<210> SEQ ID NO 173
<211> LENGTH: 46
<212> TYPE: DNA
<213> ORGANISM: Artificial
<220> FEATURE:
<223> OTHER INFORMATION: Synthetic oligonucleotide

<400> SEQUENCE: 173
acgacgtcga gatcttggca ttggacttaa cctatagaca aagaat　　　　　　　　　46

<210> SEQ ID NO 174
<211> LENGTH: 46
<212> TYPE: DNA
<213> ORGANISM: Artificial
<220> FEATURE:
<223> OTHER INFORMATION: Synthetic oligonucleotide

<400> SEQUENCE: 174
gcgcataggc atcggtacgg agatggttta tctaatgggt tggact　　　　　　　　　46

<210> SEQ ID NO 175
<211> LENGTH: 46
<212> TYPE: DNA
<213> ORGANISM: Artificial
<220> FEATURE:
<223> OTHER INFORMATION: Synthetic oligonucleotide

<400> SEQUENCE: 175
caccgcatcc tgaggccggt gtggagggca cgaagtctgg gggact　　　　　　　　　46

<210> SEQ ID NO 176
<211> LENGTH: 40
<212> TYPE: DNA
<213> ORGANISM: Artificial
<220> FEATURE:
<223> OTHER INFORMATION: Synthetic oligonucleotide

<400> SEQUENCE: 176
atattctagg ttggtaggga aggcatgtat ctaattcctg　　　　　　　　　　　　　40

<210> SEQ ID NO 177
<211> LENGTH: 10
<212> TYPE: PRT
<213> ORGANISM: Artificial

```
<220> FEATURE:
<223> OTHER INFORMATION: Synthetic peptide

<400> SEQUENCE: 177

Cys Tyr Phe Gln Asn Cys Pro Arg Gly Lys
1               5                   10

<210> SEQ ID NO 178
<211> LENGTH: 23
<212> TYPE: DNA
<213> ORGANISM: Artificial
<220> FEATURE:
<223> OTHER INFORMATION: Synthetic oligonucleotide

<400> SEQUENCE: 178
tagggaagag aaggacatat gat                                           23

<210> SEQ ID NO 179
<211> LENGTH: 23
<212> TYPE: DNA
<213> ORGANISM: Artificial
<220> FEATURE:
<223> OTHER INFORMATION: Synthetic oligonucleotide

<400> SEQUENCE: 179
ttgactagta catgaccact tga                                           23

<210> SEQ ID NO 180
<211> LENGTH: 40
<212> TYPE: DNA
<213> ORGANISM: Artificial
<220> FEATURE:
<223> OTHER INFORMATION: Synthetic oligonucleotide

<400> SEQUENCE: 180
caaatcggtg ccggccggga aggggcaaaa acagtgcaac                         40

<210> SEQ ID NO 181
<211> LENGTH: 10
<212> TYPE: PRT
<213> ORGANISM: Artificial
<220> FEATURE:
<223> OTHER INFORMATION: Synthetic peptide

<400> SEQUENCE: 181

Arg Pro Pro Gly Phe Ser Pro Phe Arg Lys
1               5                   10

<210> SEQ ID NO 182
<211> LENGTH: 23
<212> TYPE: DNA
<213> ORGANISM: Artificial
<220> FEATURE:
<223> OTHER INFORMATION: Synthetic oligonucleotide

<400> SEQUENCE: 182
tagggaagag aaggacatat gat                                           23

<210> SEQ ID NO 183
<211> LENGTH: 23
<212> TYPE: DNA
<213> ORGANISM: Artificial
<220> FEATURE:
<223> OTHER INFORMATION: Synthetic oligonucleotide

<400> SEQUENCE: 183
```

```
ttgactagta catgaccact tga                                          23

<210> SEQ ID NO 184
<211> LENGTH: 40
<212> TYPE: DNA
<213> ORGANISM: Artificial
<220> FEATURE:
<223> OTHER INFORMATION: Synthetic oligonucleotide

<400> SEQUENCE: 184
gccgtaggcg taagaccaca acttcgctat ccacatggcg                        40

<210> SEQ ID NO 185
<211> LENGTH: 40
<212> TYPE: DNA
<213> ORGANISM: Artificial
<220> FEATURE:
<223> OTHER INFORMATION: Synthetic oligonucleotide

<400> SEQUENCE: 185
gctaacaaga ggacgtggtg taccatcata gagacggtca                        40

<210> SEQ ID NO 186
<211> LENGTH: 40
<212> TYPE: DNA
<213> ORGANISM: Artificial
<220> FEATURE:
<223> OTHER INFORMATION: Synthetic oligonucleotide

<400> SEQUENCE: 186
agatgcagca acgacatagt acgatatggt tcacattggt                        40

<210> SEQ ID NO 187
<211> LENGTH: 40
<212> TYPE: DNA
<213> ORGANISM: Artificial
<220> FEATURE:
<223> OTHER INFORMATION: Synthetic oligonucleotide

<400> SEQUENCE: 187
atcaagtgat gctccaataa tcgtctggat gatccccat                         40

<210> SEQ ID NO 188
<211> LENGTH: 40
<212> TYPE: DNA
<213> ORGANISM: Artificial
<220> FEATURE:
<223> OTHER INFORMATION: Synthetic oligonucleotide

<400> SEQUENCE: 188
atgcacattt cccaggcagc tttgctgtca gccatcagag                        40

<210> SEQ ID NO 189
<211> LENGTH: 40
<212> TYPE: DNA
<213> ORGANISM: Artificial
<220> FEATURE:
<223> OTHER INFORMATION: Synthetic oligonucleotide

<400> SEQUENCE: 189
cggtgggggg agggagtggg cttaaggtct tcgtttgtga                        40

<210> SEQ ID NO 190
<211> LENGTH: 40
<212> TYPE: DNA
<213> ORGANISM: Artificial
```

```
<220> FEATURE:
<223> OTHER INFORMATION: Synthetic oligonucleotide

<400> SEQUENCE: 190
cggtgggggg agggaaggga tatgttaatt tcgtcgtggc                              40

<210> SEQ ID NO 191
<211> LENGTH: 40
<212> TYPE: DNA
<213> ORGANISM: Artificial
<220> FEATURE:
<223> OTHER INFORMATION: Synthetic oligonucleotide

<400> SEQUENCE: 191
ggacggtgag gagggttgtt gattttggtg tttattttct                              40

<210> SEQ ID NO 192
<211> LENGTH: 40
<212> TYPE: DNA
<213> ORGANISM: Artificial
<220> FEATURE:
<223> OTHER INFORMATION: Synthetic oligonucleotide

<400> SEQUENCE: 192
gcagtggtgg gggaaggggg tggtgggcgt ctgatttgcg                              40

<210> SEQ ID NO 193
<211> LENGTH: 40
<212> TYPE: DNA
<213> ORGANISM: Artificial
<220> FEATURE:
<223> OTHER INFORMATION: Synthetic oligonucleotide

<400> SEQUENCE: 193
cgttgggggg aggtgggtgc ggagtagttt atttcggtgg                              40

<210> SEQ ID NO 194
<211> LENGTH: 40
<212> TYPE: DNA
<213> ORGANISM: Artificial
<220> FEATURE:
<223> OTHER INFORMATION: Synthetic oliognucleotide

<400> SEQUENCE: 194
ccacggaata atgatggtgg ttgctccccg acgcagggc                               40

<210> SEQ ID NO 195
<211> LENGTH: 40
<212> TYPE: DNA
<213> ORGANISM: Artificial
<220> FEATURE:
<223> OTHER INFORMATION: Synthetic oliognucleotide

<400> SEQUENCE: 195
gacgtattat gtgttaaccg ctattcgccg cagaatttag                              40

<210> SEQ ID NO 196
<211> LENGTH: 40
<212> TYPE: DNA
<213> ORGANISM: Artificial
<220> FEATURE:
<223> OTHER INFORMATION: Synthetic oliognucleotide

<400> SEQUENCE: 196
gtctacgcac cgatcgcagg ttagattcat aatggtgtga                              40
```

<210> SEQ ID NO 197
<211> LENGTH: 40
<212> TYPE: DNA
<213> ORGANISM: Artificial
<220> FEATURE:
<223> OTHER INFORMATION: Synthetic oliognucleotide

<400> SEQUENCE: 197
cgcaccgatc gcaggttcac gtggtataac actttgtaag                    40

<210> SEQ ID NO 198
<211> LENGTH: 40
<212> TYPE: DNA
<213> ORGANISM: Artificial
<220> FEATURE:
<223> OTHER INFORMATION: Synthetic oliognucleotide

<400> SEQUENCE: 198
acgcaccgat cgcaggtttc gagtagtttg ttaccgttca                    40

<210> SEQ ID NO 199
<211> LENGTH: 40
<212> TYPE: DNA
<213> ORGANISM: Artificial
<220> FEATURE:
<223> OTHER INFORMATION: Synthetic oliognucleotide

<400> SEQUENCE: 199
atcgagttag ggccacgcac cgatcgcagg ttgggcctaa                    40

<210> SEQ ID NO 200
<211> LENGTH: 40
<212> TYPE: DNA
<213> ORGANISM: Artificial
<220> FEATURE:
<223> OTHER INFORMATION: Synthetic oliognucleotide

<400> SEQUENCE: 200
gcaagaagag tcatctgttg tgacgcaccg atcgcaggtt                    40

<210> SEQ ID NO 201
<211> LENGTH: 40
<212> TYPE: DNA
<213> ORGANISM: Artificial
<220> FEATURE:
<223> OTHER INFORMATION: Synthetic oliognucleotide

<400> SEQUENCE: 201
acaggctagg acaatgtgaa acgcccgtgt tgctcggtta                    40

<210> SEQ ID NO 202
<211> LENGTH: 40
<212> TYPE: DNA
<213> ORGANISM: Artificial
<220> FEATURE:
<223> OTHER INFORMATION: Synthetic oliognucleotide

<400> SEQUENCE: 202
cgctcgtgtt gctcgatcag ttggcttgta acagagagtc                    40

<210> SEQ ID NO 203
<211> LENGTH: 40
<212> TYPE: DNA
<213> ORGANISM: Artificial
<220> FEATURE:
<223> OTHER INFORMATION: Synthetic oliognucleotide

```
<400> SEQUENCE: 203
acgcaccgat cgcaggttca cgtggtataa cactttgtaa                              40

<210> SEQ ID NO 204
<211> LENGTH: 40
<212> TYPE: DNA
<213> ORGANISM: Artificial
<220> FEATURE:
<223> OTHER INFORMATION: Synthetic oliognucleotide

<400> SEQUENCE: 204
atacctgctg cgtgcttatc cctgctaaaa ccgttatcgc                              40

<210> SEQ ID NO 205
<211> LENGTH: 40
<212> TYPE: DNA
<213> ORGANISM: Artificial
<220> FEATURE:
<223> OTHER INFORMATION: Synthetic oliognucleotide

<400> SEQUENCE: 205
ctggacataa catcttcatg ctgcgtgttt ccctgcttgc                              40

<210> SEQ ID NO 206
<211> LENGTH: 40
<212> TYPE: DNA
<213> ORGANISM: Artificial
<220> FEATURE:
<223> OTHER INFORMATION: Synthetic oliognucleotide

<400> SEQUENCE: 206
gtcggagacg taacacccaa cttggaccat atgctgcgtg                              40

<210> SEQ ID NO 207
<211> LENGTH: 40
<212> TYPE: DNA
<213> ORGANISM: Artificial
<220> FEATURE:
<223> OTHER INFORMATION: Synthetic oliognucleotide

<400> SEQUENCE: 207
atcctcatcc caaccgctgc gtgctctaag tcctgttcgt                              40

<210> SEQ ID NO 208
<211> LENGTH: 40
<212> TYPE: DNA
<213> ORGANISM: Artificial
<220> FEATURE:
<223> OTHER INFORMATION: Synthetic oliognucleotide

<400> SEQUENCE: 208
attgctgcgt gcatagagga ggtcatactg atgctgcgtt                              40

<210> SEQ ID NO 209
<211> LENGTH: 40
<212> TYPE: DNA
<213> ORGANISM: Artificial
<220> FEATURE:
<223> OTHER INFORMATION: Synthetic oliognucleotide

<400> SEQUENCE: 209
ccatcttgat atctctgctg cgtgcatgac tgttttttgca                             40

<210> SEQ ID NO 210
```

```
<211> LENGTH: 40
<212> TYPE: DNA
<213> ORGANISM: Artificial
<220> FEATURE:
<223> OTHER INFORMATION: Synthetic oliognucleotide

<400> SEQUENCE: 210
ttctctgctg cgtgcctcga aaacaaatta ttcctgcccg                40

<210> SEQ ID NO 211
<211> LENGTH: 40
<212> TYPE: DNA
<213> ORGANISM: Artificial
<220> FEATURE:
<223> OTHER INFORMATION: Synthetic oliognucleotide

<400> SEQUENCE: 211
gtgtggtggg ggggggggc agtgaattga tagtggccgt                40

<210> SEQ ID NO 212
<211> LENGTH: 40
<212> TYPE: DNA
<213> ORGANISM: Artificial
<220> FEATURE:
<223> OTHER INFORMATION: Synthetic oliognucleotide

<400> SEQUENCE: 212
cacactgagg ggatggcgtg tgagggggtg acgtatattt                40

<210> SEQ ID NO 213
<211> LENGTH: 40
<212> TYPE: DNA
<213> ORGANISM: Artificial
<220> FEATURE:
<223> OTHER INFORMATION: Synthetic oliognucleotide

<400> SEQUENCE: 213
ttcttgctgc gtgccctcat atgattctgc tgcctgtgtc                40

<210> SEQ ID NO 214
<211> LENGTH: 40
<212> TYPE: DNA
<213> ORGANISM: Artificial
<220> FEATURE:
<223> OTHER INFORMATION: Synthetic oliognucleotide

<400> SEQUENCE: 214
tgctgcgtgt catccctctt atcattgtcc tgcgttcctt                40

<210> SEQ ID NO 215
<211> LENGTH: 40
<212> TYPE: DNA
<213> ORGANISM: Artificial
<220> FEATURE:
<223> OTHER INFORMATION: Synthetic oliognucleotide

<400> SEQUENCE: 215
atgctgcgtg ccccaatcac actaccaacc ctgtttaccg                40

<210> SEQ ID NO 216
<211> LENGTH: 40
<212> TYPE: DNA
<213> ORGANISM: Artificial
<220> FEATURE:
<223> OTHER INFORMATION: Synthetic oliognucleotide

<400> SEQUENCE: 216
```
ttctccatgc tgcgtcatct aaccgtactc gtgcttatcc   40

<210> SEQ ID NO 217
<211> LENGTH: 40
<212> TYPE: DNA
<213> ORGANISM: Artificial
<220> FEATURE:
<223> OTHER INFORMATION: Synthetic oliognucleotide

<400> SEQUENCE: 217
gctaataagt caataaatca acatgtgtcc tgctgcgtgc   40

<210> SEQ ID NO 218
<211> LENGTH: 40
<212> TYPE: DNA
<213> ORGANISM: Artificial
<220> FEATURE:
<223> OTHER INFORMATION: Synthetic oliognucleotide

<400> SEQUENCE: 218
tttgctgcgt gctaccatcg agactcaaac tgctttgggc   40

<210> SEQ ID NO 219
<211> LENGTH: 40
<212> TYPE: DNA
<213> ORGANISM: Artificial
<220> FEATURE:
<223> OTHER INFORMATION: Synthetic oliognucleotide

<400> SEQUENCE: 219
tgctgcgtgc tacctcattc cctctctgta tacttgtccg   40

<210> SEQ ID NO 220
<211> LENGTH: 40
<212> TYPE: DNA
<213> ORGANISM: Artificial
<220> FEATURE:
<223> OTHER INFORMATION: Synthetic oliognucleotide

<400> SEQUENCE: 220
acttaccctg cgatcccaac tatgctgcgt gcccttgccc   40

<210> SEQ ID NO 221
<211> LENGTH: 40
<212> TYPE: DNA
<213> ORGANISM: Artificial
<220> FEATURE:
<223> OTHER INFORMATION: Synthetic oliognucleotide

<400> SEQUENCE: 221
ttgatcatgc tgcgtgctcc catatctgct cagctaacgt   40

<210> SEQ ID NO 222
<211> LENGTH: 40
<212> TYPE: DNA
<213> ORGANISM: Artificial
<220> FEATURE:
<223> OTHER INFORMATION: Synthetic oliognucleotide

<400> SEQUENCE: 222
gcgtagacta taccatgctg cgtgatccat acctttgacg   40

<210> SEQ ID NO 223
<211> LENGTH: 40
<212> TYPE: DNA

<213> ORGANISM: Artificial
<220> FEATURE:
<223> OTHER INFORMATION: Synthetic oliognucleotide

<400> SEQUENCE: 223
aacgacacac taaacccacc cacccacacc acaccacctt        40

<210> SEQ ID NO 224
<211> LENGTH: 40
<212> TYPE: DNA
<213> ORGANISM: Artificial
<220> FEATURE:
<223> OTHER INFORMATION: Synthetic oliognucleotide

<400> SEQUENCE: 224
aacccacatt actctatgct gcgtgtcgtc cccgtggtgc        40

<210> SEQ ID NO 225
<211> LENGTH: 40
<212> TYPE: DNA
<213> ORGANISM: Artificial
<220> FEATURE:
<223> OTHER INFORMATION: Synthetic oliognucleotide

<400> SEQUENCE: 225
ctgctgcgtg catgtcgatc gtttatgctc tgctcttccc        40

<210> SEQ ID NO 226
<211> LENGTH: 40
<212> TYPE: DNA
<213> ORGANISM: Artificial
<220> FEATURE:
<223> OTHER INFORMATION: Synthetic oliognucleotide

<400> SEQUENCE: 226
catatgatca tcctcgtgca tcggattgtt ccttgatagc        40

<210> SEQ ID NO 227
<211> LENGTH: 40
<212> TYPE: DNA
<213> ORGANISM: Artificial
<220> FEATURE:
<223> OTHER INFORMATION: Synthetic oliognucleotide

<400> SEQUENCE: 227 atacccccacc ttatgctgcg tgccatcctc ccgttccgtg       40

<210> SEQ ID NO 228
<211> LENGTH: 40
<212> TYPE: DNA
<213> ORGANISM: Artificial
<220> FEATURE:
<223> OTHER INFORMATION: Synthetic oliognucleotide

<400> SEQUENCE: 228
ccccatgctg cgtgcccctg agaatattct gctgttcatc        40

<210> SEQ ID NO 229
<211> LENGTH: 40
<212> TYPE: DNA
<213> ORGANISM: Artificial
<220> FEATURE:
<223> OTHER INFORMATION: Synthetic oliognucleotide

<400> SEQUENCE: 229
actcgttaat cctatccacg tgccatctcg cagcttaatc        40

<210> SEQ ID NO 230
<211> LENGTH: 40
<212> TYPE: DNA
<213> ORGANISM: Artificial
<220> FEATURE:
<223> OTHER INFORMATION: Synthetic oliognucleotide

<400> SEQUENCE: 230
acgttgcggg gggggtgggg ggggatggct agcgcggcat                                40

<210> SEQ ID NO 231
<211> LENGTH: 40
<212> TYPE: DNA
<213> ORGANISM: Artificial
<220> FEATURE:
<223> OTHER INFORMATION: Synthetic oliognucleotide

<400> SEQUENCE: 231
ctacacacat agcgaccaca tcacacgtgc atctctagct                                40

<210> SEQ ID NO 232
<211> LENGTH: 40
<212> TYPE: DNA
<213> ORGANISM: Artificial
<220> FEATURE:
<223> OTHER INFORMATION: Synthetic oliognucleotide

<400> SEQUENCE: 232
tacatttccc acagcaatgc atccacgtgc atcctatcgt                                40

<210> SEQ ID NO 233
<211> LENGTH: 40
<212> TYPE: DNA
<213> ORGANISM: Artificial
<220> FEATURE:
<223> OTHER INFORMATION: Synthetic oliognucleotide

<400> SEQUENCE: 233
catggctatc cccgctgcgt gaatcgtgtc atccttaccc                                40

<210> SEQ ID NO 234
<211> LENGTH: 40
<212> TYPE: DNA
<213> ORGANISM: Artificial
<220> FEATURE:
<223> OTHER INFORMATION: Synthetic oliognucleotide

<400> SEQUENCE: 234
tagatattga tccatgctgc gtgccacaaa ctgattgacc                                40

<210> SEQ ID NO 235
<211> LENGTH: 40
<212> TYPE: DNA
<213> ORGANISM: Artificial
<220> FEATURE:
<223> OTHER INFORMATION: Synthetic oliognucleotide

<400> SEQUENCE: 235
cacacgacaa gacacgacac cacaccctcc caccccact                                 40

<210> SEQ ID NO 236
<211> LENGTH: 40
<212> TYPE: DNA
<213> ORGANISM: Artificial
<220> FEATURE:

<223> OTHER INFORMATION: Synthetic oliognucleotide

<400> SEQUENCE: 236
ggacaatgca taataatcca cgtgcactcc ctgttcctcg                            40

<210> SEQ ID NO 237
<211> LENGTH: 40
<212> TYPE: DNA
<213> ORGANISM: Artificial
<220> FEATURE:
<223> OTHER INFORMATION: Synthetic oliognucleotide

<400> SEQUENCE: 237
cggtggtgtt ggatgcagtg tgtttgttgc gtgttgtggc                            40

<210> SEQ ID NO 238
<211> LENGTH: 40
<212> TYPE: DNA
<213> ORGANISM: Artificial
<220> FEATURE:
<223> OTHER INFORMATION: Synthetic oliognucleotide

<400> SEQUENCE: 238
tgtgggtgag gggagatcgt tgcctaattc agtgtgcaca                            40

<210> SEQ ID NO 239
<211> LENGTH: 40
<212> TYPE: DNA
<213> ORGANISM: Artificial
<220> FEATURE:
<223> OTHER INFORMATION: Synthetic oliognucleotide

<400> SEQUENCE: 239
gtagataagt gtgtggcgtg ataacgggga gtgcagtgtg                            40

<210> SEQ ID NO 240
<211> LENGTH: 40
<212> TYPE: DNA
<213> ORGANISM: Artificial
<220> FEATURE:
<223> OTHER INFORMATION: Synthetic oliognucleotide

<400> SEQUENCE: 240
catcggtacg gacatcatgc tgcgtgctac aaccectcgt                            40

<210> SEQ ID NO 241
<211> LENGTH: 40
<212> TYPE: DNA
<213> ORGANISM: Artificial
<220> FEATURE:
<223> OTHER INFORMATION: Synthetic oliognucleotide

<400> SEQUENCE: 241
tgaccactaa gtctgctgcg tgcaacatct gtccttatct                            40

<210> SEQ ID NO 242
<211> LENGTH: 40
<212> TYPE: DNA
<213> ORGANISM: Artificial
<220> FEATURE:
<223> OTHER INFORMATION: Synthetic oliognucleotide

<400> SEQUENCE: 242
tgctgcgtgc ccatcctgcc tacattgatc tgctattccg                            40

```
<210> SEQ ID NO 243
<211> LENGTH: 40
<212> TYPE: DNA
<213> ORGANISM: Artificial
<220> FEATURE:
<223> OTHER INFORMATION: Synthetic oliognucleotide

<400> SEQUENCE: 243
tcctcaacat atgacaaatg ctgcgtgctg ttcttcctcc                    40

<210> SEQ ID NO 244
<211> LENGTH: 12
<212> TYPE: DNA
<213> ORGANISM: Artificial
<220> FEATURE:
<223> OTHER INFORMATION: Synthetic oligonucleotide

<400> SEQUENCE: 244
cttcctcatt ca                                                  12

<210> SEQ ID NO 245
<211> LENGTH: 12
<212> TYPE: DNA
<213> ORGANISM: Artificial
<220> FEATURE:
<223> OTHER INFORMATION: Synthetic oligonucleotide

<400> SEQUENCE: 245
taactaggtg ca                                                  12

<210> SEQ ID NO 246
<211> LENGTH: 12
<212> TYPE: DNA
<213> ORGANISM: Artificial
<220> FEATURE:
<223> OTHER INFORMATION: Synthetic oligonucleotide

<400> SEQUENCE: 246
ttgctcttag cc                                                  12

<210> SEQ ID NO 247
<211> LENGTH: 12
<212> TYPE: DNA
<213> ORGANISM: Artificial
<220> FEATURE:
<223> OTHER INFORMATION: Synthetic oligonucleotide

<400> SEQUENCE: 247
cccttgggac ta                                                  12

<210> SEQ ID NO 248
<211> LENGTH: 12
<212> TYPE: DNA
<213> ORGANISM: Artificial
<220> FEATURE:
<223> OTHER INFORMATION: Synthetic oligonucleotide

<400> SEQUENCE: 248
aggatcccgg tt                                                  12

<210> SEQ ID NO 249
<211> LENGTH: 12
<212> TYPE: DNA
<213> ORGANISM: Artificial
<220> FEATURE:
<223> OTHER INFORMATION: Synthetic oligonucleotide
```

<400> SEQUENCE: 249
cgattgctgc tg                                                            12

<210> SEQ ID NO 250
<211> LENGTH: 12
<212> TYPE: DNA
<213> ORGANISM: Artificial
<220> FEATURE:
<223> OTHER INFORMATION: Synthetic oligonucleotide

<400> SEQUENCE: 250
ggctcacaat tt                                                            12

<210> SEQ ID NO 251
<211> LENGTH: 12
<212> TYPE: DNA
<213> ORGANISM: Artificial
<220> FEATURE:
<223> OTHER INFORMATION: Synthetic oligonucleotide

<400> SEQUENCE: 251
cacaaatcaa gc                                                            12

<210> SEQ ID NO 252
<211> LENGTH: 12
<212> TYPE: DNA
<213> ORGANISM: Artificial
<220> FEATURE:
<223> OTHER INFORMATION: Synthetic oligonucleotide

<400> SEQUENCE: 252
tcctctgcgg ta                                                            12

<210> SEQ ID NO 253
<211> LENGTH: 12
<212> TYPE: DNA
<213> ORGANISM: Artificial
<220> FEATURE:
<223> OTHER INFORMATION: Synthetic oligonucleotide

<400> SEQUENCE: 253
tccacatcat tc                                                            12

<210> SEQ ID NO 254
<211> LENGTH: 12
<212> TYPE: DNA
<213> ORGANISM: Artificial
<220> FEATURE:
<223> OTHER INFORMATION: Synthetic oligonucleotide

<400> SEQUENCE: 254
attccgagtg ca                                                            12

<210> SEQ ID NO 255
<211> LENGTH: 12
<212> TYPE: DNA
<213> ORGANISM: Artificial
<220> FEATURE:
<223> OTHER INFORMATION: Synthetic oligonucleotide

<400> SEQUENCE: 255
aggtactcta ag                                                            12

<210> SEQ ID NO 256
<211> LENGTH: 12

```
<212> TYPE: DNA
<213> ORGANISM: Artificial
<220> FEATURE:
<223> OTHER INFORMATION: Synthetic oligonucleotide

<400> SEQUENCE: 256
gggtaatgat gc                                                             12

<210> SEQ ID NO 257
<211> LENGTH: 12
<212> TYPE: DNA
<213> ORGANISM: Artificial
<220> FEATURE:
<223> OTHER INFORMATION: Synthetic oligonucleotide

<400> SEQUENCE: 257
tggaccgcac aa                                                             12

<210> SEQ ID NO 258
<211> LENGTH: 12
<212> TYPE: DNA
<213> ORGANISM: Artificial
<220> FEATURE:
<223> OTHER INFORMATION: Synthetic oligonucleotide

<400> SEQUENCE: 258
gcgcatagta ta                                                             12

<210> SEQ ID NO 259
<211> LENGTH: 12
<212> TYPE: DNA
<213> ORGANISM: Artificial
<220> FEATURE:
<223> OTHER INFORMATION: Synthetic oligonucleotide

<400> SEQUENCE: 259
tggcattaca cg                                                             12

<210> SEQ ID NO 260
<211> LENGTH: 12
<212> TYPE: DNA
<213> ORGANISM: Artificial
<220> FEATURE:
<223> OTHER INFORMATION: Synthetic oligonucleotide

<400> SEQUENCE: 260
gatcgcaggc ta                                                             12

<210> SEQ ID NO 261
<211> LENGTH: 12
<212> TYPE: DNA
<213> ORGANISM: Artificial
<220> FEATURE:
<223> OTHER INFORMATION: Synthetic oligonucleotide

<400> SEQUENCE: 261
ctatcggctt ta                                                             12

<210> SEQ ID NO 262
<211> LENGTH: 12
<212> TYPE: DNA
<213> ORGANISM: Artificial
<220> FEATURE:
<223> OTHER INFORMATION: Synthetic oligonucleotide

<400> SEQUENCE: 262
```
cattgggaga tt                                                              12

<210> SEQ ID NO 263
<211> LENGTH: 12
<212> TYPE: DNA
<213> ORGANISM: Artificial
<220> FEATURE:
<223> OTHER INFORMATION: Synthetic oligonucleotide

<400> SEQUENCE: 263
gccttaagat ag                                                              12

<210> SEQ ID NO 264
<211> LENGTH: 12
<212> TYPE: DNA
<213> ORGANISM: Artificial
<220> FEATURE:
<223> OTHER INFORMATION: Synthetic oligonucleotide

<400> SEQUENCE: 264
aagtcttcag ac                                                              12

<210> SEQ ID NO 265
<211> LENGTH: 12
<212> TYPE: DNA
<213> ORGANISM: Artificial
<220> FEATURE:
<223> OTHER INFORMATION: Synthetic oligonucleotide

<400> SEQUENCE: 265
ggatggtctg ta                                                              12

<210> SEQ ID NO 266
<211> LENGTH: 12
<212> TYPE: DNA
<213> ORGANISM: Artificial
<220> FEATURE:
<223> OTHER INFORMATION: Synthetic oligonucleotide

<400> SEQUENCE: 266
cctttcacgg ac                                                              12

<210> SEQ ID NO 267
<211> LENGTH: 12
<212> TYPE: DNA
<213> ORGANISM: Artificial
<220> FEATURE:
<223> OTHER INFORMATION: Synthetic oligonucleotide

<400> SEQUENCE: 267
aaatgctcgg gc                                                              12

<210> SEQ ID NO 268
<211> LENGTH: 12
<212> TYPE: DNA
<213> ORGANISM: Artificial
<220> FEATURE:
<223> OTHER INFORMATION: Synthetic oligonucleotide

<400> SEQUENCE: 268
cagatagact ag                                                              12

<210> SEQ ID NO 269
<211> LENGTH: 12
<212> TYPE: DNA
<213> ORGANISM: Artificial

```
<220> FEATURE:
<223> OTHER INFORMATION: Synthetic oligonucleotide

<400> SEQUENCE: 269
cagagtgata gc                                                             12

<210> SEQ ID NO 270
<211> LENGTH: 12
<212> TYPE: DNA
<213> ORGANISM: Artificial
<220> FEATURE:
<223> OTHER INFORMATION: Synthetic oligonucleotide

<400> SEQUENCE: 270
cagagacctg ta                                                             12

<210> SEQ ID NO 271
<211> LENGTH: 12
<212> TYPE: DNA
<213> ORGANISM: Artificial
<220> FEATURE:
<223> OTHER INFORMATION: Synthetic oligonucleotide

<400> SEQUENCE: 271
gcccattctt tg                                                             12

<210> SEQ ID NO 272
<211> LENGTH: 12
<212> TYPE: DNA
<213> ORGANISM: Artificial
<220> FEATURE:
<223> OTHER INFORMATION: Synthetic oligonucleotide

<400> SEQUENCE: 272
ccggaaggaa tg                                                             12

<210> SEQ ID NO 273
<211> LENGTH: 12
<212> TYPE: DNA
<213> ORGANISM: Artificial
<220> FEATURE:
<223> OTHER INFORMATION: Synthetic oligonucleotide

<400> SEQUENCE: 273
tgcgtcacca tc                                                             12

<210> SEQ ID NO 274
<211> LENGTH: 12
<212> TYPE: DNA
<213> ORGANISM: Artificial
<220> FEATURE:
<223> OTHER INFORMATION: Synthetic oligonucleotide

<400> SEQUENCE: 274
ccgcgtatgt aa                                                             12

<210> SEQ ID NO 275
<211> LENGTH: 12
<212> TYPE: DNA
<213> ORGANISM: Artificial
<220> FEATURE:
<223> OTHER INFORMATION: Synthetic oligonucleotide

<400> SEQUENCE: 275
aatagcggcc ga                                                             12
```

```
<210> SEQ ID NO 276
<211> LENGTH: 12
<212> TYPE: DNA
<213> ORGANISM: Artificial
<220> FEATURE:
<223> OTHER INFORMATION: Synthetic oligonucleotide

<400> SEQUENCE: 276
gcatccaatt ag                                                          12

<210> SEQ ID NO 277
<211> LENGTH: 12
<212> TYPE: DNA
<213> ORGANISM: Artificial
<220> FEATURE:
<223> OTHER INFORMATION: Synthetic oligonucleotide

<400> SEQUENCE: 277
gtagactgcg ct                                                          12

<210> SEQ ID NO 278
<211> LENGTH: 12
<212> TYPE: DNA
<213> ORGANISM: Artificial
<220> FEATURE:
<223> OTHER INFORMATION: Synthetic oligonucleotide

<400> SEQUENCE: 278
gcttctactg ta                                                          12

<210> SEQ ID NO 279
<211> LENGTH: 12
<212> TYPE: DNA
<213> ORGANISM: Artificial
<220> FEATURE:
<223> OTHER INFORMATION: Synthetic oligonucleotide

<400> SEQUENCE: 279
ctaaagtacc tc                                                          12

<210> SEQ ID NO 280
<211> LENGTH: 10
<212> TYPE: PRT
<213> ORGANISM: Artificial
<220> FEATURE:
<223> OTHER INFORMATION: Synthetic peptide

<400> SEQUENCE: 280

Arg Pro Pro Gly Phe Ser Pro Phe Arg Cys
1               5                   10

<210> SEQ ID NO 281
<211> LENGTH: 11
<212> TYPE: PRT
<213> ORGANISM: Artificial
<220> FEATURE:
<223> OTHER INFORMATION: Synthetic peptide

<400> SEQUENCE: 281

Glu His Trp Ser Tyr Gly Leu Arg Pro Gly Cys
1               5                   10

<210> SEQ ID NO 282
<211> LENGTH: 9
<212> TYPE: PRT
<213> ORGANISM: Artificial
```

```
<220> FEATURE:
<223> OTHER INFORMATION: Synthetic peptide

<400> SEQUENCE: 282

Tyr Phe Gln Asn Cys Pro Arg Gly Cys
1               5

<210> SEQ ID NO 283
<211> LENGTH: 10
<212> TYPE: PRT
<213> ORGANISM: Artificial
<220> FEATURE:
<223> OTHER INFORMATION: Synthetic peptide

<400> SEQUENCE: 283

Tyr Gln Asn Thr Ser Gln Asn Thr Ser Cys
1               5                   10

<210> SEQ ID NO 284
<211> LENGTH: 10
<212> TYPE: PRT
<213> ORGANISM: Artificial
<220> FEATURE:
<223> OTHER INFORMATION: Synthetic peptide

<400> SEQUENCE: 284

Lys Gln Asn Thr Tyr Gln Asn Thr Ser Cys
1               5                   10

<210> SEQ ID NO 285
<211> LENGTH: 10
<212> TYPE: PRT
<213> ORGANISM: Artificial
<220> FEATURE:
<223> OTHER INFORMATION: Synthetic peptide

<400> SEQUENCE: 285

Gln Asn Thr Ser Tyr Gln Asn Thr Ser Cys
1               5                   10

<210> SEQ ID NO 286
<211> LENGTH: 10
<212> TYPE: PRT
<213> ORGANISM: Artificial
<220> FEATURE:
<223> OTHER INFORMATION: Synthetic peptide

<400> SEQUENCE: 286

Lys Ile Glu Asn Glu Phe His Asn Pro Pro
1               5                   10

<210> SEQ ID NO 287
<211> LENGTH: 10
<212> TYPE: PRT
<213> ORGANISM: Artificial
<220> FEATURE:
<223> OTHER INFORMATION: Synthetic peptide

<400> SEQUENCE: 287

Lys Ile Glu Asn Glu Phe His Asn Pro Pro
1               5                   10

<210> SEQ ID NO 288
<211> LENGTH: 10
<212> TYPE: PRT
<213> ORGANISM: Artificial
<220> FEATURE:
```

```
<223> OTHER INFORMATION: Synthetic peptide

<400> SEQUENCE: 288

Lys Ile Glu Asn Glu Phe His Asn Pro Pro
1               5                   10

<210> SEQ ID NO 289
<211> LENGTH: 8
<212> TYPE: PRT
<213> ORGANISM: Artificial
<220> FEATURE:
<223> OTHER INFORMATION: Synthetic peptide

<400> SEQUENCE: 289

Lys Ile Glu Asn Glu Phe His Asn
1               5

<210> SEQ ID NO 290
<211> LENGTH: 8
<212> TYPE: PRT
<213> ORGANISM: Artificial
<220> FEATURE:
<223> OTHER INFORMATION: Synthetic peptide

<400> SEQUENCE: 290

Lys Ile Glu Asn Glu Phe His Asn
1               5

<210> SEQ ID NO 291
<211> LENGTH: 10
<212> TYPE: PRT
<213> ORGANISM: Artificial
<220> FEATURE:
<223> OTHER INFORMATION: Synthetic peptide

<400> SEQUENCE: 291

Lys Arg Phe Pro Ser Phe Gly Pro Pro Arg
1               5                   10
```